(12) United States Patent
Lee et al.

(10) Patent No.: US 9,732,069 B2
(45) Date of Patent: Aug. 15, 2017

(54) CARBAZOLE COMPOUND AND ORGANIC LIGHT EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Kumhee Lee, Suwon-si (KR); Jiyoun Lee, Suwon-si (KR); Yoonhyun Kwak, Seoul (KR); Youngjae Park, Seoul (KR); Seokhwan Hong, Seoul (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 247 days.

(21) Appl. No.: 14/598,896

(22) Filed: Jan. 16, 2015

(65) Prior Publication Data

US 2015/0336937 A1 Nov. 26, 2015

(30) Foreign Application Priority Data

May 21, 2014 (KR) .................... 10-2014-0061165
Aug. 18, 2014 (KR) .................... 10-2014-0106963

(51) Int. Cl.
*H01L 51/50* (2006.01)
*C07D 405/14* (2006.01)
(Continued)

(52) U.S. Cl.
CPC ......... *C07D 405/14* (2013.01); *C07D 409/14* (2013.01); *C07D 413/14* (2013.01);
(Continued)

(58) Field of Classification Search
None
See application file for complete search history.

(56) References Cited

U.S. PATENT DOCUMENTS

2011/0168990 A1* 7/2011 Tanaka ................ C09K 11/06
257/40
2013/0062597 A1* 3/2013 Yoshida ............. C07D 405/14
257/40

FOREIGN PATENT DOCUMENTS

JP 2009267255 A 11/2009
JP 2012049518 A 3/2012
(Continued)

*Primary Examiner* — Gregory Clark
(74) *Attorney, Agent, or Firm* — Cantor Colburn LLP

(57) ABSTRACT

A carbazole compound represented by Formula 1

Formula 1

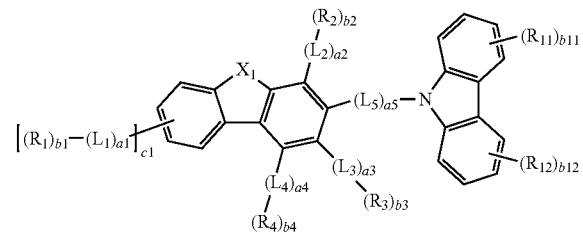

wherein, in Formula 1, $X_1$, $L_1$ to $L_5$, $R_1$ to $R_4$, $R_{11}$, $R_{12}$, a1 to a5, b1 to b4, b11, b12, and c1 are described in the specification.

20 Claims, 2 Drawing Sheets

(51) Int. Cl.
  *H01L 51/00* (2006.01)
  *C07D 413/14* (2006.01)
  *C07D 409/14* (2006.01)
  *C07D 417/14* (2006.01)
  *C07D 471/04* (2006.01)
  *C07D 495/04* (2006.01)
(52) U.S. Cl.
  CPC ......... *C07D 417/14* (2013.01); *C07D 471/04* (2013.01); *C07D 495/04* (2013.01); *H01L 51/0072* (2013.01); *H01L 51/0073* (2013.01); *H01L 51/0067* (2013.01); *H01L 51/5012* (2013.01); *H01L 51/5016* (2013.01); *H01L 2251/5384* (2013.01)

(56) References Cited

FOREIGN PATENT DOCUMENTS

| JP | 2012169325 A | 9/2012 |
| JP | 2013016717 A | 1/2013 |

* cited by examiner

CARBAZOLE COMPOUND AND ORGANIC LIGHT EMITTING DEVICE INCLUDING THE SAME

CROSS-REFERENCE TO RELATED APPLICATIONS

This application claims priority to Korean Patent Application No. 10-2014-0061165, filed on May 21, 2014, and Korean Patent Application No. 10-2014-0106963, filed on Aug. 18, 2014, in the Korean Intellectual Property Office, and all the benefits accruing therefrom under 35 U.S.C. §119, the contents of which are incorporated herein in their entirety by reference.

BACKGROUND

1. Field

The present disclosure relates to a carbazole compound and an organic light-emitting device including the carbazole compound.

2. Description of the Related Art

Organic light-emitting devices (OLEDs) are self-emitting devices, which have advantages such as wide viewing angles, excellent contrast, quick response, high brightness, excellent driving voltage characteristics, and can provide multicolored images.

A typical organic light-emitting device may include an anode, a cathode, and an organic layer disposed between the anode and the cathode and including an emission layer. The organic light-emitting device may include a hole transport region between the anode and the emission layer, and an electron transport region between the emission layer and the cathode. Holes injected from the anode move to the emission layer via the hole transport region, while electrons injected from the cathode move to the emission layer via the electron transport region. Carriers such as the holes and electrons recombine in the emission layer to generate excitons. When the excitons drop from an excited state to a ground state, light is emitted.

Various types of organic light emitting devices are known. However, there still remains a need in OLEDs having low driving voltage, high efficiency, high brightness, and long lifespan.

SUMMARY

Provided is a novel carbazole compound, and an organic light-emitting device including the novel carbazole compound.

Additional aspects will be set forth in part in the description which follows and, in part, will be apparent from the description, or may be learned by practice of the presented embodiments.

According to an aspect of the present disclosure, there is provided a carbazole compound represented by Formula 1:

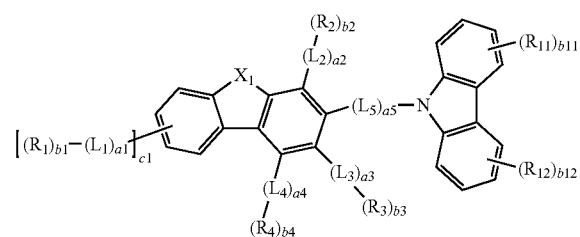

Formula 1 wherein, in Formula 1, $X_1$ is O or S;

$L_1$ to $L_5$ are each independently selected from a substituted or unsubstituted $C_1$-$C_{60}$ alkylene group, a substituted or unsubstituted $C_2$-$C_{60}$ alkenylene group, a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic condensed heteropolycyclic group;

a1 to a5 are each independently an integer selected from 0 to 5;

$R_1$ to $R_4$, $R_{11}$, and $R_{12}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, and —$B(Q_6)(Q_7)$;

at least one of $R_2$ to $R_4$ is independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group and a substituted or unsubstituted monovalent non-aromatic condensed heteropolycyclic group;

b1 to b4, b11, b12 and c1 are each independently an integer selected from 1 to 4; at least one of substituents of the substituted $C_1$-$C_{60}$ alkylene group, the substituted $C_2$-$C_{60}$ alkenylene group, the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, and a monovalent nonaromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, and a monovalent nonaromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent nonaromatic condensed polycyclic group, and a monovalent aromatic condensed heteropolycyclic group.

According to another aspect of the present disclosure, an organic light-emitting device includes:

a first electrode;
a second electrode; and
an organic layer disposed between the first electrode and the second electrode, wherein the organic layer includes an emission layer and at least one carbazole compound of Formula 1 described above.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
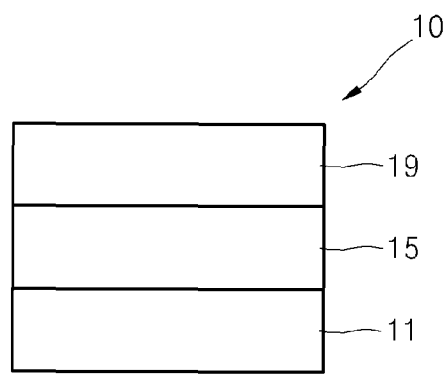
FIG. 1 is a schematic view of an organic light-emitting device according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

According to an embodiment of the present disclosure, there is provided a carbazole compound represented by Formula 1:

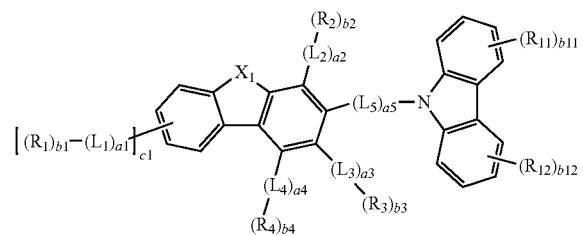

Formula 1

In Formula 1,
$X_1$ may be O or S; and
$L_1$ to $L_5$ may be each independently selected from a substituted or unsubstituted $C_1$-$C_{60}$ alkylene group, a substituted or unsubstituted $C_2$-$C_{60}$ alkenylene group, a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic condensed heteropolycyclic group.

For example, $L_1$ to $L_5$ in Formula 1 may be each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{20}$ aryl group, a phenyl group-substituted phenyl group, a $C_2$-$C_{20}$ heteroaryl group, a monovalent nonaromatic condensed polycyclic group, a monovalent nonaromatic condensed heteropolycyclic group, and —Si($Q_{33}$)($Q_{34}$)($Q_{35}$), wherein $Q_{33}$ to $Q_{35}$ may be each independently a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

In some embodiments, $L_1$ to $L_5$ in Formula 1 may be each independently a group represented by one of Formulae 2-1 to 2-37:

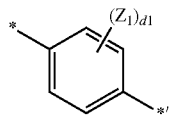
Formula 2-1

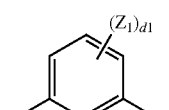
Formula 2-2

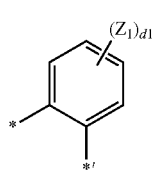
Formula 2-3

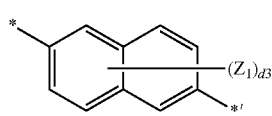
Formula 2-4

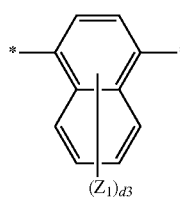
Formula 2-5

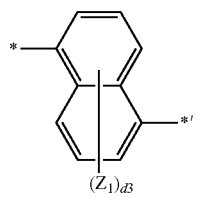
Formula 2-6

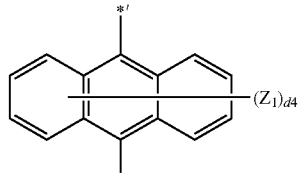
Formula 2-7

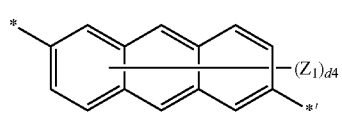
Formula 2-8

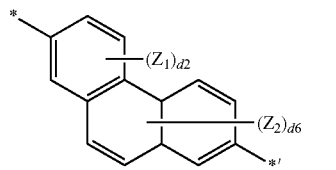
Formula 2-9

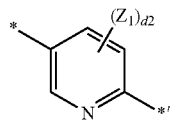
Formula 2-10

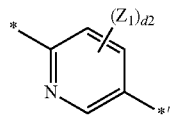
Formula 2-11

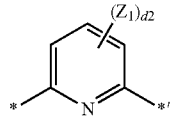
Formula 2-12

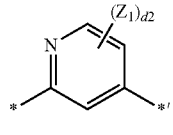
Formula 2-13

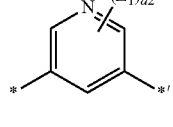
Formula 2-14

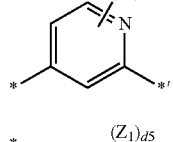
Formula 2-15

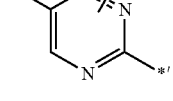
Formula 2-16

Formula 2-17
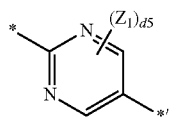
Formula 2-18
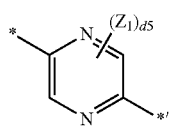
Formula 2-19
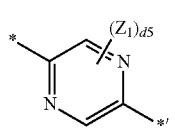
Formula 2-20
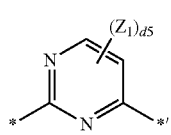
Formula 2-21
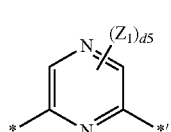
Formula 2-22
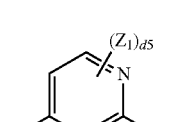
Formula 2-23
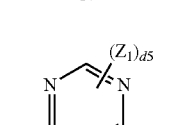
Formula 2-24
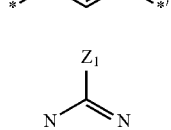
Formula 2-25
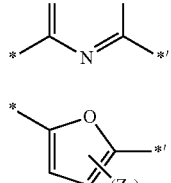
Formula 2-26
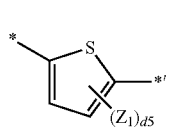
Formula 2-27
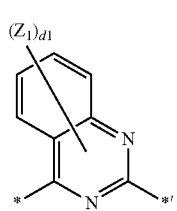
Formula 2-28
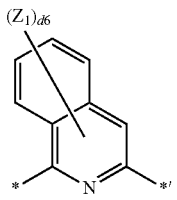
Formula 2-29
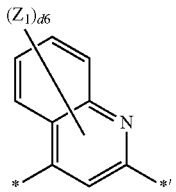
Formula 2-30

Formula 2-31
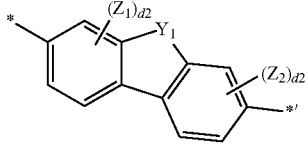
Formula 2-32
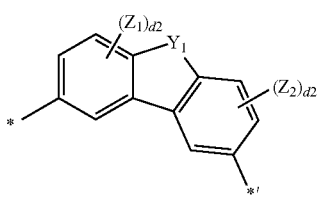
Formula 2-33
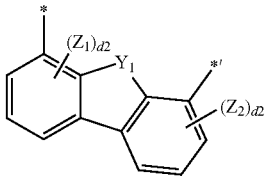
Formula 2-34
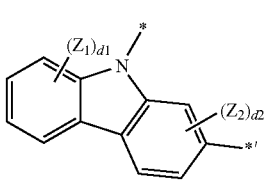
Formula 2-35
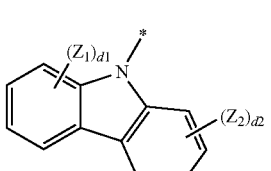

-continued

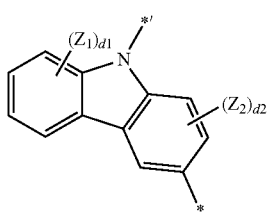
Formula 2-36

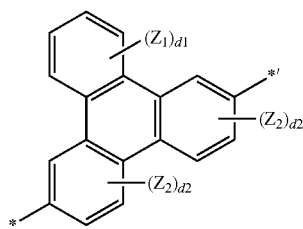
Formula 2-37

In Formulae 2-1 to 2-37, $Y_1$ may be O, S, S(=O), S(=O)$_2$, C($Z_3$)($Z_4$), N($Z_5$), or Si($Z_6$)($Z_7$);

$Z_1$ to $Z_7$ may be each independently selected from a hydrogen, a deuterium, —F, —Cl, —Br, —I, a hydroxyl group, a cyano group, a nitro group, an amino group, an amidino groups, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a phenyl group-substituted phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, and —Si($Q_{33}$)($Q_{34}$)($Q_{45}$), wherein $Q_{33}$ to $Q_{45}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

d1 may be an integer selected from 1 to 4;
d2 may be an integer selected from 1 to 3;
d3 may be an integer selected from 1 to 6;
d4 may be an integer selected from 1 to 8;
d5 may be 1 or 2;
d6 may be an integer selected from 1 to 5; and
* indicates a binding site with an adjacent atom.

In some other embodiments, $L_1$ to $L_5$ in Formula 1 may be each independently selected from a phenylene group, a naphthylene group, a phenanthrenylene group, an anthracenylene group, a triphenylenylene group, a carbazolylene group, a pyridinylene group, a pyrimidinylene group, a triazinylene group, a quinazolinylene group, a quinolinylene group, an isoquinolinylene group, a naphthyridinylene group, and an oxadiazolylene group; and a phenylene group, a naphthylene group, a phenanthrenylene group, an anthracenylene group, a triphenylenylene group, a carbazolylene group, a pyridinylene group, a pyrimidinylene group, a triazinylene group, a quinazolinylene group, a quinolinylene group, an isoquinolinylene group, a naphthyridinylene group, and an oxadiazolylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a phenyl group-substituted phenyl group, a naphthyl group, an anthracenyl group, a triphenylenyl group and a phenanthrenyl group. However, embodiments of the present disclosure are not limited thereto.

In some other embodiments, $L_1$ to $L_5$ in Formula 1 may be each independently a group represented by one of Formulae 3-1 to 3-33, but are not limited thereto:

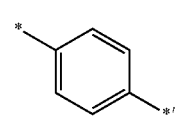
Formula 3-1

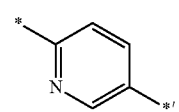
Formula 3-2

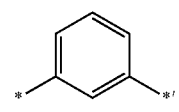
Formula 3-3

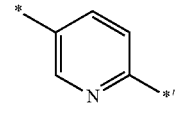
Formula 3-4

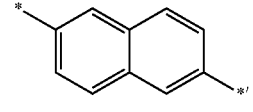
Formula 3-5

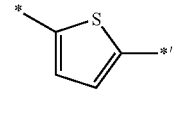
Formula 3-6

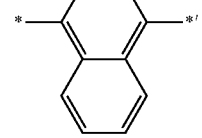
Formula 3-7

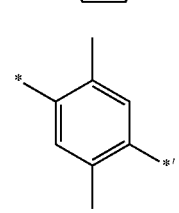
Formula 3-8

-continued
Formula 3-9
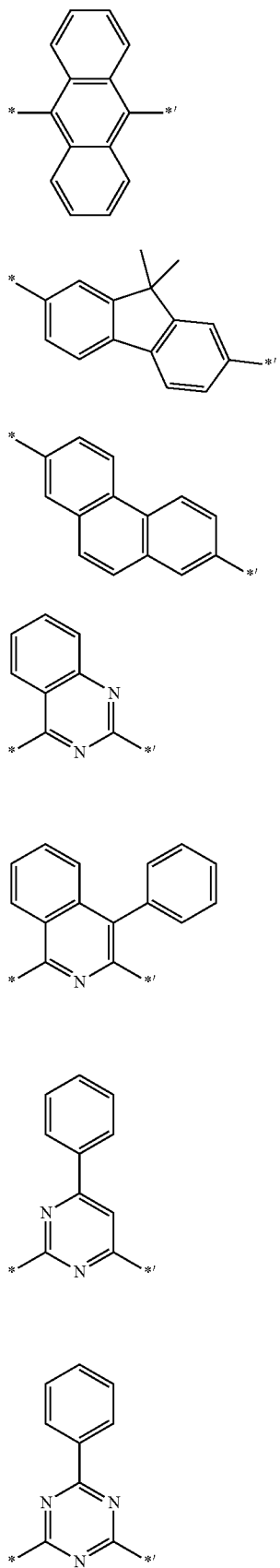
Formula 3-10
Formula 3-11
Formula 3-12
Formula 3-13
Formula 3-14
Formula 3-15
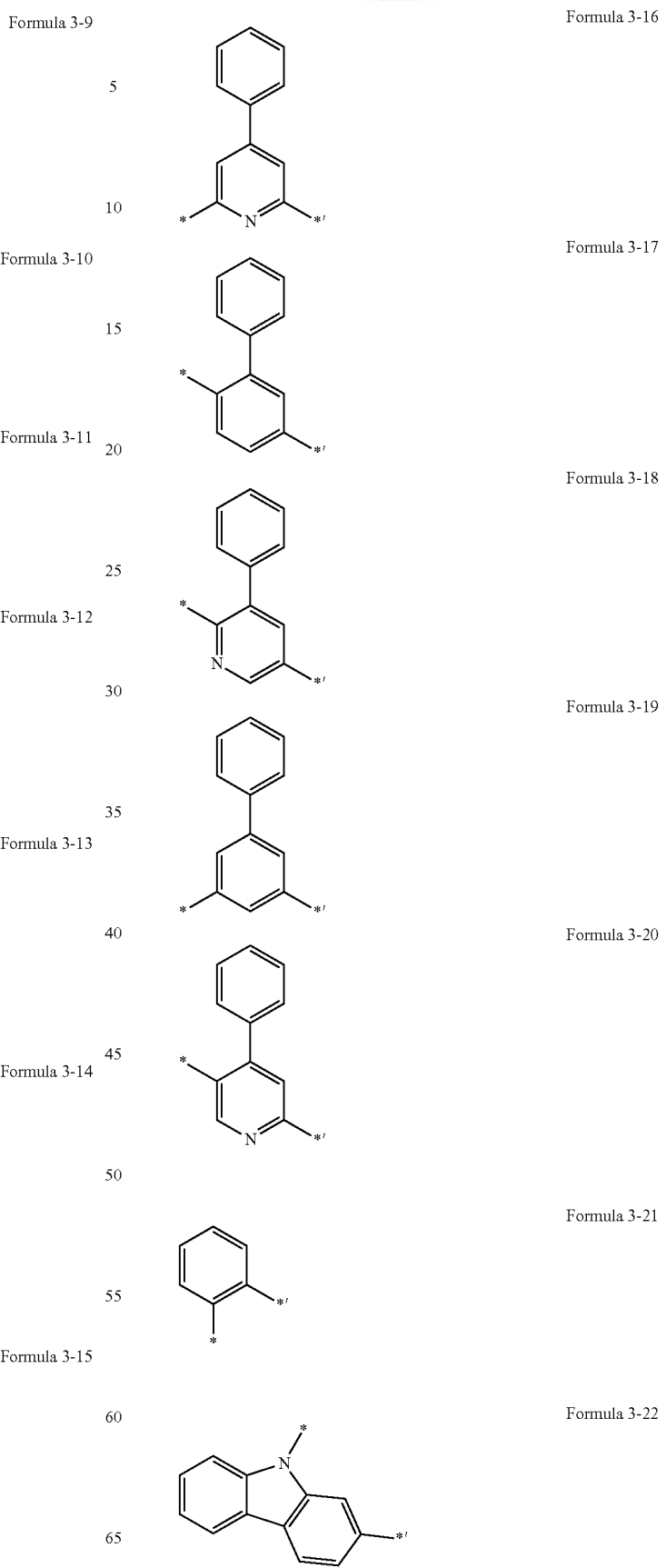
Formula 3-16
Formula 3-17
Formula 3-18
Formula 3-19
Formula 3-20
Formula 3-21
Formula 3-22

Formula 3-23
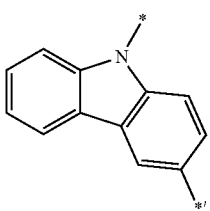

Formula 3-24
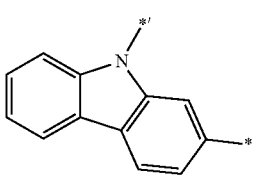

Formula 3-25
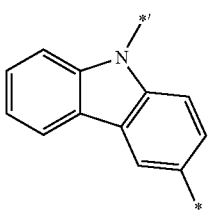

Formula 3-26
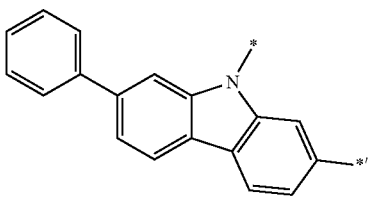

Formula 3-27
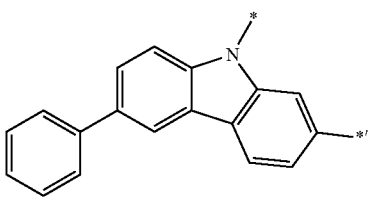

Formula 3-28
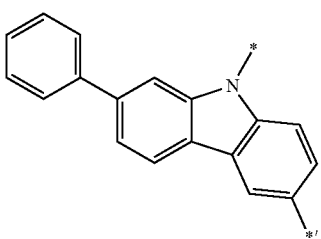

Formula 3-29
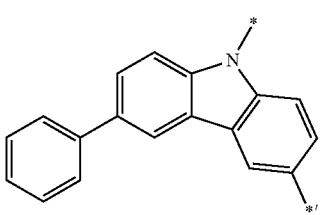

Formula 3-30
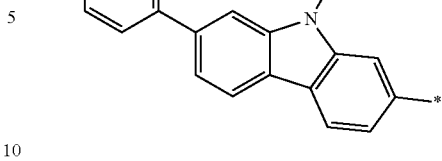

Formula 3-31
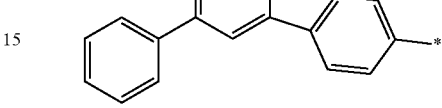

Formula 3-32
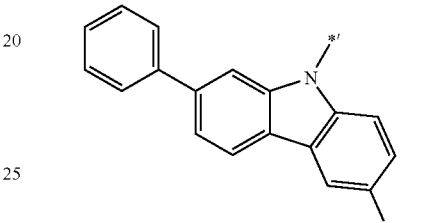

Formula 3-33
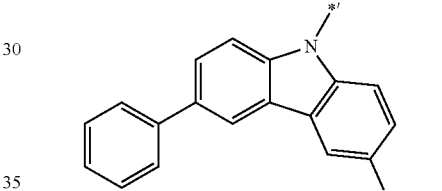

In Formulae 3-1 to 3-33, * and *' each independently indicate a binding site with an adjacent atom.

In Formula 1, a1, which indicates the number of groups $L_1$, may be 0, 1, 2, 3, 4, or 5, in some embodiments—0, 1, or 2, and in some other embodiments—0 or 1. When a1 is 0, $L_1$ is a single bond. When a1 is 2 or greater, at least two groups $L_1$ may be identical or different. a2 to a5 in Formula 1 may be understood based on the above description of a1 and the structure the compound represented by Formula 1.

In some embodiments, a1 to a5 in Formula 1 may be each independently 0, 1, or 2, for example, 0 or 1, but are not limited thereto.

In Formula 1, $R_1$ to $R_4$, $R_{11}$, and $R_{12}$ may be each independently selected from a hydrogen, a deuterium, a fluoro group (—F), a chloro group (—Cl), a bromo group (—Br), an iodo group (—I), a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$), and at least one of $R_2$ to $R_4$ may be independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group and a substituted or unsubstituted monovalent non-aromatic condensed heteropolycyclic group.

For example, $R_1$ to $R_4$, $R_{11}$, and $R_{12}$ in Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_2$-$C_{20}$ heteroaryl group, a substituted or unsubstituted monovalent nonaromatic condensed polycyclic group, and a substituted or unsubstituted monovalent nonaromatic condensed heteropolycyclic group; and at least one of $R_2$ to $R_4$ may be independently selected from a substituted or unsubstituted $C_6$-$C_{60}$ aryl group, a substituted or unsubstituted $C_2$-$C_{60}$ heteroaryl group, a substituted or unsubstituted monovalent nonaromatic condensed cyclic group, and a substituted or unsubstituted monovalent nonaromatic condensed heterocyclic group.

In some embodiments, $R_1$ to $R_4$, $R_{11}$, and $R_{12}$ in Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a $C_1$-$C_{20}$ alkyl group-substituted phenyl group, a phenyl group-substituted phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group and —Si($Q_{33}$)($Q_{34}$)($Q_{35}$), and —Si($Q_3$)($Q_4$)($Q_5$), wherein $Q_3$ to $Q_5$ and $Q_{33}$ to $Q_{35}$ may be each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

In some embodiments, at least one of $R_2$ to $R_4$ in Formula 1 may be independently selected from a triphenylenyl group, a carbazolyl group, a pyrrolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, a phenanthrolinyl group, a phenazinyl group, a benzoimidazolyl group, a benzothiazolyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, and a triphenylenyl group, a carbazolyl group, a pyrrolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, a phenanthrolinyl group, a phenazinyl group, a benzoimidazolyl group, a benzothiazolyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, each substituted with at least one of a deuterium, —F, —Cl, —Br, —I, a hydroxyl group, a cyano group, a nitro group, an amino group, an amidino group, a hydrazine group, a hydrazone group, carboxylic acid group or a salt thereof, a sulfonic acid group or a salt thereof, a phosphoric acid group or a salt thereof, $C_1$-$C_{20}$ alkyl group, $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$).

In some other embodiments, at least one of $R_2$ to $R_4$ in Formula 1 may be independently selected from a pyridinyl group, a pyrazinyl group, a pyrimidinyl group, a pyridazinyl group, a quinolinyl group, an isoquinolinyl group, a naphthyridinyl group, a quinoxalinyl group, a quinazolinyl group, a benzothiazolyl group, an isobenzothiazolyl group, a benzoxazolyl group, an isobenzooxazolyl group, an oxadiazolyl group, a triazinyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, and a pyridinyl group, a pyrazinyl group, a pyrimidinyl group, a pyridazinyl group, a quinolinyl group, an isoquinolinyl group, a naphthyridinyl group, a quinoxalinyl group, a quinazolinyl group, a benzothiazolyl group, an isobenzothiazolyl group, a benzoxazolyl group, an isobenzooxazolyl group, an oxadiazolyl group, a triazinyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, each substituted with at least one of a deuterium, —F, —Cl, —Br, —I, a hydroxyl group, a cyano group, a nitro group, an amino group, an amidino group, a hydrazine group, a hydrazone group, carboxylic acid group or a salt thereof, a sulfonic acid group or a salt thereof, a phosphoric acid group or a salt thereof, $C_1$-$C_{20}$ alkyl group, $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$). However, embodiments of the present disclosure are not limited thereto.

In some other embodiments, at least one of $R_2$ to $R_4$ in Formula 1 may be independently selected from a thiophenyl group, a furanyl group, a carbazolyl group, an acridinyl, a dibenzofuranyl group, a dibenzothiophenyl group, a benzocarbazolyl group and a dibenzocarbazolyl group, and a thiophenyl group, a furanyl group, a carbazolyl group, an acridinyl, a dibenzofuranyl group, a dibenzothiophenyl group, a benzocarbazolyl group, and a dibenzocarbazolyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group and —Si($Q_{33}$)($Q_{34}$)($Q_{35}$)

In some other embodiments, at least one of $R_2$ to $R_4$ in Formula 1 may be independently selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group and an ovalenyl group, and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$)

In some other embodiments, at least one of $R_2$ to $R_4$ in Formula 1 may be independently selected from a thiophenyl group, a furanyl group, a carbazolyl group, an acridinyl, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, and a thiophenyl group, a furanyl group, a carbazolyl group, an acridinyl, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$). However, embodiments of the present disclosure are not limited thereto.

For example, $R_1$ to $R_4$, $R_{11}$ and $R_{12}$ in Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a group represented by any of Formulae 4-1 to 4-48, Formulae 5-1 to 5-6, and Formulae 6-1 to 6-5, and —Si($Q_3$)($Q_4$)($Q_5$), wherein $Q_3$ to $Q_5$ may be each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group; and at least one of $R_2$ to $R_4$ may be independently selected from the group represented by any of Formulae 4-1 to 4-48, Formulae 5-1 to 5-6, and Formulae 6-1 to 6-5. However, embodiments of the present disclosure are not limited thereto.

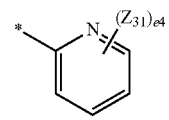

Formula 4-1

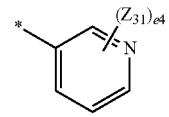

Formula 4-2

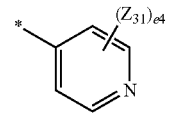

Formula 4-3

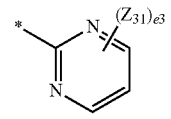

Formula 4-4

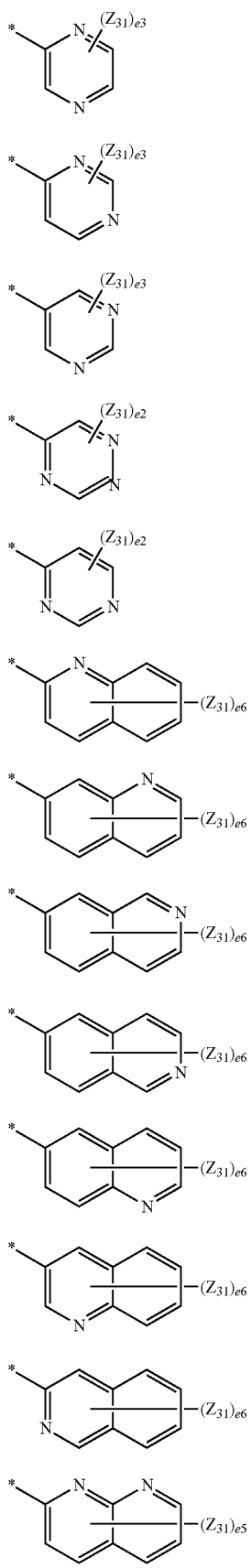
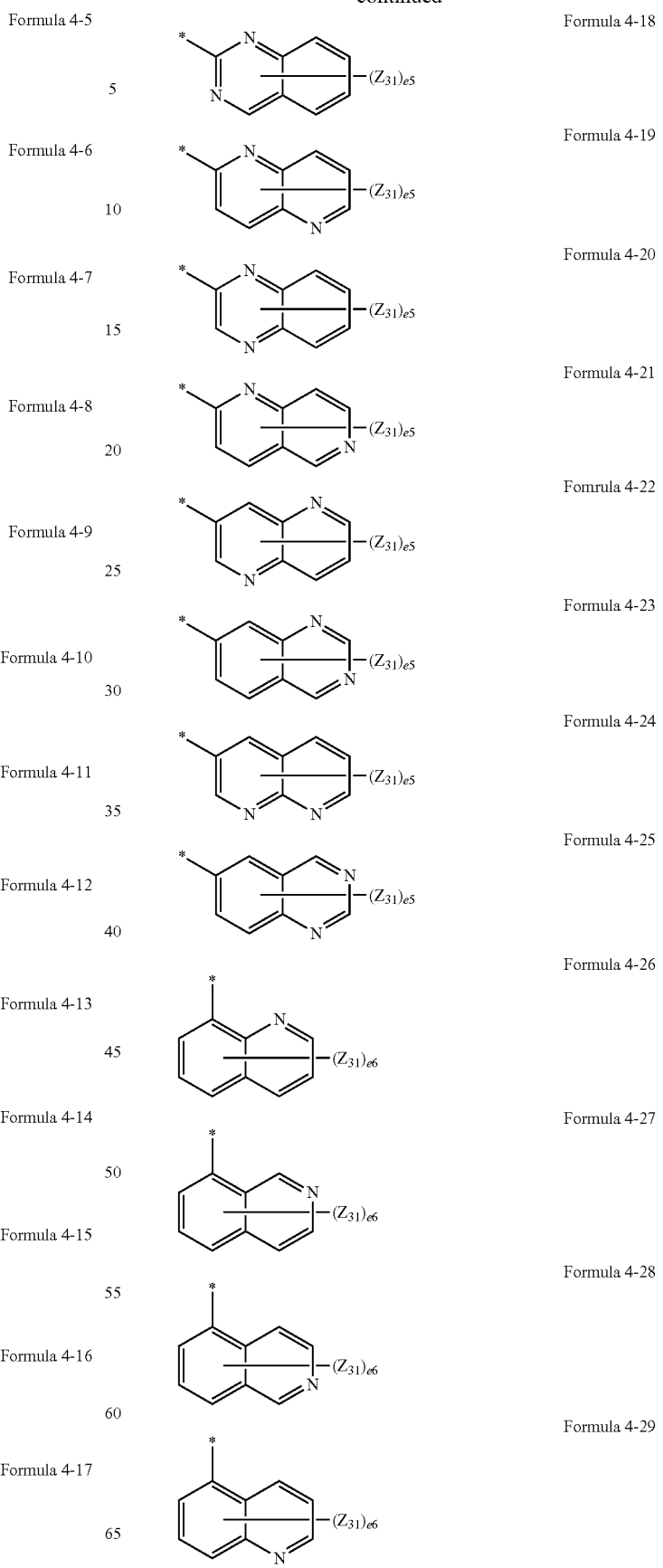

Formula 4-30
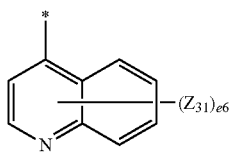
Formula 4-31
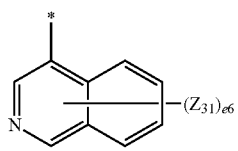
Formula 4-32
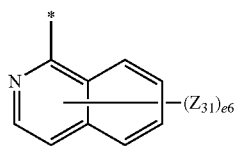
Formula 4-33
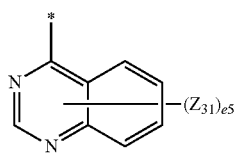
Formula 4-34
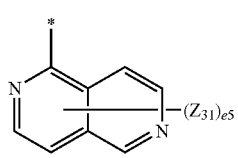
Formula 4-35
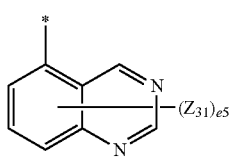
Formula 4-36
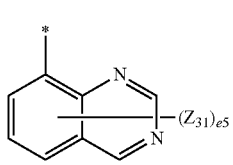
Formula 4-37
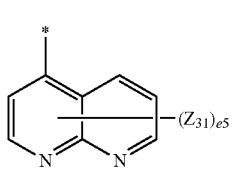
Formula 4-38
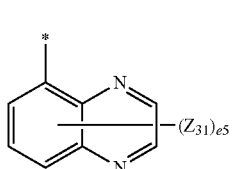
Formula 4-39
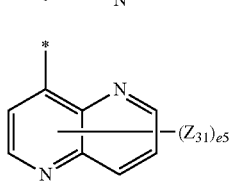
Formula 4-40
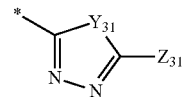
Formula 4-41
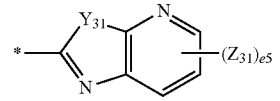
Formula 4-42
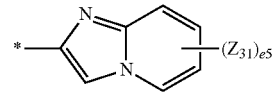
Formula 4-43
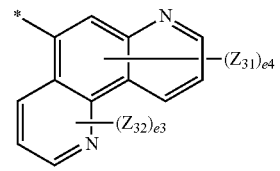
Formula 4-44
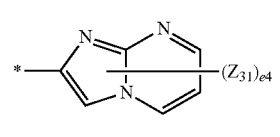
Formula 4-45
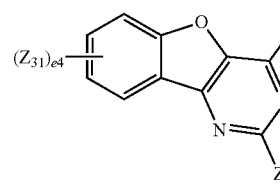
Formula 4-46
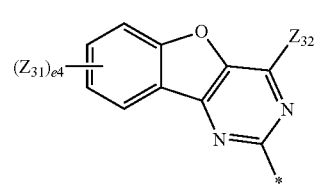
Formula 4-47
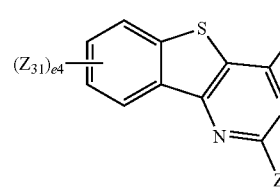
Formula 4-48
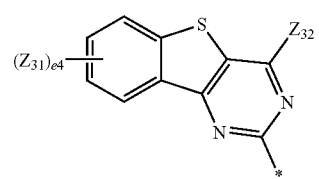
Formula 5-1
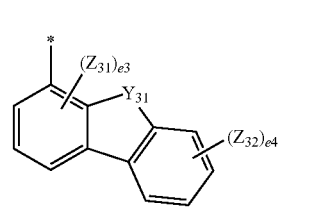

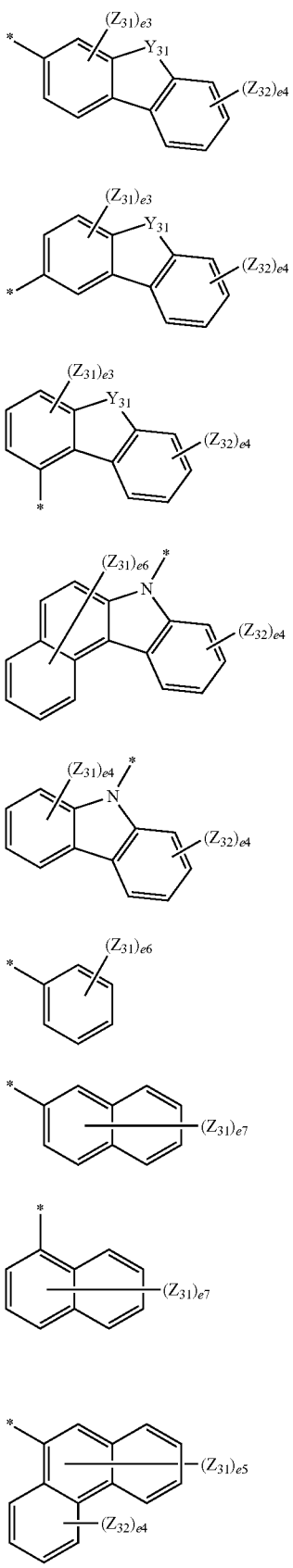

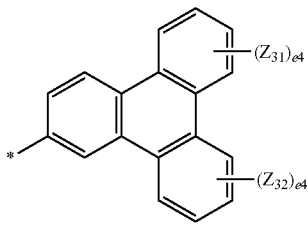

In Formulae 4-1 to 4-48, Formulae 5-1 to 5-6, and Formulae 6-1 to 6-5, $Y_{31}$ may be O, S, $C(Z_{33})(Z_{34})$, $N(Z_{35})$, or $Si(Z_{36})(Z_{37})$;

$Z_{31}$ to $Z_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a $C_1$-$C_{20}$ alkyl group-substituted phenyl group, a phenyl group-substituted phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, and —$Si(Q_{33})(Q_{34})(Q_{35})$, wherein $Q_{33}$ to $Q_{35}$ may be each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

e2 may be 1 or 2;

e3 may be an integer selected from 1 to 3;

e4 may be an integer selected from 1 to 4;

e5 may be an integer selected from 1 to 5.

e6 may be an integer selected from 1 to 6;

e7 may be an integer selected from 1 to 7; and

* indicates a binding site with an adjacent atom.

In Formula 1, b1, which indicates the number of groups $R_1$, may be 1, 2, 3, or 4, and in some embodiments—1 or 2, and in some other embodiments—1. When b1 is 2 or greater, at least two groups $R_1$ may be identical or different. b2 to b4 in Formula 1 may be understood based on the above-description of b1 and the structure of Formula 1.

In some embodiments, b1 to b4 in Formula 1 may be each independently 1 or 2, for example, 1. However, embodiments of the present disclosure are not limited thereto.

In Formula 1, c1, which indicates the number of groups -[$(L_1)_{a1}$-$(R_1)_{b1}$], may be 1, 2, 3, or 4, in some embodiments—1 or 2, and in some other embodiments—1. When c1 is 2 or greater, at least two groups -[$(L_1)_{a1}$-$(R_1)_{b1}$] may be identical or different.

In some embodiments, in Formula 1, c1 may be 1, a1 may be 0, and $R_1$ may be a hydrogen.

In some embodiments, $R_{11}$ and $R_{12}$ in Formula 1 may be both hydrogen.

In some embodiments, in Formula 1, a1 may be 0;

c1, b11, and b12 may be 1; and $R_1$, $R_{11}$ and $R_{12}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group. However, embodiments of the present disclosure are not limited thereto.

In some embodiments, in Formula 1, a2 and a3 may be 0, and $R_2$ and $R_3$ may each be a hydrogen.

In some embodiments, in Formula 1, a3 and a4 may be 0, and $R_3$ and $R_4$ may each be a hydrogen.

In some embodiments, in Formula 1, a2 and a4 may be 0, and $R_2$ and $R_4$ may each be a hydrogen.

In some embodiments, the carbazole compound may be represented by Formula 1A or 1B:

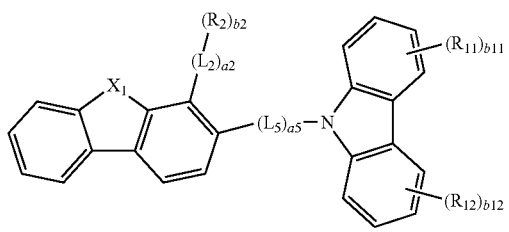

Formula 1A

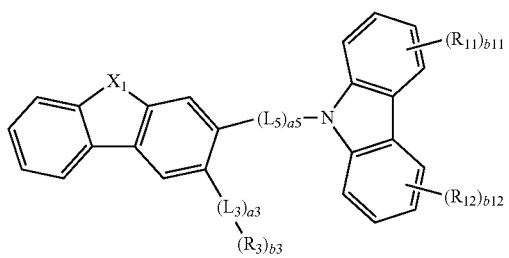

Formula 1B

In Formula 1A, $X_1$, $L_3$, $L_5$, a3, a5, b2, b3, $R_{11}$, $R_{12}$, b11, and b12 are the same as those defined above; and $R_2$ and $R_3$ may be selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent nonaromatic condensed polycyclic group, and a substituted or unsubstituted monovalent nonaromatic condensed heteropolycyclic group.

For example, in Formulae 1A and 1B, $L_3$ and $L_5$ may be each independently selected from a phenylene group, a naphthylene group, a phenanthrenylene group, an anthracenylene group, a triphenylenylene group, and a carbazolylene group, and a phenylene group, a naphthylene group, a phenanthrenylene group, an anthracenylene group, a triphenylenylene group, and a carbazolylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a phenyl group-substituted phenyl group, a naphthyl group, an anthracenyl group, a triphenylenyl group and a phenanthrenyl group;

a3 and a5 may be each independently 0, 1, or 2;

$R_{11}$ and $R_{12}$ may be each independently selected from a hydrogen, a deuterium, —F, —Cl, —Br, —I, a hydroxyl group, a cyano group, a nitro group, an amino group, an amidino group, a hydrazine group, a hydrazone group, carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group;

$R_2$ and $R_3$ may be each independently selected from a group represented by any of Formulae 4-1 to 4-48, Formulae 5-1 to 5-6, and Formulae 6-1 to 6-5; and b11 and b12 may be 1. However, embodiments of the present disclosure are not limited thereto.

In some embodiments, in Formulae 1A and 1B, $R_{11}$ and $R_{12}$ may each be a hydrogen, but are not limited thereto.

For example, the carbazole compound of Formula 1 may be one of Compounds 1 to 131, but is not limited thereto:

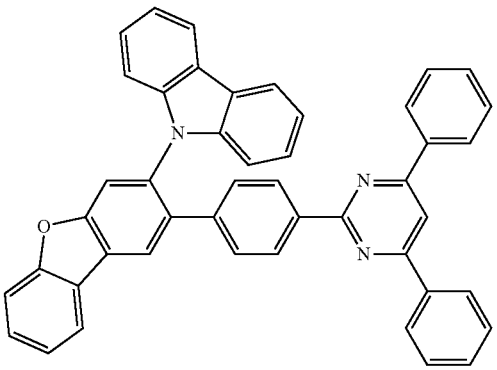

1

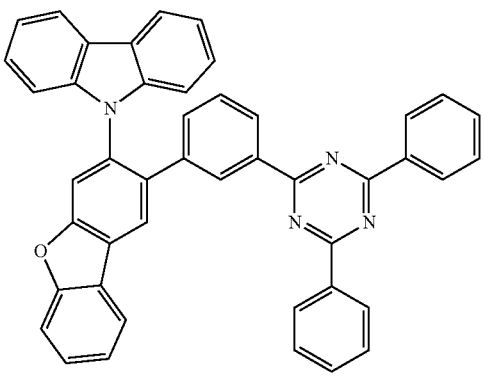

2

31
-continued
3
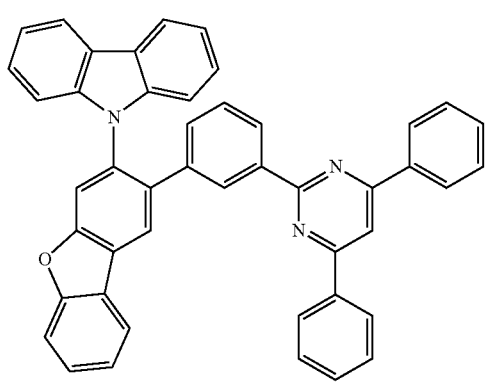
4
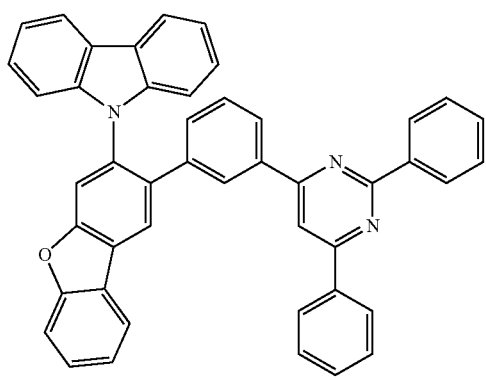
5
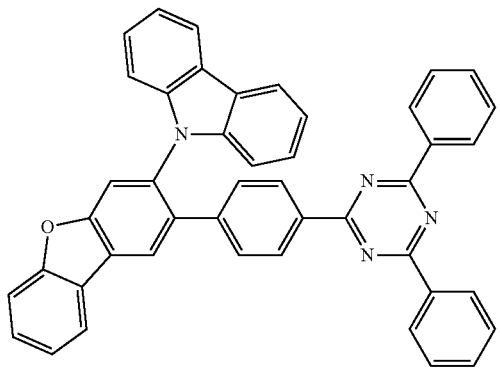
6
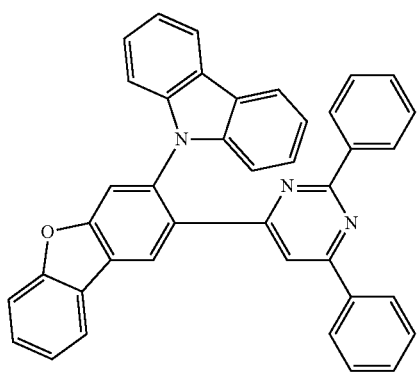
32
-continued
7
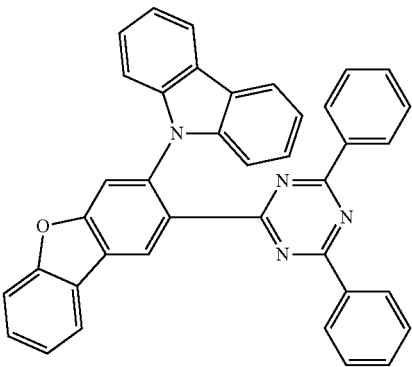
8
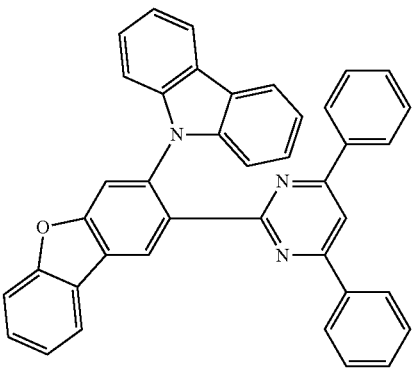
9
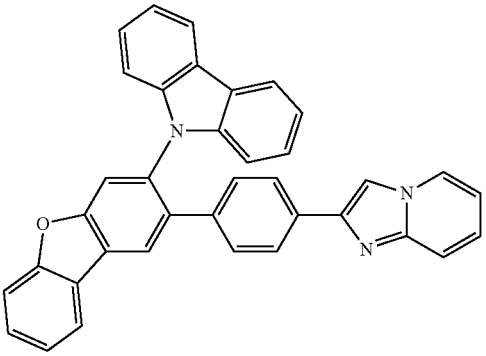
10
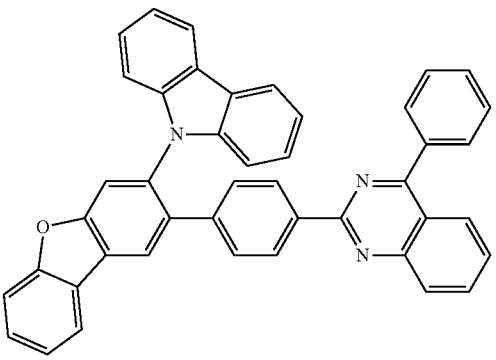

11
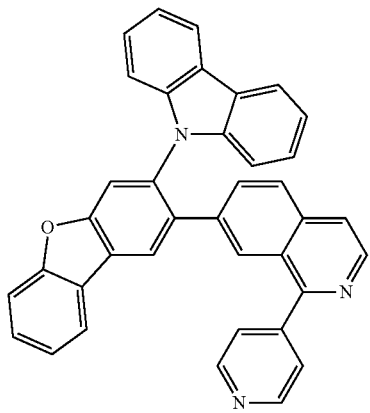
12
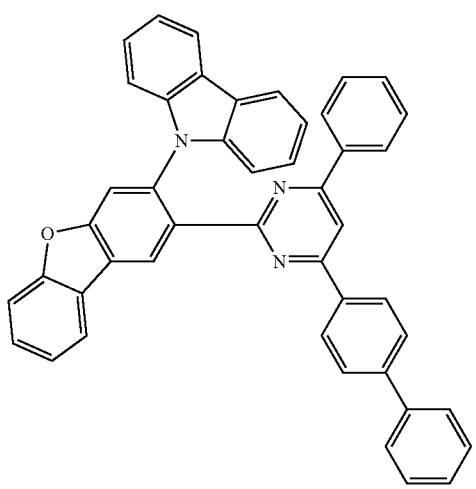
13
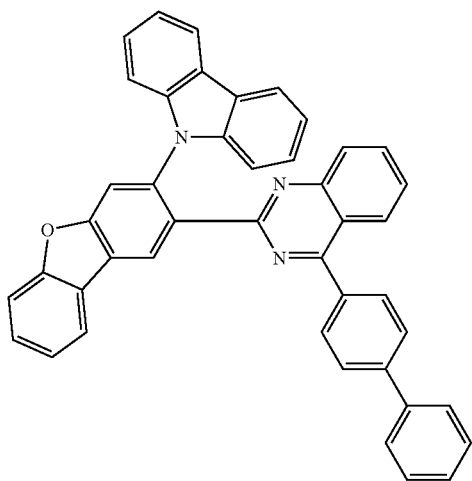
14
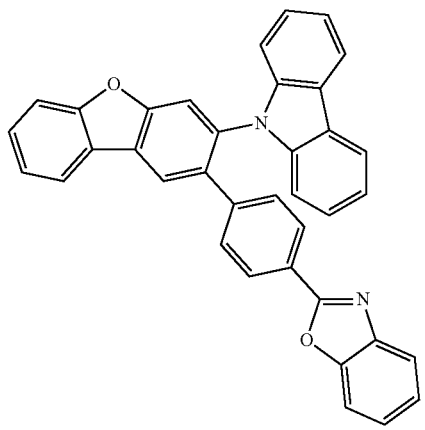
15
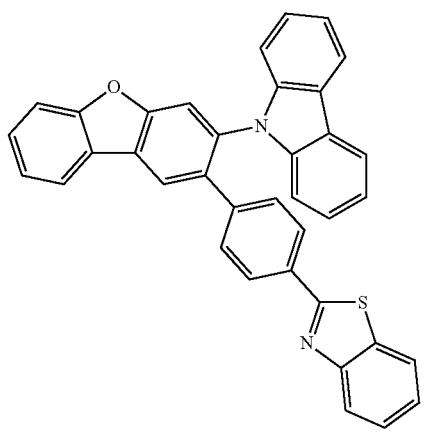
16
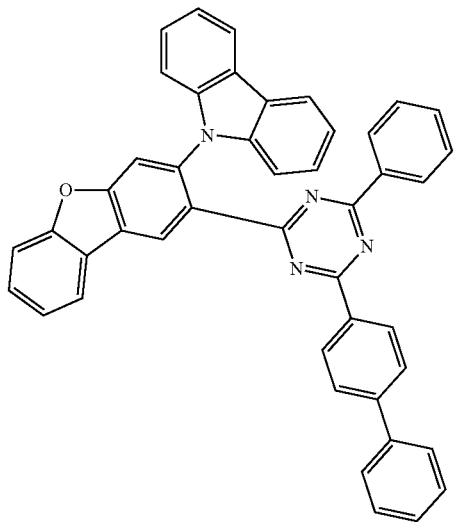

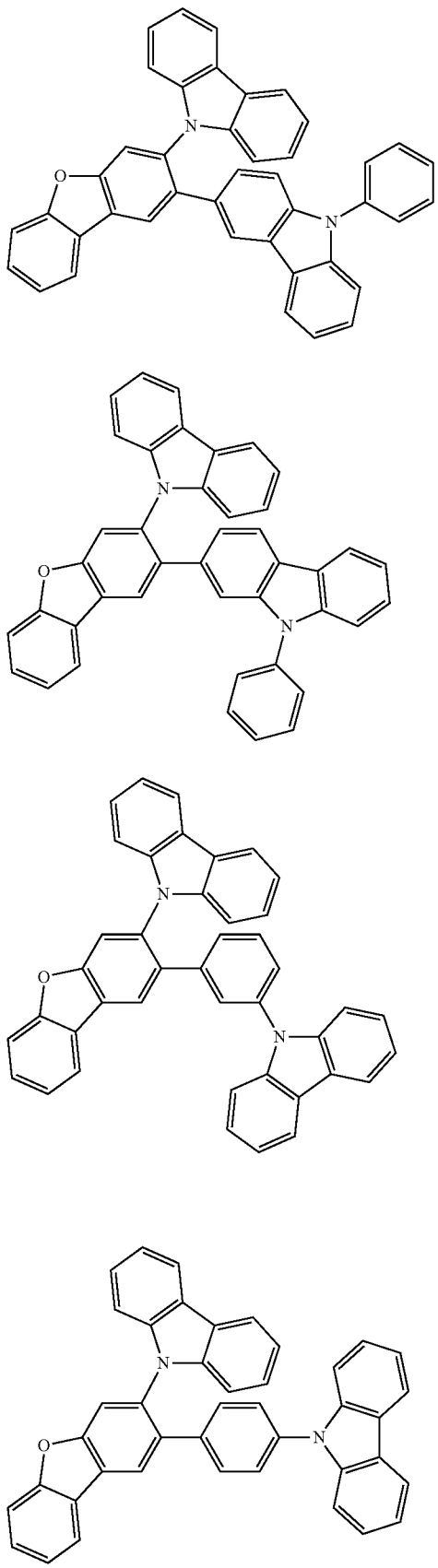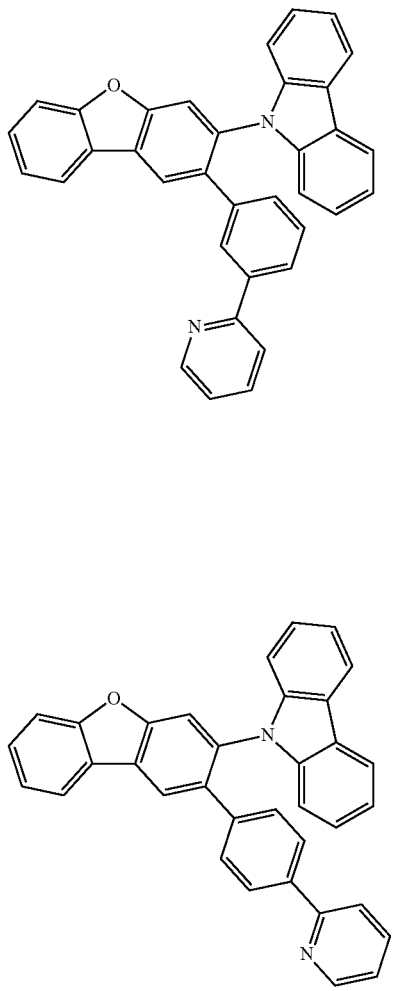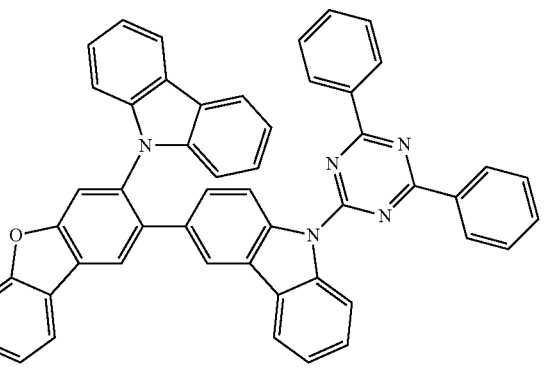

24
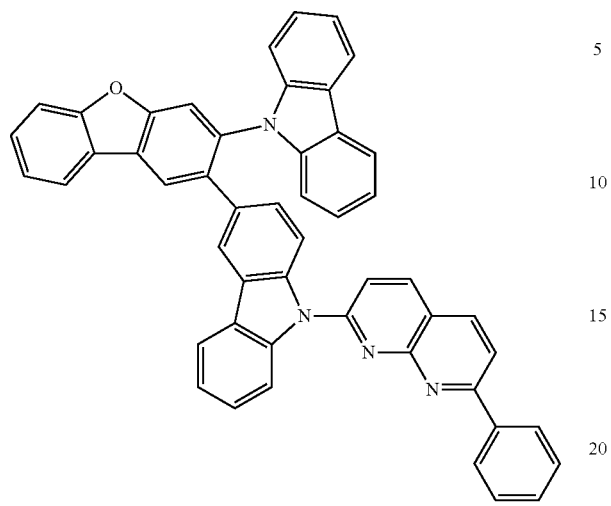
25
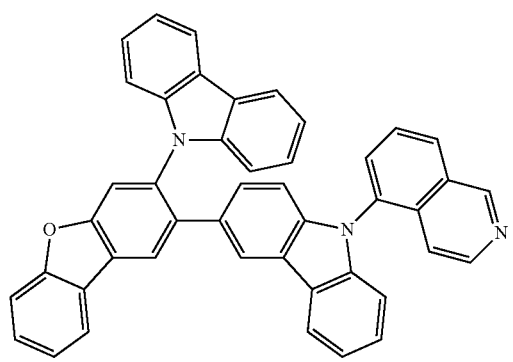
26
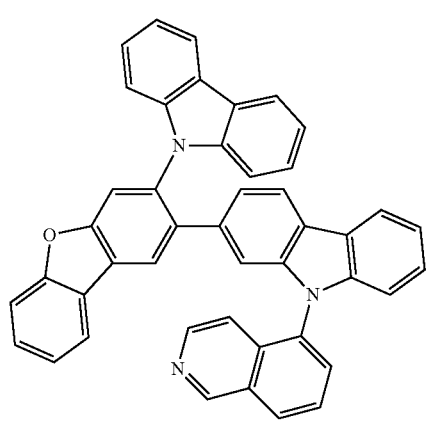
27
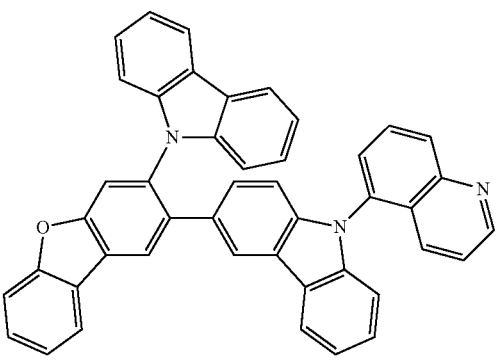
28
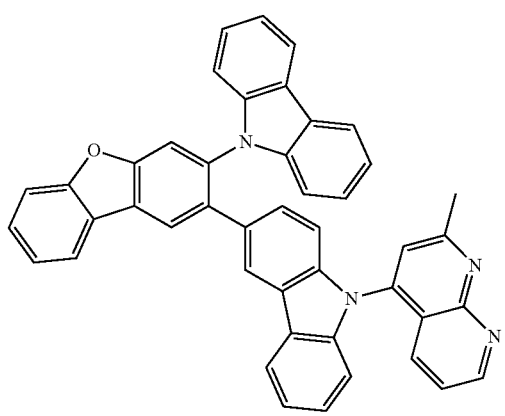
29
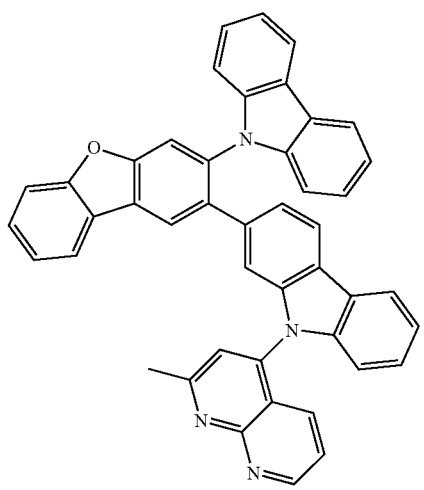

30
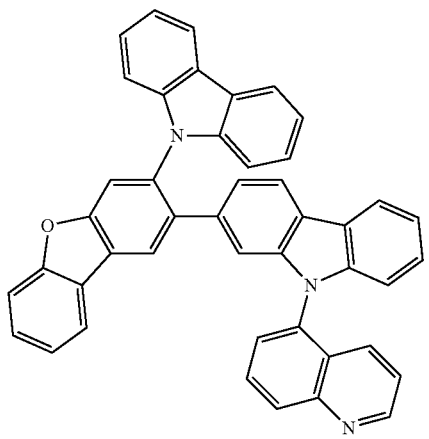
31
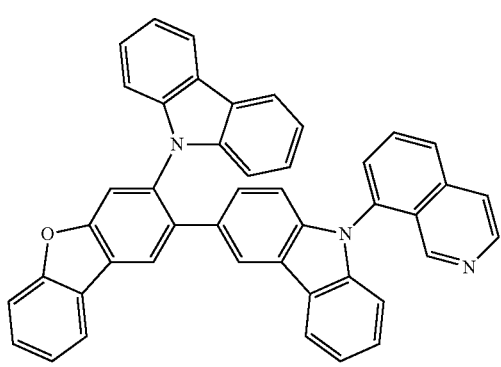
32
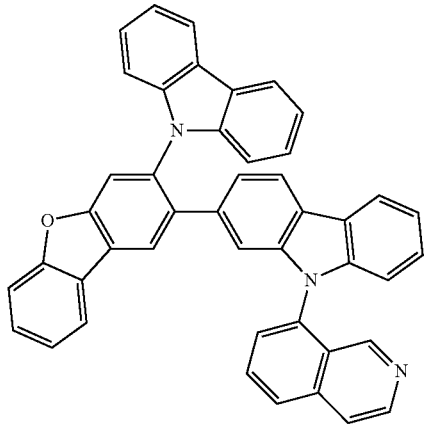
33
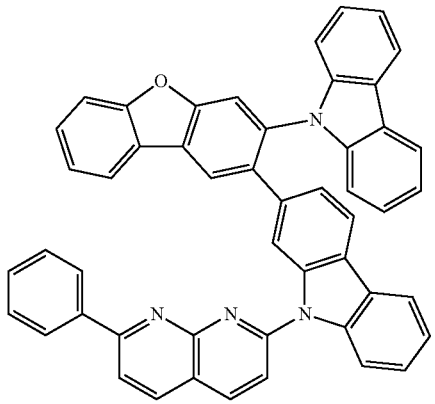
34
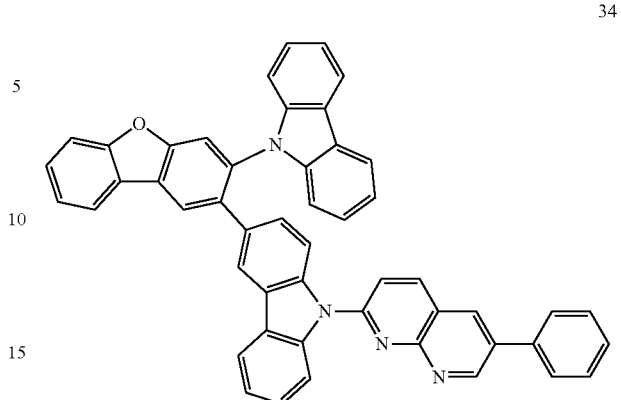
35
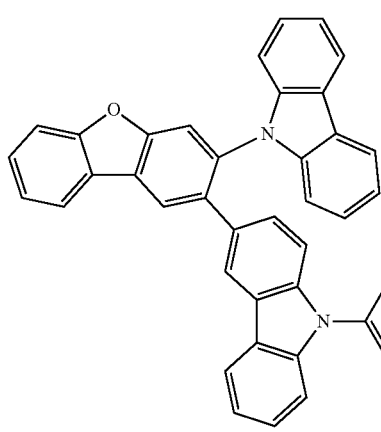
36
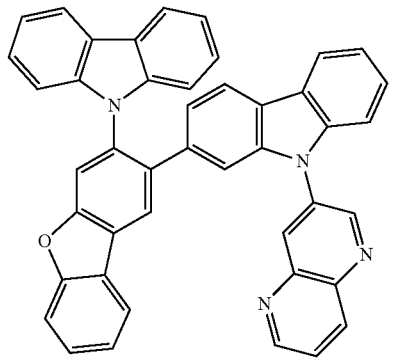
37
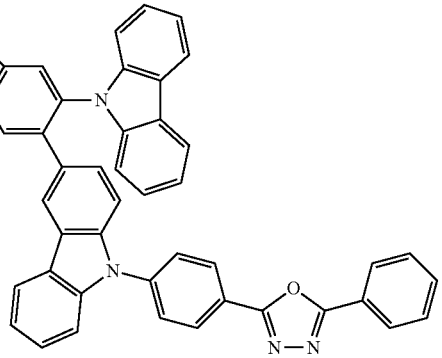

38
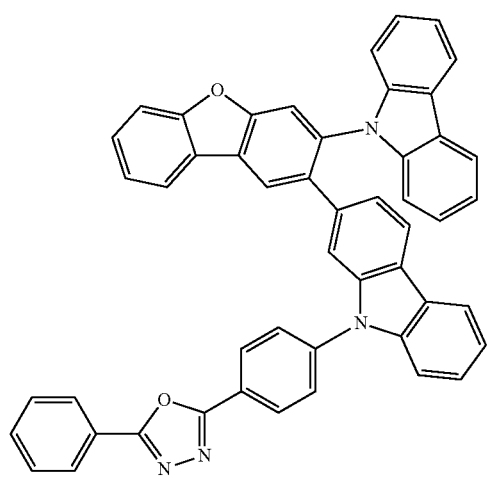
39
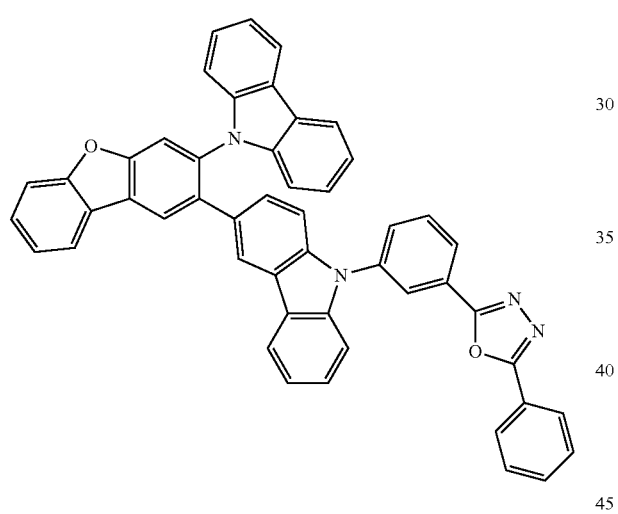
40
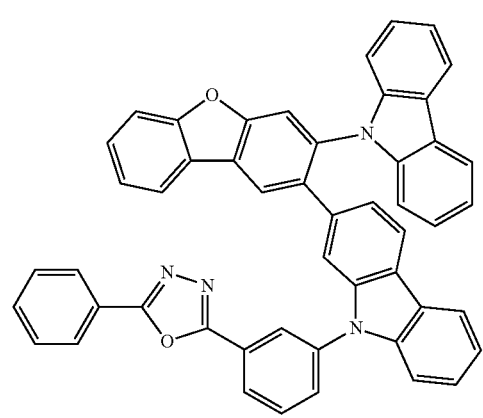
41
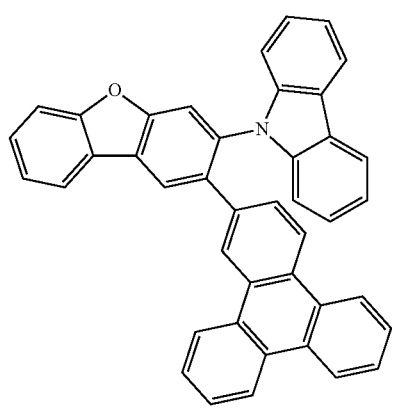
42
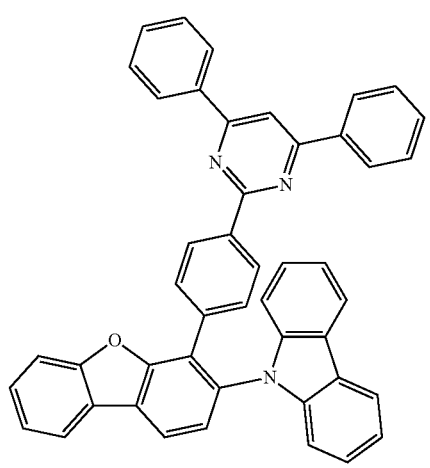
43
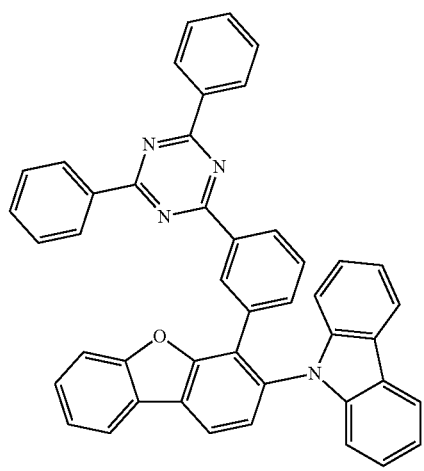

44
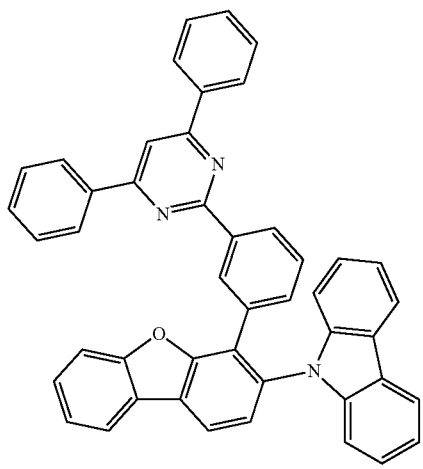
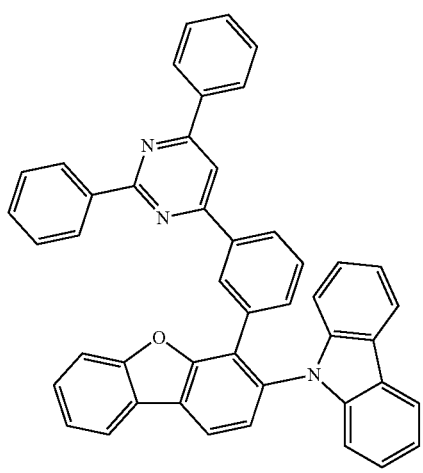
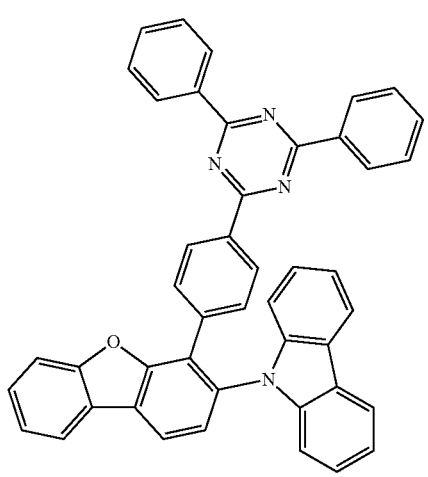
47
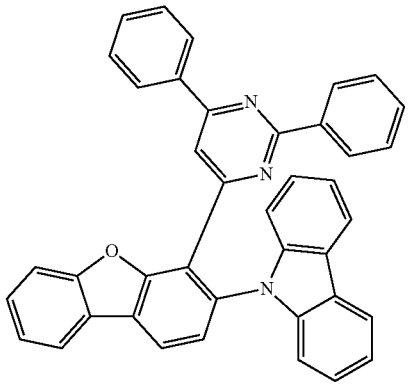
48
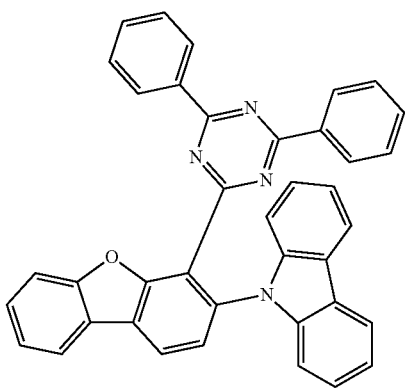
49
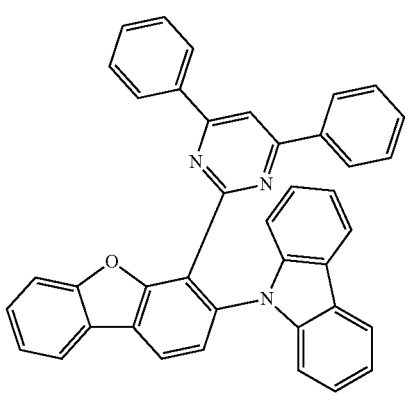
50
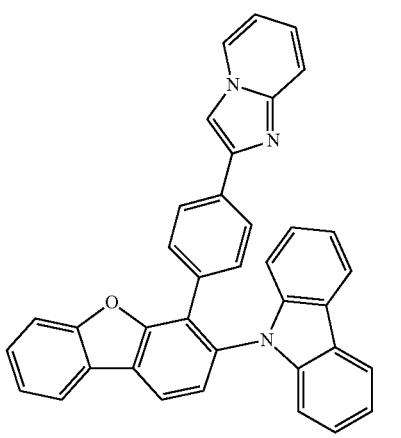

51
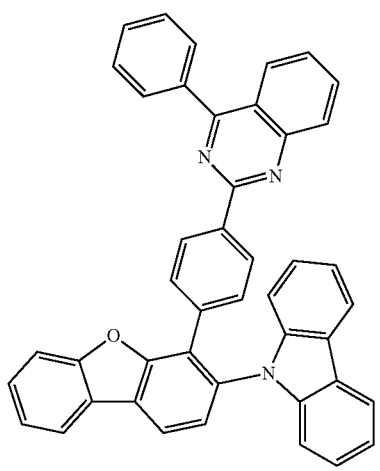
52
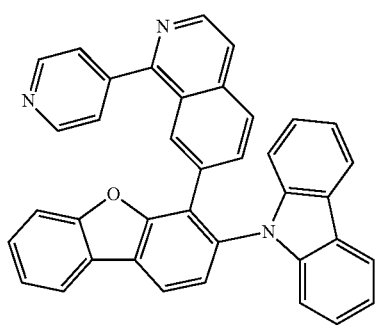
53
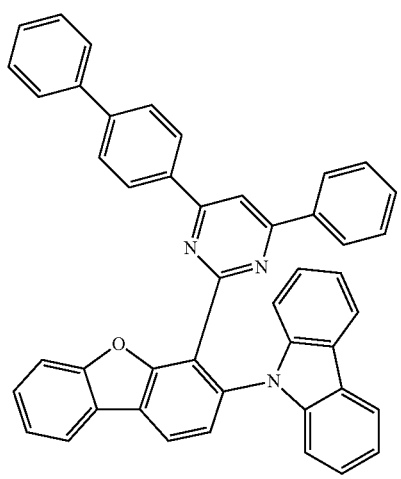
54
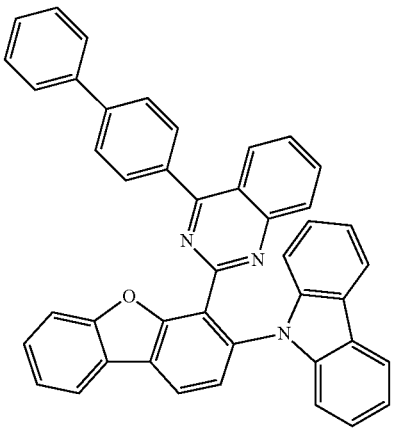
55
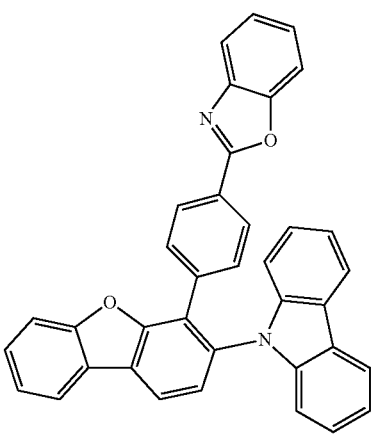
56
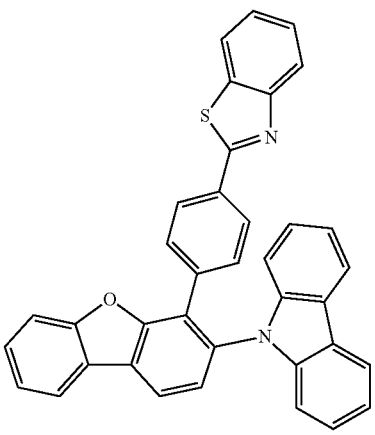

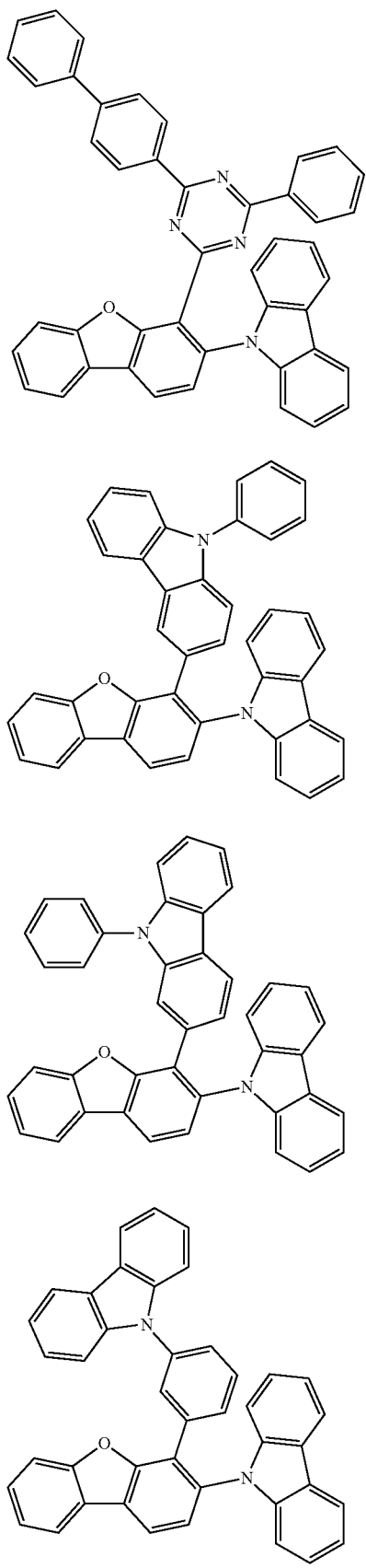
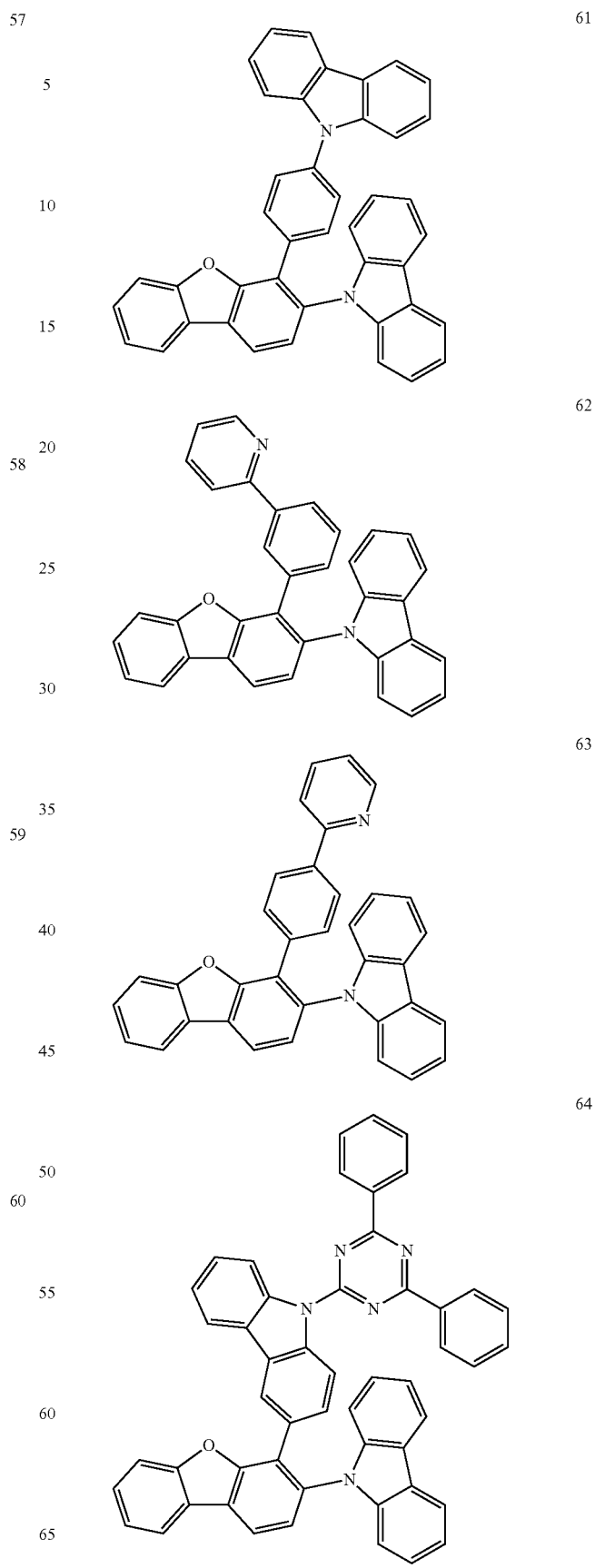

65
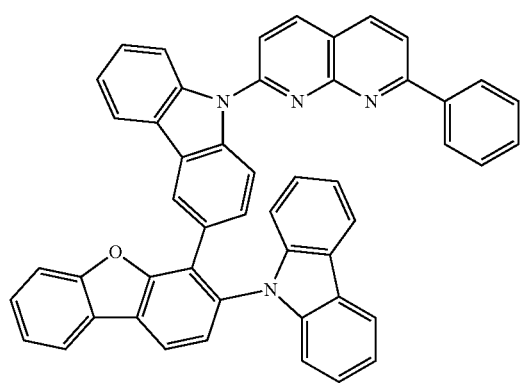
66
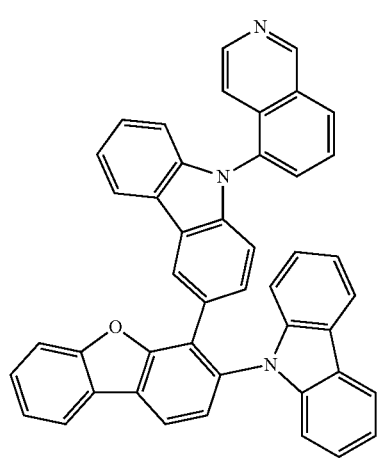
67
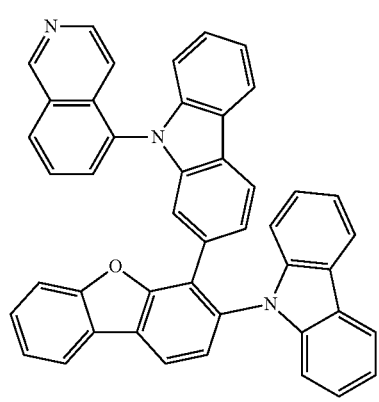
68
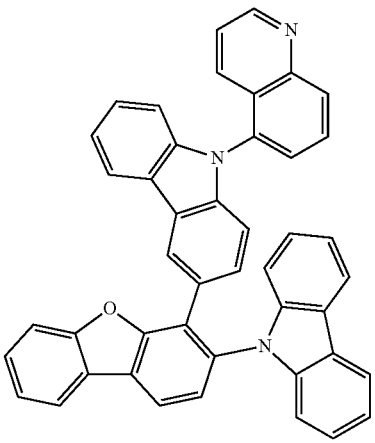
69
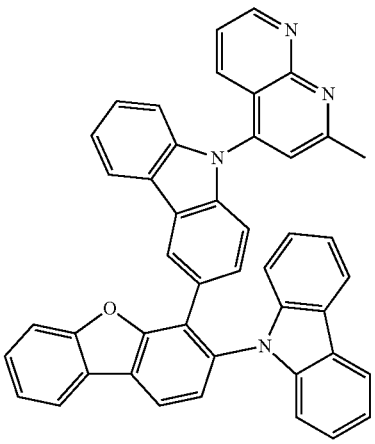
70
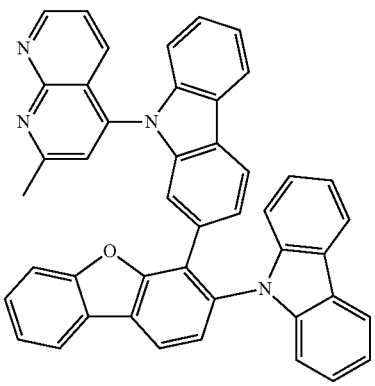
71
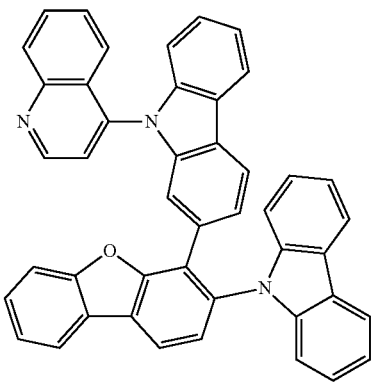

-continued
72
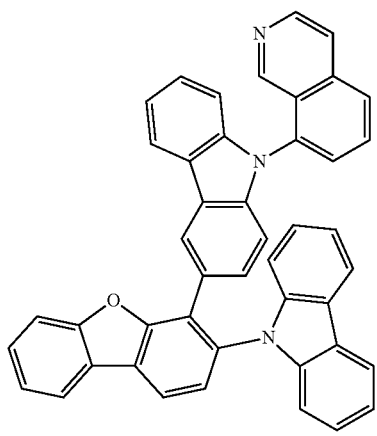
73
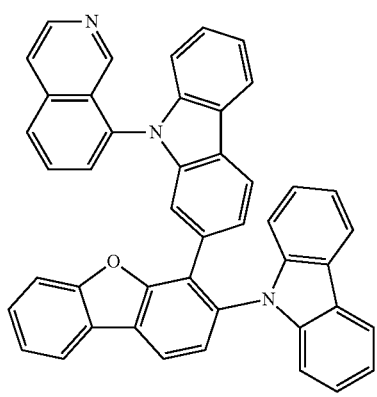
74
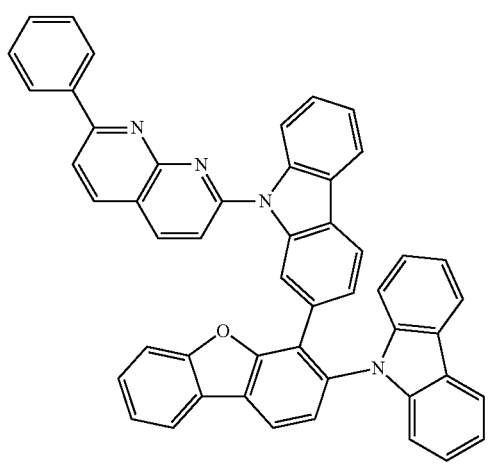
-continued
75
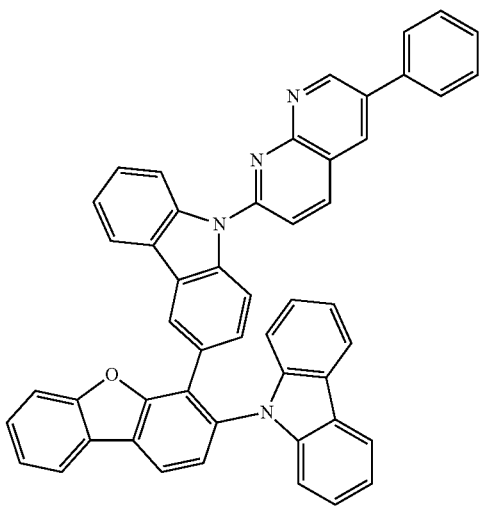
76
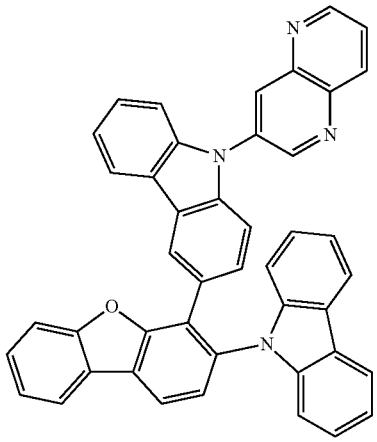
77
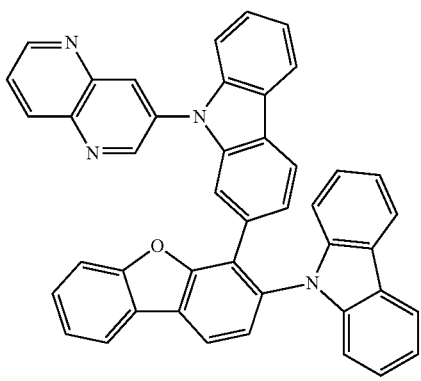

78
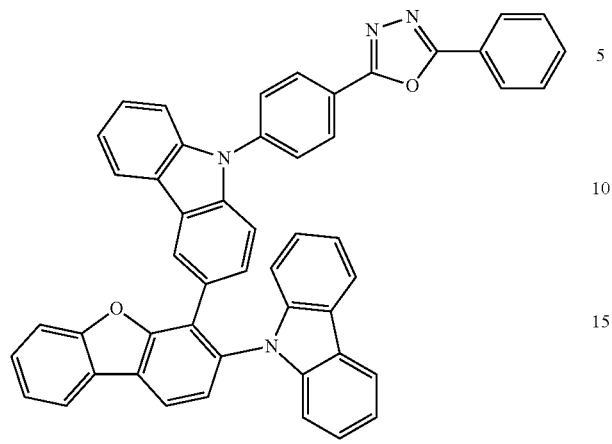
79
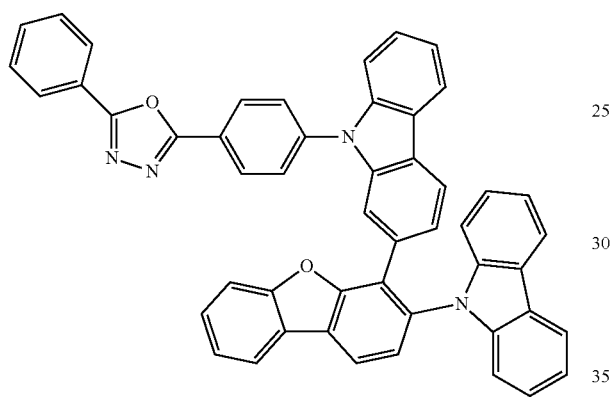
80
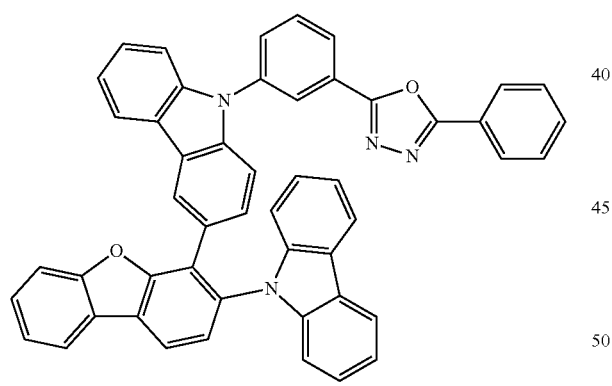
81
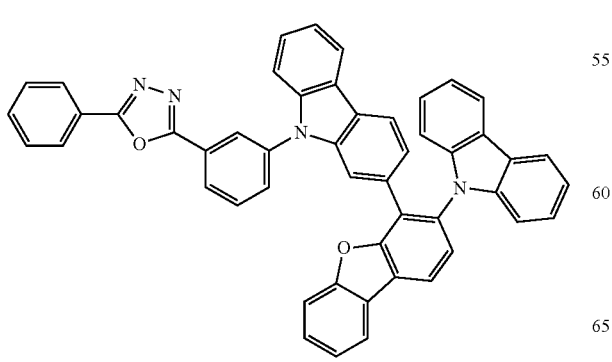
82
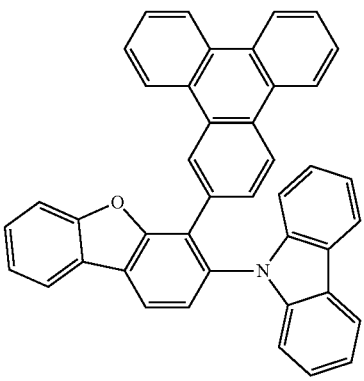
83
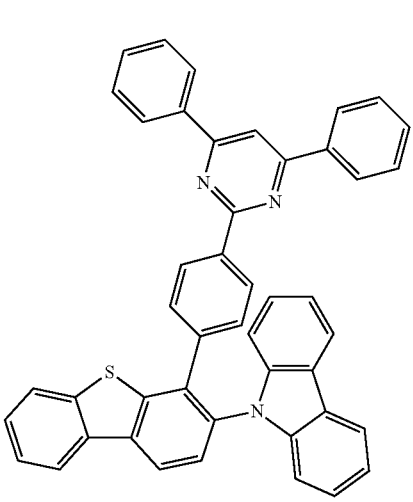
84
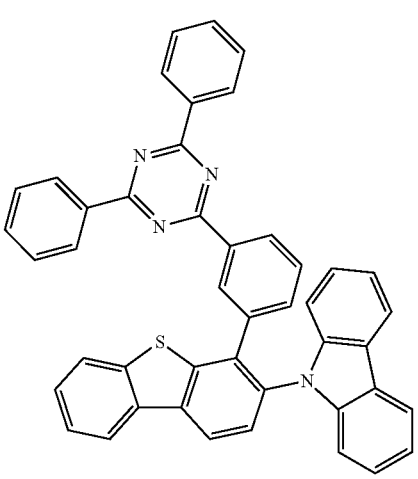

85
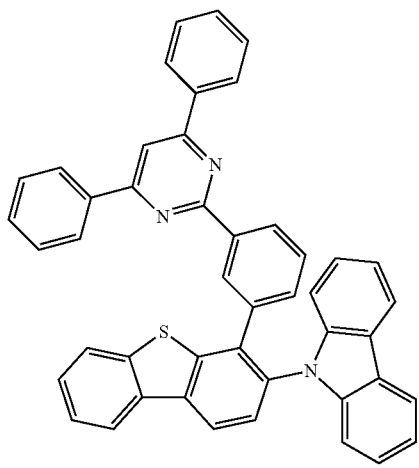
86
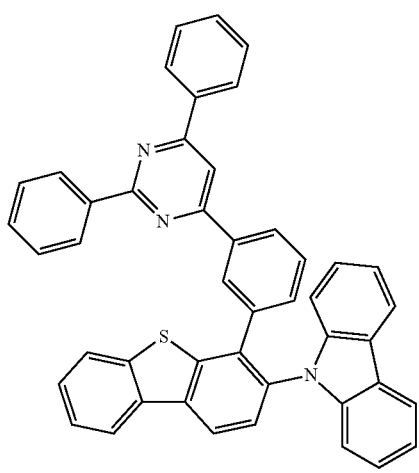
87
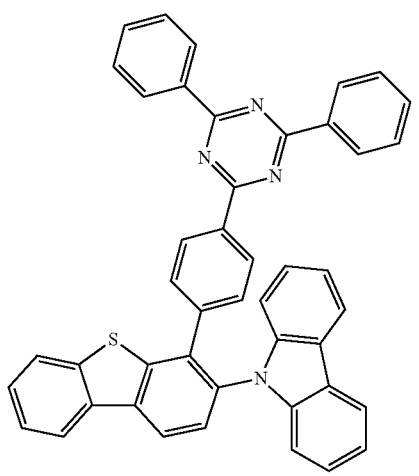
88
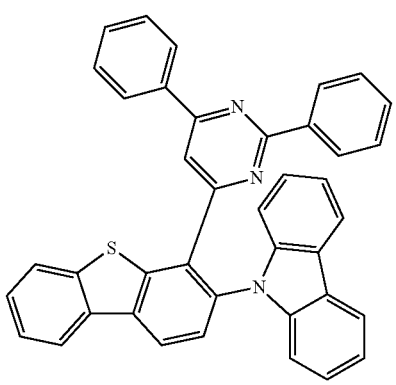
89
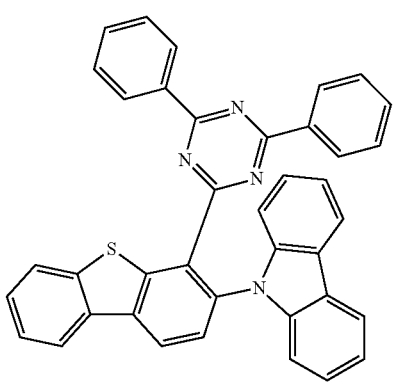
90
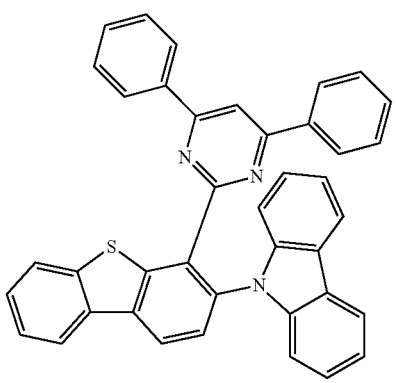
91
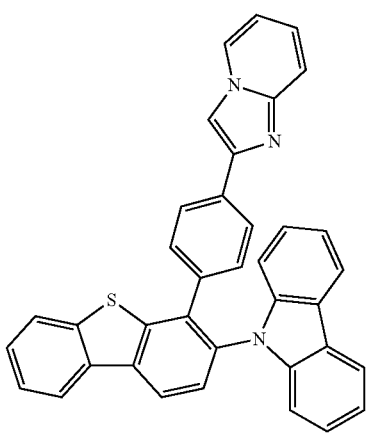

92
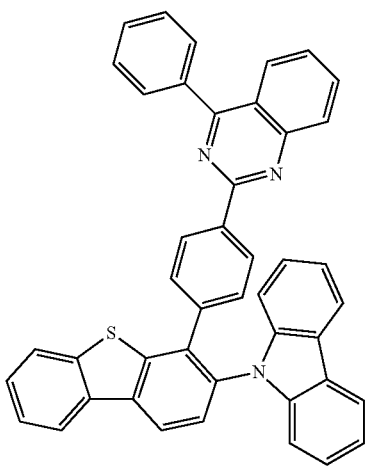
95
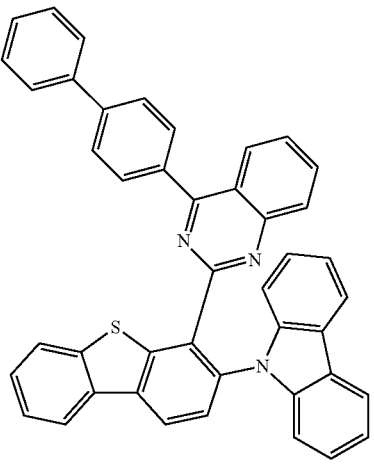
93
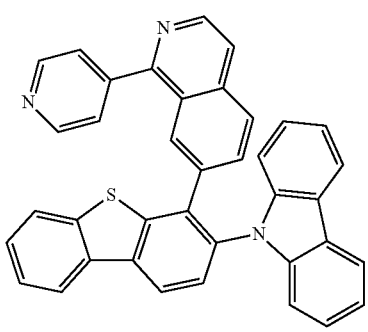
96
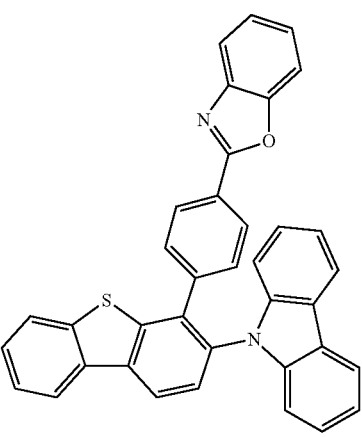
94
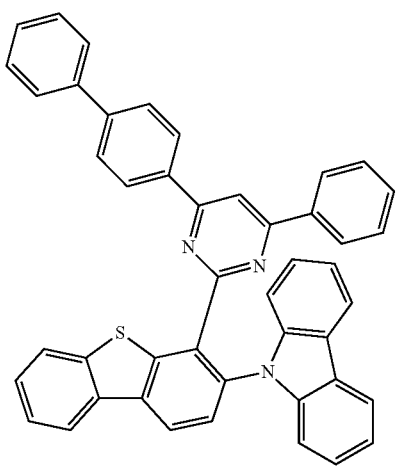
97
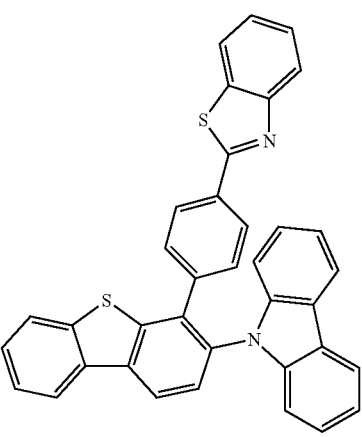

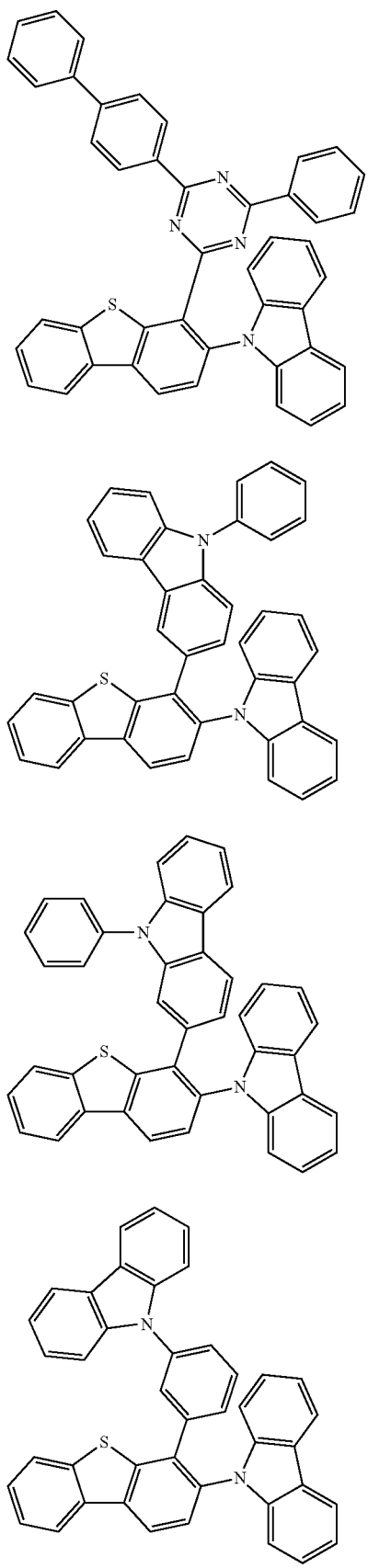
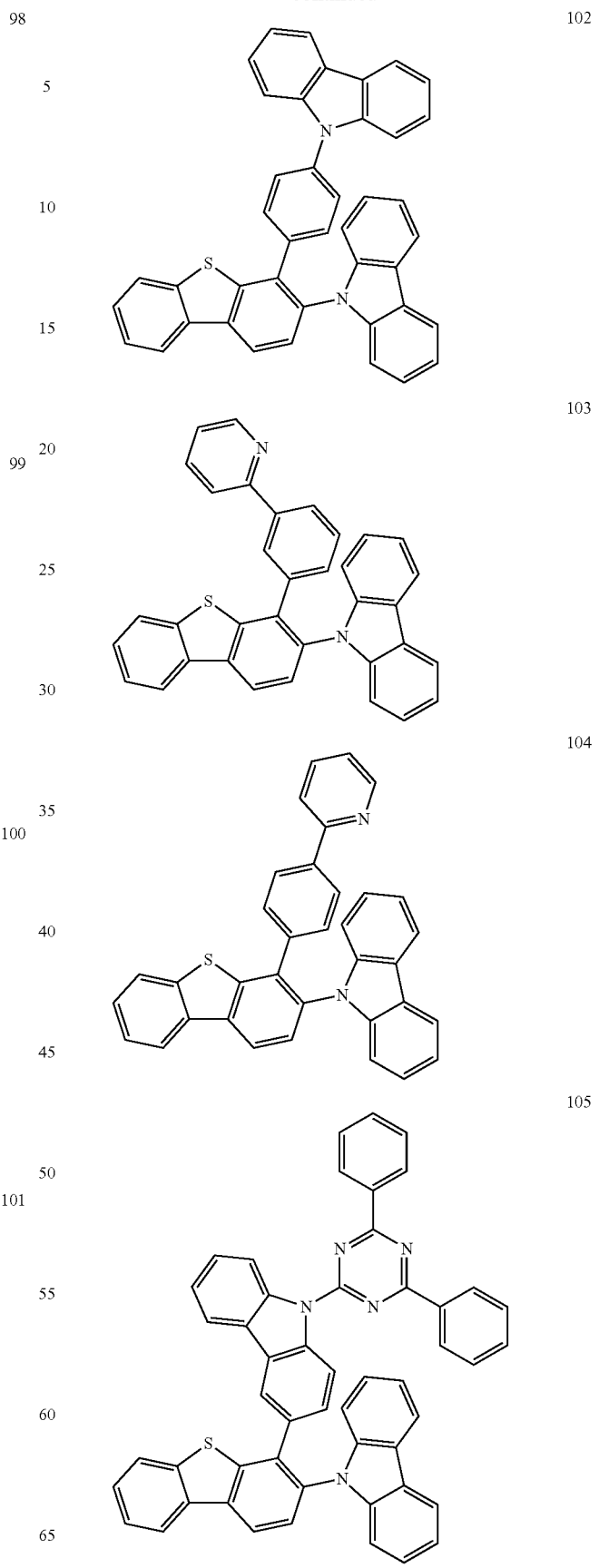

106
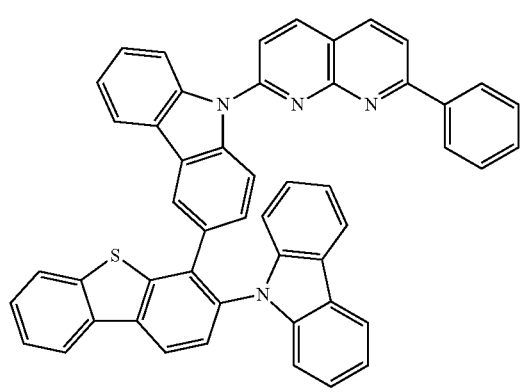
107
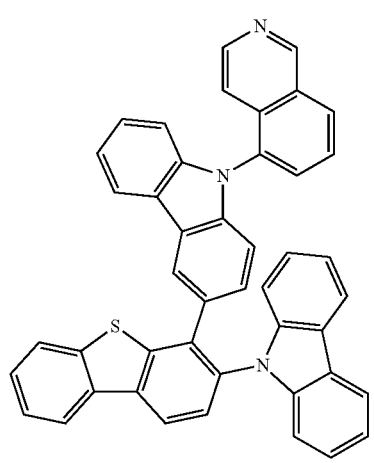
108
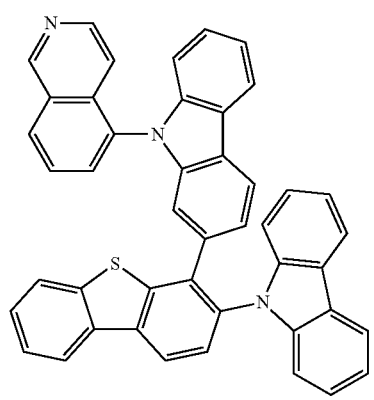
109
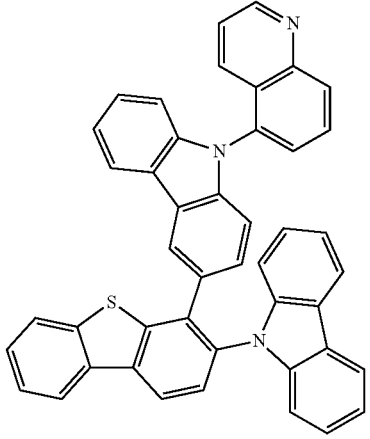
110
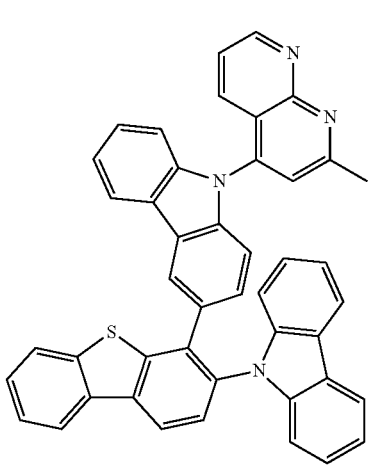
111
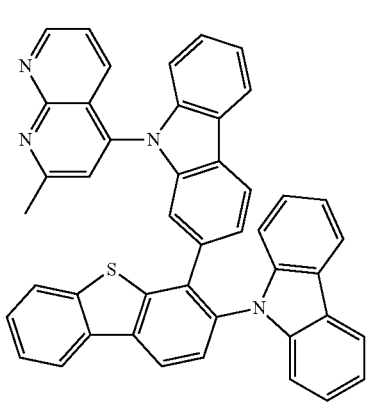

112 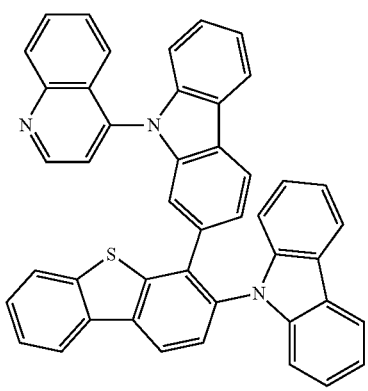
115 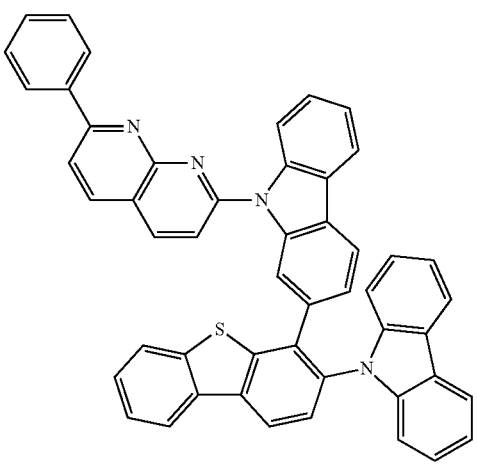
113 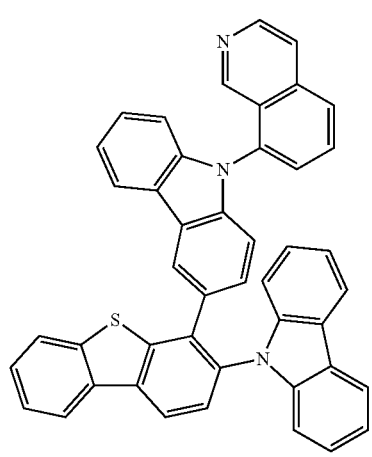
116 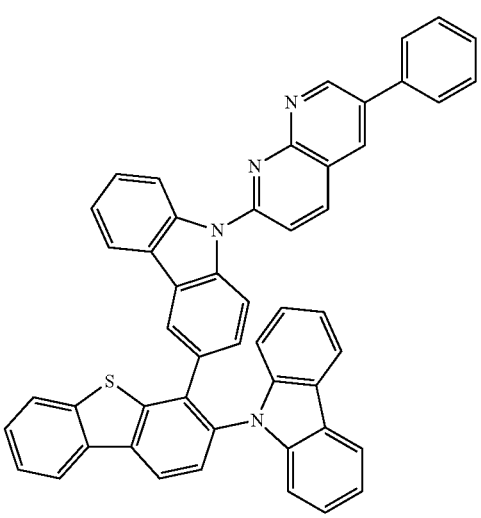
114 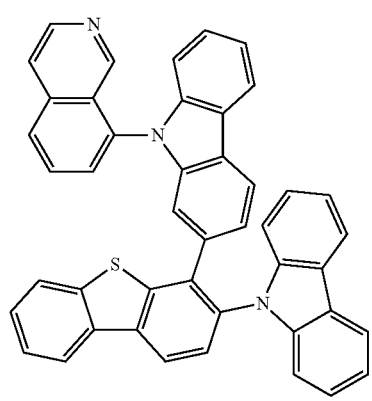
117 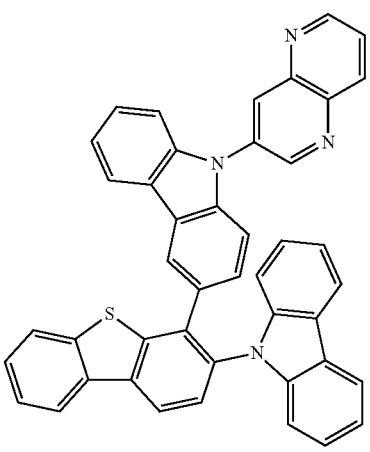

118
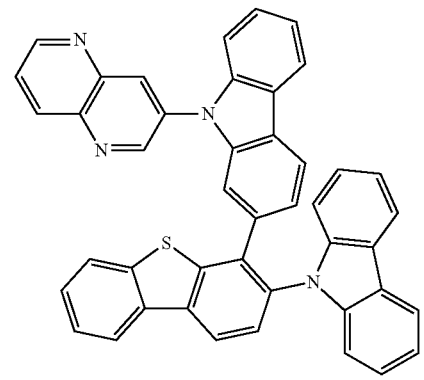
119
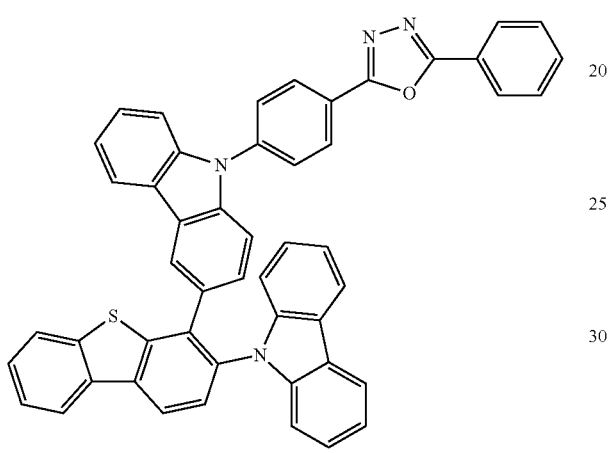
120
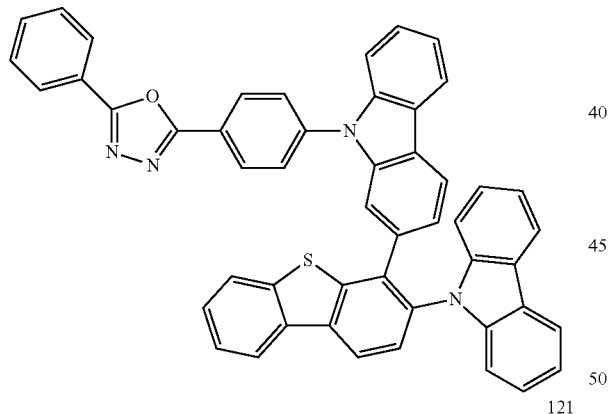
121
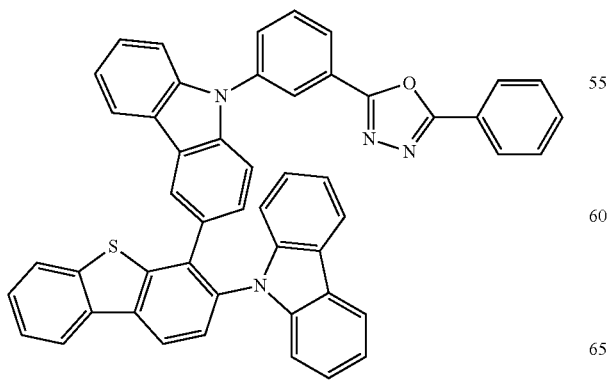
122
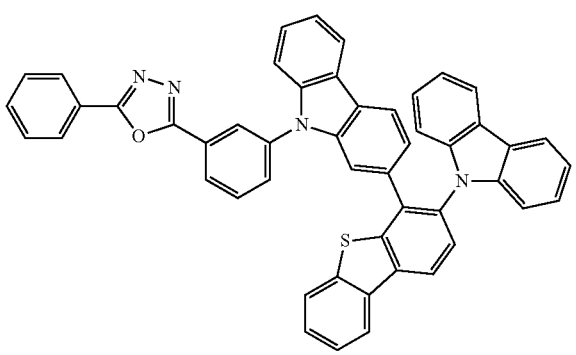
123
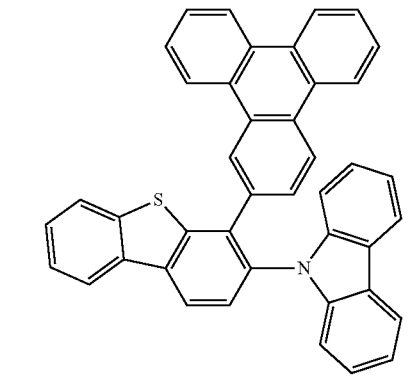
124
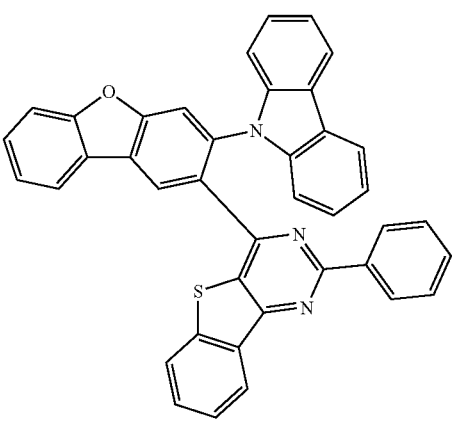
125
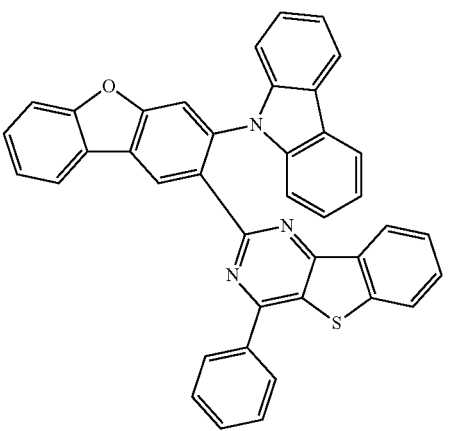

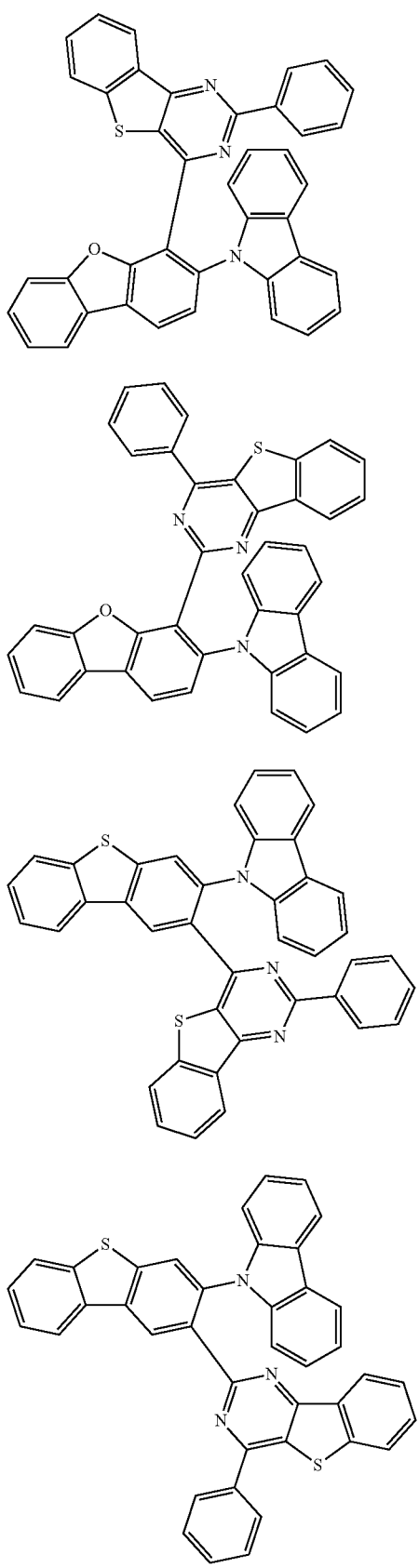

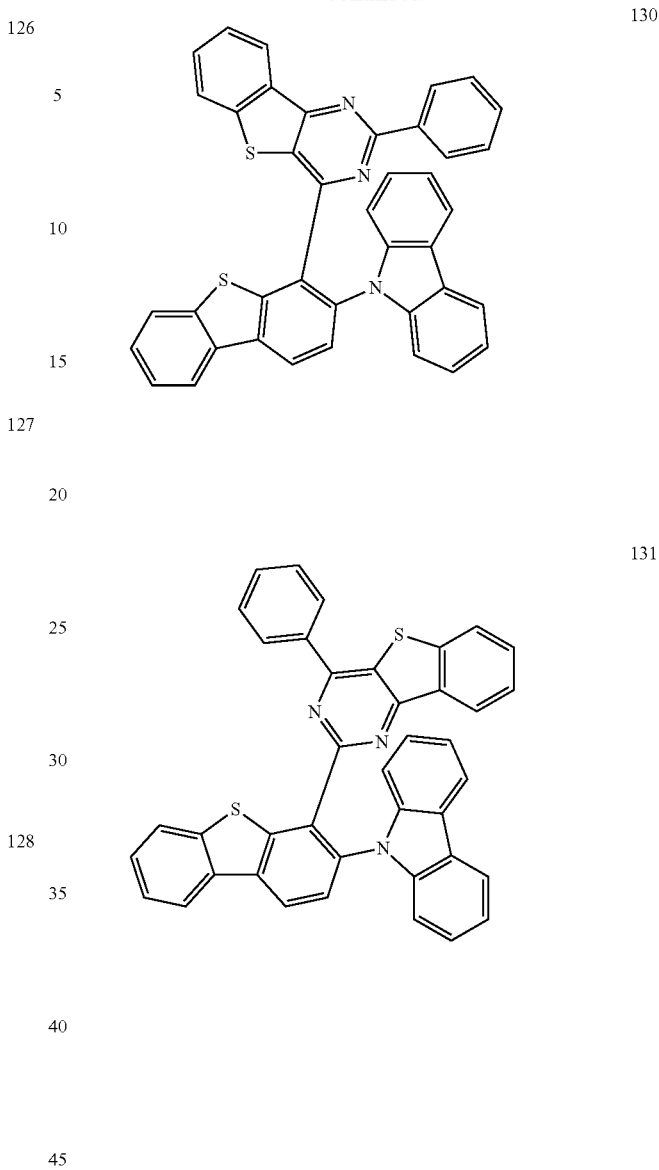

In the carbazole compound of Formula 1, 1) "a carbazole ring" may be linked to "$3^{rd}$ carbon" of "A ring", optionally via $-(L_5)_{a5}$- (refer to Formula 1'), and 2) at least one of $R_2$ to $R_4$ may be independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted a monovalent non-aromatic condensed polycyclic group, and a substituted or unsubstituted a monovalent non-aromatic condensed heteropolycyclic group (in other words, at least one of $R_2$ to $R_4$ in Formula 1 is essentially a "cyclic group"). Accordingly, the electron density of "A ring" in Formula 1 may be effectively controlled. In addition, the charge transporting ability of the carbazole compound of Formula 1 may be controlled by varying substituents $R_2$ to $R_4$.

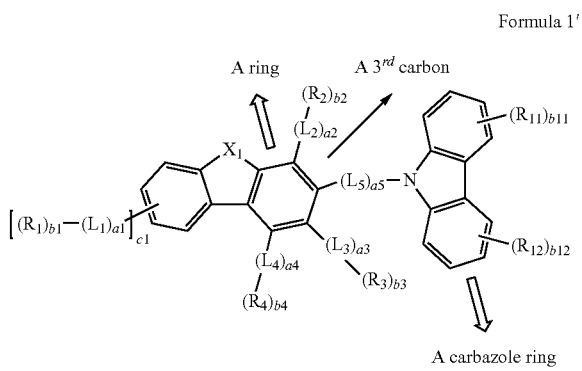

Formula 1'

For example, the results of Gaussian simulation on the highest occupied molecular orbital (HOMO), the lowest unoccupied molecular orbital (LUMO), the triplet (T1) energy levels, and the singlet (S1) energy levels of some of Compounds 1 to 131 are shown in Table 1:

TABLE 1

| Compound | HOMO (eV) | LUMO (eV) | $T_1$ (eV) | $S_1$ (eV) |
|---|---|---|---|---|
| Compound 1 | −5.299 | −1.649 | 2.857 | 3.231 |
| Compound 2 | −5.369 | −1.845 | 2.957 | 3.101 |
| Compound 3 | −5.294 | −1.694 | 2.936 | 3.23 |
| Compound 4 | −5.501 | −1.598 | 2.965 | 3.217 |
| Compound 7 | −5.32 | −1.800 | 2.860 | 2.95 |
| Compound 9 | −5.297 | −1.222 | 2.840 | 3.387 |
| Compound 10 | −5.287 | −1.904 | 2.53 | 3.018 |
| Compound 11 | −5.504 | −1.803 | 2.561 | 3.205 |
| Compound 12 | −5.218 | −1.748 | 2.806 | 2.941 |
| Compound 13 | −5.185 | −1.967 | 2.556 | 2.666 |
| Compound 16 | −5.309 | −1.878 | 2.812 | 2.913 |
| Compound 17 | −5.224 | −1.187 | 3.031 | 3.290 |
| Compound 18 | −5.283 | −1.224 | 2.988 | 3.255 |
| Compound 19 | −5.336 | −1.357 | 2.988 | 3.255 |
| Compound 22 | −5.328 | −1.924 | 3.004 | 3.089 |
| Compound 25 | −5.31 | −1.722 | 2.644 | 3.075 |
| Compound 27 | −5.299 | −1.709 | 2.747 | 3.052 |
| Compound 28 | −5.377 | −1.893 | 2.791 | 3.023 |
| Compound 29 | −5.393 | −1.916 | 2.82 | 3.079 |
| Compound 37 | −5.353 | −1.777 | 2.674 | 3.157 |
| Compound 38 | −5.326 | −1.686 | 2.699 | 3.156 |
| Compound 39 | −5.255 | −1.818 | 2.787 | 3.048 |
| Compound 40 | −5.322 | −1.730 | 2.808 | 3.122 |
| Compound 41 | −5.377 | −1.290 | 2.789 | 3.365 |
| Compound 124 | −5.317 | −1.730 | 2.911 | 3.007 |
| Compound 125 | −5.241 | −1.789 | 2.853 | 2.916 |

A synthesis method of the carbazole compound of Formula 1 may be understood by those of ordinary skill in the art based on the synthesis examples to be described below.

The carbazole compound of Formula 1 is suitable for use of an organic layer, for example, as a host in an emission layer of an organic light-emitting device. According to another embodiment of the present disclosure, an organic light-emitting device includes:

a first electrode, a second electrode, and an organic layer disposed between the first electrode and the second electrode, wherein the organic layer includes an emission layer and at least one carbazole compound of Formula 1.

The organic light-emitting device, which includes the organic layer including the at least one carbazole compound of Formula 1, may have improved consumption power, efficiency, luminance, and lifetime characteristics.

The carbazole compound of Formula 1 may be used between a pair of electrodes of an organic light-emitting device. For example, the carbazole compound of Formula 1 may be included in at least one of the emission layer, a hole transport region between the first electrode and the emission layer (for example, including at least one of a hole injection layer, a hole transport layer, and an electron blocking layer), and an electron transport region between the emission layer and the second electrode (for example, including at least one of a hole blocking layer, an electron transport layer, and an electron injection layer). For example, the carbazole compound of Formula 1 may be included in the emission layer. In this regard, the emission layer may further include a dopant, and the carbazole compound of Formula 1 in the emission layer may serve as a host. The emission layer may be a green emission layer emitting green light, or a red emission layer emitting red light. The dopant may be a phosphorescent dopant.

As used herein, "(the organic layer) including at least one carbazole compound means that "(the organic layer) including one of the carbazole compounds of Formula 1, or at least two different carbazole compounds of Formula 1".

In some embodiments, the organic layer may include only Compound 1 above as a carbazole compound of Formula 1. Compound 1 may be in the emission layer of the organic light-emitting device. In some embodiments, the organic layer may include Compounds 1 and 2 as the carbazole compound of Formula 1. In this regard, Compounds 1 and 2 may be present in the same layer (for example, in the emission layer) or may be present in different layers.

For example, the first electrode may be an anode as a hole injection electrode, and the second electrode may be a cathode as an electron injection electrode, or vice versa. That is, the first electrode may be a cathode as an electron injection electrode, and the second electrode may be an anode as a hole injection electrode.

For example, the first electrode may be an anode, the second electrode may be a cathode, and the organic layer may include:

i) a hole transport region disposed between the first electrode and the emission layer and including at least one of a hole injection layer, a hole transport layer, and an electron blocking layer; and ii) an electron transport region disposed between the emission layer and the second electrode and including at least one of a hole blocking layer, an electron transport layer, and an electron injection layer.

The term "organic layer" as used herein refers to a single layer and/or a plurality of layers disposed between the first and second electrodes of the organic light-emitting device. The "organic layer" may include an organic compound, and/or an organometallic complex including a metal.

FIG. 1 is a schematic view of an organic light-emitting device 10 according to an embodiment of the present disclosure. Hereinafter, a structure of an organic light-emitting device according to an embodiment of the present disclosure and a method of manufacturing the same will now be described with reference to FIG. 1. Referring to FIG. 1, the organic light-emitting device 10 has a structure in which a substrate 11, a first electrode 11, an organic layer 15, and a second electrode 19 are sequentially stacked in this order.

A substrate (not shown) may be disposed under the first electrode 11 or on the second electrode 190 in FIG. 1. The substrate may be any substrate that is used in conventional organic light emitting devices. In some embodiments the substrate may be a glass substrate or a transparent plastic substrate with strong mechanical strength, thermal stability, transparency, surface smoothness, ease of handling, and water resistance.

The first electrode 11 may be formed by depositing or sputtering a first electrode-forming material on the substrate 11. The first electrode 11 may be an anode. A material having a high work function may be selected as a material for the first electrode to facilitate hole injection. The first electrode 11 may be a reflective electrode, a semi-transmissive electrode, or a transmissive electrode. For example, the material for the first electrode 13 may be indium tin oxide (ITO), indium zinc oxide (IZO), tin oxide ($SnO_2$), or zinc oxide (ZnO). In some embodiments, the material for the first electrode 13 may be a metal or an alloy thereof, for example, magnesium (Mg), aluminum (Al), aluminum-lithium (Al—Li), calcium (Ca), magnesium-indium (Mg—In), magnesium-Silver (Mg—Ag), or the like.

The first electrode 11 may have a single-layer structure or a multi-layer structure including at least two layers. For example, the first electrode 11 may have a three-layered structure of ITO, Ag, and ITO layers, but is not limited thereto.

The organic layer 15 may be disposed on the first electrode 11.

The organic layer 15 may include a hole transport region; an EML, and an electron transport region.

The hole transport region may be disposed between the first electrode 11 and the EML.

The hole transport region may include at least one of a hole injection layer (HIL), a hole transport layer (HTL), an electron blocking layer (EBL), and a buffer layer.

The hole transport region may include exclusively the HIL or the HTL. In some embodiments, the electron transport region may have a structure including a HIL/HTL or a HIL/HTL/EBL, wherein the layers forming the structure of the electron transport region may be sequentially stacked on the first electrode 10 in the stated order.

When the hole transport region includes the HIL, the HIL may be formed on the first electrode 11 by any of a variety of methods, for example, vacuum deposition, spin coating, casting, Langmuir-Blodgett (LB) deposition, or the like.

When the HIL is formed using vacuum deposition, vacuum deposition conditions may vary depending on the material that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Angstroms per second (A/sec). However, the deposition conditions are not limited thereto.

When the HIL is formed using spin coating, the coating conditions may vary depending on the material that is used to form the HIL, and the desired structure and thermal properties of the HIL to be formed. For example, the coating rate may be in the range of about 2,000 revolutions per minute (rpm) to about 5,000 rpm, and a temperature at which heat treatment is performed to remove a solvent after coating may be in a range of about 80° C. to about 200° C. However, the coating conditions are not limited thereto.

Conditions for forming the HTL and the EBL may be the same as those for the HIL described above.

In some embodiments, the hole transport region may include at least one of m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (PANI/PSS), a compound represented by Formula 201 below, and a compound represented by Formula 202 below.

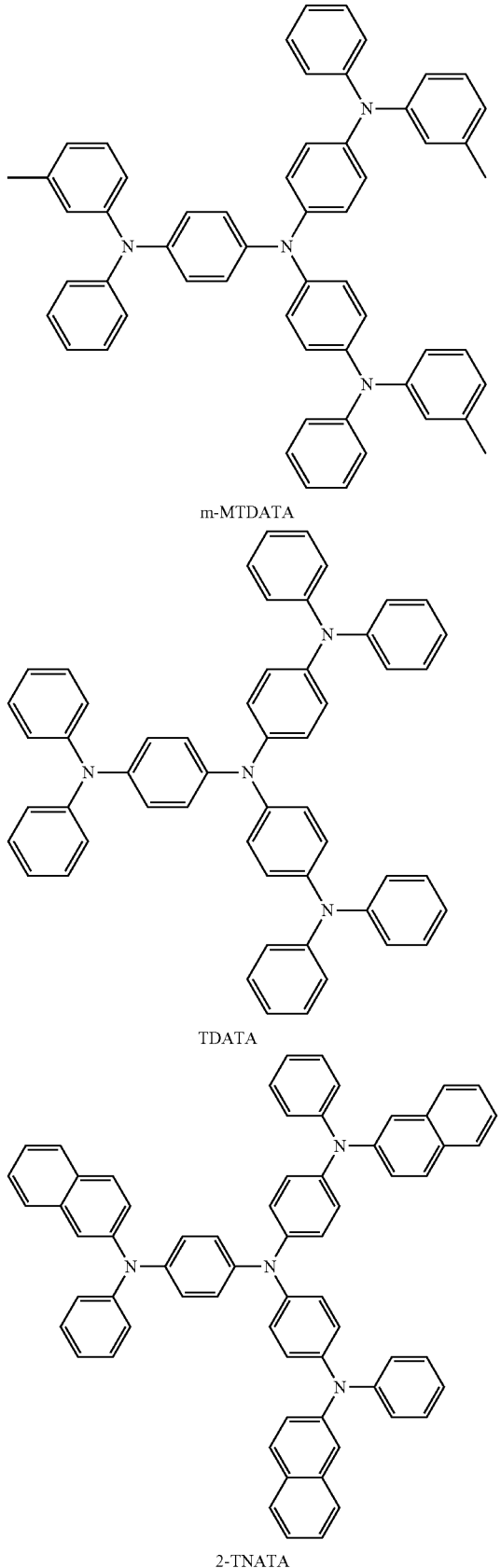

m-MTDATA

TDATA

2-TNATA

-continued
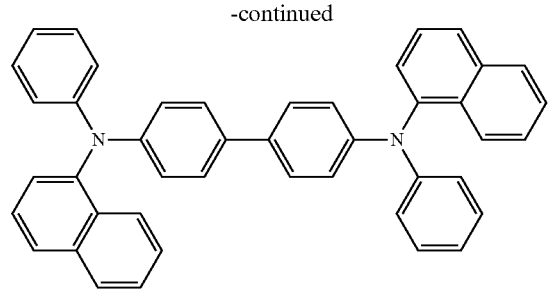
NPB
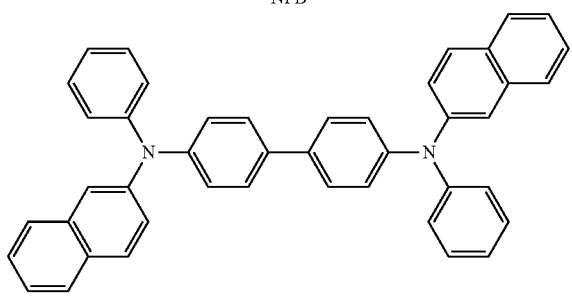
β-NPB
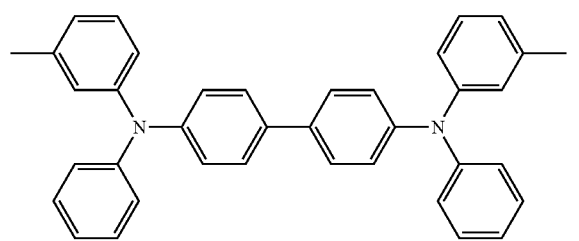
TPD
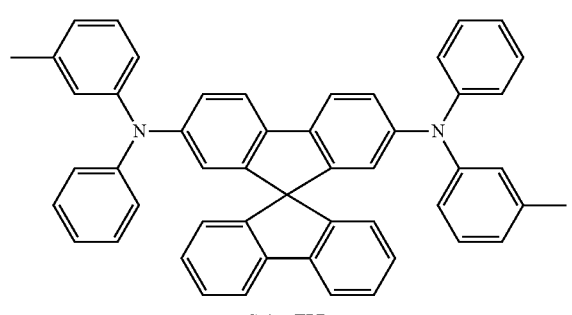
Spiro-TPD
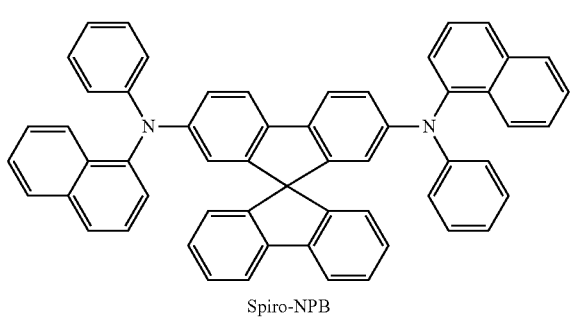
Spiro-NPB
-continued
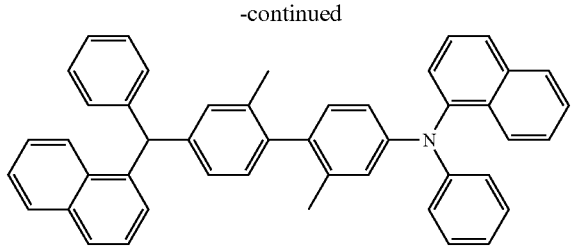
methylated NPB
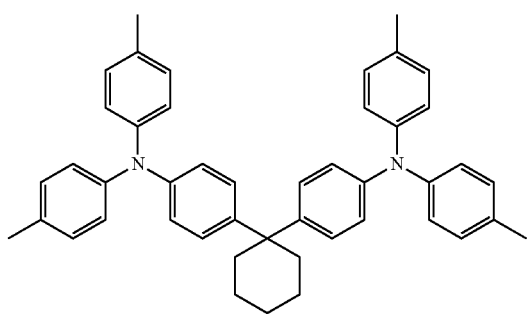
TAPC
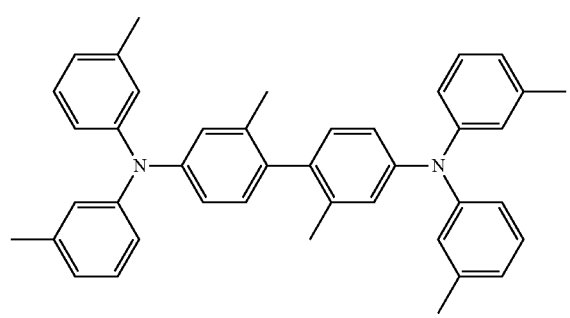
HMTPD
Formula 201
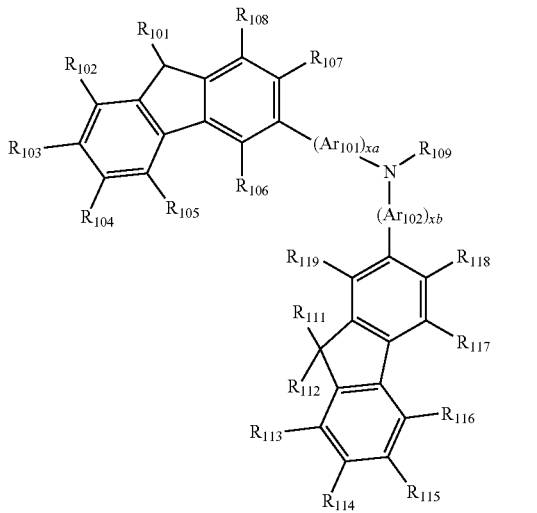

-continued

Formula 202

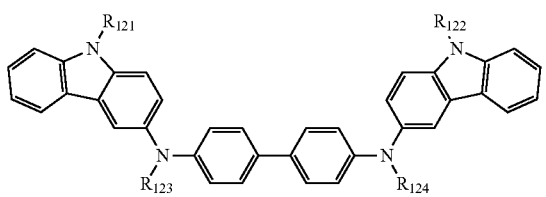

In Formula 201 above, $Ar_{101}$ and $Ar_{102}$ may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group, and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

In Formula 201, xa and xb may be each independently an integer from 0 to 5, for example, may be 0, 1, or 2. For example, xa may be 1, and xb may be 0, but are not limited thereto.

In Formulae 201 and 202, $R_{101}$ to $R_{108}$, $R_{111}$ to $R_{119}$, and $R_{121}$ to $R_{124}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, or the like), and a $C_1$-$C_{10}$ alkoxy group (for example, a methoxy group, an ethoxy group, a propoxy group, a butoxy group, a pentoxy group, or the like), a $C_1$-$C_{10}$ alkyl group and a $C_1$-$C_{10}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a naphthyl group, an anthracenyl group, a fluorenyl group, and a pyrenyl group, and a phenyl group, a naphthyl group, an anthracenyl group, a fluorenyl group, and a pyrenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group. However, embodiments of the present disclosure are not limited thereto.

In Formula 201 above, $R_{109}$ may be selected from a phenyl group, a naphthyl group, an anthracenyl group, and a pyridinyl group, and a phenyl group, a naphthyl group, an anthracenyl group, and a pyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group.

In some embodiments, the compound of Formula 201 may be represented by Formula 201A, but is not limited thereto:

Formula 201A

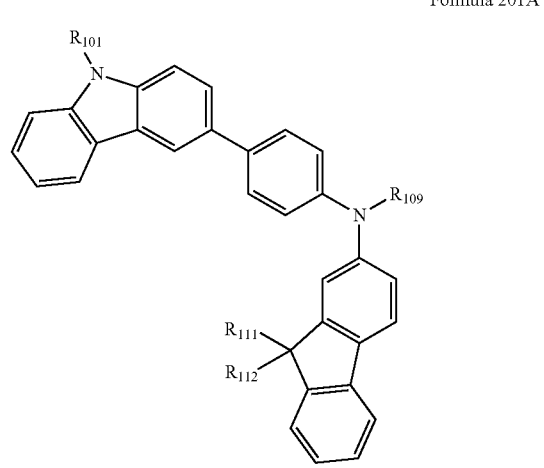

In Formula 201A, $R_{101}$, $R_{111}$, $R_{112}$, and $R_{109}$ may be the same as those defined above.

For example, the compound of Formula 201 and the compound of Formula 202 may include Compounds HT1 to HT20 below, but are not limited thereto:

HT1

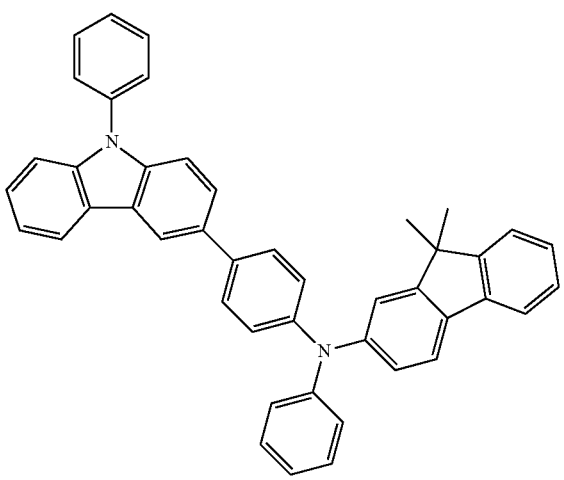

HT2
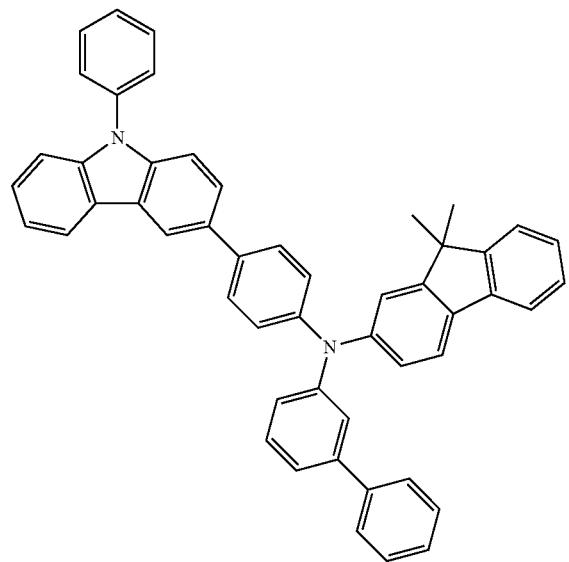
HT3
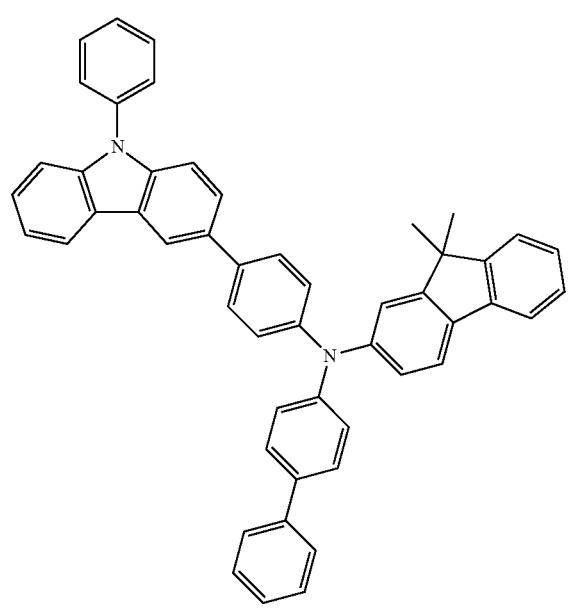
HT4
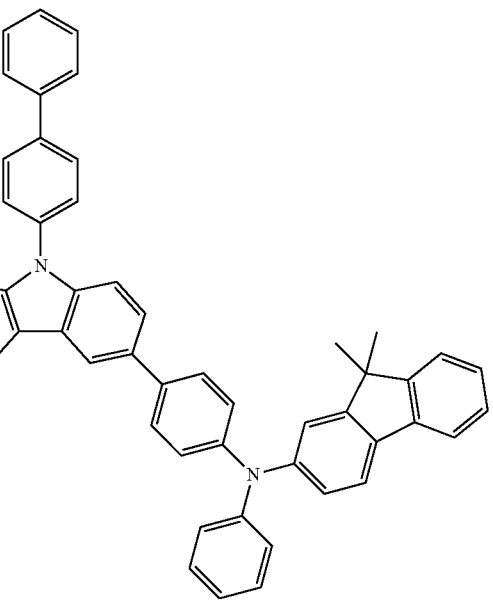
HT5
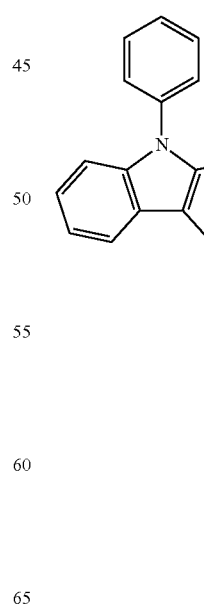

HT6
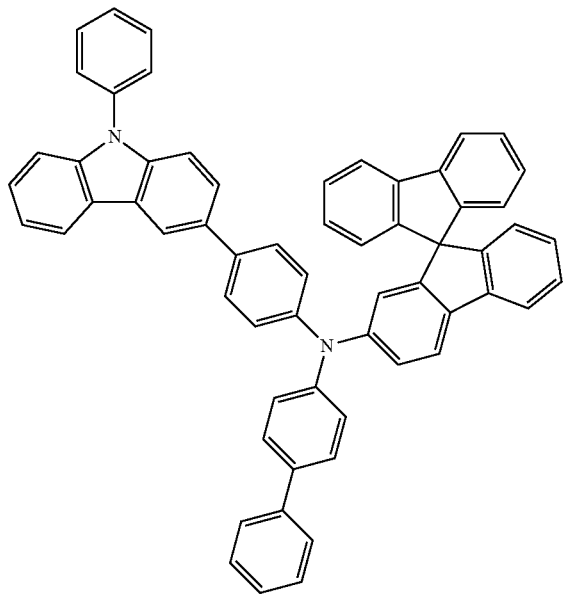
HT8
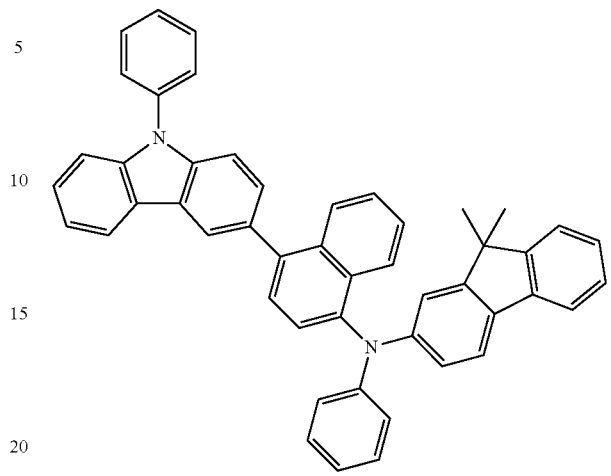
HT9
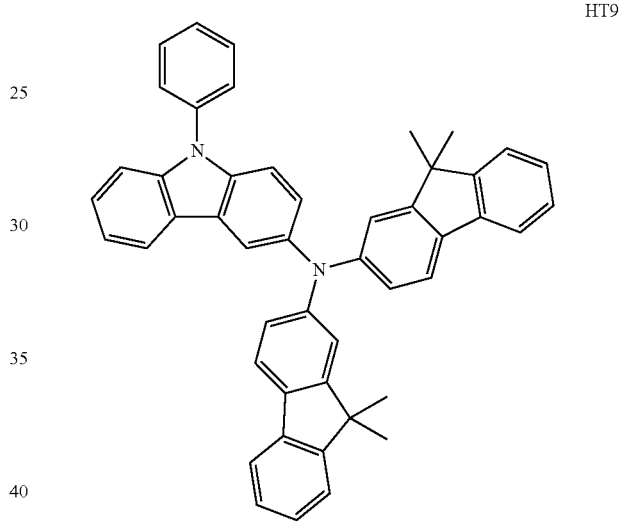
HT7
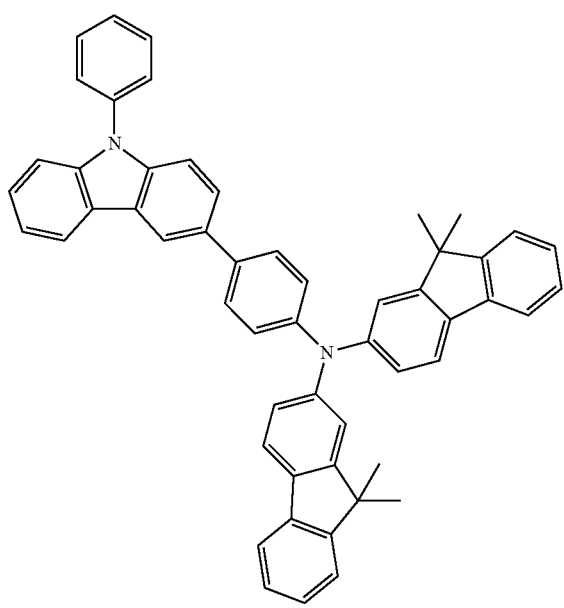
HT10
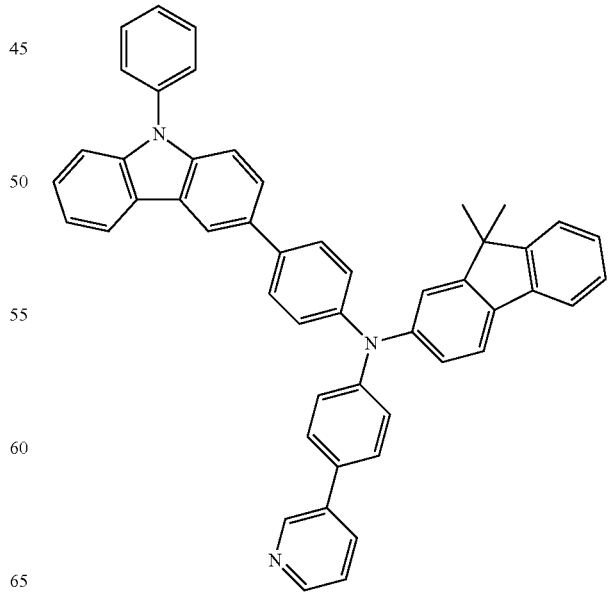

HT11
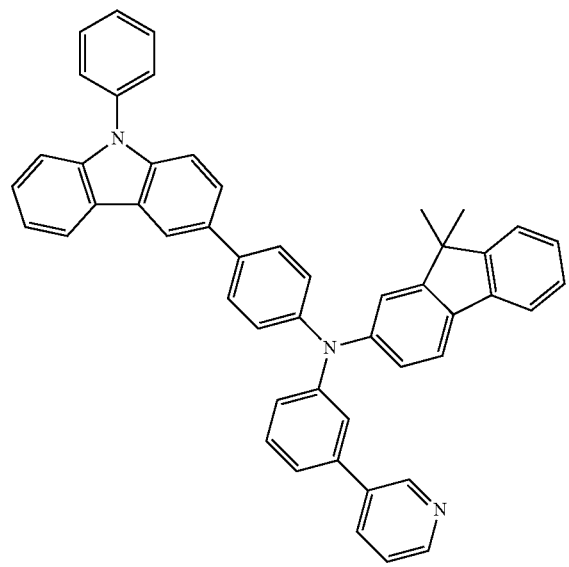
HT12
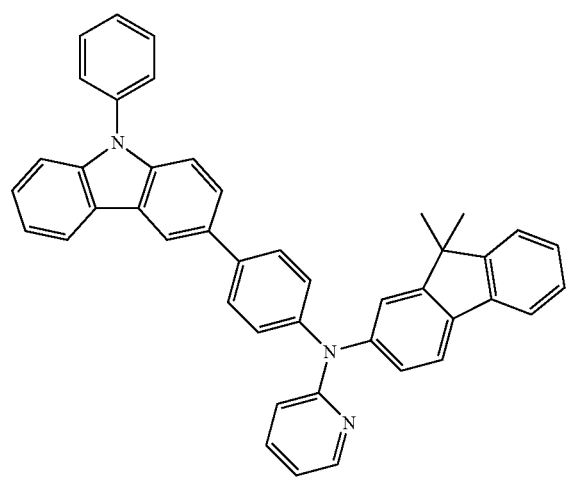
HT13
HT14
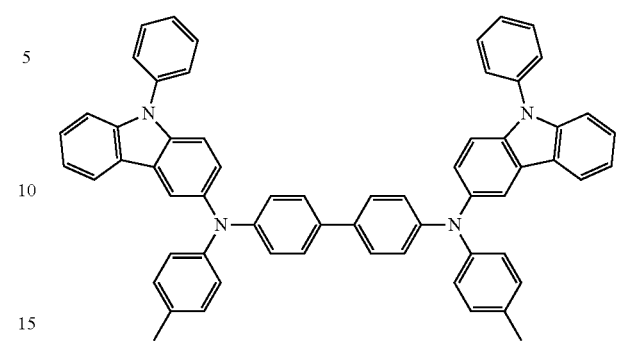
HT15
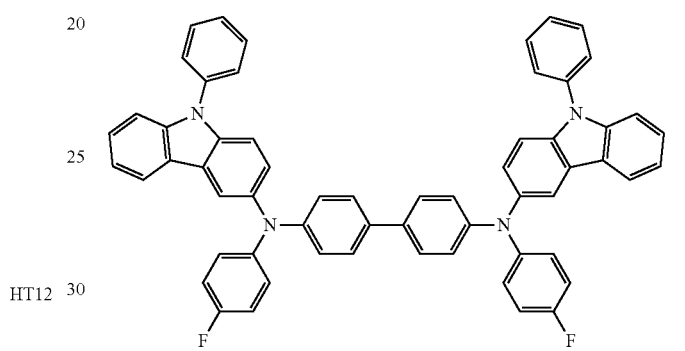
HT16
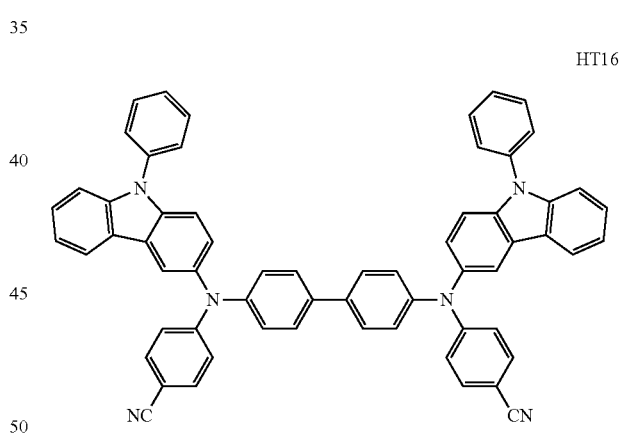
HT17
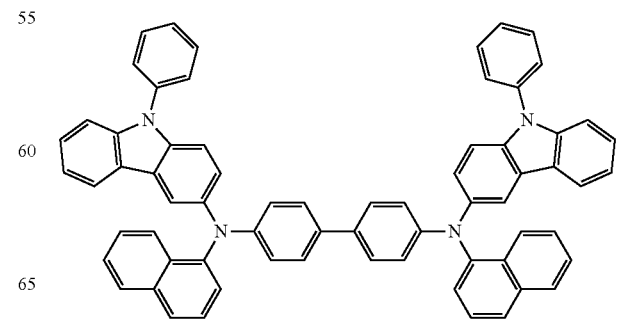

-continued

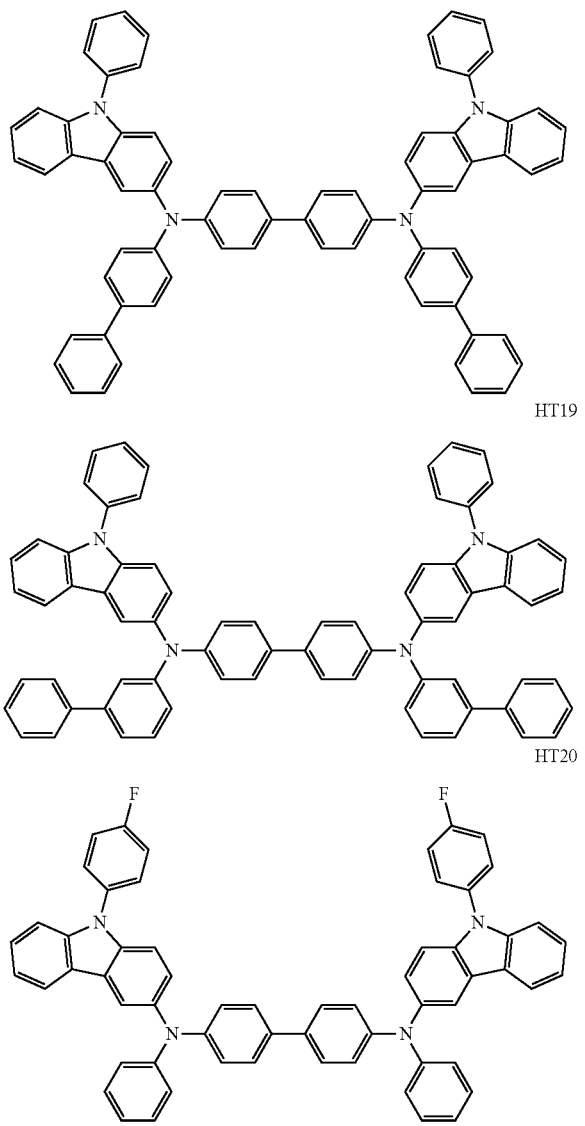

HT18

HT19

HT20

A thickness of the hole transport region may be from about 100 Angstroms (Å) to about 10,000 Å, and in some embodiments, from about 100 Å to about 1,000 Å. When the hole transport region includes a HIL and a HTL, a thickness of the HIL may be from about 100 Å to about 10,000 Å, and in some embodiments, from about 100 Å to about 1,000 Å, and a thickness of the HTL may be from about 50 Å to about 2,000 Å, and in some embodiments, from about 100 Å to about 1,500 Å. When the thicknesses of the hole transport region, the HIL, and the HTL are within these ranges, satisfactory hole transport characteristics may be obtained without a substantial increase in driving voltage.

The hole transport region may further include a charge-generating material to improve conductivity, in addition to the materials as described above. The charge-generating material may be homogeneously or non-homogeneously dispersed in the hole transport region.

The charge-generating material may be, for example, a p-dopant. The p-dopant may be one of a quinine derivative, a metal oxide, and a cyano group-containing compound, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

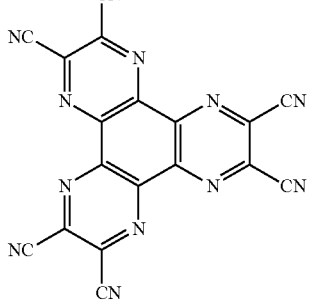

Compound HT-D1

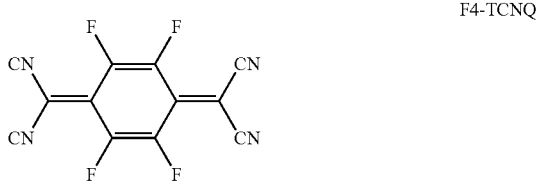

F4-TCNQ

The hole transport region may further include a buffer layer.

The buffer layer may compensate for an optical resonance distance of light according to a wavelength of the light emitted from the EML, and thus may increase efficiency.

The EML may be formed on the hole transport region by using vacuum deposition, spin coating, casting, LB deposition, or the like. When the EML is formed using vacuum deposition or spin coating, the conditions for deposition and coating may be similar to those for the formation of the HIL, though the conditions for the deposition and coating may vary depending on the material that is used to form the EML.

When the organic light-emitting device is a full color organic light-emitting device, the emission layer may be patterned into a red emission layer, a green emission layer, and a blue emission layer. In some embodiments, the EML may have a stack structure including a red emission layer, a green emission layer, and/or a blue emission layer that are stacked upon one another to emit white light, but is not limited thereto.

The EML may include a carbazole compound of Formula 1. The EML may further include a dopant. The dopant may include at least one of a phosphorescent dopant and a fluorescent dopant.

The EML may include a host and a dopant. The host may include at least one carbazole compound of Formula 1.

In some embodiments, the EML may include a first host and a second host. The first host and the second host may be different from each other, and the at least one carbazole compound represented by Formula 1 may be included in the EML. The first host may include at least one carbazole compound represented by Formula 1 in which at least one of $R_2$ to $R_4$ may be independently selected from a pyridinyl group, a pyrazinyl group, a pyrimidinyl group, a pyridazinyl group, a quinolinyl group, an isoquinolinyl group, a naphthyridinyl group, a quinoxalinyl group, a quinazolinyl group, a benzothiazolyl group, an isobenzothiazolyl group, a benzoxazolyl group, an isobenzooxazolyl group, an oxadiazolyl group, a triazinyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, and a pyridinyl group, a pyrazinyl group, a pyrimidinyl group, a pyridazinyl group, a quinolinyl group, an isoquinolinyl group, a naphthyridinyl group, a quinoxalinyl group, a quinazolinyl group, a benzothiazolyl group, an isobenzothiazolyl group, a benzoxazolyl group, an isobenzooxazolyl group, an oxadiazolyl group, a triazinyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, each substituted with at least one of a deuterium, —F, —Cl, —Br, —I, a hydroxyl group, a cyano group, a nitro group, an amino group, an amidino group, a hydrazine group, a hydrazone group, carboxylic acid group or a salt thereof, a sulfonic acid group or a salt thereof, a phosphoric acid group or a salt thereof, $C_1$-$C_{20}$ alkyl group, $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$); and the second host may include at least one carbazole compound represented by Formula 1 in which at least one of $R_2$ to $R_4$ may be independently selected from a thiophenyl group, a furanyl group, a carbazolyl group, acridinyl, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, and a thiophenyl group, a furanyl group, a carbazolyl group, acridinyl, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$), wherein $Q_{33}$ to $Q_{35}$ may be each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

In some embodiments, the EML may include a first host and a second host. The first host and the second host may be different from each other, and the at least one carbazole compound represented by Formula 1 may be in the EML. The first host may include at least one of the carbazole based compound represented by Formula 1 in which at least one of $R_2$ to $R_4$ in Formula 1 may be independently selected from a group represented by any of Formulae 4-1 to 4-48, and the second host may include at least one carbazole compound represented by Formula 1 in which at least one of $R_2$ to $R_4$ in Formula 1 may be independently selected from a group represented by any of Formulae 5-1 to 5-6, and Formulae 6-1 to 6-5.

When the EML includes a first host and a second host as described above, the balance of transport of holes and electrons into the EML may be effectively achieved, and thus the organic light-emitting device may have improved efficiency, improved luminance, and improved lifetime.

In some embodiments, the EML may include host 1 and host 2, wherein the host 1 and the host 2 may be different from each other, and wherein the at least one carbazole compound represented by Formula 1 may be in the EML. The host 1 may include a carbazole compound represented by Formula 1, and the host 2 may include at least one of a first compound represented by Formula 41 and a second compound represented by Formula 61.

Formula 41

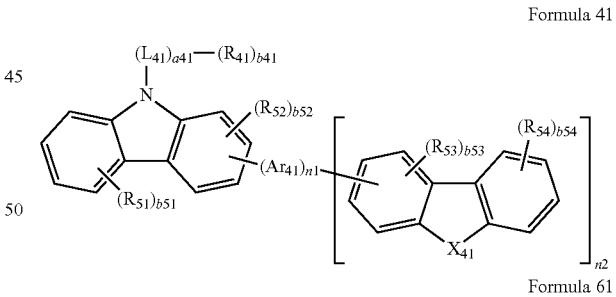

Formula 61

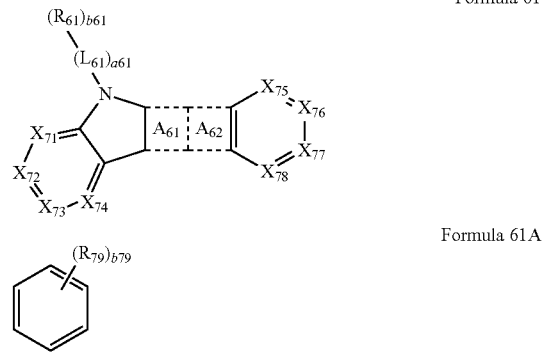

Formula 61A

-continued

Formula 61B

In Formulae 41, 61, 61A, and 61B, $X_{41}$ may be $N-[(L_{42})_{a42}-(R_{42})_{b42}]$, S, O, S(=O), S(=O)$_2$, C(=O), C($R_{43}$)($R_{44}$), Si($R_{43}$)($R_{44}$), P($R_{43}$), P(=O)($R_{43}$), or C=N($R_{43}$);

ring $A_{61}$ in Formula 61 may be represented by Formula 61A;

ring $A_{62}$ in Formula 61 may be represented by Formula 61B;

$X_{61}$ may be $N-[(L_{62})_{a62}-(R_{62})_{b62}]$, S, O, S(=O), S(=O)$_2$, C(=O), C($R_{63}$)($R_{64}$), Si($R_{63}$)($R_{64}$), P($R_{63}$), P(=O)($R_{63}$), or C=N($R_{63}$);

$X_{71}$ may be C($R_{71}$) or N;
$X_{72}$ may be C($R_{72}$) or N;
$X_{73}$ may be C($R_{73}$) or N;
$X_{74}$ may be C($R_{74}$) or N;
$X_{75}$ may be C($R_{75}$) or N;
$X_{76}$ may be C($R_{76}$) or N;
$X_{77}$ may be C($R_{77}$) or N;
$X_{78}$ may be C($R_{78}$) or N;

$Ar_{41}$, $L_{41}$, $L_{42}$, $L_{61}$, and $L_{62}$ may be each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent nonaromatic condensed polycyclic group, and a substituted or unsubstituted divalent nonaromatic condensed heteropolycyclic group;

n1 and n2 may be each independently an integer selected from 0 to 3;

a41, a42, a61, and a62 may be each independently an integer selected from 0 to 3;

$R_{41}$ to $R_{44}$, $R_{51}$ to $R_{54}$, $R_{61}$ to $R_{64}$, and $R_{71}$ to $R_{79}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent nonaromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

b41, b42, b51 to b54, b61, b62, and b79 may be each independently an integer selected from 1 to 3;

at least one of substituents of the substituted $C_1$-$C_{60}$ alkylene group, the substituted $C_2$-$C_{60}$ alkenylene group, the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —N($Q_{11}$)($Q_{12}$), —Si($Q_{13}$)($Q_{14}$)($Q_{15}$), and —B($Q_{16}$)($Q_{17}$), a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, and a monovalent nonaromatic condensed heteropolycyclic group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, and a monovalent nonaromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent nonaromatic condensed polycyclic group, and a monovalent aromatic condensed heteropolycyclic group.

In some embodiments, $R_{41}$ to $R_{44}$, $R_{51}$ to $R_{54}$, $R_{61}$ to $R_{64}$, and $R_{71}$ to $R_{79}$ in above Formulae may be each independently selected from a hydrogen, a deuterium, —F, —Cl, —Br, —I, a hydroxyl group, a cyano group, a nitro group, an amino group, an amidino group, a hydrazine group, a hydrazone group, carboxylic acid group or a salt thereof, a sulfonic acid group or a salt thereof, a phosphoric acid group or a salt thereof, $C_1$-$C_{20}$ alkyl group and $C_1$-$C_{20}$ alkoxy group, a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, carboxylic acid group or a salt thereof, a sulfonic acid group or a salt thereof and a phosphoric acid group or a salt thereof, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, carboxylic acid group or a salt thereof, a sulfonic acid or a salt thereof, a phosphoric acid or a salt thereof, $C_1$-$C_{20}$ alkyl group, $C_1$-$C_{20}$ alkoxy group, —Si($Q_{33}$)($Q_{34}$)($Q_{35}$), a phenyl group, a phenyl group-substituted phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, and —Si($Q_3$)($Q_4$)($Q_5$), wherein $Q_3$ to $Q_5$, and $Q_{33}$ to $Q_{35}$ may be each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group. However, embodiments of the present disclosure are not limited thereto.

For example, the first compound may be represented by one of Formulae 41-1 to 41-12, and the second compound may be represented by one of Formula 61-1 to 61-6:
Formula 41-1
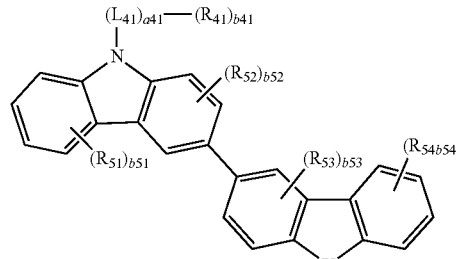
Formula 41-2
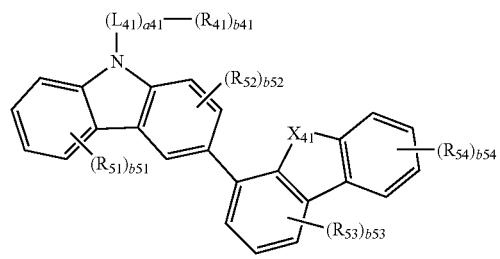
Formula 41-3
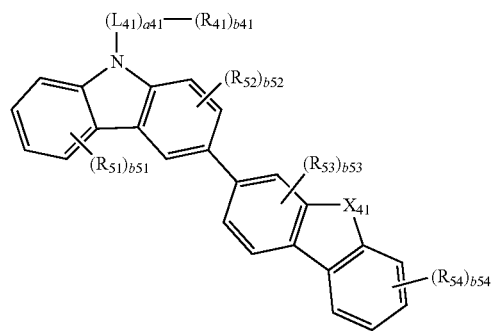
Formula 41-4
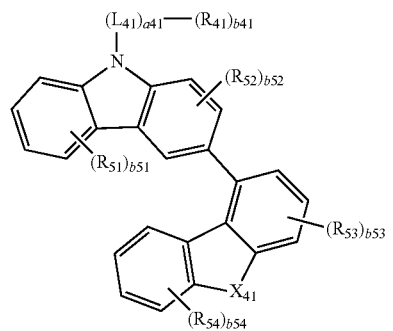
Formula 41-5
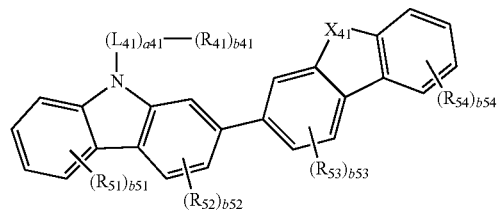
Formula 41-6
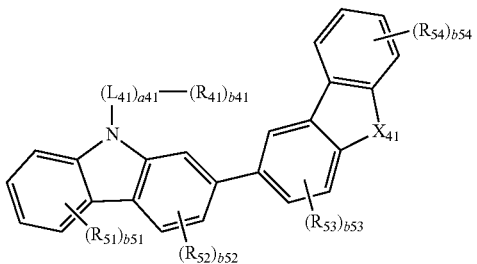
Formula 41-7
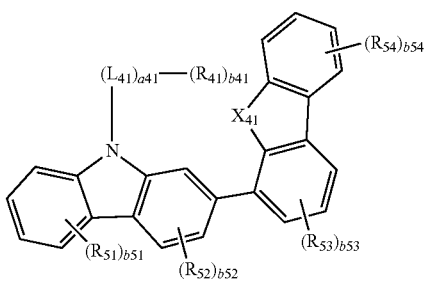
Formula 41-8
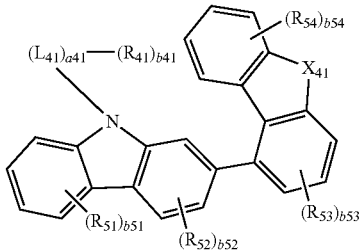
Formula 41-9
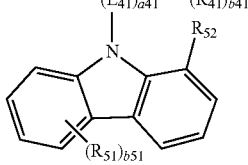
Formula 41-10
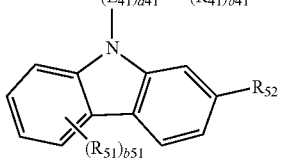
Formula 41-11
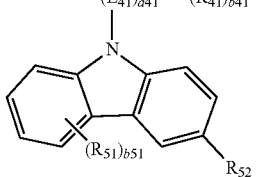

-continued

Formula 41-12

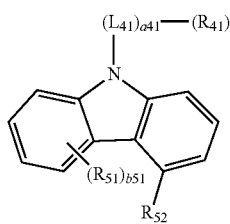

Formula 61-1

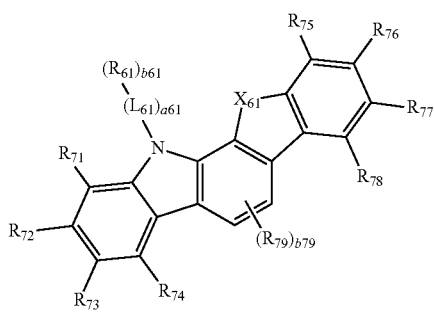

Formula 61-2

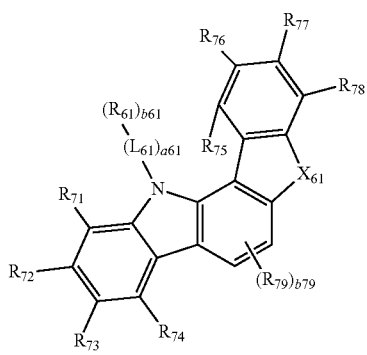

Formula 61-3

Formula 61-4

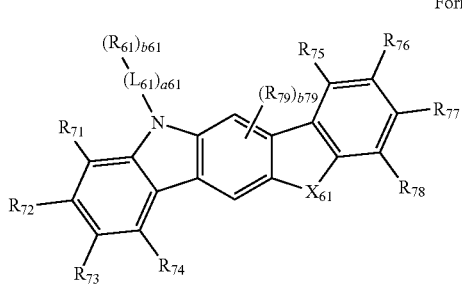

Formula 61-5

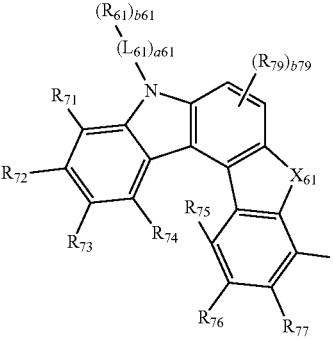

Formula 61-6

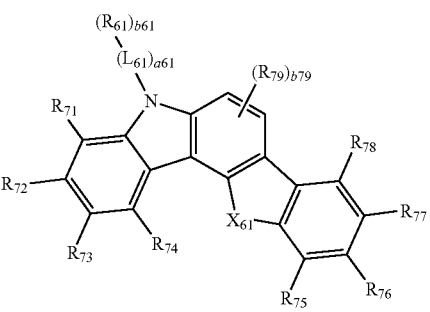

In Formulae 41-1 to 41-12 and Formulae 61-1 to 61-6, $X_{41}$, $X_{61}$, $L_{41}$, $L_{42}$, a41, a42, $L_{61}$, $L_{62}$, a61, a62, $R_{41}$ to $R_{44}$, b41, b42, $R_{61}$ to $R_{64}$, b61, b62, $R_{71}$ to $R_{79}$, and b79 may be the same as those described herein.

For example, in the carbazole compound of Formula 1 of the host 1, at least one of $R_2$ to $R_4$ may be independently selected from a pyridinyl group, a pyrazinyl group, a pyrimidinyl group, a pyridazinyl group, a quinolinyl group, an isoquinolinyl group, a naphthyridinyl group, a quinoxalinyl group, a quinazolinyl group, a benzothiazolyl group, an isobenzothiazolyl group, a benzoxazolyl group, an isobenzooxazolyl group, an oxadiazolyl group, a triazinyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, and a pyridinyl group, a pyrazinyl group, a pyrimidinyl group, a pyridazinyl group, a quinolinyl group, an isoquinolinyl group, a naphthyridinyl group, a quinoxalinyl group, a quinazolinyl group, a benzothiazolyl group, an isobenzothiazolyl group, a benzoxazolyl group, an isobenzooxazolyl group, an oxadiazolyl group, a triazinyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, each substituted with at least one of a deuterium, —F, —Cl, —Br, —I, a hydroxyl group, a cyano group, a nitro group, an amino group, an amidino group, a hydrazine group, a hydrazone group, carboxylic acid group or a salt thereof, a sulfonic acid group or a salt thereof, a phosphoric acid or a salt thereof, $C_1$-$C_{20}$ alkyl group, $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$)

At least one of $R_{41}$, $R_{42}$, and $R_{52}$ in the first compound of Formula 41 when the host 2 includes a first compound represented by Formula 41 and at least one of $R_{61}$ and $R_{62}$ in the second compound of Formula 61 when the host 2 includes a second compound represented by Formula 61 may be each independently selected from a thiophenyl group, a furanyl group, a carbazolyl group, acridinyl, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group; and a thiophenyl group, a furanyl group, a carbazolyl group, acridinyl, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, each substituted with at least one of a deuterium, —F, —Cl, —Br, —I, a hydroxyl group, a cyano group, a nitro group, an amino group, an amidino group, a hydrazine group, a hydrazone group, carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$), wherein $Q_{33}$ to $Q_{35}$ may be each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

In some other embodiments, at least one of $R_2$ to $R_4$ in the carbazole compound of Formula 1 of the host 1 may be independently selected from a thiophenyl group, a furanyl group, a carbazolyl group, acridinyl, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, and a thiophenyl group, a furanyl group, a carbazolyl group, acridinyl, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$)

At least one of $R_{41}$, $R_{42}$, and $R_{52}$ in the first compound of Formula 41 when the host 2 includes a first compound represented by Formula 41, and at least one of $R_{61}$ and $R_{62}$ in the second compound of Formula 61 when the host 2 includes a second compound of Formula 61 may be each independently selected from a pyrrolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, phenanthridinyl, phenanthrolinyl, phenazinyl, a benzoimidazolyl group, an isobenzothiazolyl group, a benzoxazolyl group, an isobenzooxazolyl group, a triazolyl group, a tetrazolyl group, an oxadiazolyl group, a triazinyl group, an imidazopyridinyl group, and an imidazopyrimidinyl group, and a pyrrolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, phenanthridinyl, phenanthrolinyl, phenazinyl, a benzoimidazolyl group, an isobenzothiazolyl group, a benzoxazolyl group, an isobenzooxazolyl group, a triazolyl group, a tetrazolyl group, an oxadiazolyl group, a triazinyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, carboxylic acid group or a salt thereof, a sulfonic acid group or a salt thereof, a phosphoric acid group or a salt thereof, $C_1$-$C_{20}$ alkyl group, $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$), wherein $Q_{33}$ to $Q_{35}$ may be each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

In some embodiments, at least one of $R_2$ to $R_4$ in the carbazole compound of Formula 1 of the host 1 may be independently a group represented by one of Formulae 4-1 to 4-48; and at least one of $R_{41}$, $R_{42}$ and $R_{52}$ in the first compound of Formula 41 when the host 2 include a first compound of Formula 41, and at least one of $R_{61}$ and $R_{62}$ in the second compound of Formula 61 when the host 2 include a second compound of Formula 61 may be each independently a group represented by one of Formulae 5-1 to 5-6 and Formulae 6-1 to 6-5.

In some other embodiments, at least one of $R_2$ to $R_4$ in the carbazole compound of Formula 1 of the host 1 may be independently a group represented by one of Formulae 5-1 to 5-6 and Formulae 6-1 to 6-5; and at least one of $R_{41}$, $R_{42}$, and $R_{52}$ in the first compound of Formula 41 when the host 2 includes a first compound of Formula 41, and at least one of $R_{61}$ and $R_{62}$ in the second compound of Formula 61 when the host 2 includes a second compound of Formula 61 may be each independently a group represented by one of Formulae 4-1 to 4-48.

In some embodiments, the first compound represented by Formula 41 may include one of Compounds A1 to A83, and the second compound may include at least one of Compounds B1 to B20. However, embodiments of the present disclosure are not limited thereto:

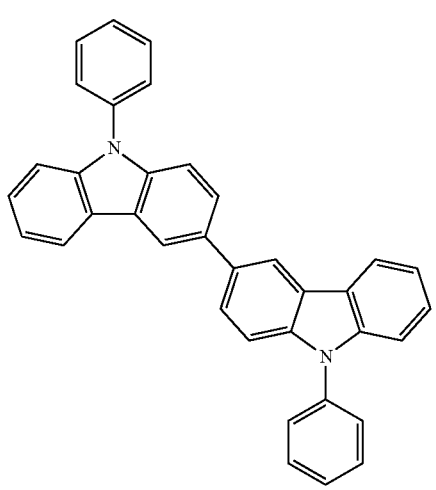

A1

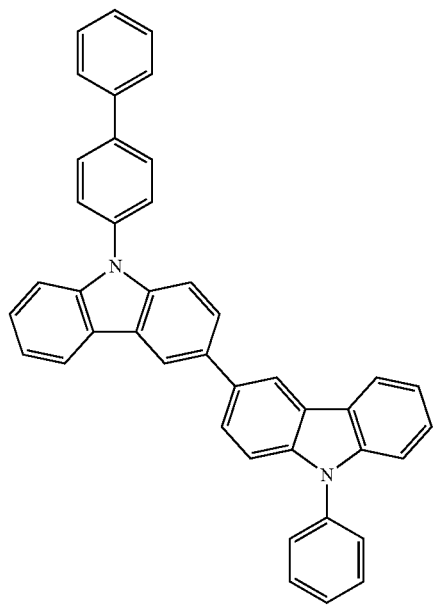

A2

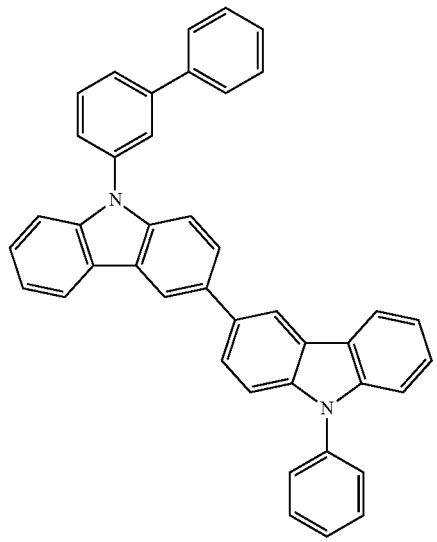

A3

A4
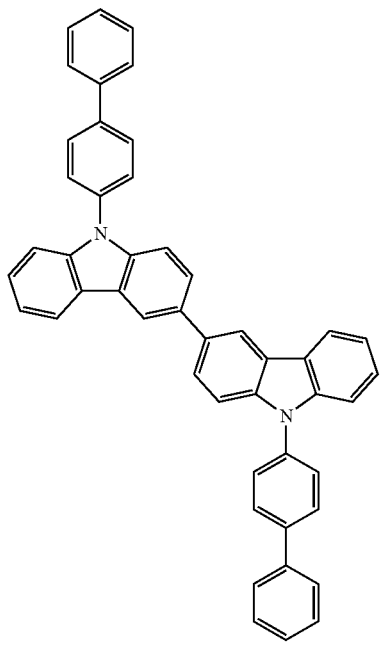
A5
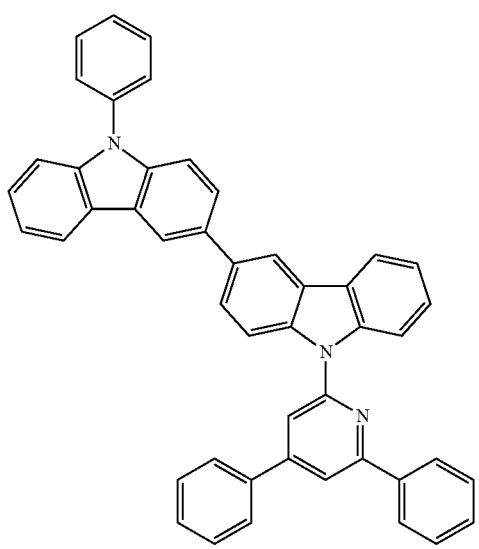
A6
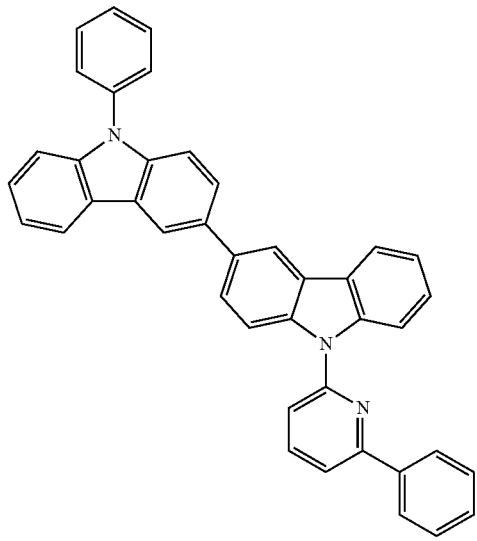
A7
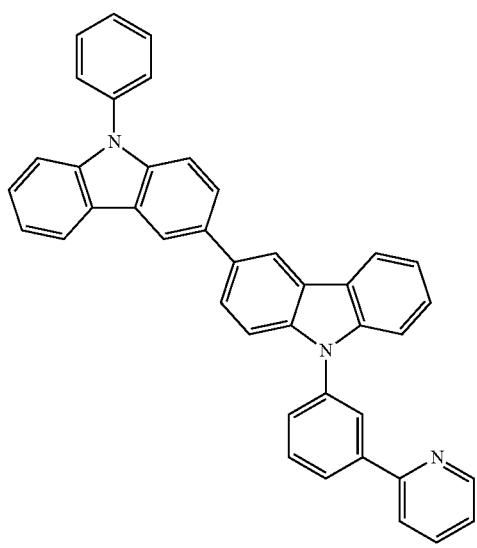

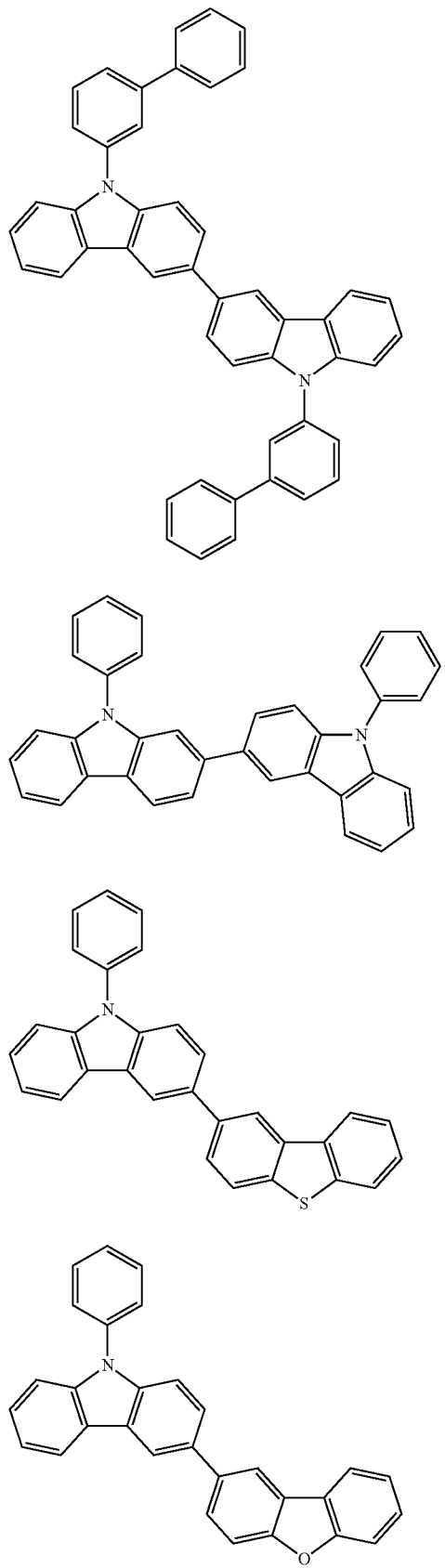
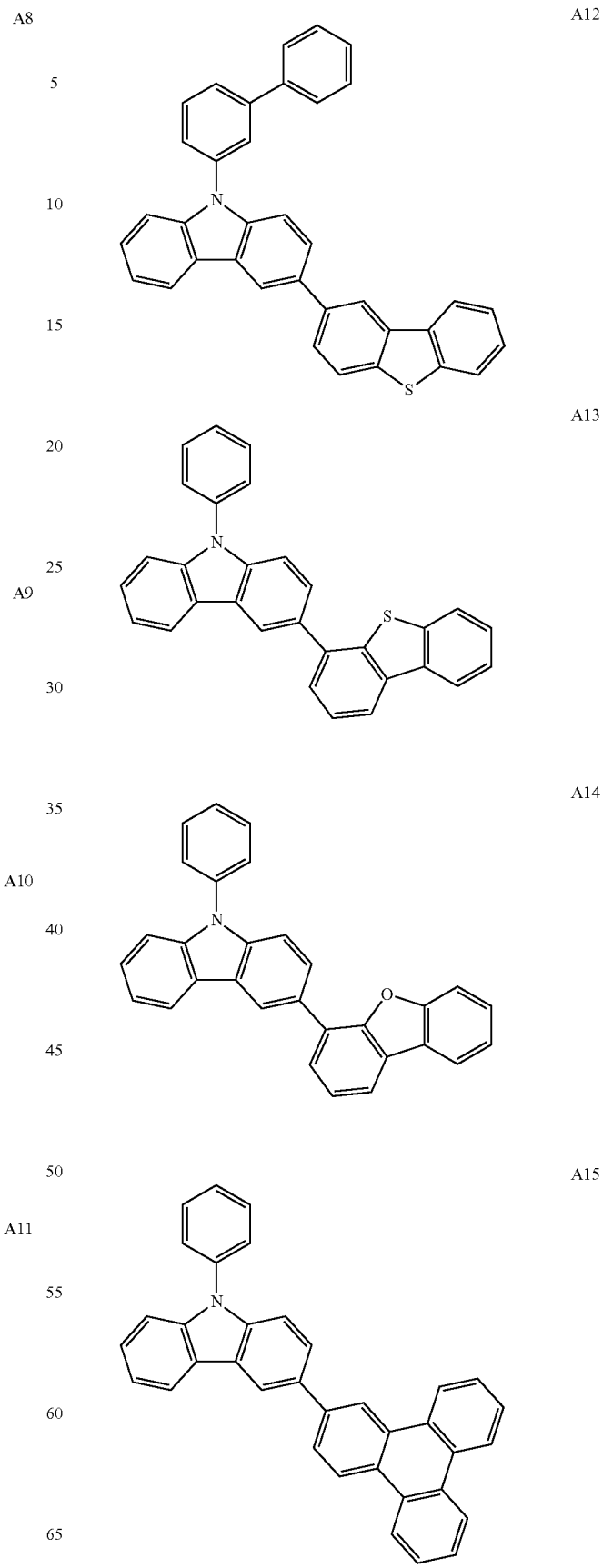

A16
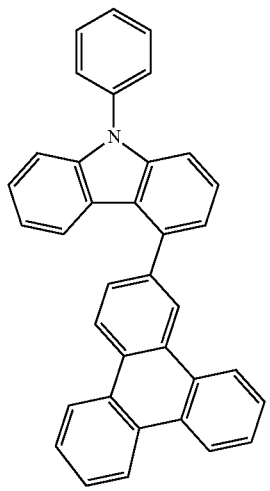
A19
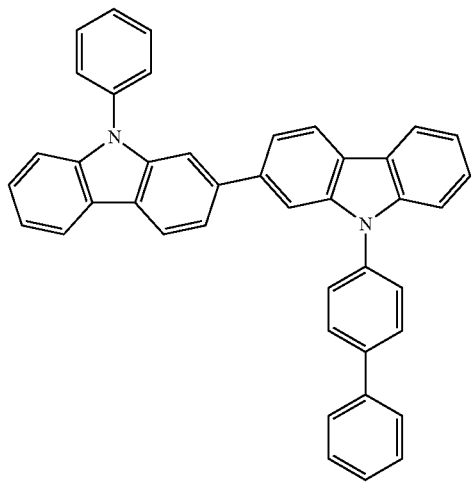
A17
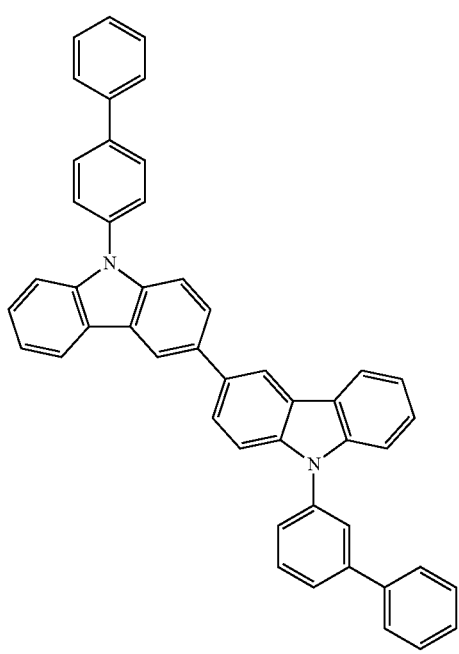
A20
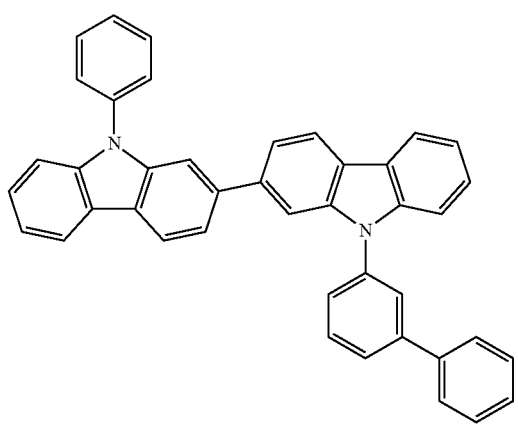
A18
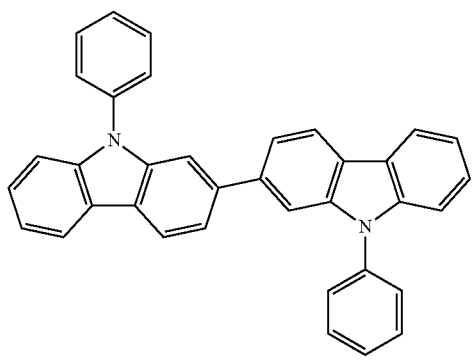
A21
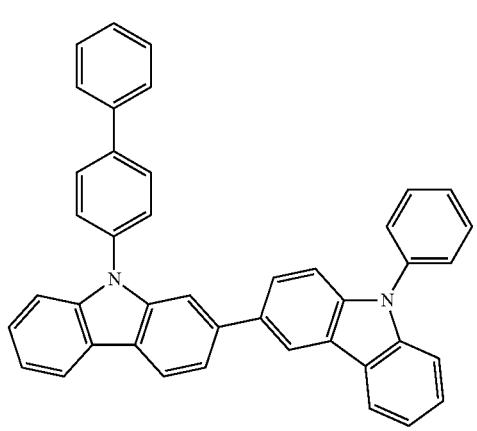

A22
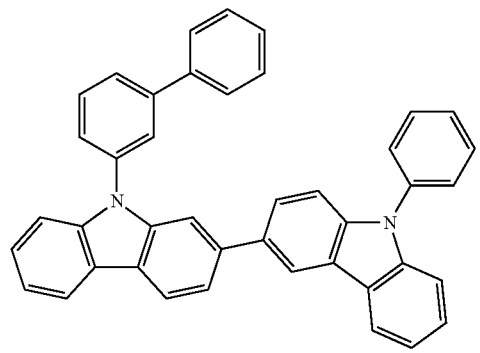
A23
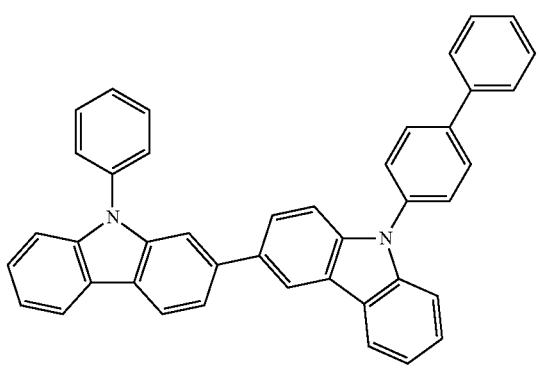
A24
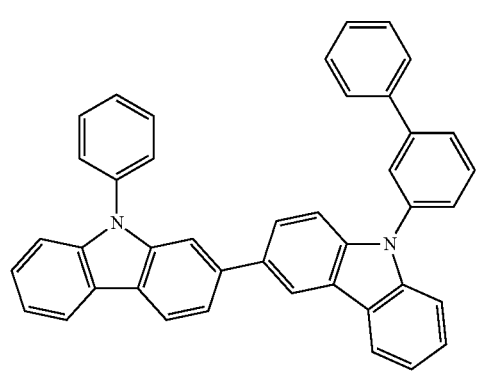
A25
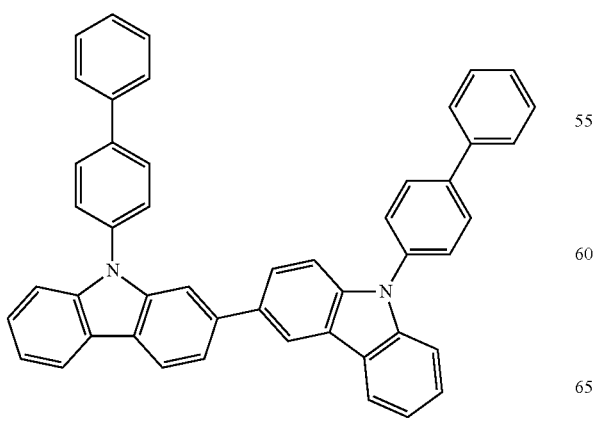
A26
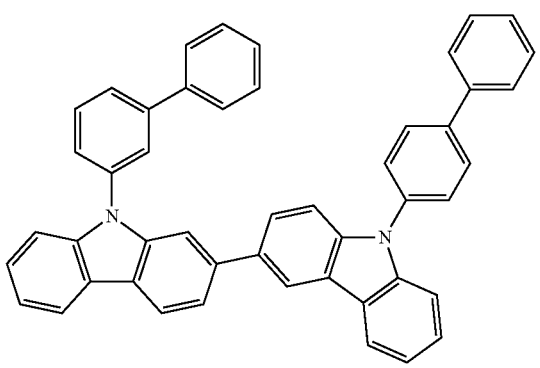
A27
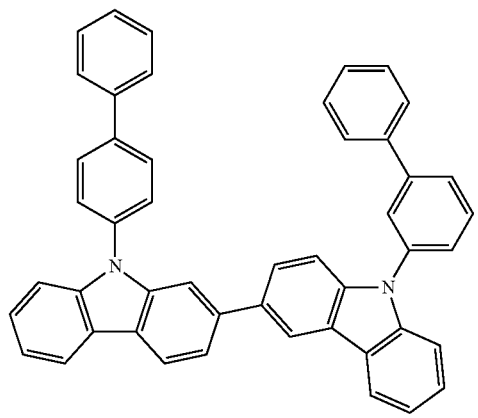
A28
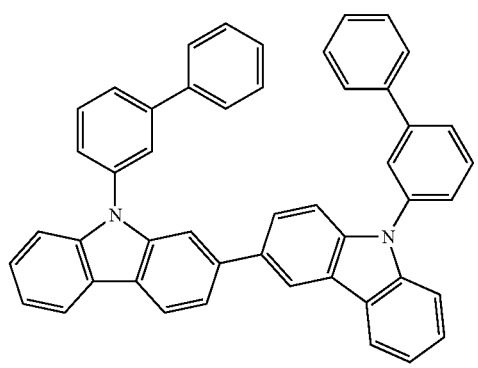

A29
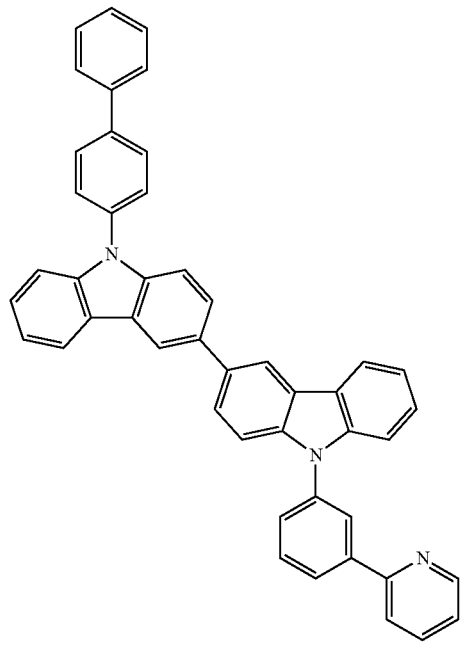
A31
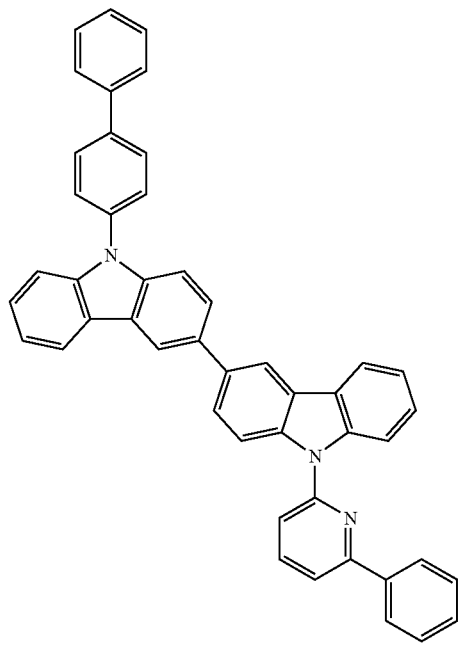
A30
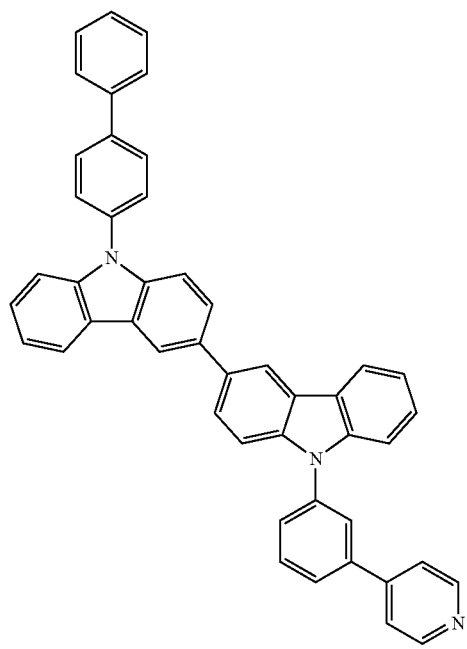
A32
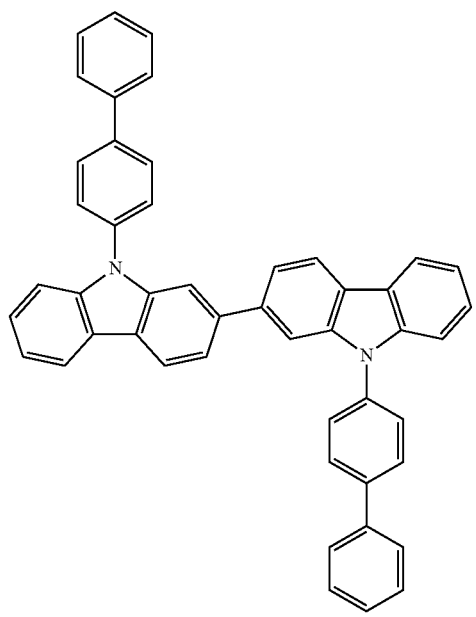

A33
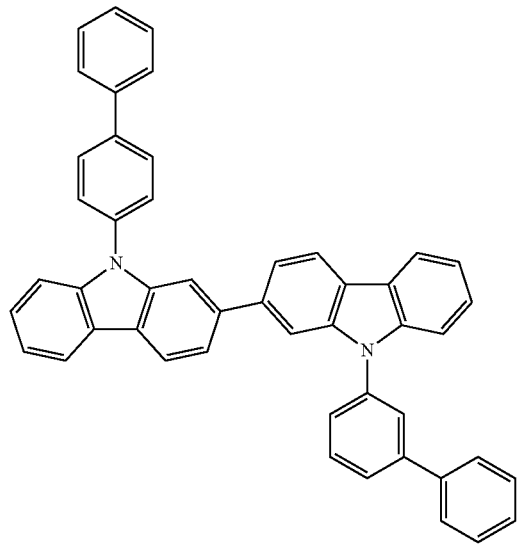
A34
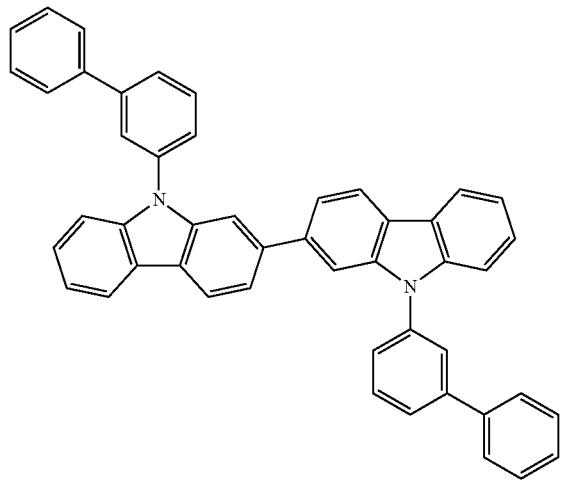
A35
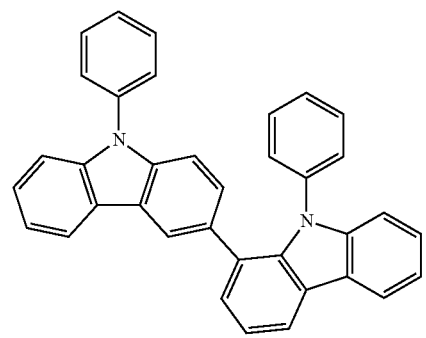
A36
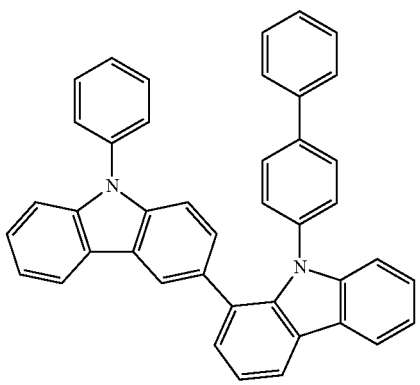
A37
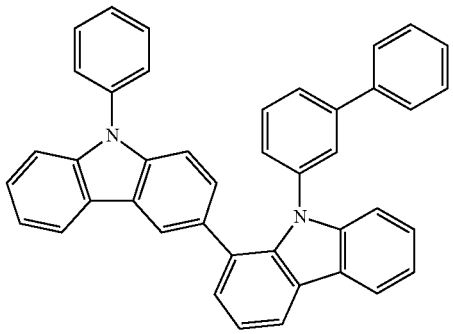
A38
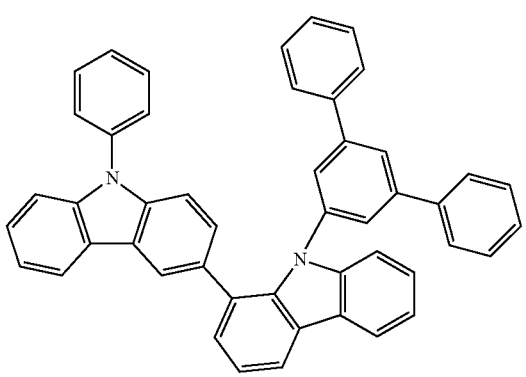
A39
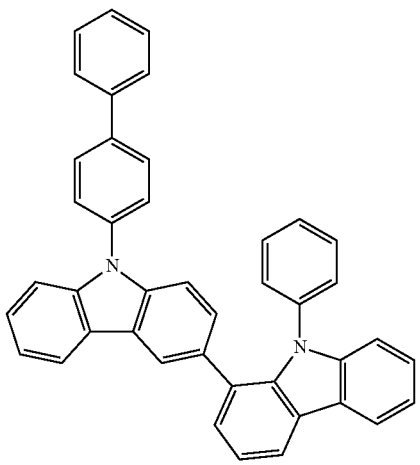

111
-continued
A40
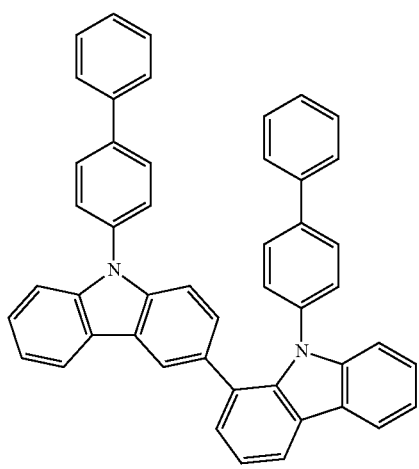
A41
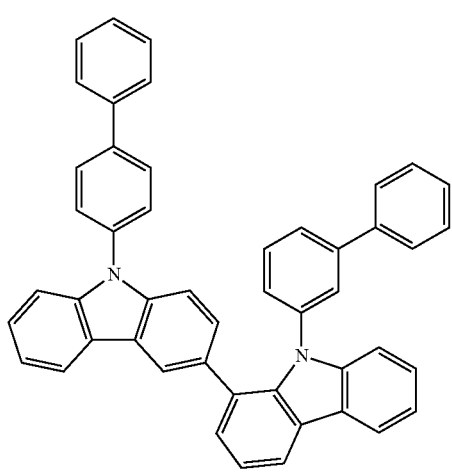
A42
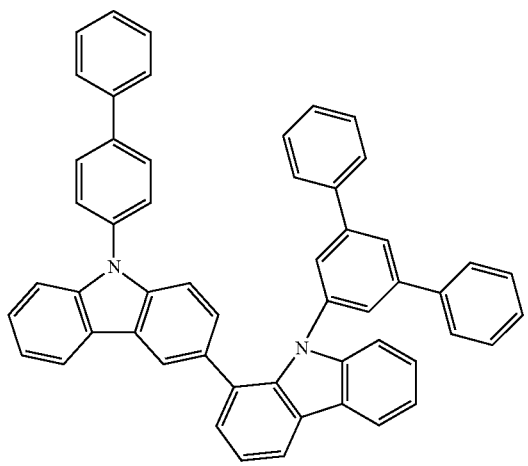
112
-continued
A43
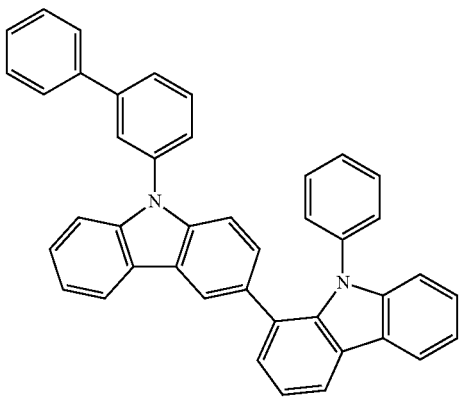
A44
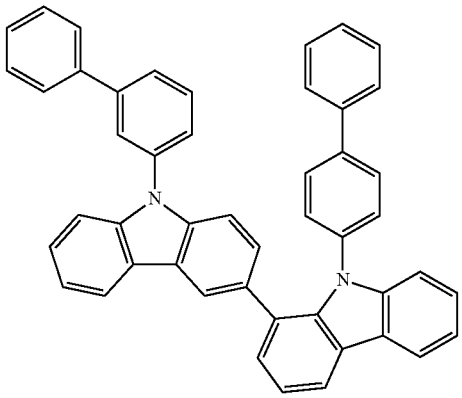
A45
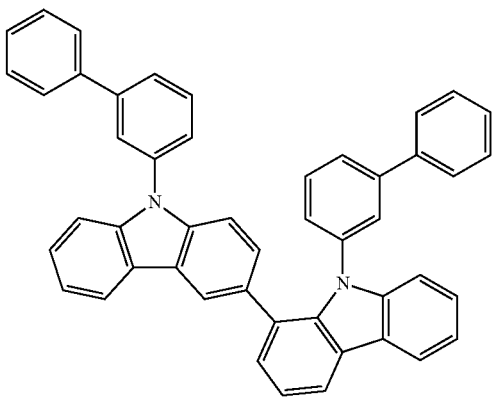
A46
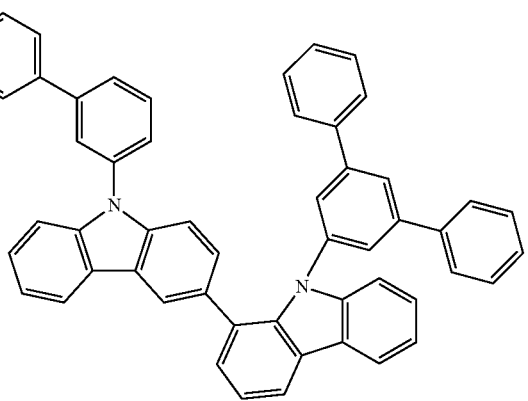

A47
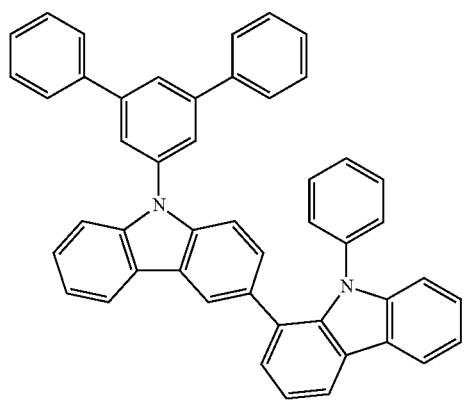
A48
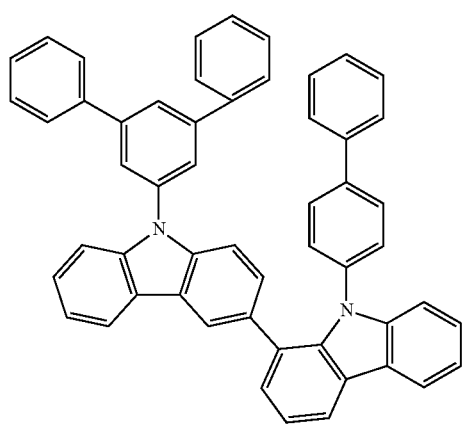
A49
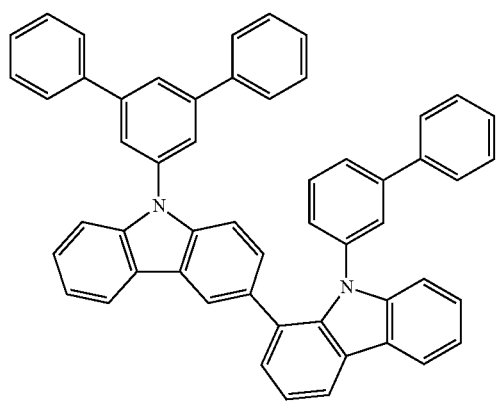
A50
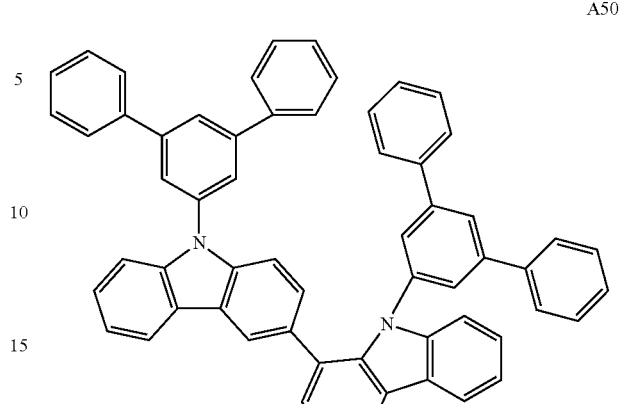
A51
A52
A53

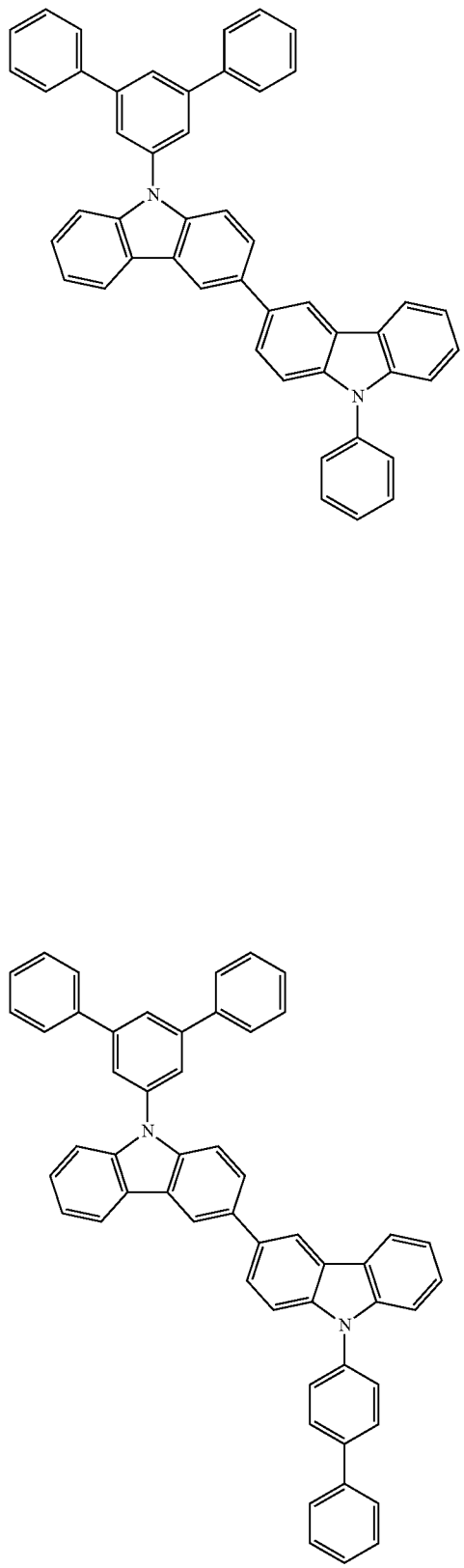
A54
A55
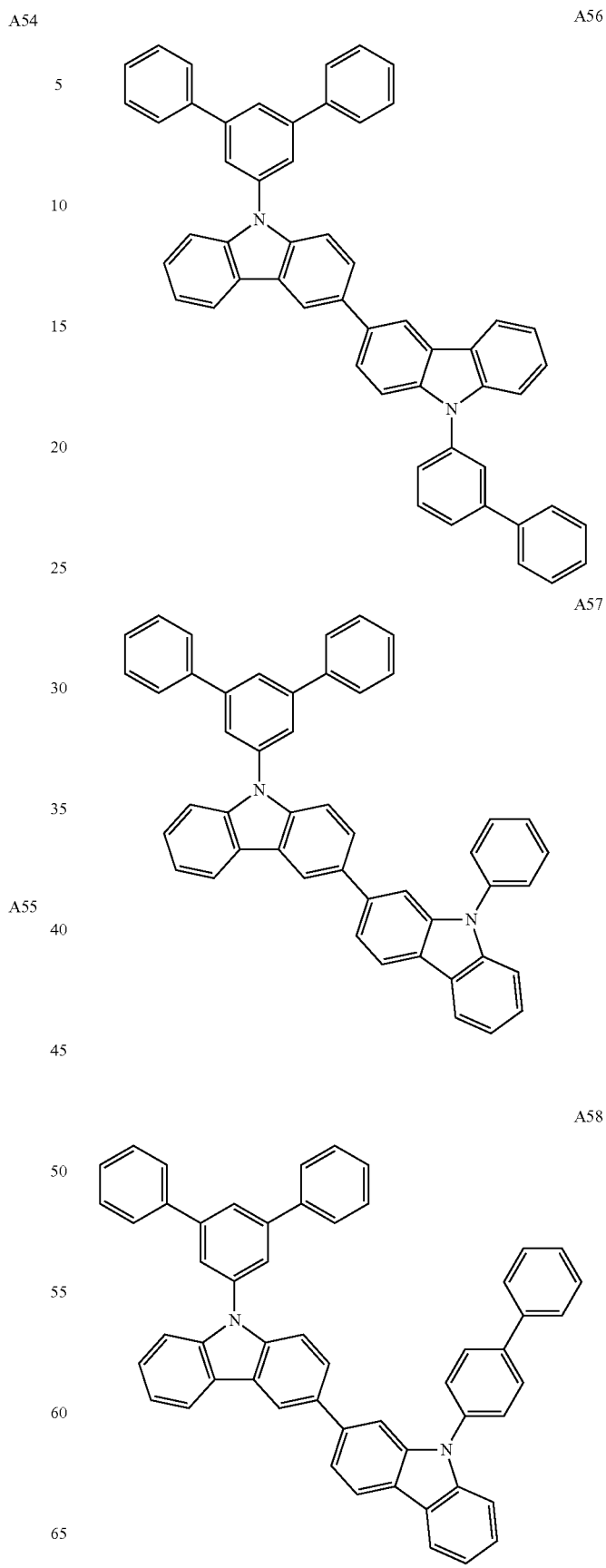
A56
A57
A58

A59
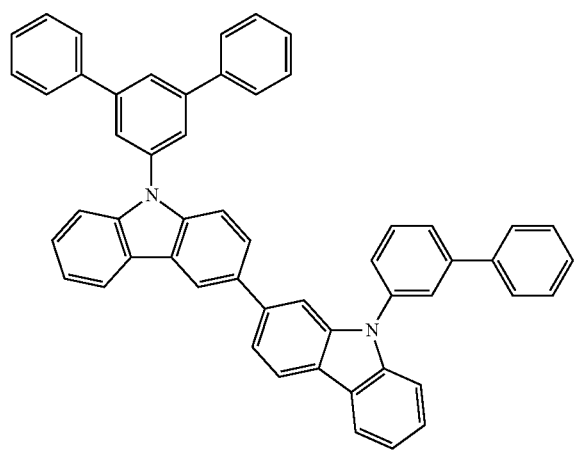
A60
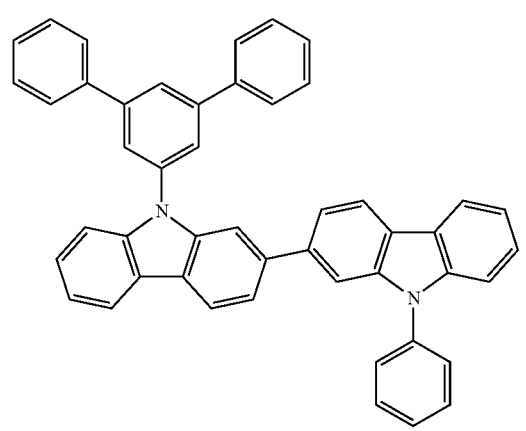
A61
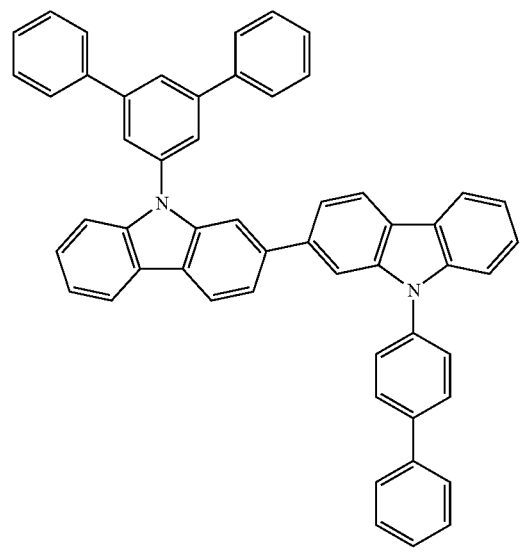
A62
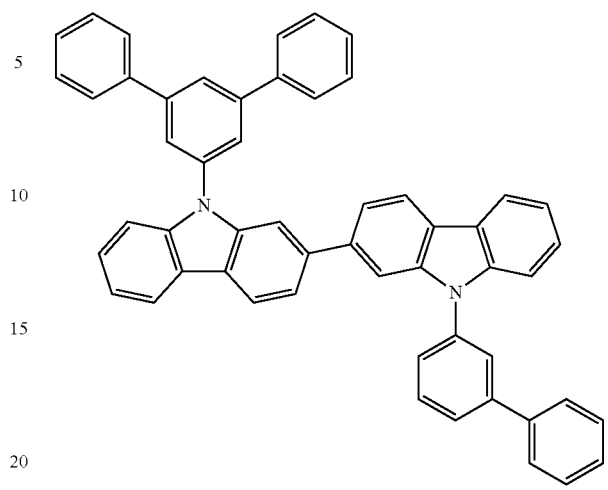
A63
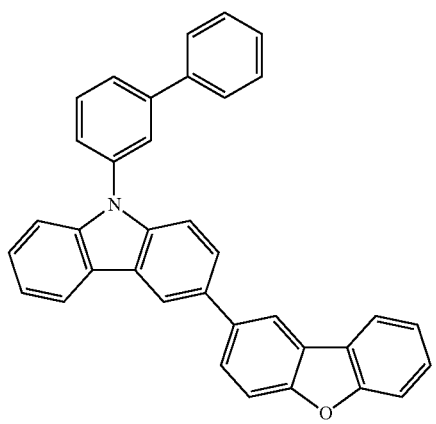
A64
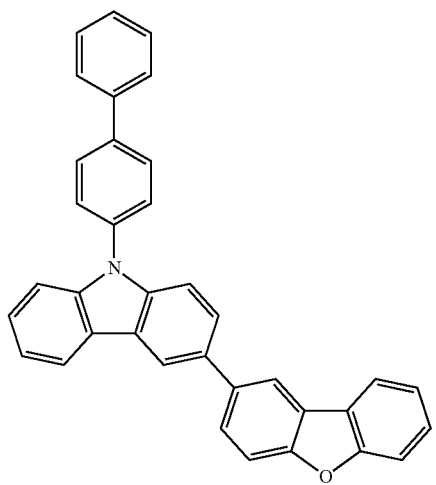

A65
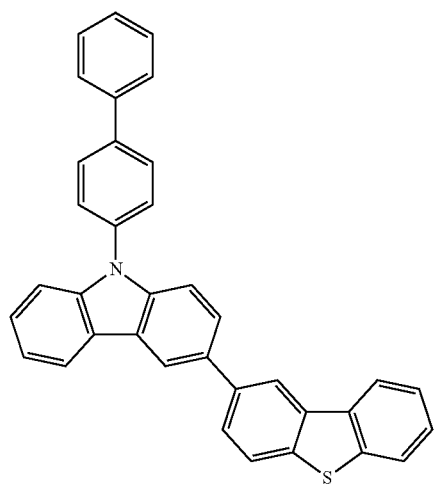
A66
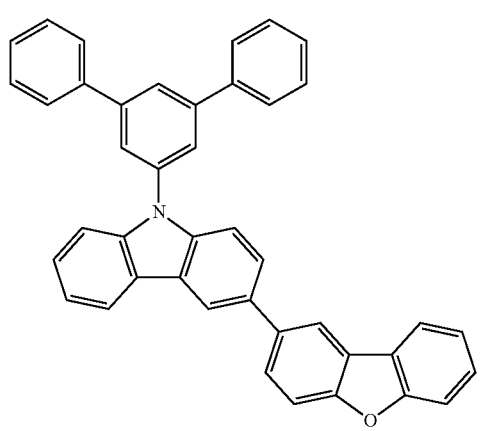
A67
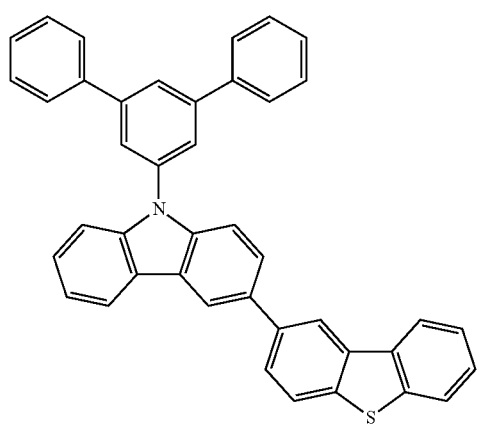
A68
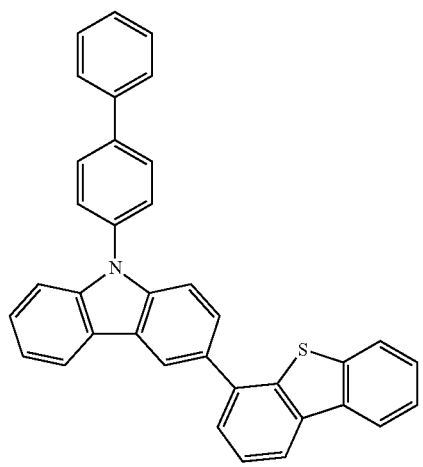
A69
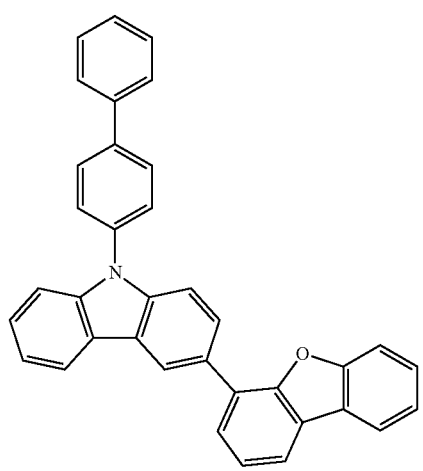
A70
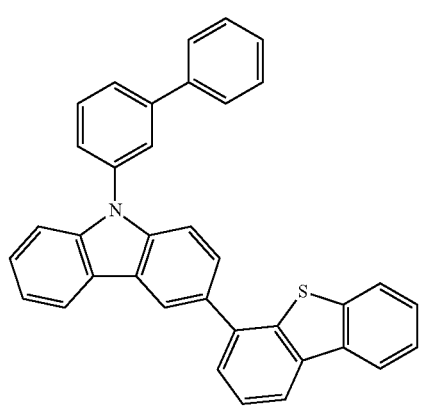

A71
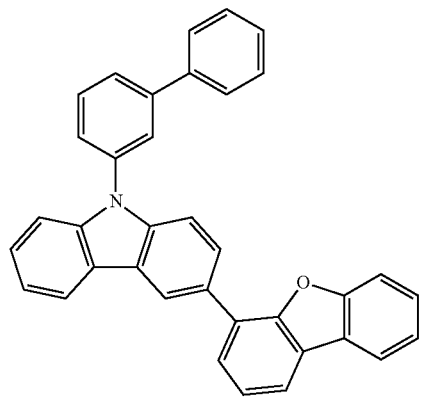
A72
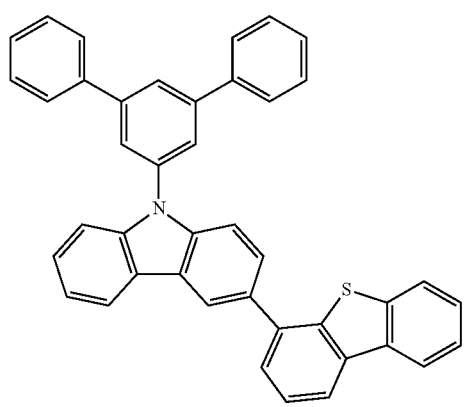
A73
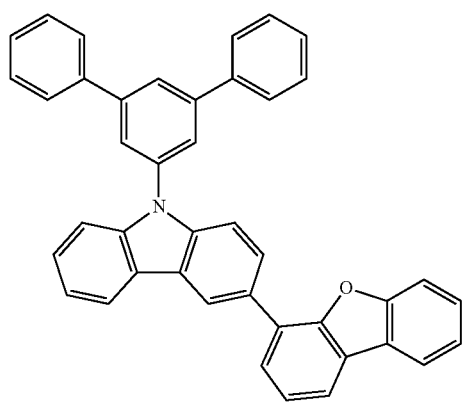
A74
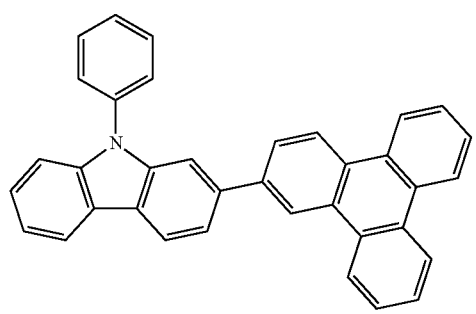
A75
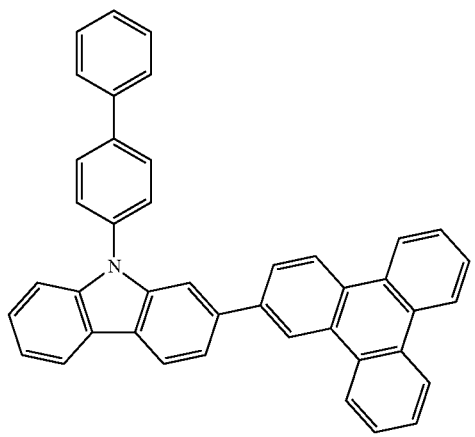
A76
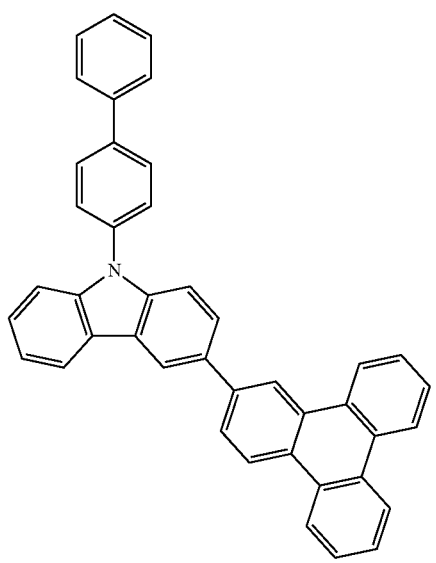
A77
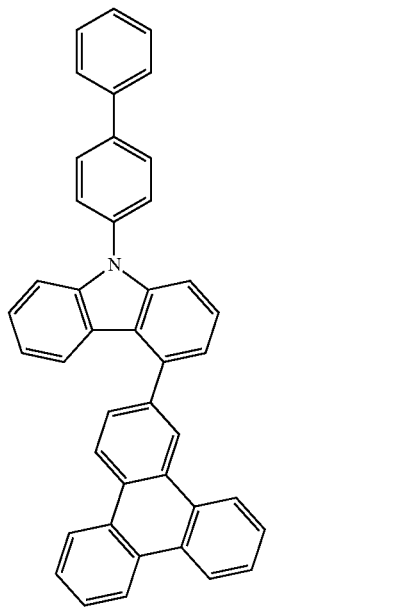

-continued
A78
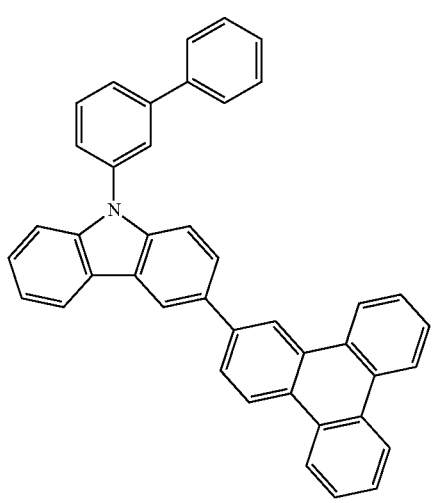
A79
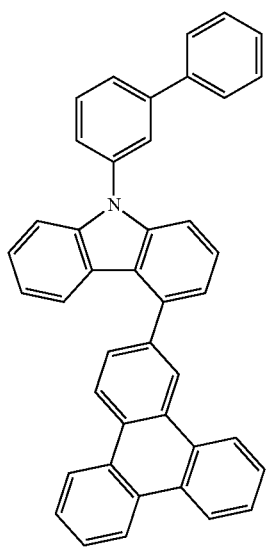
A80
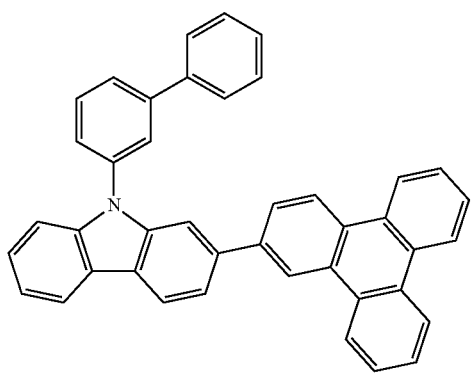
A81
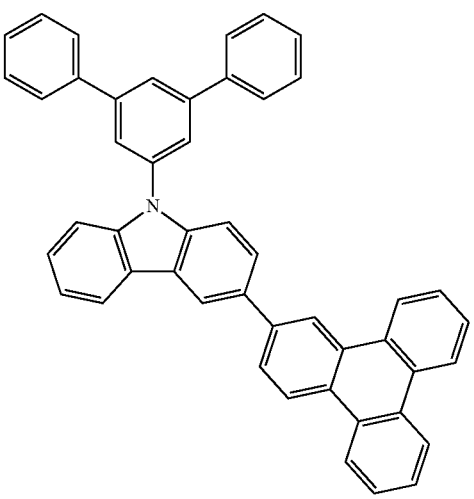
A82
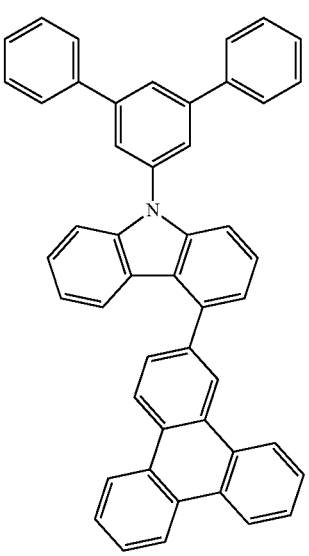
A83
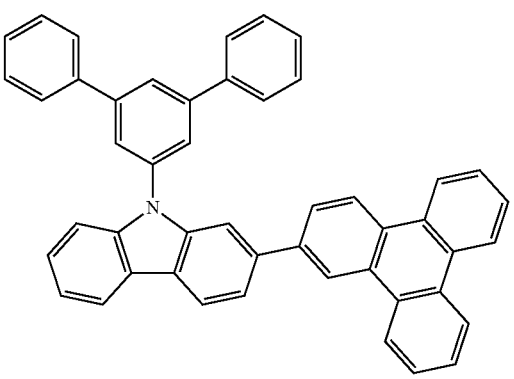

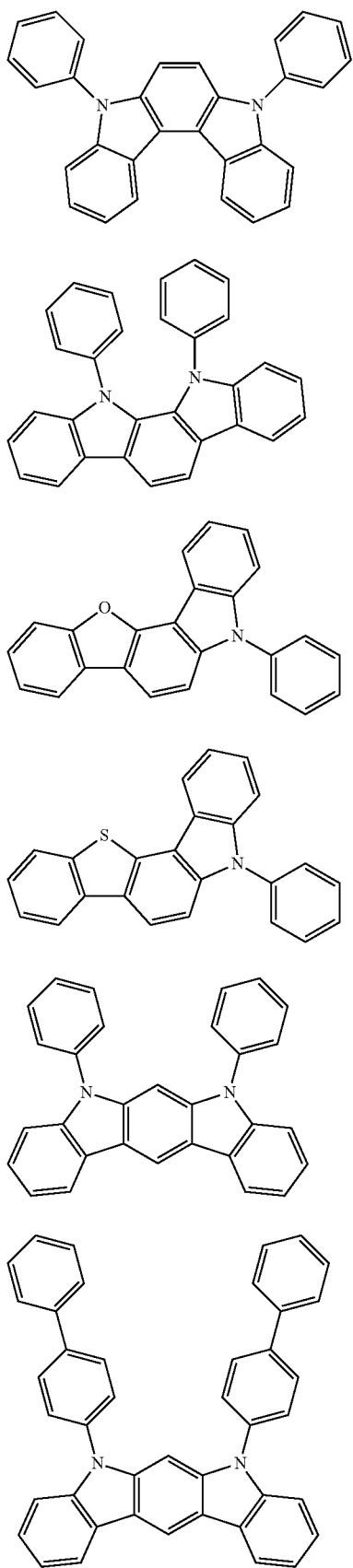
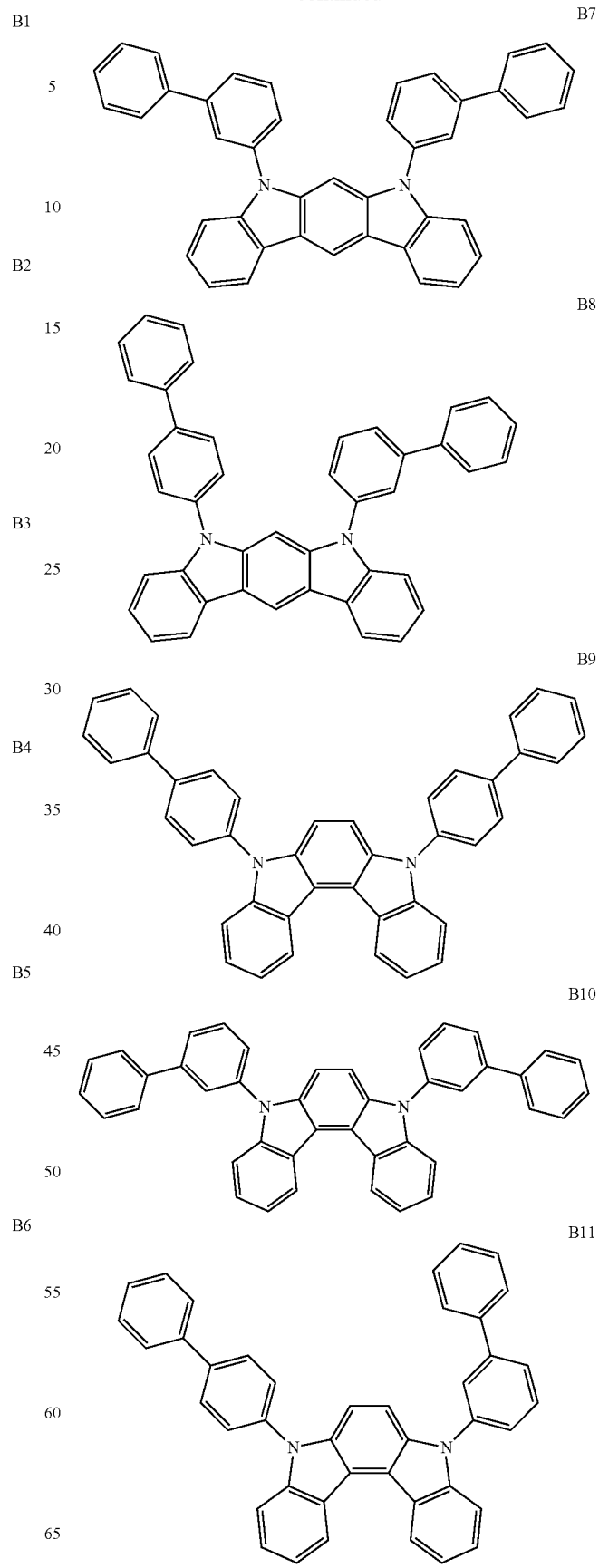

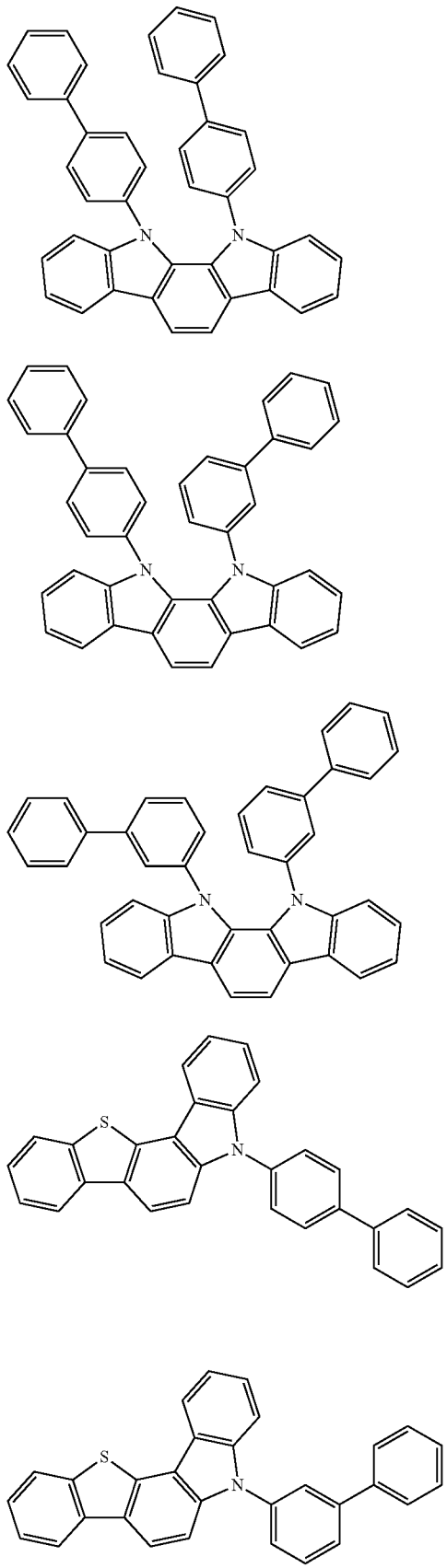
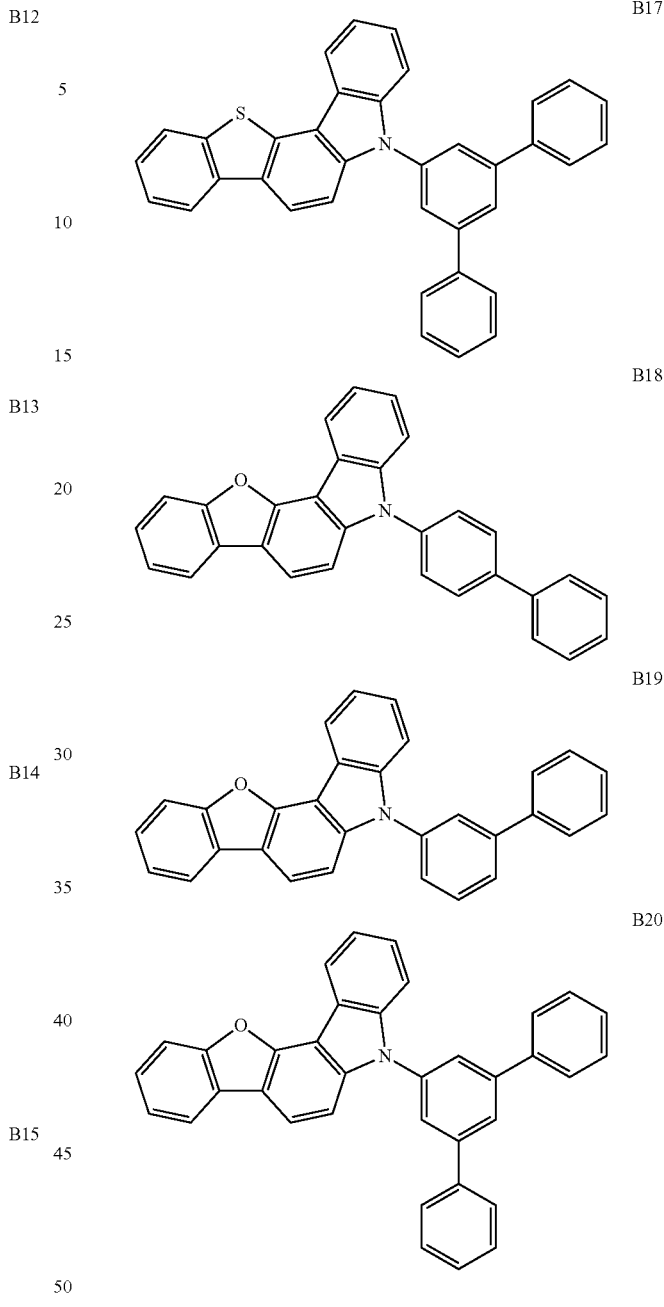

For example, the EML may include one of Compounds 1 to 131 as the host 1, and one of Compounds A1 to A83 and Compounds B1 to B20 as the host 2. However, embodiments of the present disclosure are not limited thereto.

When the EML includes both a host 1 and a host 2 as described above, the balance of injecton of holes and electons into the EML may be effectively controlled, and thus the organic light-emitting device may have improved emission efficiency, and improved lifetime characteristics.

A weight ratio of the first host to the second host in the EML, and a weight ratio of the host 1 and the host 2 in the EML may be each independently selected from a range of about 1:99 to about 99:1, and in some embodiments, a range of about 10:90 to about 90:10. When the weight ratio of the first host to the second host and the weight ratio of the host 1 to the host 2 are within these ranges, the balance of injection of holes and electrons into the EML may be effectively controlled.

The dopant in the EML may include a fluorescent dopant emitting light based on fluorescence emission mechanism, or a phosphorescent dopant emitting light based on phosphorescence emission mechanism.

In some embodiments, the dopant of the EML may be a phosphorescent dopant, and the phosphorescent dopant may include an organometallic compound represented by Formula 81:

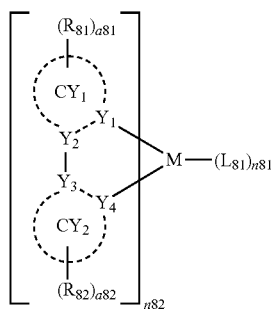

Formula 81

In Formula 81,

M may be iridium (Ir), platinum (Pt), osmium (Os), titanium (Ti), zirconium (Zr), hafnium (Hf), europium (Eu), terbium (Tb), or thulium (Tm);

$Y_1$ to $Y_4$ may be each independently carbon (C) or nitrogen (N);

$Y_1$ and $Y_2$ may be linked to each other via a single bond or a double bond, $Y_3$ and $Y_4$ may be linked to each other via a single bond or a double bond;

$CY_1$ and $CY_2$ may be each independently selected from a benzene, a naphthalene, a fluorene, a spiro-fluorene, an indene, a pyrrole, a thiophene, a furan, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzoxazole, an isobenzoxazole, a triazole, a tetrazole, oxadiazole, a triazine, a dibenzofuran, and a dibenzothiophene, wherein $CY_1$ and $CY_2$ may be optionally linked to each other via a single bond or an organic linking group;

$R_{81}$ and $R_{82}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted \monovalent non-aromatic condensed heteropolycyclic group, —N(Q$_1$)(Q$_2$), —Si(Q$_3$)(Q$_4$)(Q$_5$), and —B(Q$_6$)(Q$_7$);

a81 and a82 may be each independently an integer selected from 1 to 5;

n81 may be an integer selected from 0 to 4;

n82 may be 1, 2, or 3; and $L_{81}$ may be a monovalent organic ligand, a divalent organic ligand, or a trivalent organic ligand.

$R_{81}$ and $R_{82}$ in Formula 81 may be defined to be the same as described above with reference to $R_{41}$ above.

The phosphorescent dopant may include at least one of Compounds PD1 to PD78, but is not limited thereto:

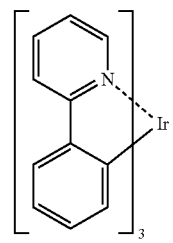

PD1

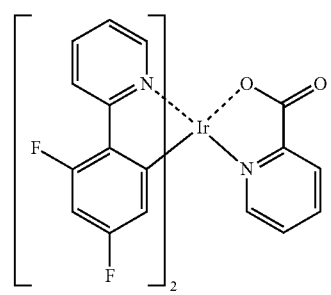

PD2

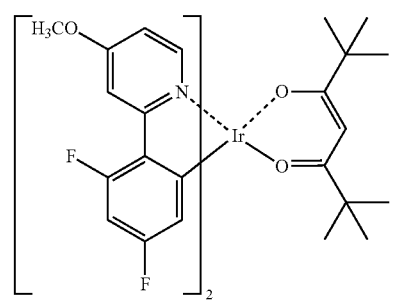

PD3

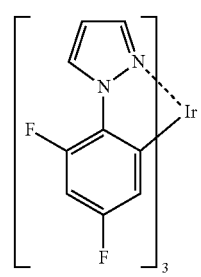

PD4

-continued
PD5
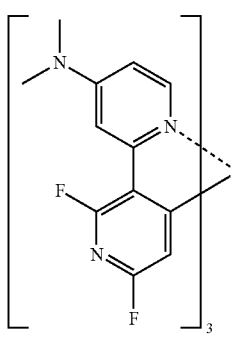
PD6
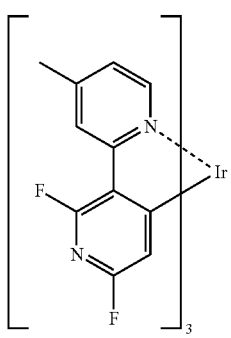
PD7
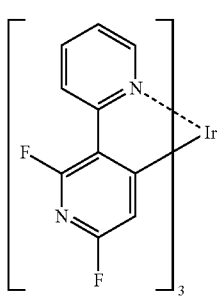
PD8
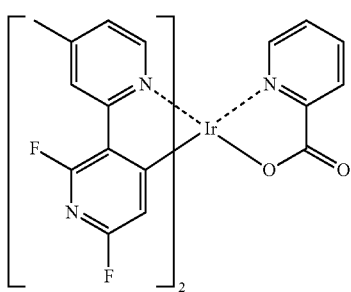
PD9
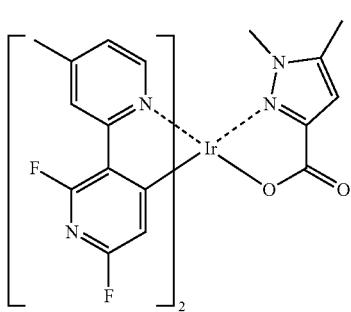
-continued
PD10
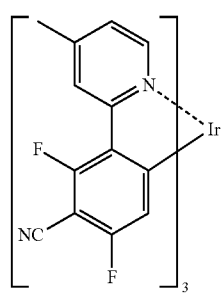
PD11
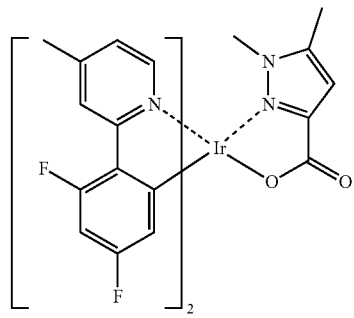
PD12
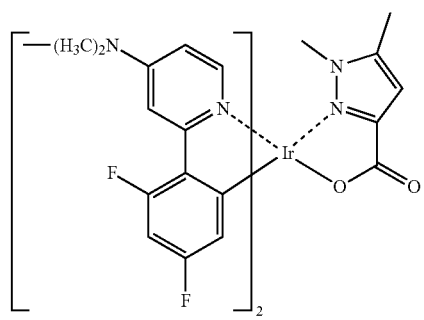
PD13
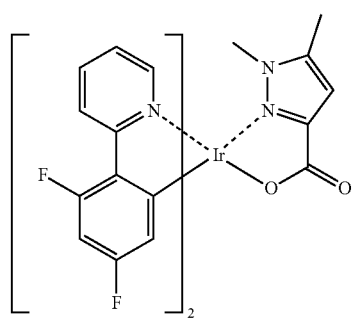
PD14
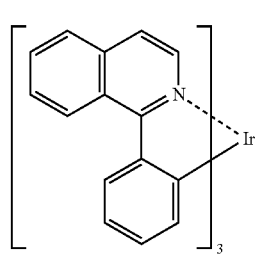

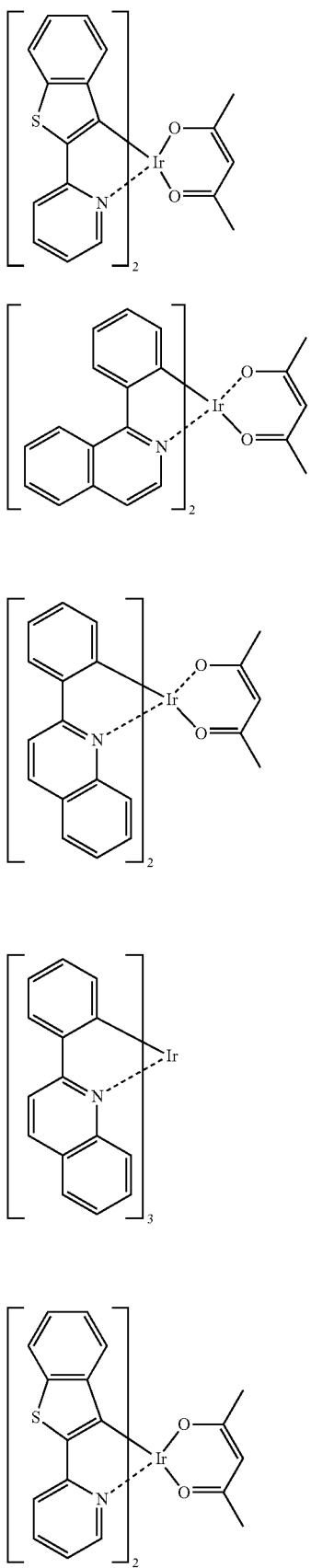
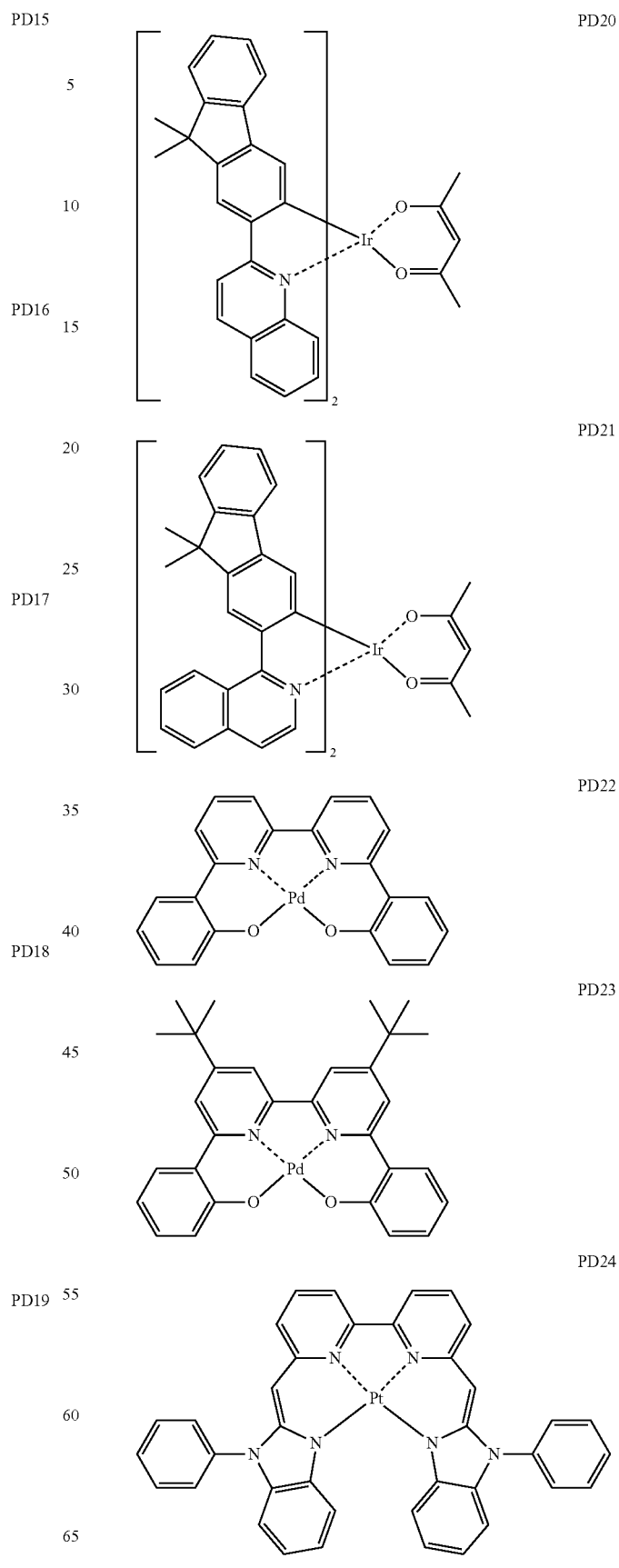

PD25 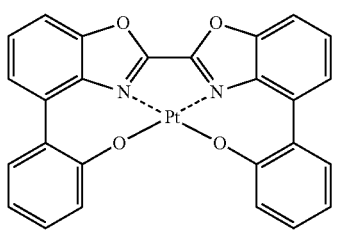
PD26 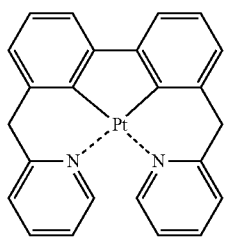
PD27 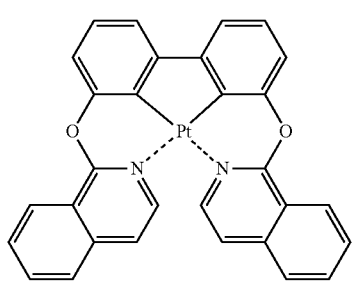
PD28 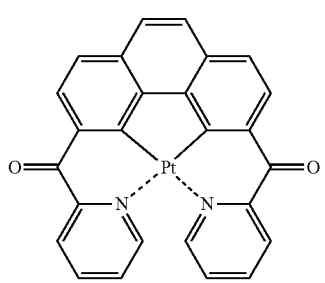
PD29 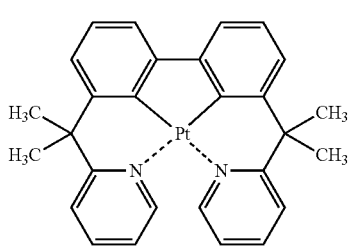
PD30 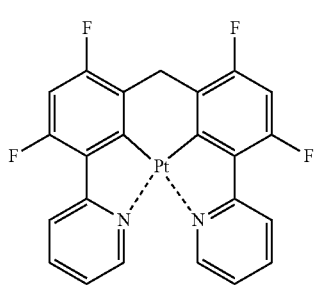
PD31 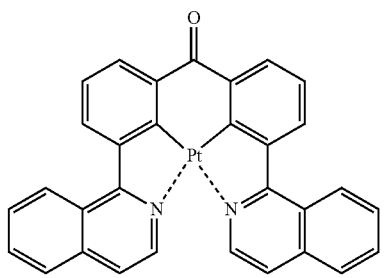
PD32 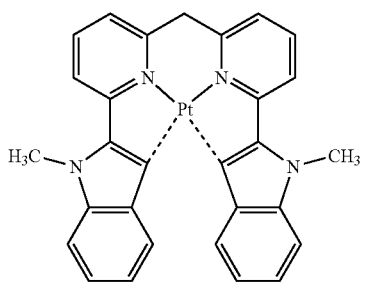
PD33 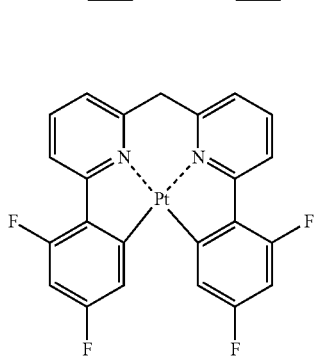
PD34 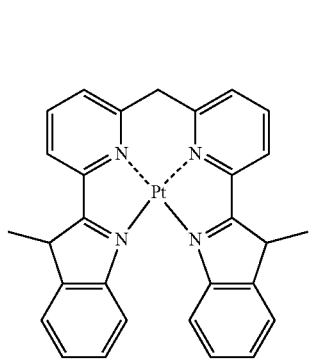
PD35 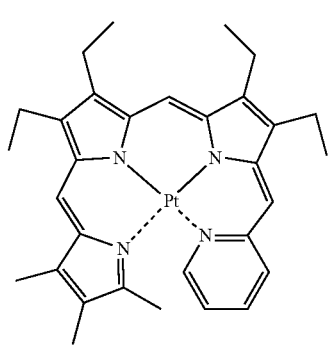

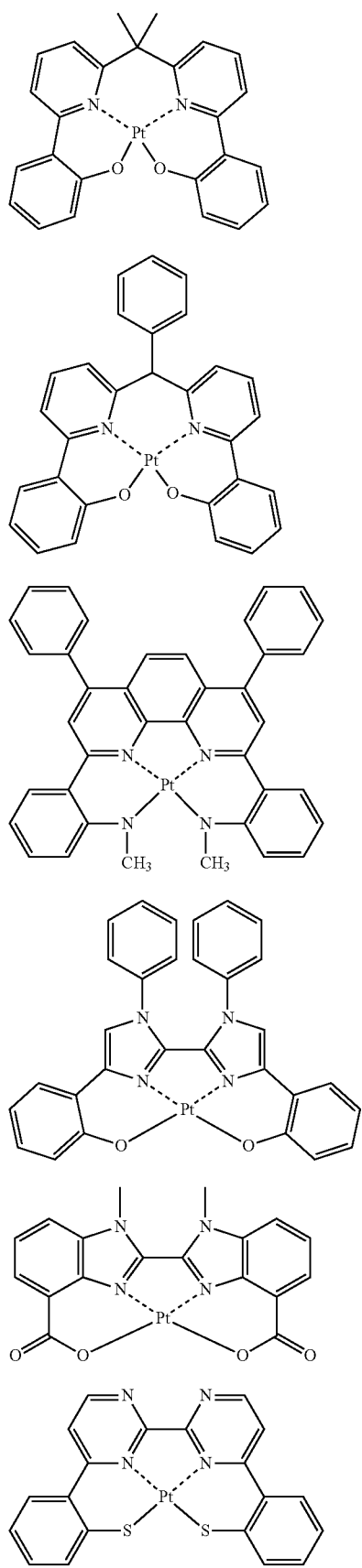
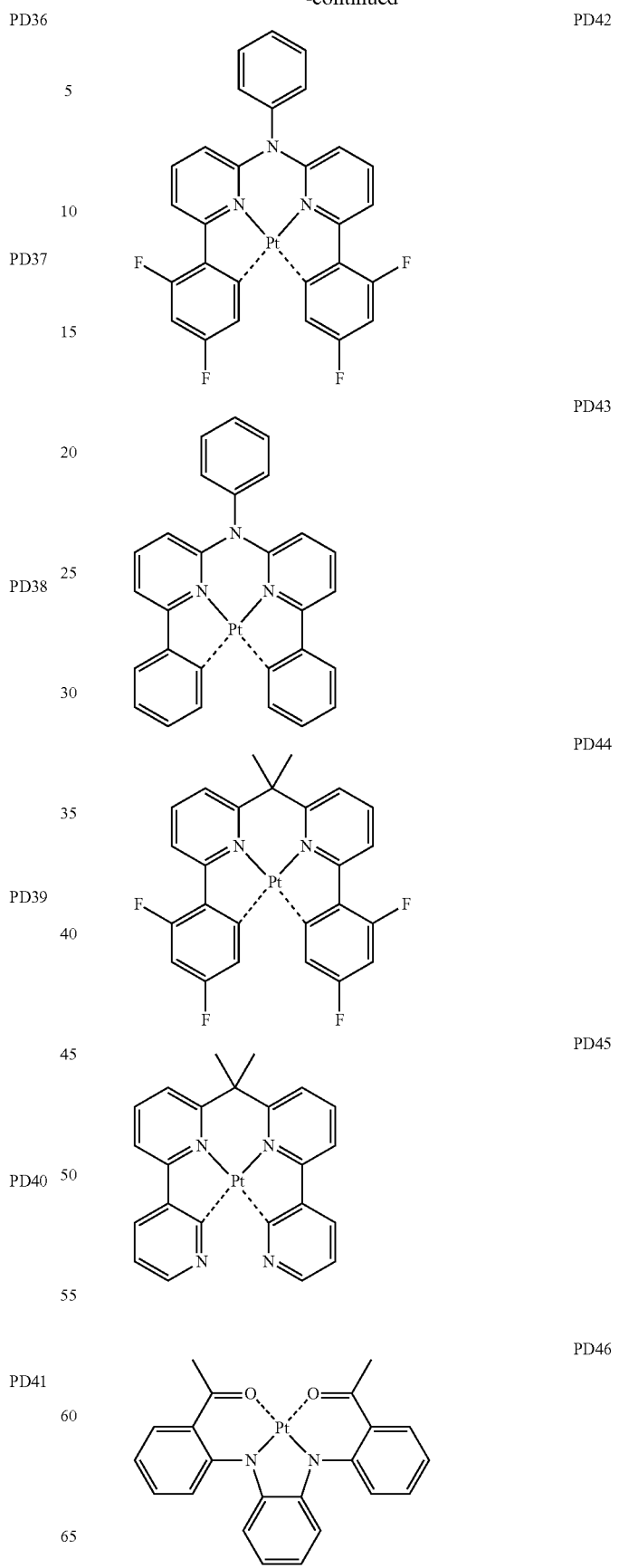

PD47 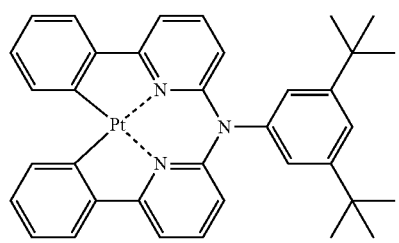
PD48 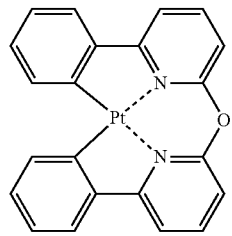
PD49 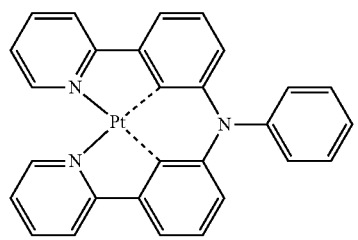
PD50 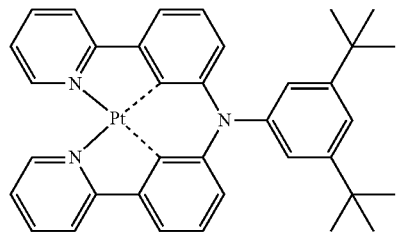
PD51 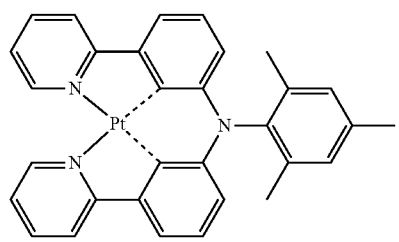
PD52 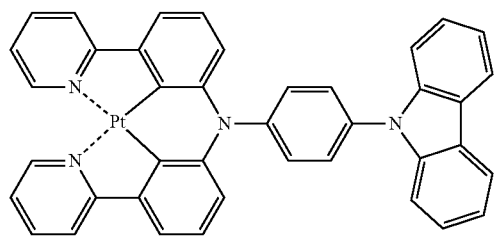
PD53 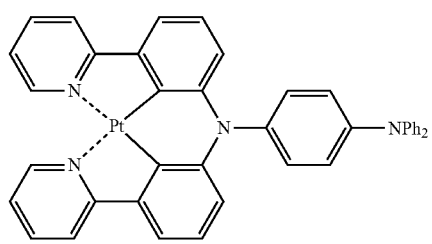
PD54 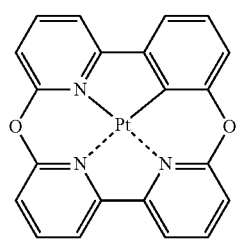
PD55 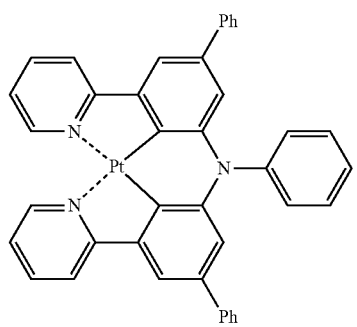
PD56 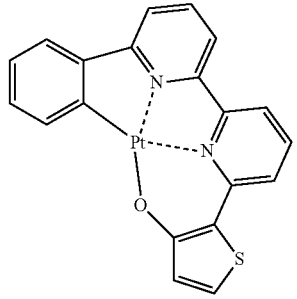
PD57 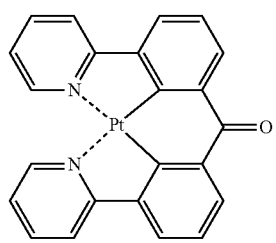

PD58 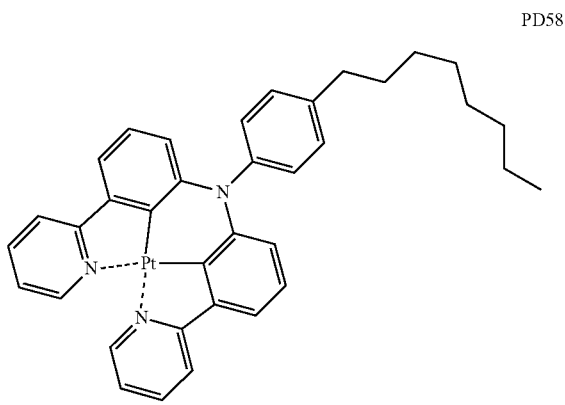
PD59 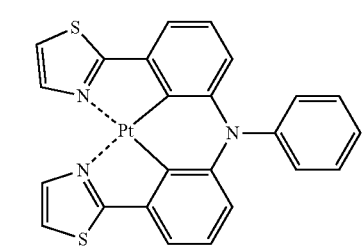
PD60 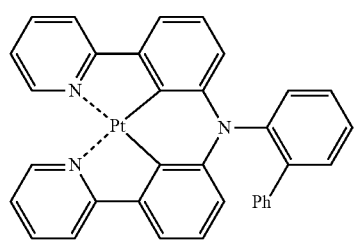
PD61 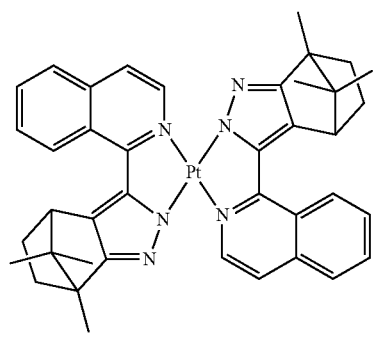
PD62 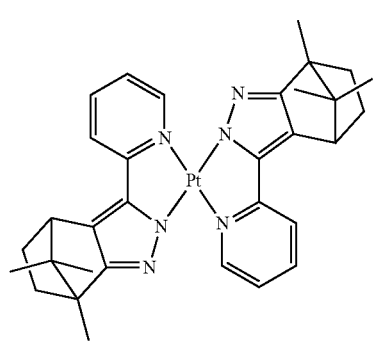
PD63 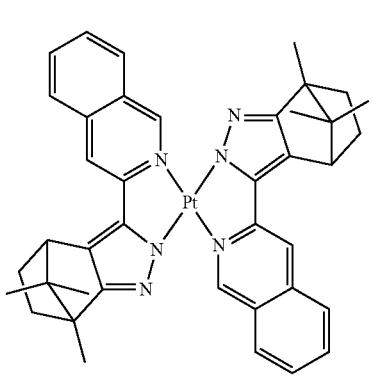
PD64 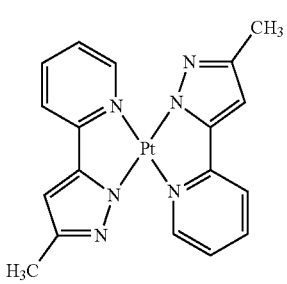
PD65 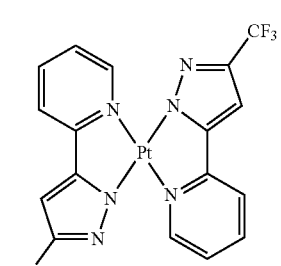
PD66 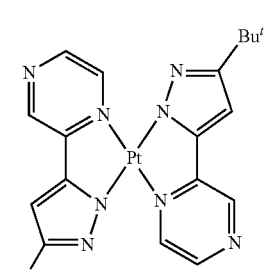
PD67 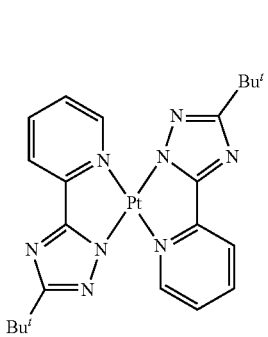

-continued
PD68 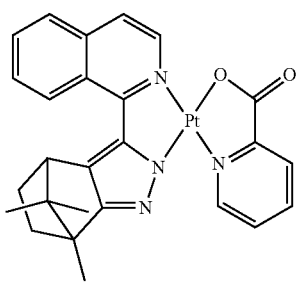
PD69 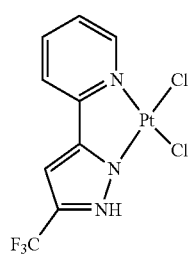
PD70 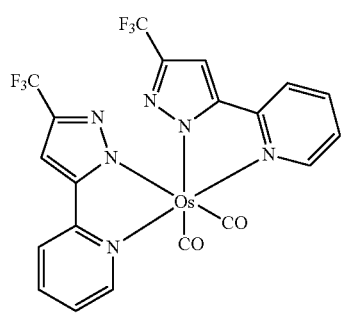
PD71 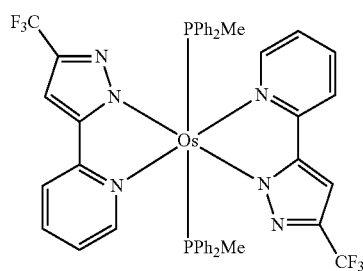
PD72 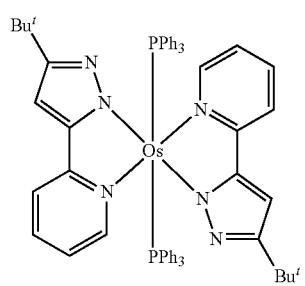
PD73 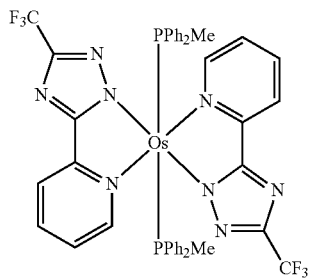
PD74 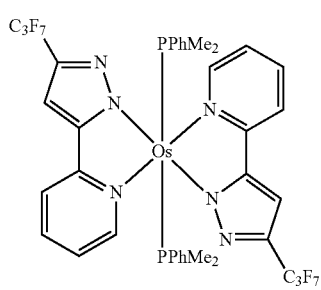
PD75 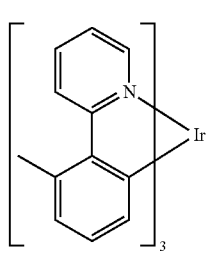
PD76 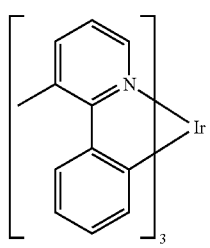
PD77
PD78 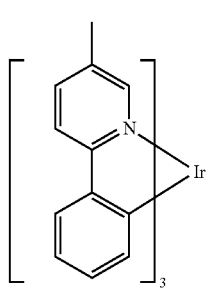

In some embodiments, the phosphorescent dopant may include PtOEP.
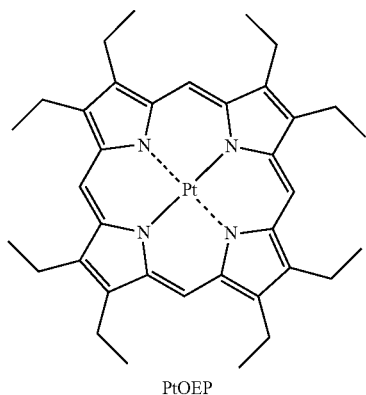
PtOEP
The fluorescent dopant may include at least one of DPAVBi, BDAVBi, TBPe, DCM, DCJTB, Coumarin 6, and C545T.
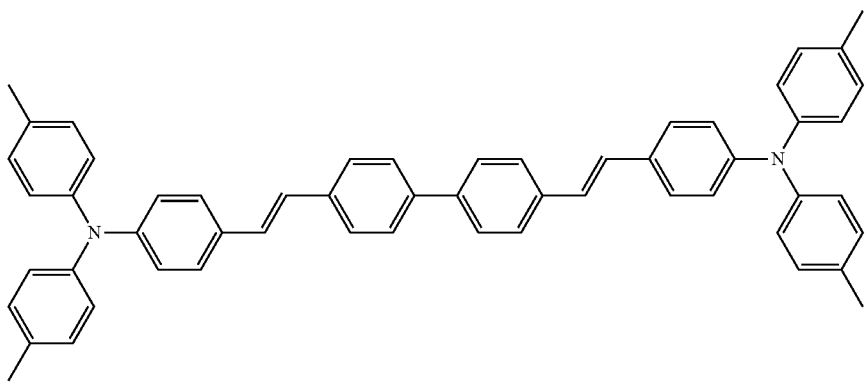
DPAVBi
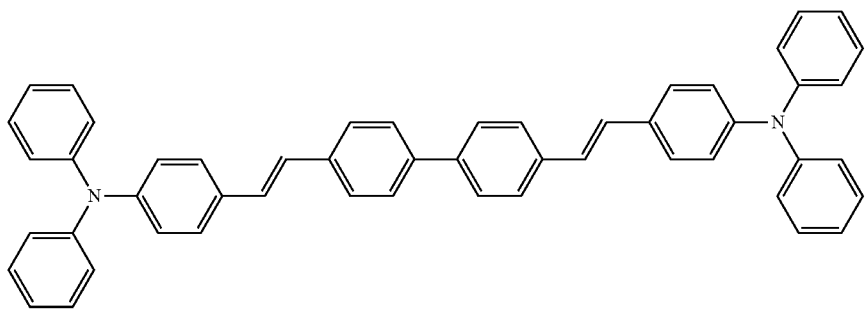
BDAVBi
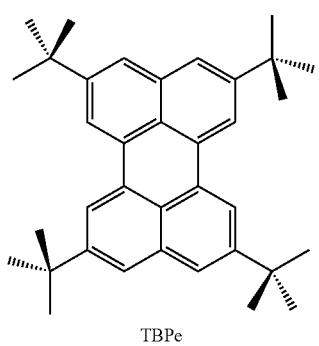
TBPe
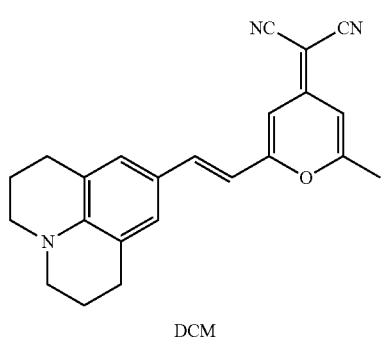
DCM

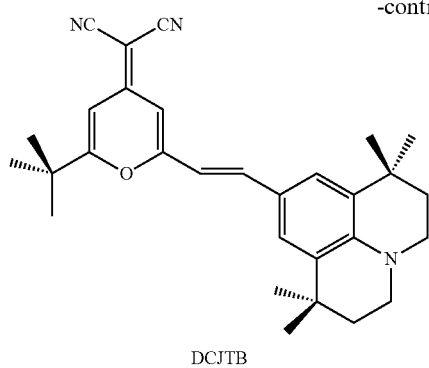

DCJTB

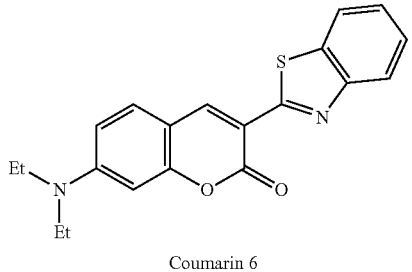

Coumarin 6

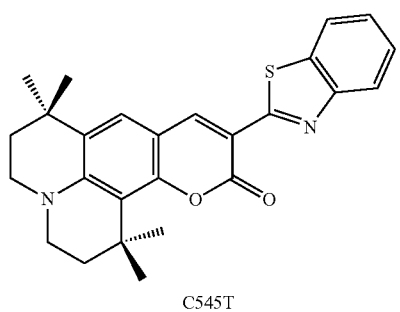

C545T

When the EML includes both a host and a dopant, the amount of the dopant may be from about 0.01 to about 20 parts by weight based on 100 parts by weight of the host. However, the amount of the dopant is not limited to this range.

The thickness of the EML may be about 100 Å to about 1,000 Å, and in some embodiments, may be from about 200 Å to about 600 Å. When the thickness of the EML is within these ranges, the EML may have improved light emitting ability without a substantial increase in driving voltage.

Next, the electron transport region may be disposed on the EML.

The electron transport region may include at least one of a HBL, an ETL, and an EIL.

In some embodiments, the electron transport region may have a structure including a HBL/ETL/EIL or an ETL/EIL, wherein the layers forming the structure of the electron transport region may be sequentially stacked on the EML in the stated order. However, embodiments of the present disclosure are not limited thereto. The ETL may have a single-layer structure or a multi-layer structure including at least two different materials.

Conditions for forming the HBL, ETL, and EIL of the electron transport region may be defined based on the above-described formation conditions for the HIL.

When the electron transport region includes the HBL, the HBL may include at least one of BCP and Bphen. However, embodiments of the present disclosure are not limited thereto.

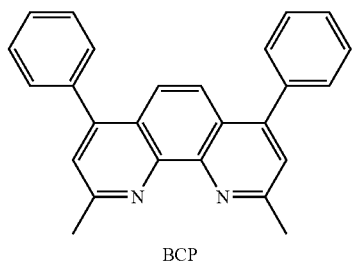

BCP

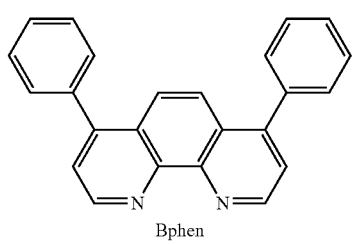

Bphen

A thickness of the HBL may be from about 20 Å to about 1,000 Å, and in some embodiments, from about 30 Å to about 300 Å. When the thickness of the HBL is within these ranges, the HBL may have improved hole blocking ability without a substantial increase in driving voltage.

The ETL may further include at least one of $Alq_3$, Balq, TAZ, and NTAZ below, in addition to BCP and Bphen described above.

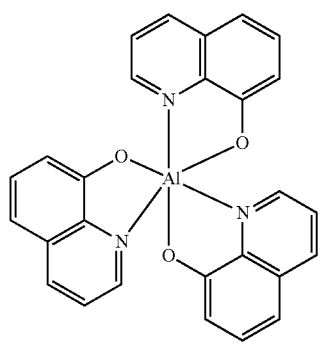

Alq₃

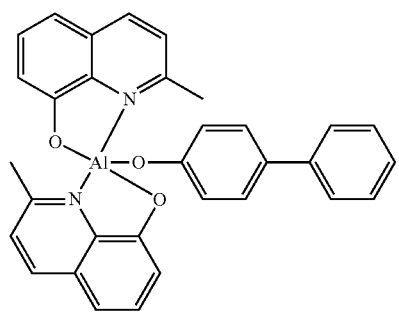

BAlq

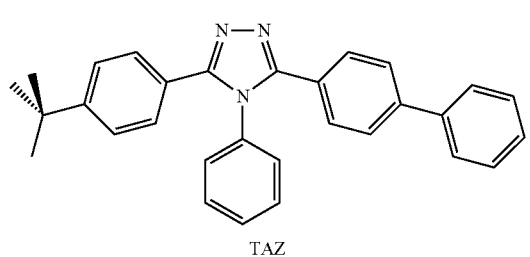

TAZ

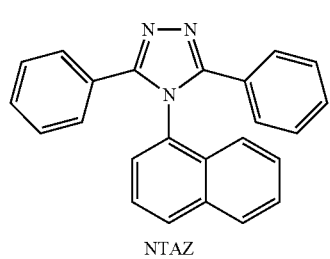

NTAZ

In some embodiments, the ETL may include at least one of Compounds ET1 and ET2 represented below, but is not limited thereto.

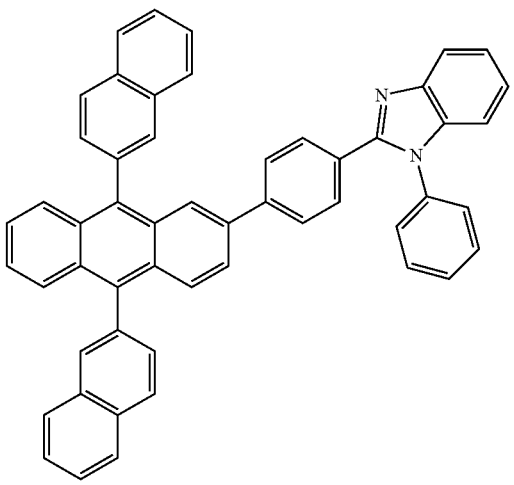

ET1

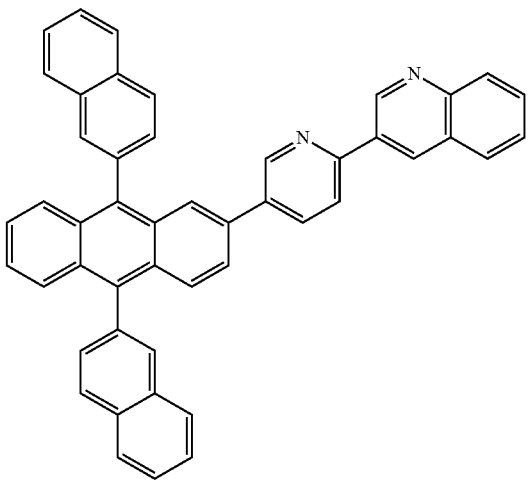

ET2

A thickness of the ETL may be from about 100 Å to about 1,000 Å, and in some embodiments, from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to the above-described materials.

The metal-containing material may include a lithium (Li) complex. Non-limiting examples of the Li complex are compound ET-D1 below (lithium quinolate (LiQ)), or compound ET-D2 below.

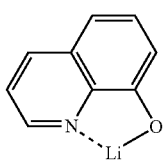

ET-D1

-continued

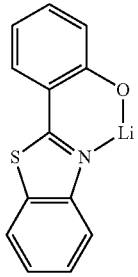

ET-D2

The electron transport region may include an EIL that may facilitate injection of electrons from the second electrode 19. The EIL may include at least one selected from LiF, NaCl, CsF, Li$_2$O, and BaO. The thickness of the EIL may be from about 1 Å to about 100 Å, and in some embodiments, from about 3 Å to about 90 Å. When the thickness of the EIL is within these ranges, the EIL may have satisfactory electron injection ability without a substantial increase in driving voltage.

The second electrode 19 is disposed on the organic layer 15. The second electrode 19 may be a cathode. A material for the second electrode 19 may be a metal, an alloy, or an electrically conductive compound that have a low work function, or a combination thereof. Non-limiting examples of the material for the second electrode 19 are lithium (Li), magnesium (Mg), aluminum (Al), aluminum (Al)-lithium (Li), calcium (Ca), magnesium (Mg)-indium (In), and magnesium (Mg)-silver (Ag), or the like. In some embodiments, to manufacture a top-emission light-emitting device, the second electrode 19 may be formed as a transmissive electrode from, for example, indium tin oxide (ITO) or indium zinc oxide (IZO).

Although the organic light-emitting device of FIG. 1 is described above, embodiments of the present disclosure are not limited thereto.

As used herein, a $C_1$-$C_{60}$ alkyl group refers to a linear or branched aliphatic hydrocarbon monovalent group having 1 to 60 carbon atoms. Non-limiting examples of the $C_1$-$C_{60}$ alkyl group a methyl group, a ethyl group, a propyl group, an isobutyl group, a sec-butyl group, a tert-butyl group, a pentyl group, an iso-amyl group, and a hexyl group. As used herein, a $C_1$-$C_{60}$ alkylene group refers to a divalent group having the same structure as the $C_1$-$C_{60}$ alkyl.

As used herein, a $C_1$-$C_{60}$ alkoxy group refers to a monovalent group represented by —$OA_{101}$ (where $A_{101}$ is a $C_1$-$C_{60}$ alkyl group as described above). Non-limiting examples of the $C_1$-$C_{60}$ alkoxy group are a methoxy group, an ethoxy group, and an isopropyloxy group.

As used herein, a $C_2$-$C_{60}$ alkenyl group refers to a structure including at least one carbon double bond in the middle or at the terminal of the $C_2$-$C_{60}$ alkyl group. Non-limiting examples of the $C_2$-$C_{60}$ alkenyl group are an ethenyl group, a propenyl group, and a butenyl group. As used herein, a $C_2$-$C_{60}$ alkylene group refers to a divalent group having the same structure as the $C_2$-$C_{60}$ alkenyl group.

As used herein, a $C_2$-$C_{60}$ alkynyl group refers to a structure including at least one carbon triple bond in the middle or at the terminal of the $C_2$-$C_{60}$ alkyl group. Non-limiting examples of the $C_2$-$C_{60}$ alkynyl group are an ethynyl group and a propynyl group. As used herein, a $C_2$-$C_{60}$ alkynylene group used herein refers to a divalent group having the same structure as the $C_2$-$C_{60}$ alkynyl group.

As used herein, a $C_3$-$C_{10}$ cycloalkyl group refers to a monovalent, monocyclic hydrocarbon group having 3 to 10 carbon atoms. Non-limiting examples of the $C_3$-$C_{10}$ cycloalkyl group are a cyclopropyl group, a cyclobutyl group, a cyclopentyl group, a cyclohexyl group, and a cycloheptyl group. As used herein, a $C_3$-$C_{10}$ cycloalkylene group refers to a divalent group having the same structure as the $C_3$-$C_{10}$ cycloalkyl group.

As used herein, a $C_2$-$C_{10}$ heterocycloalkyl group refers to a monovalent monocyclic group having 2 to 10 carbon atoms in which at least one hetero atom selected from N, O, P, and S is included as a ring-forming atom. Non-limiting examples of the $C_2$-$C_{10}$ heterocycloalkyl group are a tetrahydrofuranyl group and a tetrahydrothiophenyl group. As used herein, a $C_2$-$C_{10}$ heterocycloalkylene group refers to a divalent group having the same structure as the $C_2$-$C_{10}$ heterocycloalkyl group.

As used herein, a $C_3$-$C_{10}$ cycloalkenyl group refers to a monovalent monocyclic group having 3 to 10 carbon atoms that includes at least one double bond in the ring but that is not aromatic. Non-limiting examples of the $C_3$-$C_{10}$ cycloalkenyl group are a cyclopentenyl group, a cyclohexenyl group, and a cycloheptenyl group. As used herein, a $C_3$-$C_{10}$ cycloalkenylene group refers to a divalent group having the same structure as the $C_3$-$C_{10}$ cycloalkenyl group.

As used herein, a $C_2$-$C_{10}$ heterocycloalkenyl group used herein refers to a monovalent monocyclic group having 2 to 10 carbon atoms that includes at least one double bond in the ring and in which at least one hetero atom selected from N, O, P, and S is included as a ring-forming atom. Non-limiting examples of the $C_2$-$C_{10}$ heterocycloalkenyl group are a 2,3-dihydrofuranyl group and a 2,3-dihydrothiophenyl group. As used herein, a $C_2$-$C_{10}$ heterocycloalkenylene group used herein refers to a divalent group having the same structure as the $C_2$-$C_{10}$ heterocycloalkenyl group.

As used herein, a $C_6$-$C_{60}$ aryl group refers to a monovalent, aromatic carbocyclic aromatic group having 6 to 60 carbon atoms, and a $C_6$-$C_{60}$ arylene group refers to a divalent, aromatic carbocyclic group having 6 to 60 carbon atoms. Non-limiting examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group include at least two rings, the rings may be fused to each other.

As used herein, a $C_2$-$C_{60}$ heteroaryl group refers to a monovalent, aromatic carbocyclic group having 2 to 60 carbon atoms in which at least one hetero atom selected from N, O, P, and S is included as a ring-forming atom, and 2 to 60 carbon atoms. A $C_2$-$C_{60}$ heteroarylene group refers to a divalent, aromatic carbocyclic group having 2 to 60 carbon atoms in which at least one hetero atom selected from N, O, P, and S is included as a ring-forming atom. Non-limiting examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl and the $C_2$-$C_{60}$ heteroarylene include at least two rings, the rings may be fused to each other.

As used herein, a $C_6$-$C_{60}$ aryloxy group indicates —$OA_{102}$ (where $A_{102}$ is a $C_6$-$C_{60}$ aryl group as described above), and a $C_6$-$C_{60}$ arylthio group indicates —$SA_{103}$ (where $A_{103}$ is a $C_6$-$C_{60}$ aryl group as described above).

As used herein, a monovalent non-aromatic condensed polycyclic group refers to a monovalent group having at least two rings condensed to each other, in which only carbon atoms (for example, 8 to 60 carbon atoms) are exclusively included as ring-forming atoms and the entire molecule is non-aromatic. A non-limiting example of the monovalent non-aromatic condensed polycyclic group is a fluorenyl group. As used herein, a divalent non-aromatic condensed polycyclic group refers to a divalent group having the same structure as the monovalent non-aromatic condensed polycyclic group.

As used herein, a monovalent non-aromatic condensed heteropolycyclic group refers to a monovalent group having at least two rings condensed to each other, in which carbon atoms (for example, 2 to 60 carbon atoms) and a hetero atom selected from N, O, P, and S are as ring-forming atoms and the entire molecule is non-aromatic. A non-limiting example of the monovalent non-aromatic condensed heteropolycyclic group is a carbazolyl group. As used herein, a divalent non-aromatic condensed heteropolycyclic group refers to a divalent group having the same structure as the monovalent non-aromatic condensed heteropolycyclic group.

As used herein, at least one of substituents of the substituted $C_1$-$C_{60}$ alkylene group, the substituted $C_2$-$C_{60}$ alkenylene group, the substituted $C_2$-$C_{60}$ alkynylene group, the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —N($Q_{11}$)($Q_{12}$), —Si($Q_{13}$)($Q_{14}$)($Q_{15}$), and —B($Q_{16}$)($Q_{17}$), a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, and a monovalent nonaromatic condensed heteropolycyclic group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, and a monovalent nonaromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —N($Q_{21}$)($Q_{22}$), —Si($Q_{23}$)($Q_{24}$)($Q_{25}$), and —B($Q_{26}$)($Q_{27}$), and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{31}$ to $Q_{37}$, and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent aromatic condensed heteropolycyclic group.

As used herein, the terms "a phenyl group-substituted phenyl group" refers to "a phenyl group substituted with at least one phenyl group".

As used herein, the terms "$C_1$-$C_{20}$ alkyl group-substituted phenyl group" refers to "a phenyl group substituted with at least one $C_1$-$C_{20}$ alkyl group".

Hereinafter, the present disclosure will be described in detail with reference to the following synthesis examples and other examples of compounds and organic light-emitting devices. However, these examples are for illustrative purposes only and are not intended to limit the scope of the present disclosure. In the following synthesis examples, the expression that "'B' instead of 'A' was used" means that the amounts of 'B' and 'A' were the same in equivalent amounts.

EXAMPLES

Synthesis Example 1: Synthesis of Compound 2

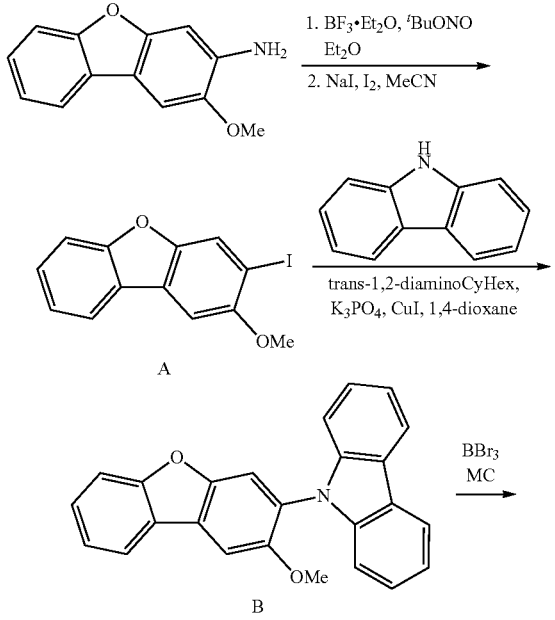

-continued

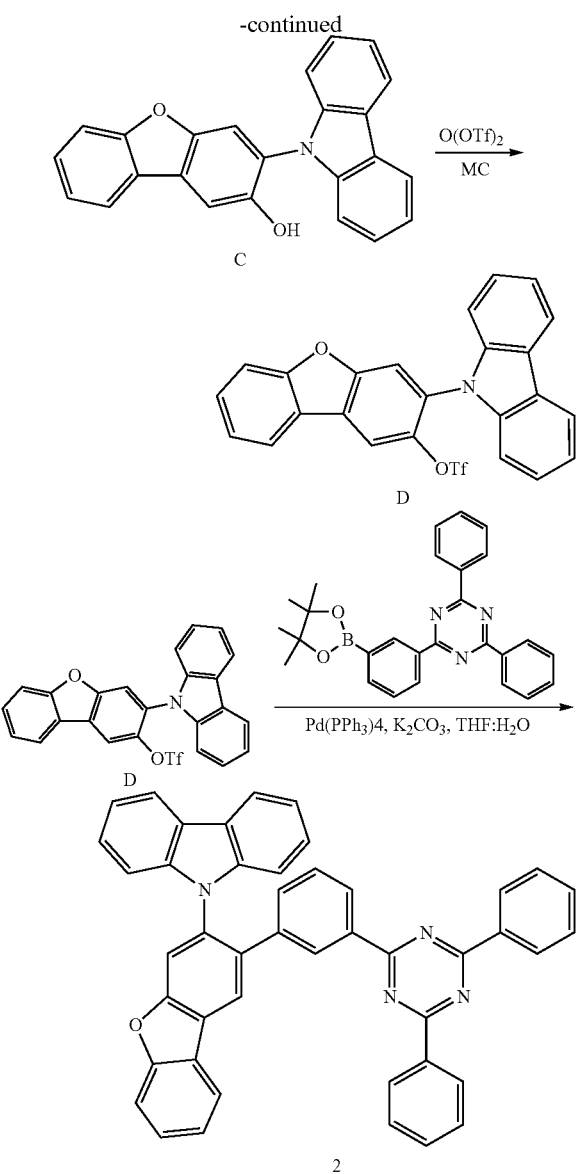

Synthesis of Intermediate A 11.1 g (52 mmol) of 3-amino-2-methoxydibenzofuran was dissolved in 130 mL of Et$_2$O in a 1 L round bottomed flask. 26.4 mL (208 mmol) of BF$_3$·Et$_2$O was slowly dropwise added thereto at about −20° C. for about 5 minutes. A mixture of 21.7 mL of tert-butyl nitrile dissolved in 64 mL of Et$_2$O was slowly added to the resulting mixture for 30 minutes, and stirred for 30 minutes. 300 mL of Et$_2$O was added thereto and the resulting mixture was stirred at about 0° C. for 10 minutes. The reaction mixture was concentrated, and a solution of 9.4 g (62.4 mmol) of NaI and 1.2 g (4.7 mmol) of I$_2$ dissolved in 340 mL of dry CH$_3$CN was slowly dropwise added thereto at room temperature for 1 hour. 200 mL of a 20% Na$_2$S$_2$C$_3$ aqueous solution was added thereto, followed by chloroform (300 mL×3), to obtain an organic layer. The organic layer was collected and dried using magnesium sulfate (MgSO$_4$), followed by evaporation to remove the solvent. The resulting residue was separated and purified using silica gel column chromatography to obtain 12.1 g of Intermediate A (Yield: 72%). This compound was identified using liquid chromatography-mass spectroscopy (LC-MS).

LC-MS (m/z)=C$_{13}$H$_{11}$NO$_2$ (M$^+$) 213.

Synthesis of Intermediate B 8.92 g (27.5 mmol) of Intermediate A, 5.06 g (30.3 mmol) of carbazole, 0.52 g (2.75 mmol) of CuI, 8.76 g (41.3 mmol) of K$_3$PO$_4$, and 74 µL (0.07 mmol) of (±)-trans-1,2-cyclohexanediamine were mixed with 140 mL of 1,4-dioxane. the temperature was increased to about 110° C. in a nitrogen atmosphere, and the resulting mixture was stirred under reflux for about 48 hours, cooled down to room temperature, and extracting with 200 mL of water and 200 mL of methylene chloride. An organic layer was collected and dried using magnesium sulfate (MgSO$_4$). The solvent was evaporated. The resulting residue was separated and purified using silica gel column chromatography to obtain 3.5 g of Intermediate B (Yield: 35%). This compound was identified using LC-MS.

LC-MS (m/z)=C$_{25}$H$_{17}$NO$_2$ (M$^+$) 363.

Synthesis of Intermediate C 15.0 mL (15.0 mmol, 1.0 M solution in dichloromethane) of boron tribromide was slowly dropwise added to a mixture of 3.64 g (10.0 mmol) of Intermediate B dissolved under nitrogen in 100 mL of methylene chloride (100 mL), for about 10 minutes, and stirred at about 0° C. for about 10 hours. 30 mL of water was added to the resulting mixture at about 0° C. and the mixture was stirred. Methylene chloride (60 mL×3) was added to obtain an organic layer. The organic layer was dried using magnesium sulfate (MgSO$_4$). The solvent was evaporated, thereby obtaining Intermediate C.

Synthesis of Intermediate D

Intermediate C and 12.8 mL (91.6 mmol) of triethylamine were mixed with 100 mL of methylene chloride in a nitrogen atmosphere. 5.14 mL (30.5 mmol) of trifluoromethanesulfonic anhydride was slowly dropwise added thereto at about 0° C., and the resulting mixture was stirred at about 0° C. for about 7 hours. 15 mL of a 1.0 M aqueous HCl was added to the resulting mixture, and the mixture was stirred. Methylene chloride (60 mL×3) was added to obtain an organic layer. The organic layer was dried using magnesium sulfate (MgSO$_4$). The solvent was removed in vacuum. The resulting residue was separated and purified using silica gel column chromatography to obtain 3.2 g of Intermediate D (Yield: 65%). This compound was identified using LC-MS.

LC-MS (m/z)=C$_{25}$H$_{14}$F$_3$NO$_4$S (M$^+$) 481.

Synthesis of Compound 2

7.0 g (14.5 mmol) of Intermediate D, 6.31 g (14.5 mmol) of 2,4-diphenyl-6-(3-(4,4,5,5-tetramethyl-1,3,2-dioxaborolan-2-yl)phenyl)-1,3,5-triazine, 0.84 g (0.725 mmol) of Pd(PPh$_3$)$_4$, and 5.01 g (36.3 mmol) of K$_2$CO$_3$ were mixed with 50 mL of THF and 25 mL of distilled water. The temperature was increased to about 80° C., and the resulting mixture was stirred under reflux for about 18 hours. The mixture was cooled down to room temperature and filtered to obtain a solid. The solid was dissolved in toluene to obtain an organic layer. The organic layer was dried using magnesium sulfate (MgSO$_4$), and the solvent was evaporated. The resulting residue was recrystallized using a mixture of toluene and MeOH to obtain 6.25 g of Compound 2 (Yield: 67%). This compound was identified using LC-MS.

LC-MS (m/z)=C$_{45}$H$_{28}$N$_4$O (M$^+$) 640.

Synthesis Example 2: Synthesis of Compound 3

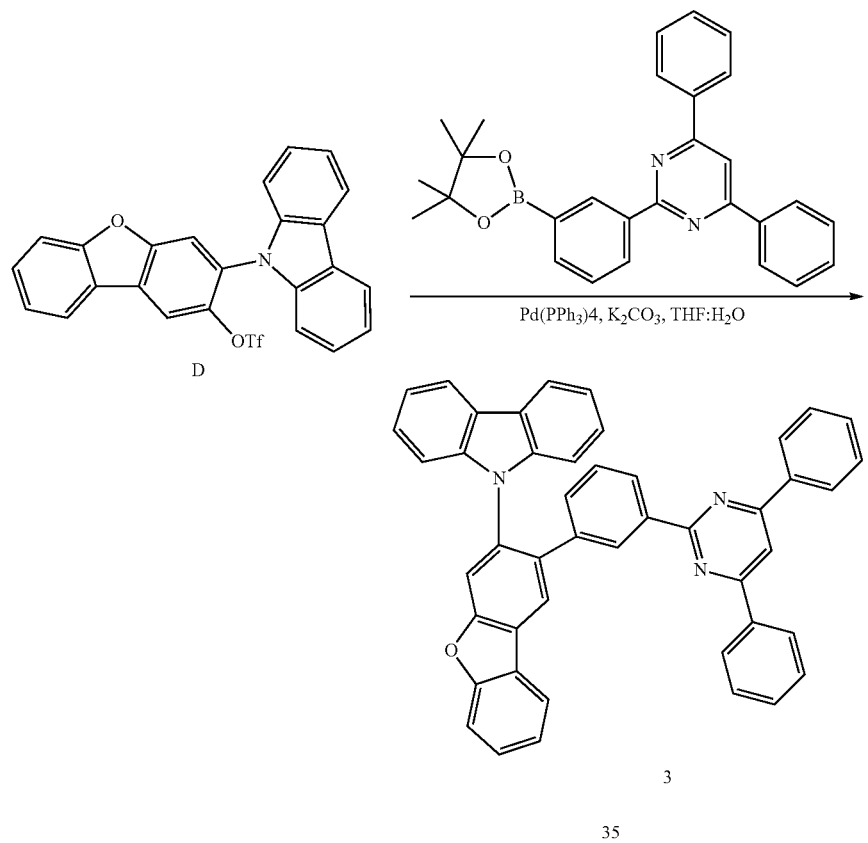

8.5 g of Compound 3 (Yield: 91%) was obtained in the same manner as Compound 2 in Synthesis Example 1, except that 6.17 g (14.5 mmol) of 4,6-diphenyl-2-(3-(4,4,5,5-tetramethyl-1,3,2-dioxaborolan-2-yl)phenyl)pyrimidine, instead of 2,4-diphenyl-6-(3-(4,4,5,5-tetramethyl-1,3,2-dioxaborolan-2-yl)phenyl)-1,3,5-triazine, was used. This compound was identified using LC-MS.

LC-MS (m/z)=$C_{45}H_{28}N_4O$ (M$^+$) 639.

Synthesis Example 3: Synthesis of Compound 27

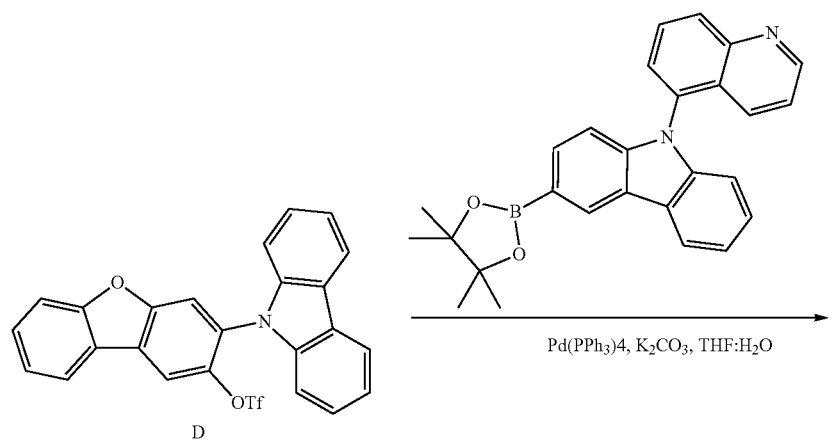

-continued

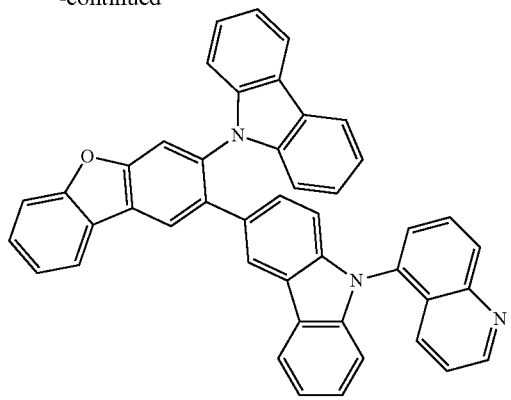

27

7.88 g (16.4 mmol) of Intermediate D, 8.95 g (21.3 mmol) of 9-(quinolin-5-yl)-3-(4,4,5,5-tetramethyl-1,3,2-dioxaborolan-2-yl)-9H-carbazole, 0.94 g (0.82 mmol) of Pd(PPh$_3$)$_4$, and 5.66 g (40.9 mmol) of K$_2$CO$_3$ were mixed with 100 mL of THF and 50 mL of distilled water. The temperature was increased to about 80° C., and the resulting mixture was stirred under reflux for about 18 hours. The mixture was cooled down to room temperature. 100 mL of distilled water was added, under stirring, followed by methylene chloride (150 mL×3) to obtain an organic layer. The organic layer was dried using magnesium sulfate (MgSO$_4$) and the solvent was removed in vacuum. The resulting residue was separated and purified using silica gel column chromatography to obtain 7.54 g of Compound 27 (Yield: 74%). This compound was identified using LC-MS.

LC-MS (m/z)=C$_{45}$H$_{28}$N$_4$O (M$^+$) 625.

Evaluation Example 1: Evaluation of HOMO, LUMO, and Triplet (T1) Energy Level

The highest occupied molecular orbital (HOMO), the lowest unoccupied molecular orbital (LUMO), and the triplet (T1) energy levels of Compounds 2, 3, and 27 were evaluated according to the methods described in Table 2 below. The results are shown in Table 3.

TABLE 2

| HOMO energy level evaluation method | A potential (V)-current (A) plot of each of the compounds was obtained using cyclic voltammetry (CV) (Electrolyte: 0.1M Bu$_4$NClO$_4$/Solvent: CH$_2$Cl$_2$/Electrode: 3-electrode system (working electrode: GC, reference electrode: Ag/AgCl, auxiliary electrode: Pt)), and a HOMO energy of the compound was calculated based on the reduction onset potential in the potential-current plot. |
| --- | --- |
| LUMO energy level evaluation method | Each of the compounds was diluted in CHCl$_3$ to a concentration of 1 × 10$^{-5}$ M, and then UV absorption spectra thereof were measured at room temperature using a spectrometer (Shimadzu UV-350 Spectrometer). A LUMO energy level of the compound was calculated based on the optical band gap (Eg) of the absorption spectrum edge. |

TABLE 2-continued

| T1 energy level evaluation method | A mixture of each of the compounds and toluene (prepared by dissolving 1 mg of the compound in 3 cubic centimeters (cc) of toluene) was put in a quartz cell, which was then placed in liquid nitrogen (77 K) for photoluminescence spectroscopy. Photoluminescence spectra of the compounds were measured using a photoluminescence spectrometer, and then compared with those at room temperature to analyze only peaks appearing at low temperature. A T1 energy level of each of the compounds was calculated based on the low-temperature peaks. |
| --- | --- |

TABLE 3

| Compound No. | HOMO (eV) (found) | LUMO (eV) (found) | T1 energy level (eV) |
| --- | --- | --- | --- |
| 2 | −5.72 | −2.15 | 2.70 |
| 3 | −5.69 | −2.15 | 2.65 |
| 27 | −5.56 | −2.21 | 2.54 |

Referring to Table 3, Compounds 2, 3, and 27 were found to have suitable electrical characteristics for use as materials for organic light-emitting devices.

Evaluation Example 2: Thermal Characteristics Evaluation

Thermal analysis of each of Compounds 2, 3, and 27 was performed using thermo gravimetric analysis (TGA) and differential scanning calorimetry (DSC) (N$_2$ atmosphere, temperature range: room temperature to 800° C. (10° C./min)-TGA, room temperature to 400° C.-DSC, Pan Type: Pt Pan in disposable Al Pan (TGA), disposable Al pan (DSC)). The results are shown in Table 4. Referring to Table 4, Compounds 2, 3, and 27 were found to have good thermal stabilities.

TABLE 4

| Compound No. | Tg (° C.) | Tm (° C.) | Tc (° C.) | Td (1%/5%, ° C.) |
| --- | --- | --- | --- | --- |
| 2 | 144.4 | 309.8 | n/a | 389/418 |
| 3 | 139.8 | 289.6 | n/a | 387/419 |
| 27 | 155.3 | N/A | N/A | 379/414 |

Evaluation Example 3: Emission Spectrum Evaluation

Emission characteristics of Compound 2 were evaluated using UV absorption spectrum and photoluminescence (PL) spectrum. First, Compound 2 was diluted in toluene to a concentration of 0.2 millimolar (mM), and a UV absorption spectrum of the solution was measured using Shimadzu UV-350 Spectrometer. The same process was repeated using Compounds 3 and 27.

Meanwhile, Compound 2 was diluted with toluene to a concentration of about 10 mM and then a PL spectrum of Compound 2 was measured at about 298K with an ISC PC1 spectrofluorometer equipped with a Xenon lamp. The same process was repeated using Compounds 3 and 27.

Figure 2:
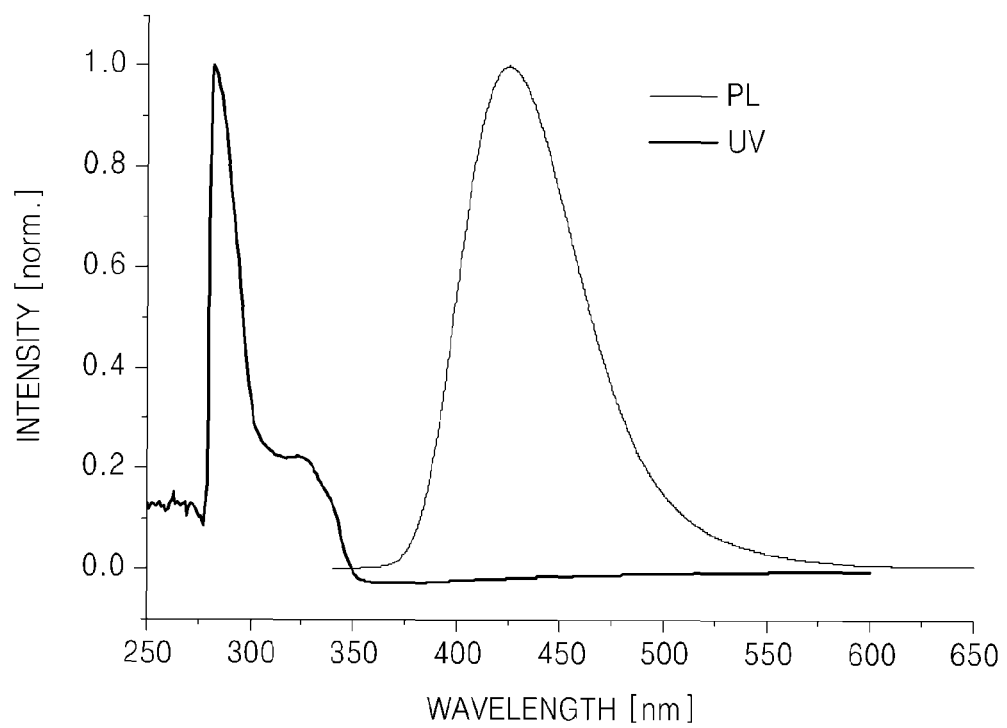
FIG. 2 is a graph of normalized intensity versus wavelength (nanometers, nm) illustrating photoluminescence (PL) and UV absorption spectra of Compound 2.
Figure 3:
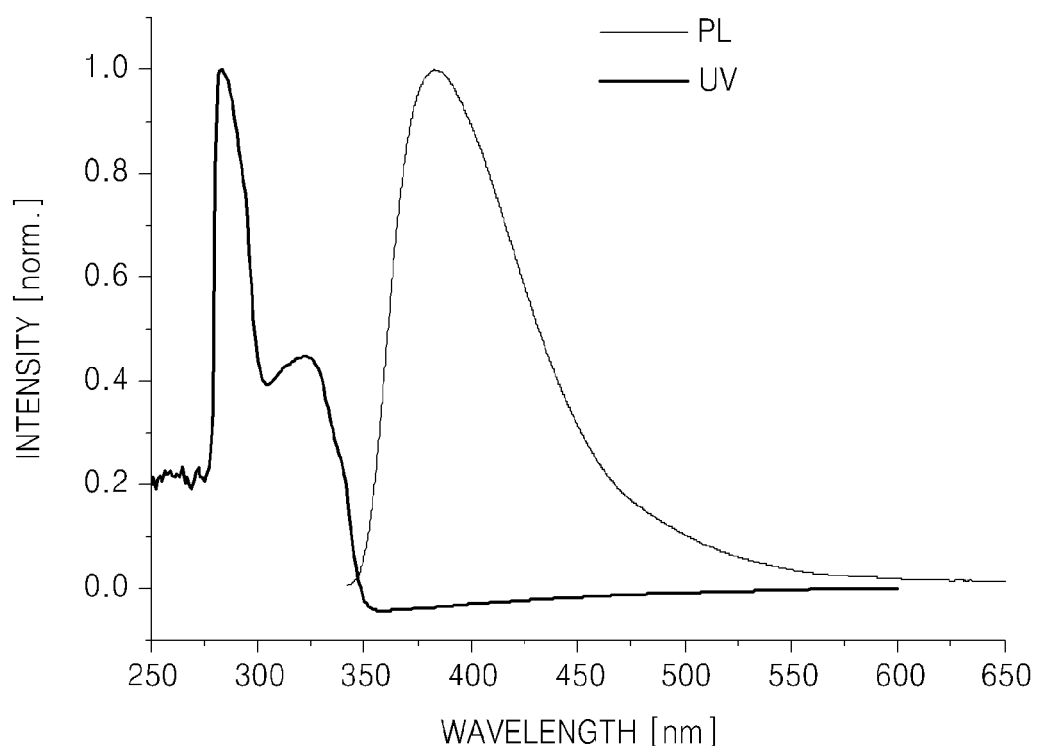
FIG. 3 is a graph of normalized intensity versus wavelength (nanometers, nm) illustrating photoluminescence (PL) and UV absorption spectra of Compound 3.

The PL spectrum and UV absorption spectrum of Compound 2 are shown in FIG. 2. The PL spectrum and UV absorption spectrum of Compound 3 are shown in FIG. 3. Peak wavelengths and peaks with a full maximum at half width (FMHW) in the UV absorption spectra and PL spectra of each compound are summarized in Table 5.

TABLE 5

| Compound No. | UV absorption spectrum λmax | PL spectrum λmax | FWHM |
|---|---|---|---|
| 2 | 323 nm | 425 nm | 67 nm |
| 3 | 322 nm | 383 nm | 70 nm |
| 27 | 328 nm | 413 nm | 54 nm |

Referring to FIGS. 2 and 3, and Table 5, Compounds 3, 2, and 27 were found to have good emission characteristics.

Example 1

After a glass substrate with an indium tin oxide (ITO) electrode (first electrode, anode) having a thickness of about 1,500 Å was ultrasonically washed with distilled water, and then with isopropyl alcohol, acetone, methanol, and the like. The washed glass substrate was dried, placed into a plasma cleaning system, and cleaned using oxygen plasma for about 5 minutes. The glass substrate was then loaded into a vacuum deposition device.

Compound NPB was vacuum-deposited on the ITO electrode of the glass substrate to form a HTL having a thickness of about 1,000 Å.

Compound 2 (host) and Ir(ppy)$_3$ (dopant, Compound PD1 herein, 10 percent by weight (wt %)) were co-deposited on the HTL to form an EML having a thickness of about 300 Å.

Subsequently, BAlq was vacuum-deposited on the EML to form a first ETL having a thickness of about 50 Å, and then Alq$_3$ was vacuum-deposited on the first ETL to form a second ETL having a thickness of about 250 Å. Then, LiF was deposited on the second ETL to form an EIL having a thickness of about 5 Å, and Al was deposited on the EIL to a thickness of about 1,000 Å to form a second electrode (cathode), thereby completing the manufacture of an organic light-emitting device.

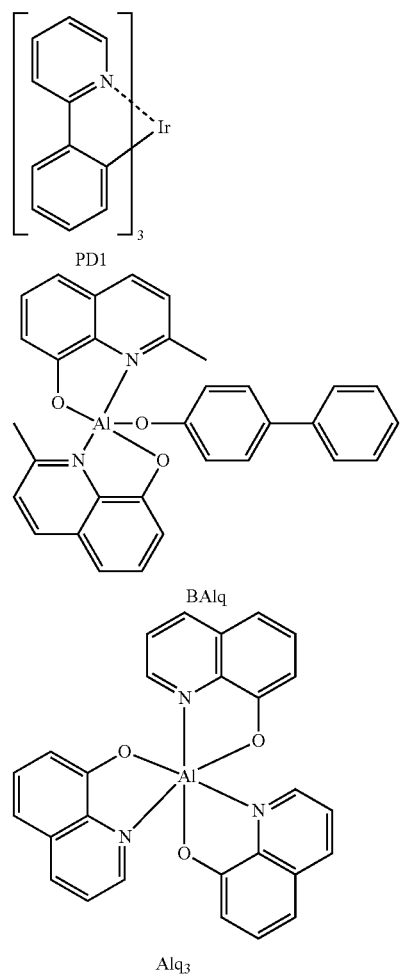

PD1

BAlq

Alq$_3$

Example 2

An organic light-emitting device was manufactured in the same manner as in Example 1, except that Compound 3, instead of Compound 2, was used as a host to form the EML.

Example 3

An organic light-emitting device was manufactured in the same manner as in Example 1, except that Compound 27, instead of Compound 2, was used as a host to form the EML.

Example 4

An organic light-emitting device was manufactured in the same manner as in Example 1, except that the thickness of the HTL was changed to about 1,350 Å, and Compound 27 and PtOEP, instead of Compound 2 and Ir(ppy)$_3$, respectively, were used to form the EML.

Comparative Example 1

An organic light-emitting device was manufactured in the same manner as in Example 1, except that Compound A, instead of Compound 2, was used as a host to form the EML.

Compound A

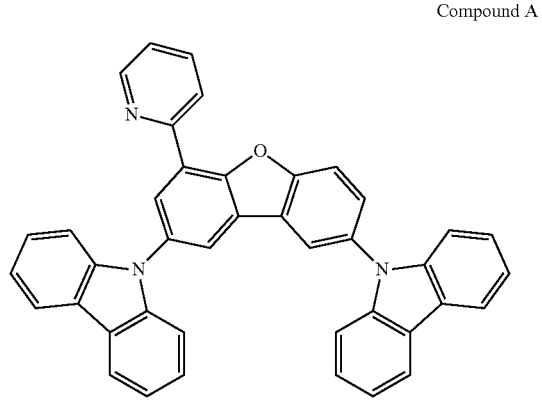 [SMILES: c1ccc(-c2cc(-n3c4ccccc4c4ccccc43)cc3c2oc2ccc(-n4c5ccccc5c5ccccc54)cc23)nc1]

Comparative Example 2

An organic light-emitting device was manufactured in the same manner as in Example 1, except that Compound B, instead of Compound 2, was used as a host to form the EML.

Compound B

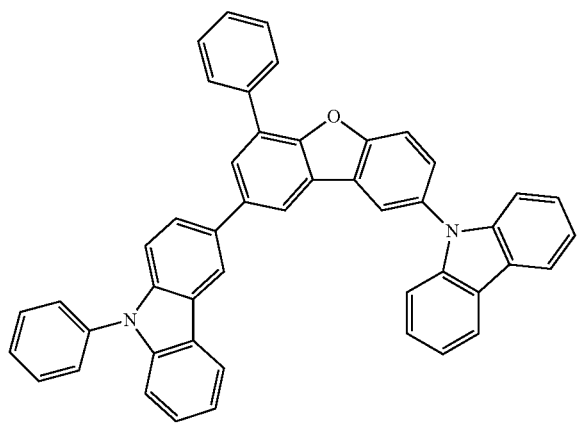

Comparative Example 3

An organic light-emitting device was manufactured in the same manner as in Example 1, except that the thickness of the HTL was changed to about 1,350 Å, and Compound A and PtOEP, instead of Compound 2 and Ir(ppy)$_3$, respectively, were used to form the EML.

Comparative Example 4

An organic light-emitting device was manufactured in the same manner as in Example 1, except that the thickness of the HTL was changed to about 1,350 Å, and Compound B and PtOEP, instead of Compound 2 and Ir(ppy)$_3$, respectively, were used to form the EML.

Comparative Example 5

An organic light-emitting device was manufactured in the same manner as in Example 1, except that CBP, instead of Compound 2, was used to form the EML.

Comparative Example 6

An organic light-emitting device was manufactured in the same manner as in Example 1, except that the thickness of the HTL was changed to about 1,350 Å, and CBP and PtOEP, instead of Compound 2 and Ir(ppy)$_3$, respectively, were used to form the EML.

Evaluation Example 4: Characteristics Evaluation of Organic Light-Emitting Devices Consumption powers, luminances, efficiencies, emission colors, and lifetimes of the organic light-emitting devices of Examples 1 to 4 and Comparative Examples 1 to 3 were evaluated using a Kethley Source-Measure Unit (SMU 236) and a PR650 Spectroscan Source Measurement Unit (available from Photo Research, Inc.). The results are shown in Table 6. $LT_{97}$ was evaluated as a function of the time until a measured initial luminance (assumed as 100%) was reduced to 97% during driving. $LT_{97}$ of green organic light-emitting devices were evaluated at 6,000 nits, and $LT_{97}$ of red organic light-emitting devices were evaluated at 1,500 nits.

TABLE 6

| | EML | | Consumption power | Luminance | Efficiency | Emission | $LT_{97}$ |
|---|---|---|---|---|---|---|---|
| Example | host | dopant | (lm/W) | (cd/m$^2$) | (cd/A) | color | (hr) |
| Example 1 | Compound 2 | Ir(ppy)$_3$ | 28.2 | 4755 | 48.5 | Green | 90 |
| Example 2 | Compound 3 | Ir(ppy)$_3$ | 28.3 | 4865 | 49.6 | Green | 88 |
| Example 3 | Compound 27 | Ir(ppy)$_3$ | 25.3 | 4715 | 47.5 | Green | 84 |
| Example 4 | Compound 27 | PtOEP | 10.9 | 2435 | 24.0 | Red | 95 |
| Comparative Example 1 | Compound A | Ir(ppy)$_3$ | 23.9 | 4815 | 48.0 | Green | 72 |
| Comparative Example 2 | Compound B | Ir(ppy)$_3$ | 22.6 | 4690 | 47.5 | Green | 74 |
| Comparative Example 3 | Compound A | PtOEP | 10.3 | 2365 | 23.0 | Red | 85 |
| Comparative Example 4 | Compound B | PtOEP | 9.95 | 2270 | 22.5 | Red | 88 |
| Comparative Example 5 | CBP | Ir(ppy)$_3$ | 22.0 | 4,766 | 47.7 | Green | 61 |
| Comparative Example 6 | CBP | PtOEP | 22.1 | 2.212 | 22.1 | Red | 89 |

Referring to Table 6, the organic light-emitting devices of Examples 1 to 3 were found to have improved consumption power, luminance, efficiency, and lifetime characteristics. In particular, the organic light-emitting device of Example 4 were found to have improved consumption power, luminance, efficiency, and lifetime characteristics, compared to the organic light-emitting devices of Comparative Examples 3, 4, and 6.

As described above, according to the one or more of the above embodiments of the present disclosure, a carbazole compound of Formula 1 may have) good electric characteristics and thermal stability. Thus an organic light-emitting device including the carbazole compound of Formula 1 may have improved consumption power, efficiency, luminance, and lifetime characteristics.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present disclosure have been described with reference to the figures, it will be understood by those of ordinary skill in the art that various changes in form and details may be made therein without departing from the spirit and scope of the present disclosure as defined by the following claims.

What is claimed is:

1. A carbazole compound represented by Formula 1:

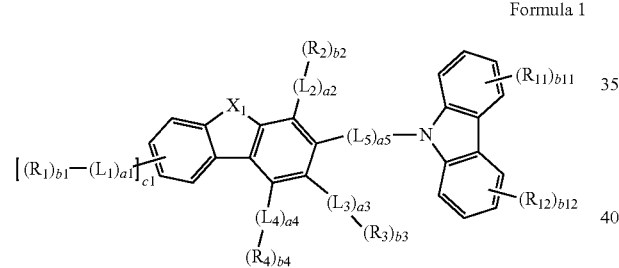

Formula 1 wherein, in Formula 1, $X_1$ is O or S;

$L_1$ to $L_5$ are each independently selected from a substituted or unsubstituted $C_1$-$C_{60}$ alkylene group, a substituted or unsubstituted $C_2$-$C_{60}$ alkenylene group, a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic condensed heteropolycyclic group;

a1 to a5 are each independently an integer selected from 0 to 5;

$R_1$ to $R_4$, $R_{11}$, and $R_{12}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

at least one of $R_2$ to $R_4$ is independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group and a substituted or unsubstituted monovalent non-aromatic condensed heteropolycyclic group;

b1 to b4, b1, b12 and c1 are each independently an integer selected from 1 to 4;

at least one of substituents of the substituted $C_1$-$C_{60}$ alkylene group, the substituted $C_2$-$C_{60}$ alkenylene group, the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, and a monovalent nonaromatic condensed heteropolycyclic group;

a $C_3$-$C_{10}$ cycloalkyl group, a $C_2$—C heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, and a monovalent nonaromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$;

wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent nonaromatic condensed polycyclic group, and a monovalent aromatic condensed heteropolycyclic group.

2. The carbazole compound of claim 1, wherein $L_1$ to $L_5$ are each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{20}$ aryl group, a phenyl group-substituted phenyl group, a $C_2$-$C_{20}$ heteroaryl group, a monovalent nonaromatic condensed polycyclic group, a monovalent nonaromatic condensed heteropolycyclic group, and —$Si(Q_{33})(Q_{34})(Q_{35})$, wherein $Q_{33}$ to $Q_{35}$ are each independently a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

3. The carbazole compound of claim 1, wherein $L_1$ to $L_5$ are each independently a group represented by one of Formulae 2-1 to 2-37:

Formula 2-1
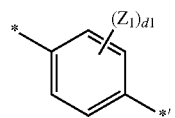

Formula 2-2
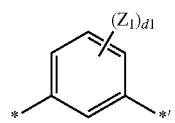

Formula 2-3
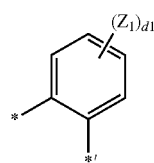

Formula 2-4
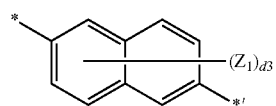

Formula 2-5
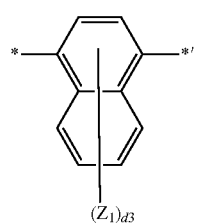

Formula 2-6
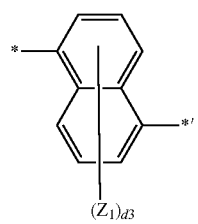

Formula 2-7
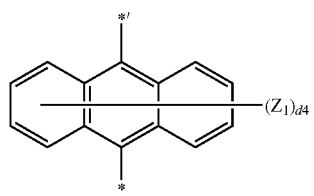

Formula 2-8
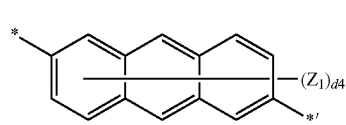

-continued

Formula 2-9
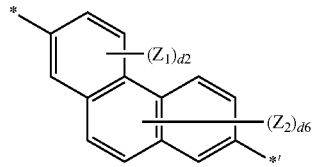

Formula 2-10
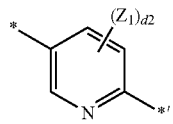

Formula 2-11
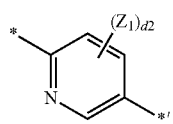

Formula 2-12
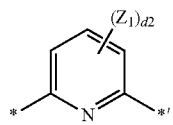

Formula 2-13
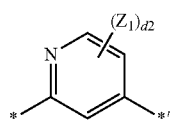

Formula 2-14
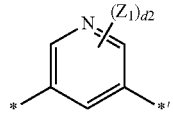

Formula 2-15
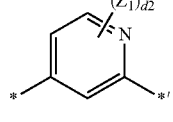

Formula 2-16
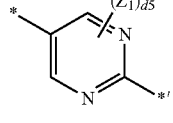

Formula 2-17
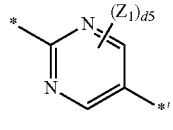

Formula 2-18
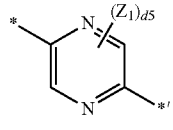

Formula 2-19
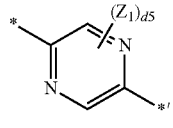

Formula 2-20
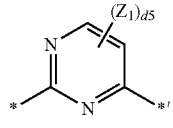

-continued

Formula 2-21
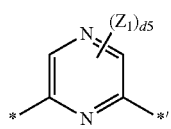

Formula 2-22
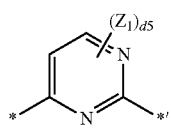

Formula 2-23
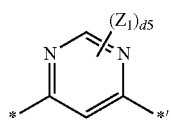

Formula 2-24
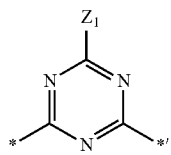

Formula 2-25
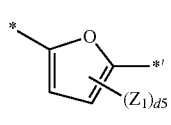

Formula 2-26
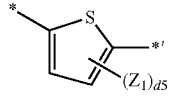

Formula 2-27
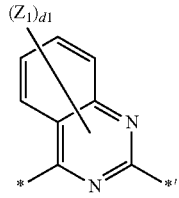

Formula 2-28
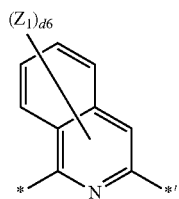

Formula 2-29
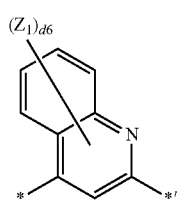

Formula 2-30
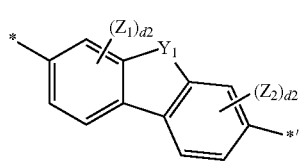

Formula 2-31
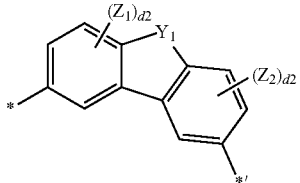

Formula 2-32
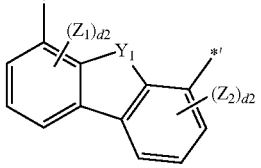

Formula 2-33
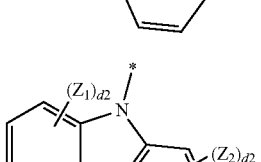

Formula 2-34
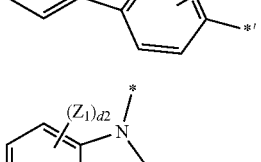

Formula 2-35
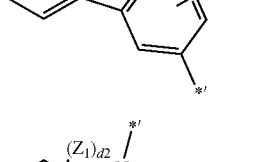

Formula 2-36
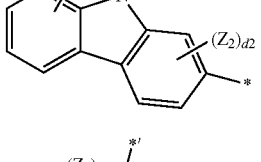

Formula 2-37
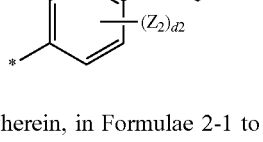

wherein, in Formulae 2-1 to 2-37, $Y_1$ is O, S, S(=O), S(=O)$_2$, C(Z$_3$)(Z$_4$), N(Z$_5$), or Si(Z$_6$)(Z$_7$);

$Z_1$ to $Z_7$ are each independently selected from a hydrogen, a deuterium, —F, —Cl, —Br, —I, a hydroxyl group, a cyano group, a nitro group, an amino group, an amidino groups, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a phenyl group-substituted phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, and —Si($Q_{33}$)($Q_{34}$)($Q_{45}$), wherein $Q_{33}$ to $Q_{45}$ are each independently a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

d1 is an integer selected from 1 to 4;
d2 is an integer selected from 1 to 3;
d3 is an integer selected from 1 to 6;
d4 is an integer selected from 1 to 8;
d5 is 1 or 2;
d6 is an integer selected from 1 to 5; and
* indicates a binding site with an adjacent atom.

4. The carbazole compound of claim 1, wherein $L_1$ to $L_5$ are each independently selected from a phenylene group, a naphthylene group, a phenanthrenylene group, an anthracenylene group, a triphenylenylene group, a carbazolylene group, a pyridinylene group, a pyrimidinylene group, a triazinylene group, a quinazolinylene group, a quinolinylene group, an isoquinolinylene group, a naphthyridinylene group, and an oxadiazolylene group; and a phenylene group, a naphthylene group, a phenanthrenylene group, an anthracenylene group, a triphenylenylene group, a carbazolylene group, a pyridinylene group, a pyrimidinylene group, a triazinylene group, a quinazolinylene group, a quinolinylene group, an isoquinolinylene group, a naphthyridinylene group, and an oxadiazolylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a phenyl group-substituted phenyl group, a naphthyl group, an anthracenyl group, a triphenylenyl group and a phenanthrenyl group.

5. The carbazole compound of claim 1, wherein a1 to a5 are each independently 0, 1, or 2.

6. The carbazole compound of claim 1, wherein $R_1$ to $R_4$, $R_{11}$, and $R_{12}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_2$-$C_{20}$ heteroaryl group, a substituted or unsubstituted monovalent nonaromatic condensed polycyclic group, and a substituted or unsubstituted monovalent nonaromatic condensed heteropolycyclic group; and at least one of $R_2$ to $R_4$ is independently selected from a substituted or unsubstituted $C_6$-$C_{60}$ aryl group, a substituted or unsubstituted $C_2$-$C_{60}$ heteroaryl group, a substituted or unsubstituted monovalent nonaromatic condensed cyclic group, and a substituted or unsubstituted monovalent nonaromatic condensed heterocyclic group.

7. The carbazole compound of claim 1, wherein $R_1$ to $R_4$, $R_{11}$ and $R_{12}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a $C_1$-$C_{20}$ alkyl group-substituted phenyl group, a phenyl group-substituted phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group and —Si($Q_{33}$)($Q_{34}$)($Q_{35}$), and —Si($Q_3$)($Q_4$)($Q_5$), wherein $Q_3$ to $Q_5$ and $Q_{33}$ to $Q_{35}$ are each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

8. The carbazole compound of claim 1, wherein at least one of $R_2$ to $R_4$ is independently selected from a triphenylenyl group, a carbazolyl group, a pyrrolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, a phenanthrolinyl group, a phenazinyl group, a benzoimidazolyl group, a benzothiazolyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, and a triphenylenyl group, a carbazolyl group, a pyrrolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, a phenanthrolinyl group, a phenazinyl group, a benzoimidazolyl group, a benzothiazolyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, each substituted with at least one of a deuterium, —F, —Cl, —Br, —I, a hydroxyl group, a cyano group, a nitro group, an amino group, an amidino group, a hydrazine group, a hydrazone group, carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$).

9. The carbazole compound of claim 1, wherein at least one of $R_2$ to $R_4$ is independently selected from a pyridinyl group, a pyrazinyl group, a pyrimidinyl group, a pyridazinyl group, a quinolinyl group, an isoquinolinyl group, a naphthyridinyl group, a quinoxalinyl group, a quinazolinyl group, a benzothiazolyl group, an isobenzothiazolyl group, a benzoxazolyl group, an isobenzooxazolyl group, an oxadiazolyl group, a triazinyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, and a pyridinyl group, a pyrazinyl group, a pyrimidinyl group, a pyridazinyl group, a quinolinyl group, an isoquinolinyl group, a naphthyridinyl group, a quinoxalinyl group, a quinazolinyl group, a benzothiazolyl group, an isobenzothiazolyl group, a benzoxazolyl group, an isobenzooxazolyl group, an oxadiazolyl group, a triazinyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, each substituted with at least one of a deuterium, —F, —Cl, —Br, —I, a hydroxyl group, a cyano group, a nitro group, an amino group, an amidino group, a hydrazine group, a hydrazone group, carboxylic acid group or a salt thereof, a sulfonic acid group or a salt thereof, a phosphoric acid group or a salt thereof, $C_1$-$C_{20}$ alkyl group, $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$).

10. The carbazole compound of claim 1, wherein at least one of $R_2$ to $R_4$ is independently selected from a thiophenyl group, a furanyl group, a carbazolyl group, acridinyl, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, and a thiophenyl group, a furanyl group, a carbazolyl group, acridinyl, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$).

11. The carbazole compound of claim 1, wherein $R_1$ to $R_4$, $R_{11}$, and $R_{12}$ in Formula 1 are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a group represented by any of Formulae 4-1 to 4-48, Formulae 5-1 to 5-6, and Formulae 6-1 to 6-5, and —Si($Q_3$)($Q_4$)($Q_5$), wherein $Q_3$ to $Q_5$ are each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group; and at least one of $R_2$ to $R_4$ is independently selected from the group represented by any of Formulae 4-1 to 4-48, Formulae 5-1 to 5-6, and Formulae 6-1 to 6-5:

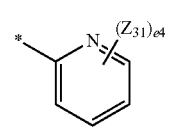

Formula 4-1

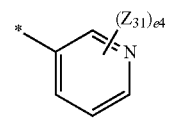

Formula 4-2

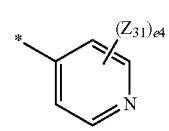

Formula 4-3

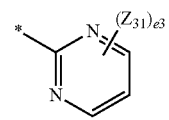

Formula 4-4

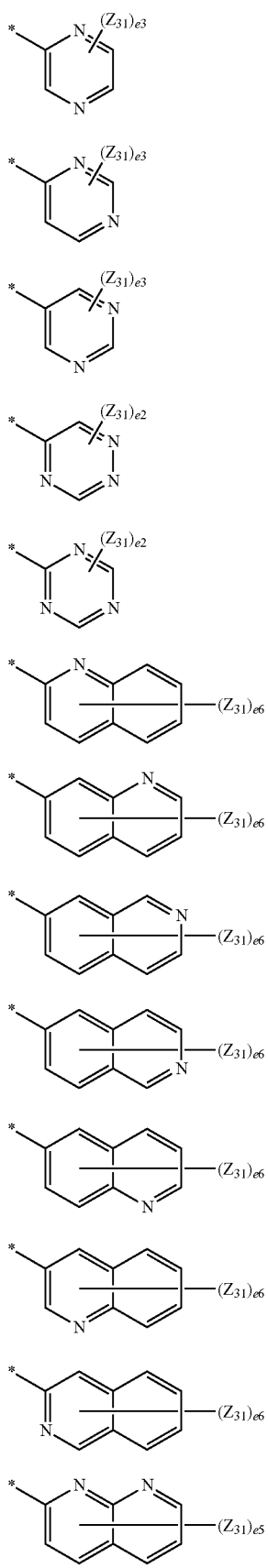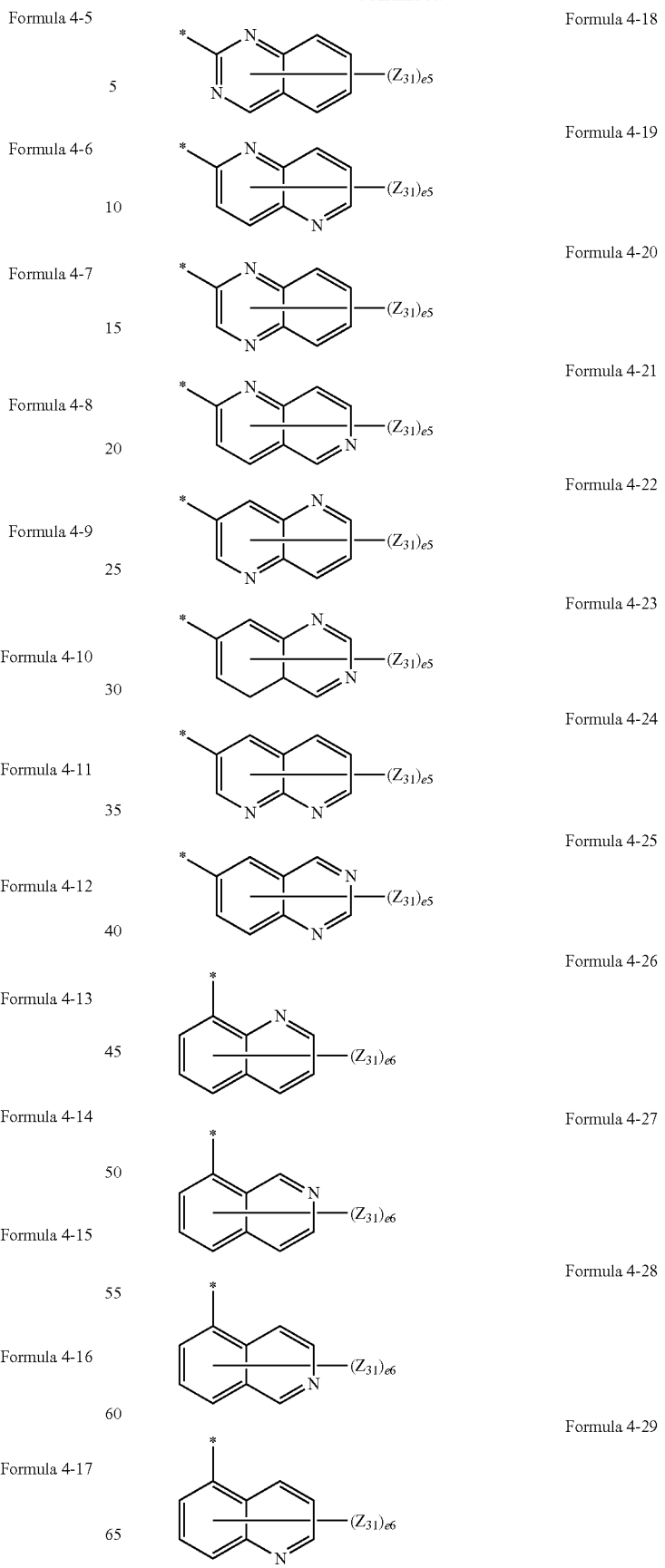

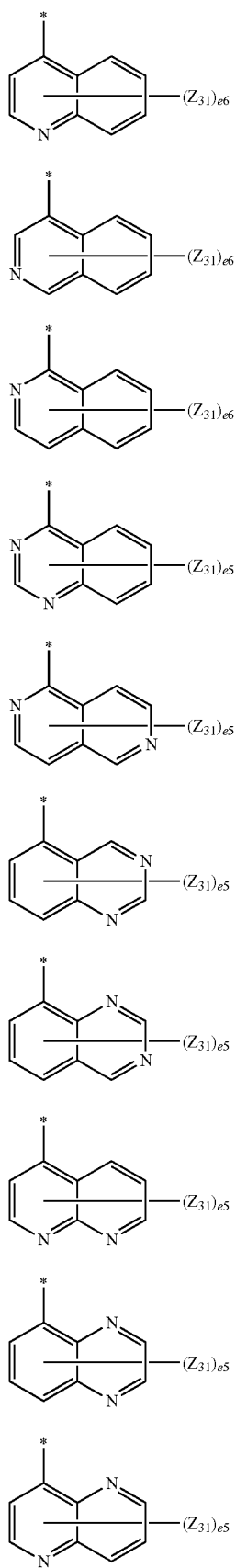
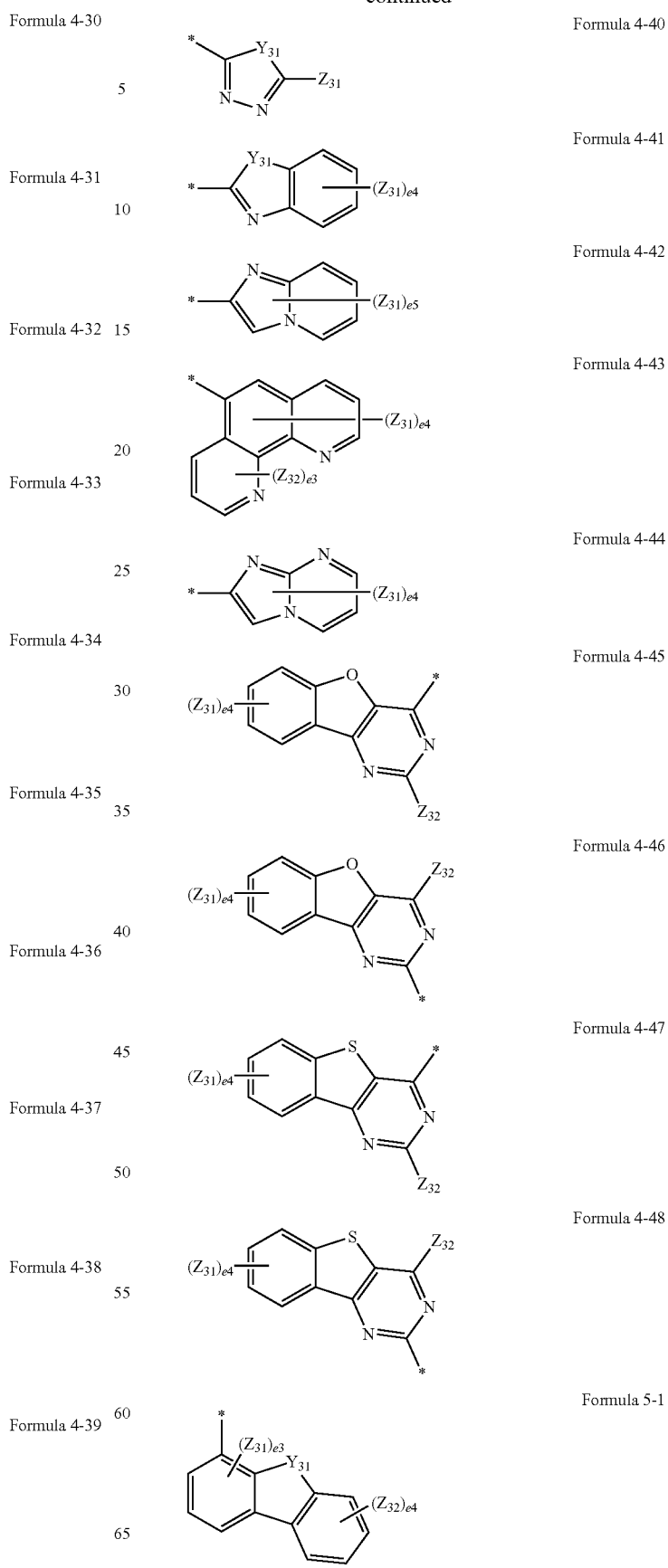

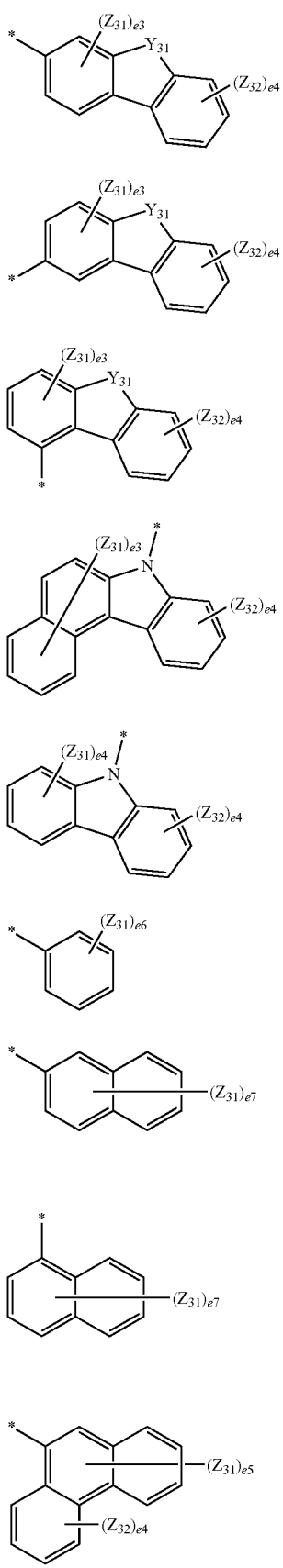

Formula 5-2

Formula 5-3

Formula 5-4

Formula 5-5

Formula 5-6

Formula 6-1

Formula 6-2

Formula 6-3

Formula 6-4

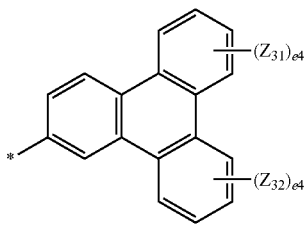

Formula 6-5 wherein, in Formulae 4-1 to 4-48, Formulae 5-1 to 5-6, and Formulae 6-1 to 6-5, $Y_{31}$ is O, S, $C(Z_{33})(Z_{34})$, $N(Z_{35})$, or $Si(Z_{36})(Z_{37})$;

$Z_{31}$ to $Z_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a $C_1$-$C_{20}$ alkyl group-substituted phenyl group, a phenyl group-substituted phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, and —$Si(Q_{33})(Q_{34})(Q_{35})$, wherein $Q_{33}$ to $Q_{35}$ are each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

e2 is 1 or 2;

e3 is an integer selected from 1 to 3;

e4 is an integer selected from 1 to 4;

e5 is an integer selected from 1 to 5;

e6 is an integer selected from 1 to 6;

e7 is an integer selected from 1 to 7; and

* indicates a binding site with an adjacent atom.

12. The carbazole compound of claim 1, wherein the carbazole compound is represented by Formula 1A or 1B:

Formula 1A

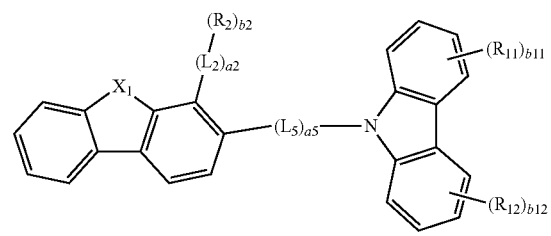

-continued

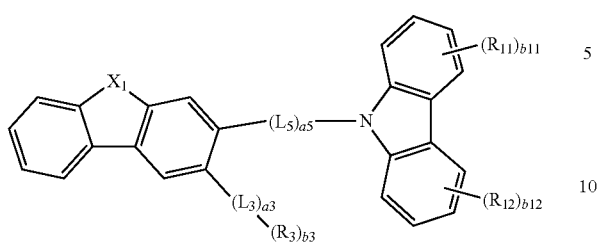
Formula 1B wherein, in Formula 1A, $X_1$, $L_3$, $L_5$, a3, a5, b2, b3, $R_{11}$, $R_{12}$, b11, and b12 are the same as in claim 1; and $R_2$ and $R_3$ are selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent nonaromatic condensed polycyclic group, and a substituted or unsubstituted monovalent nonaromatic condensed heteropolycyclic group.

13. The carbazole compound of claim 1, wherein the carbazole compound is one of Compounds 1 to 131:

1
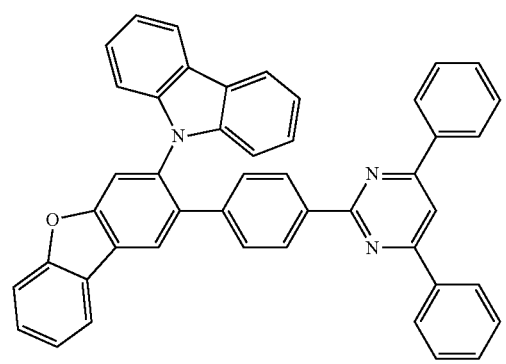

2
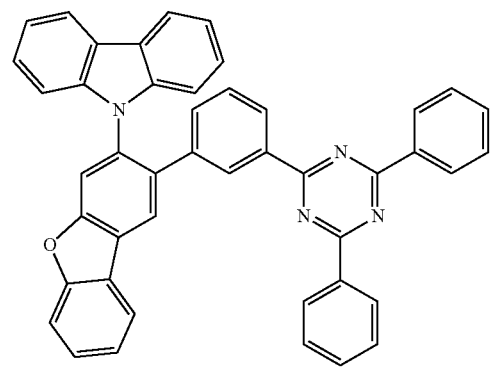

3
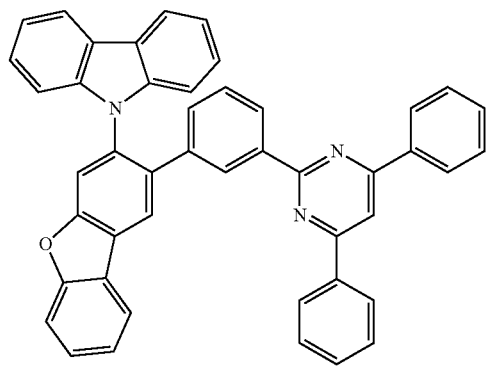

4
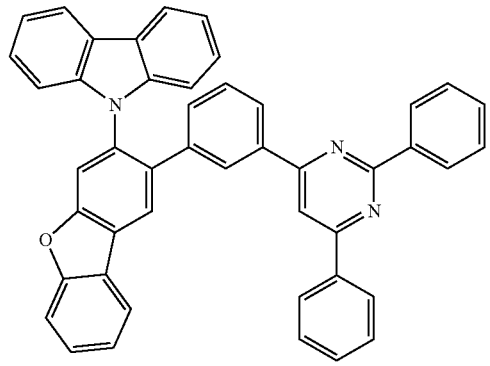

5
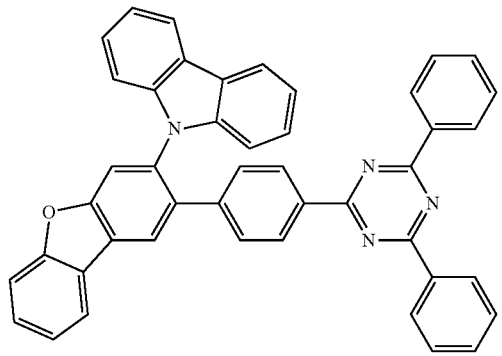

6
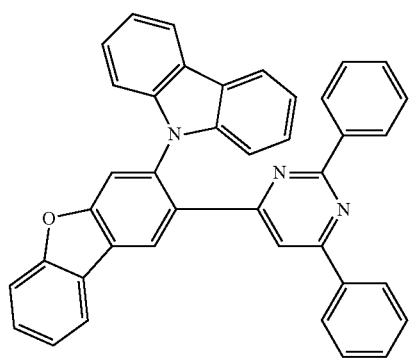

7
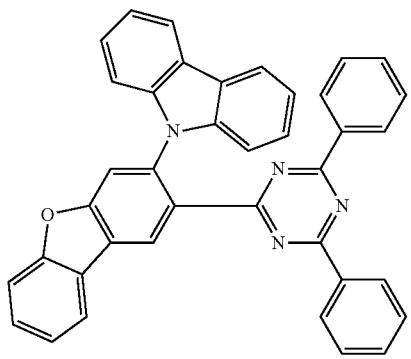
8
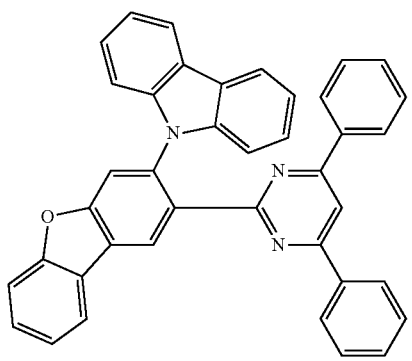
9
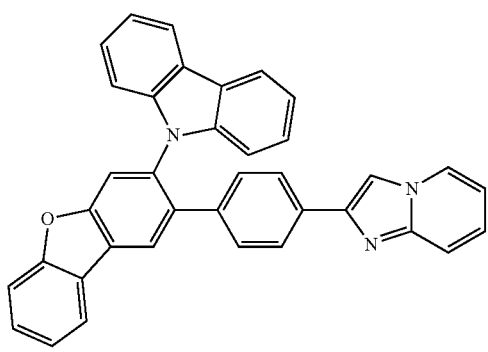
10
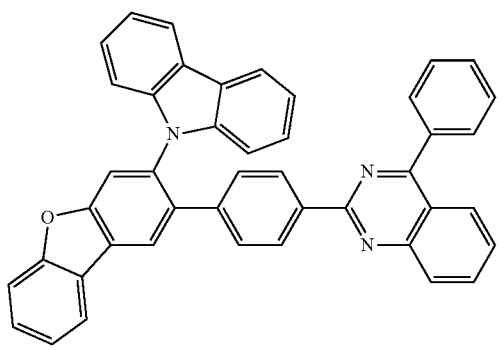
11
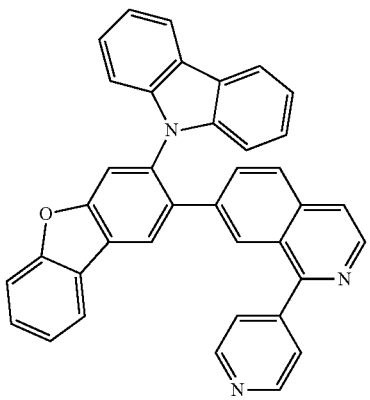
12
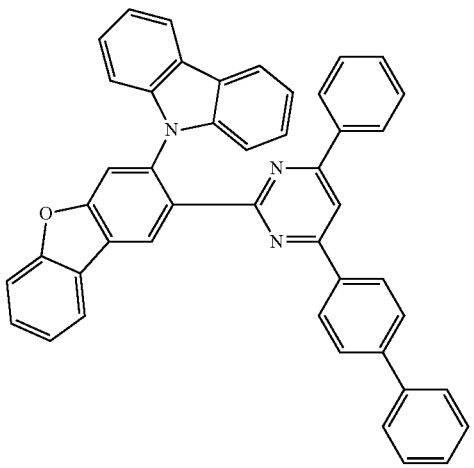
13
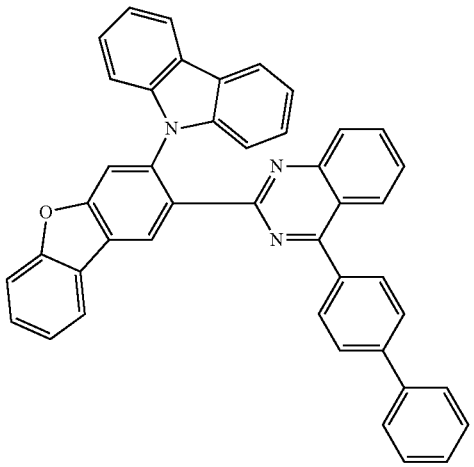

14
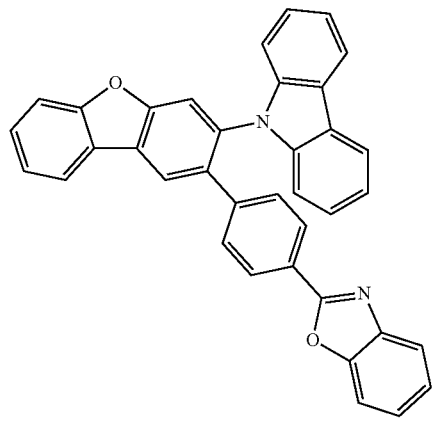
15
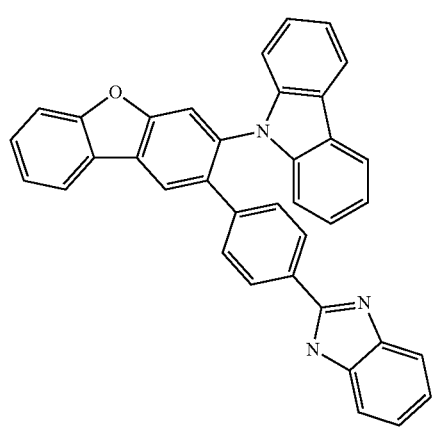
16
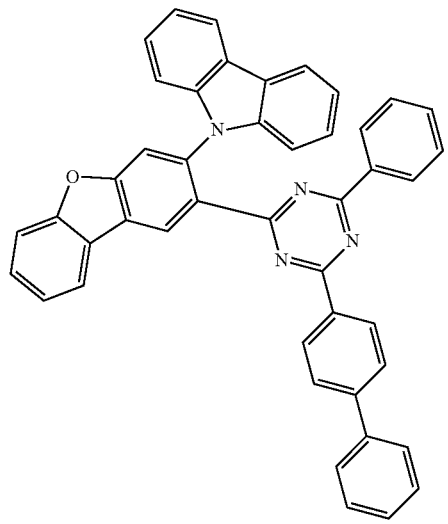
17
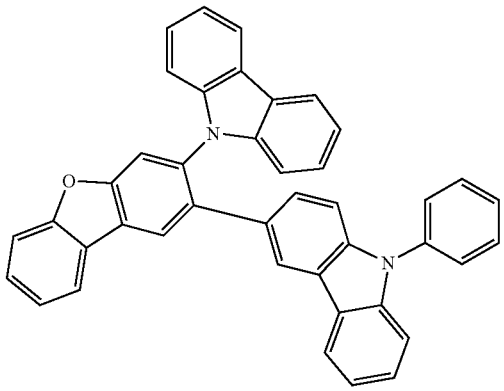
18
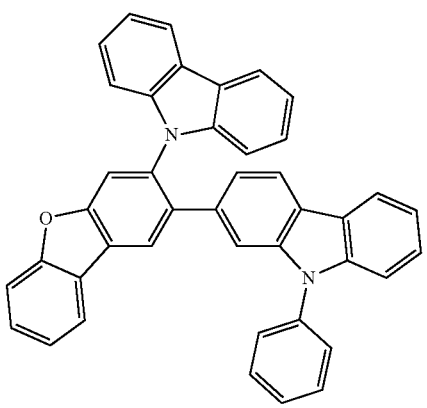
19
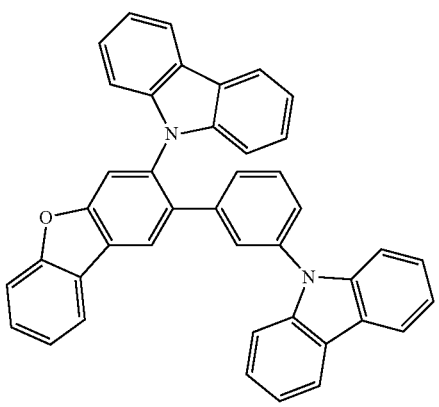
20
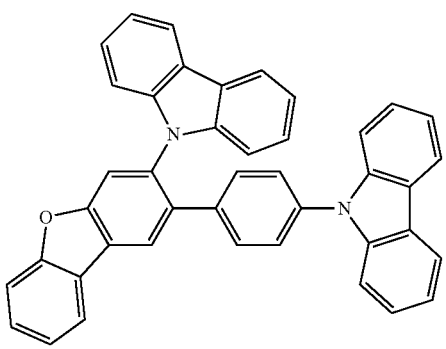

191
-continued
21
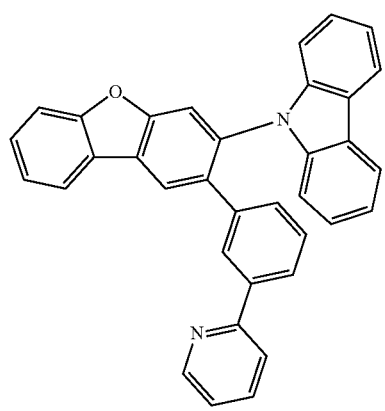
22
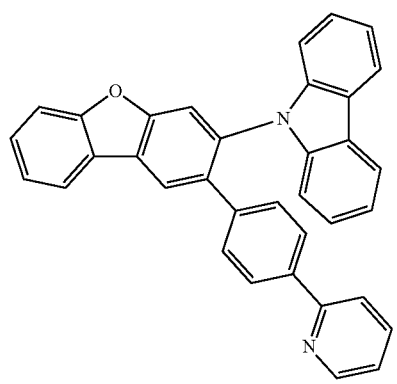
23
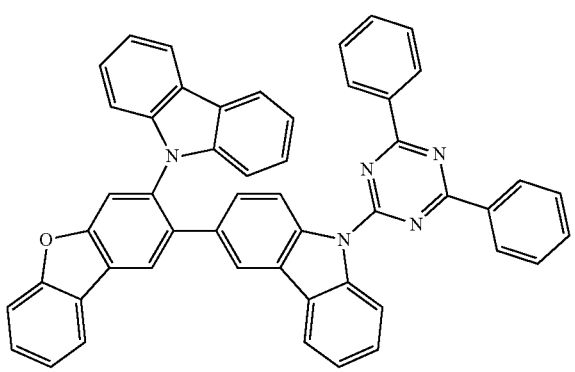
192
-continued
24
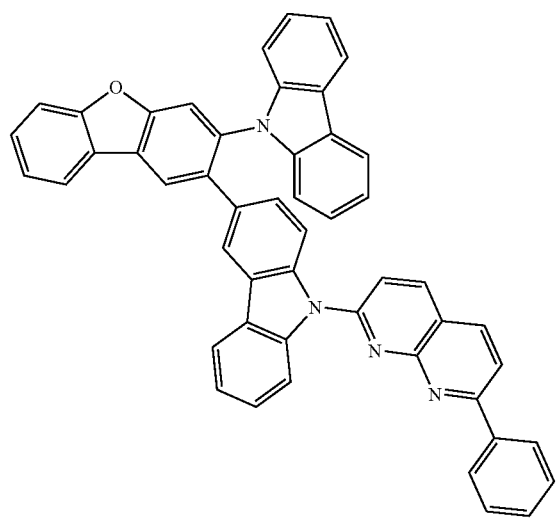
25
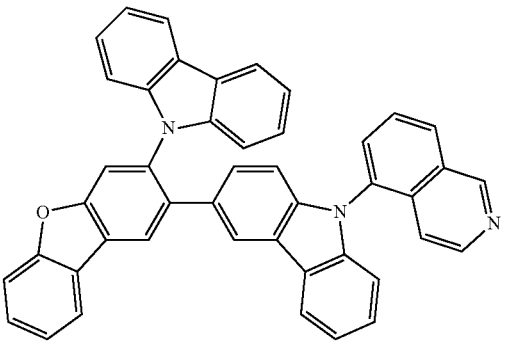
26
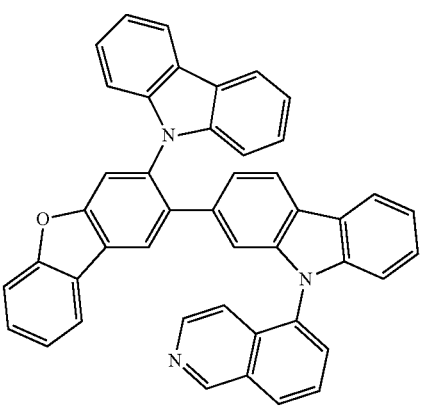

27
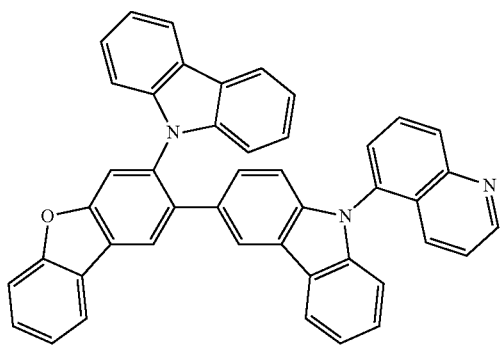
28
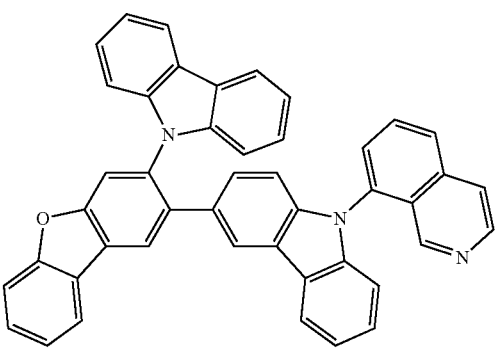
29
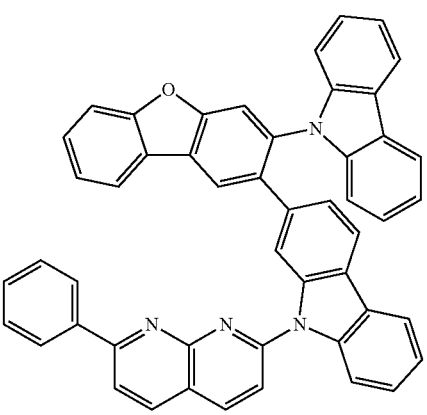
30
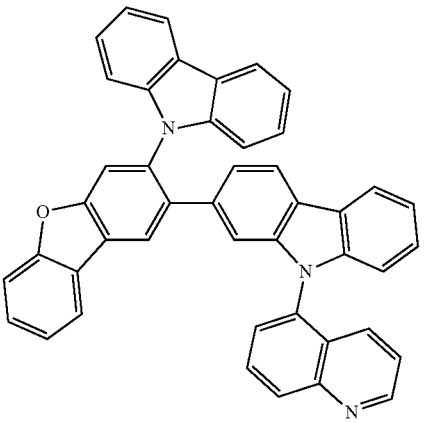
31
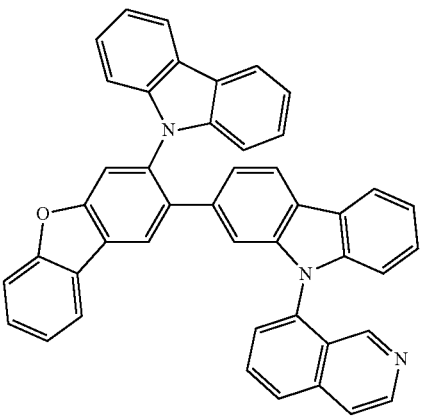

34
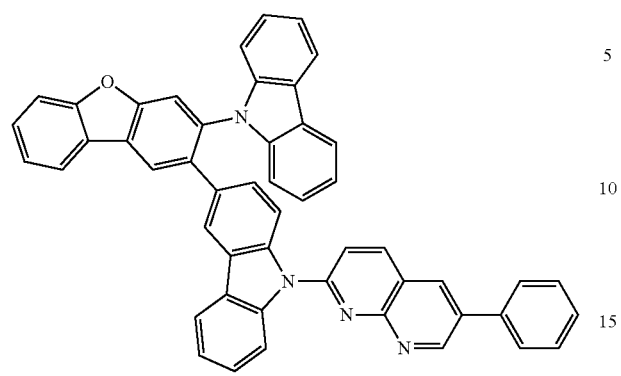
35
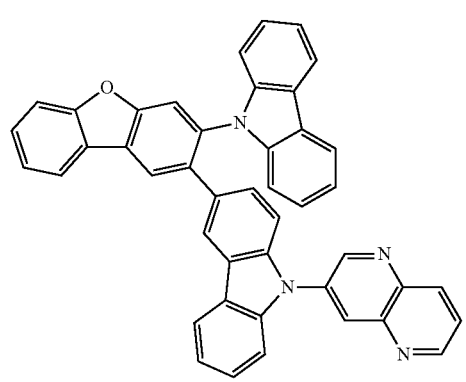
36
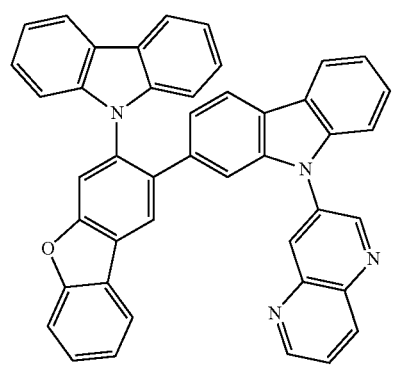
37
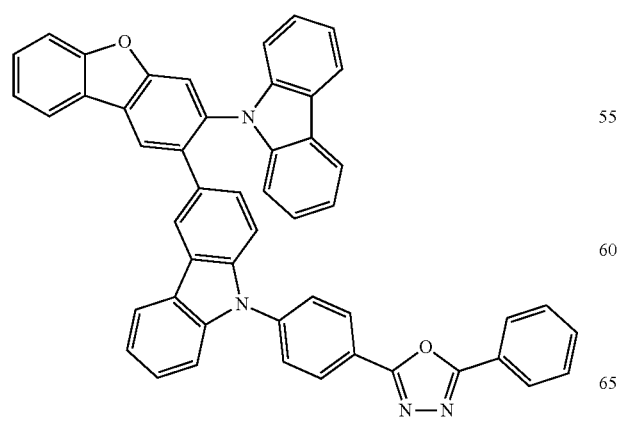
38
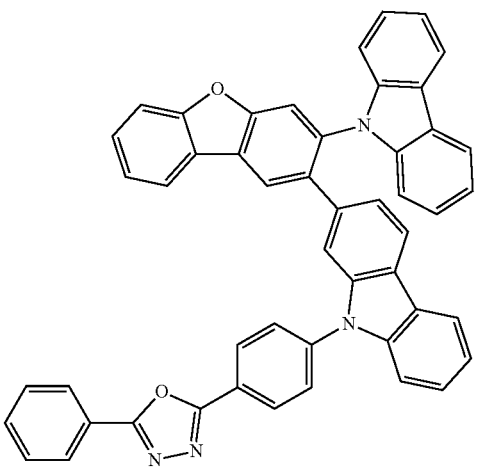
39
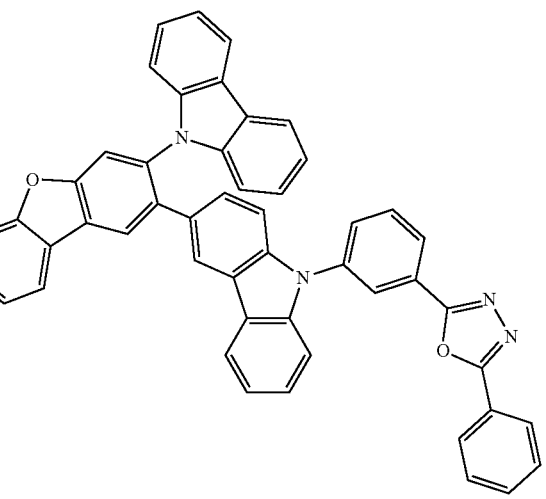
40
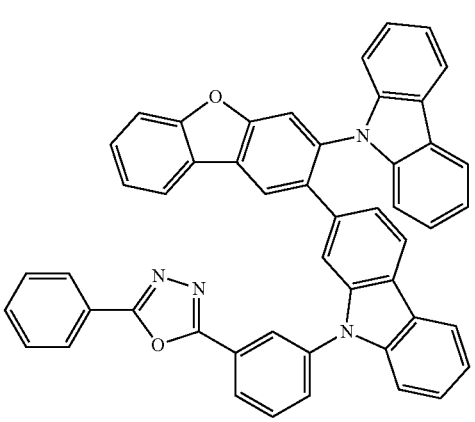

41
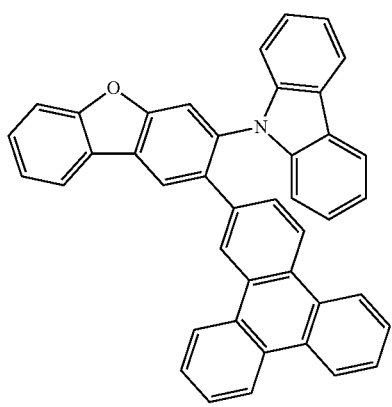
42
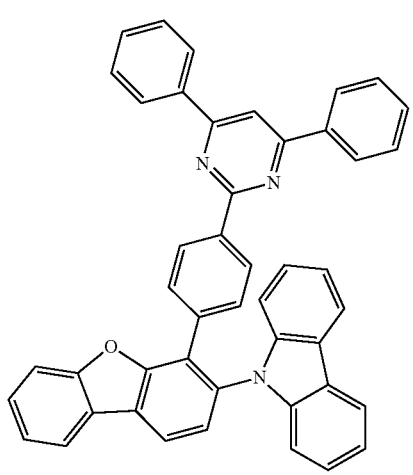
43
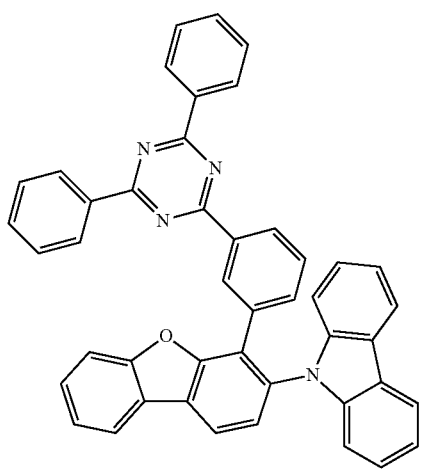
44
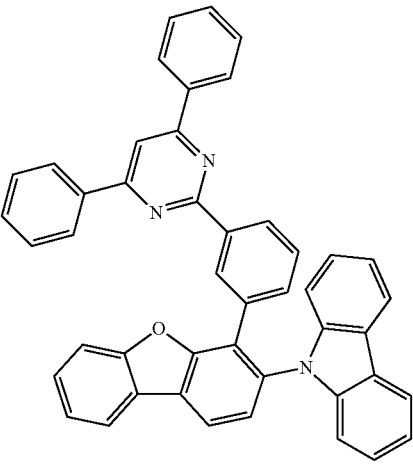
45
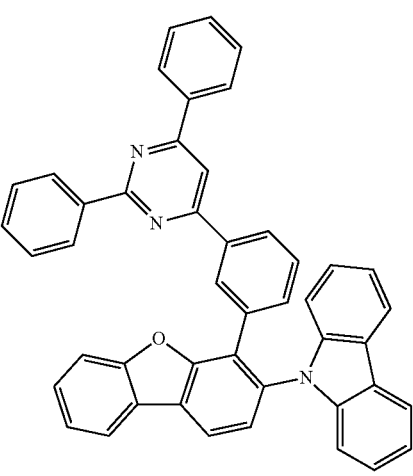
46
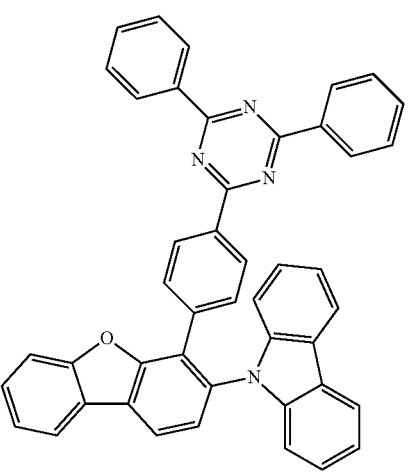

-continued
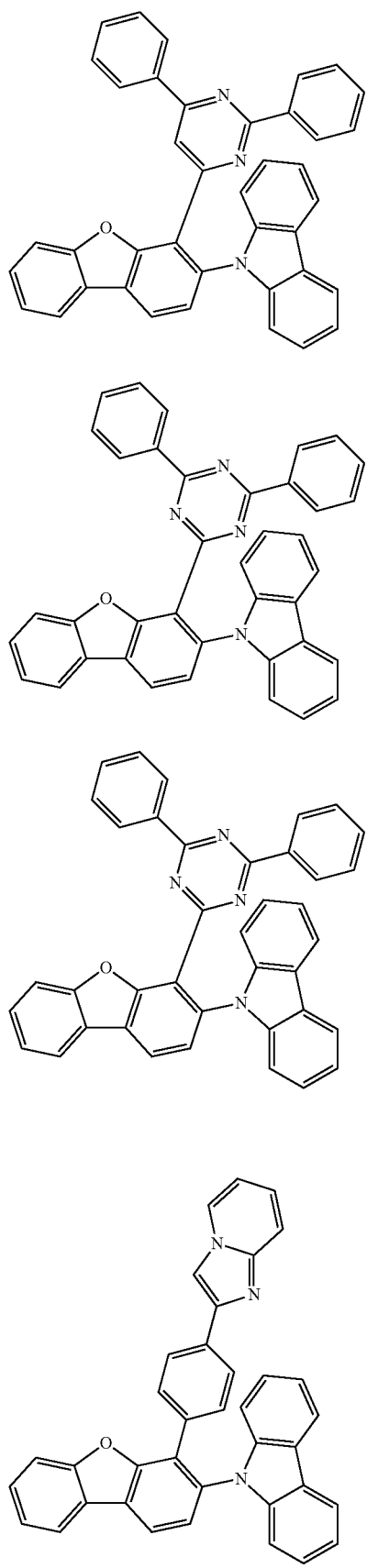
-continued
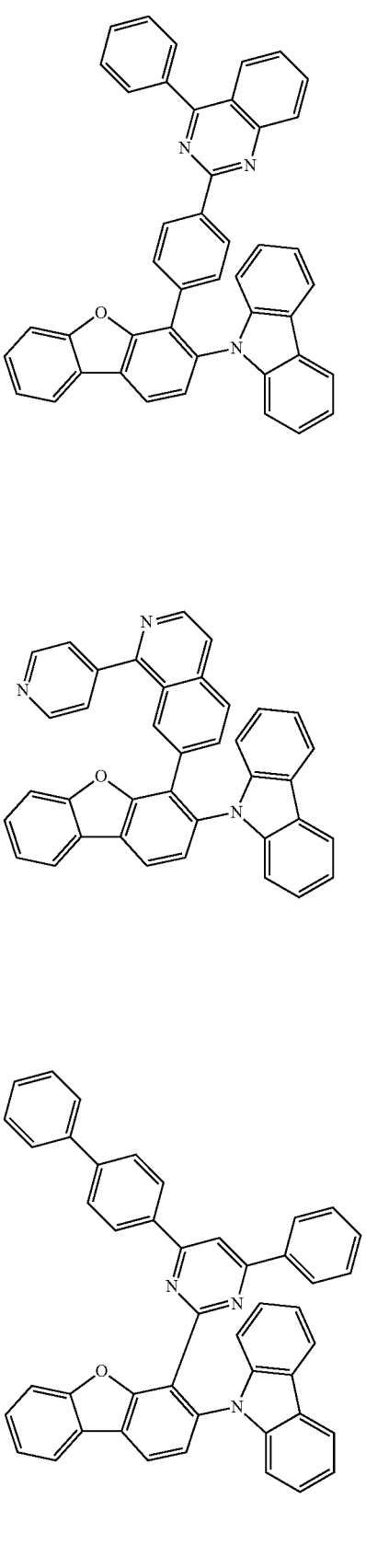

201
-continued
54
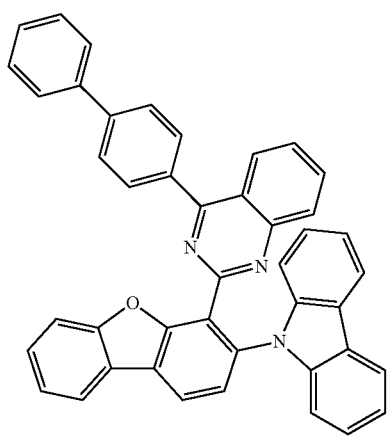
55
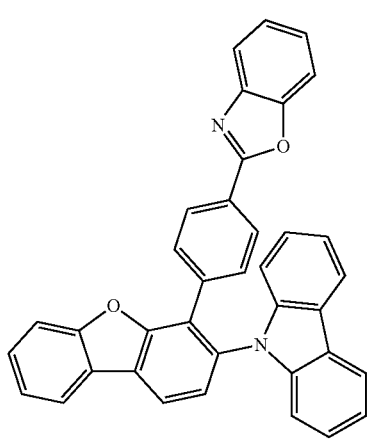
56
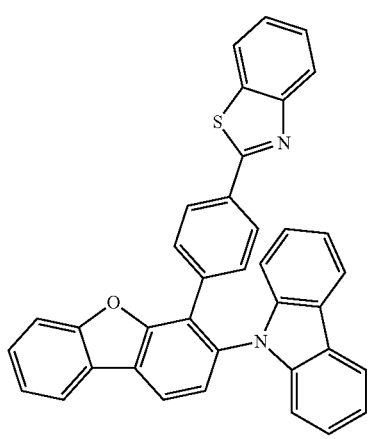
202
-continued
57
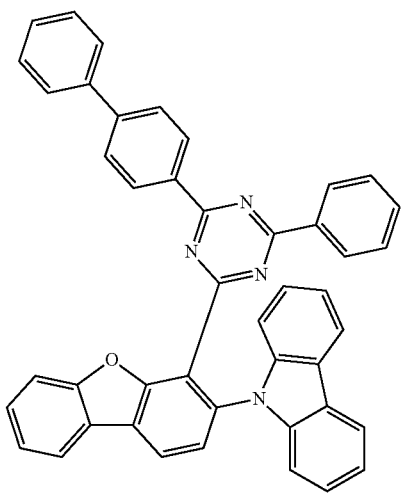
58
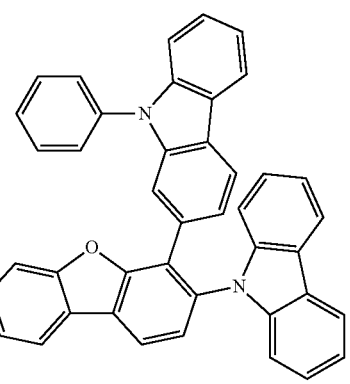
59
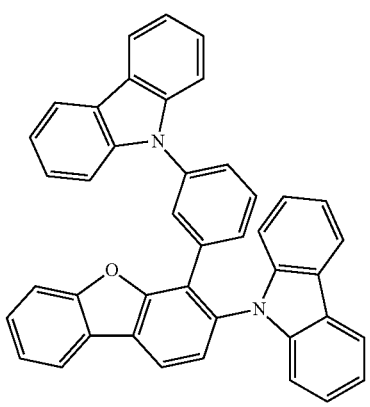
60

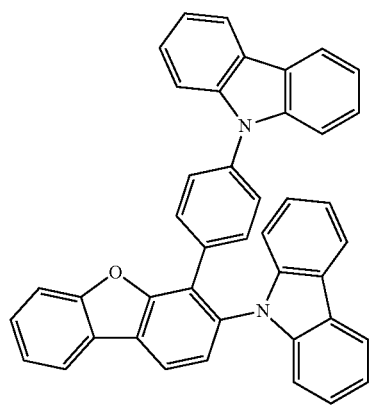
61
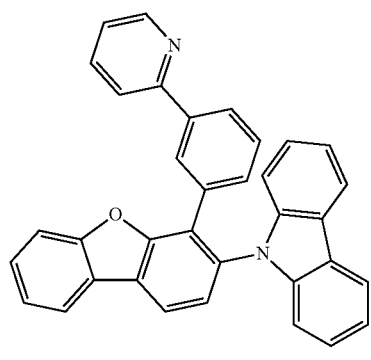
62
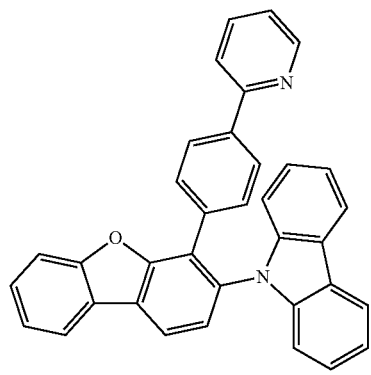
63
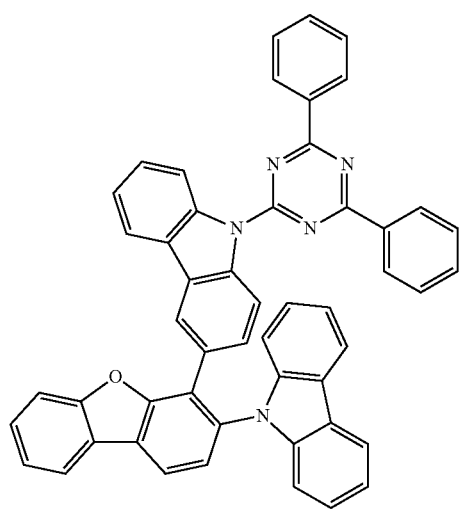
64
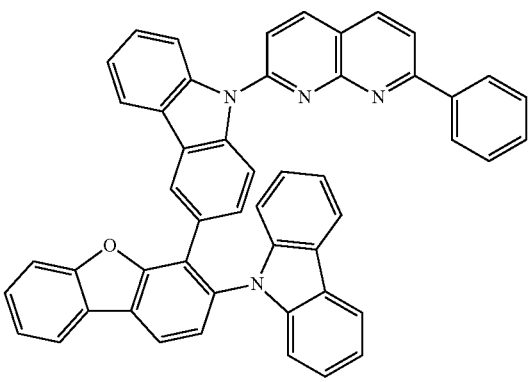
65
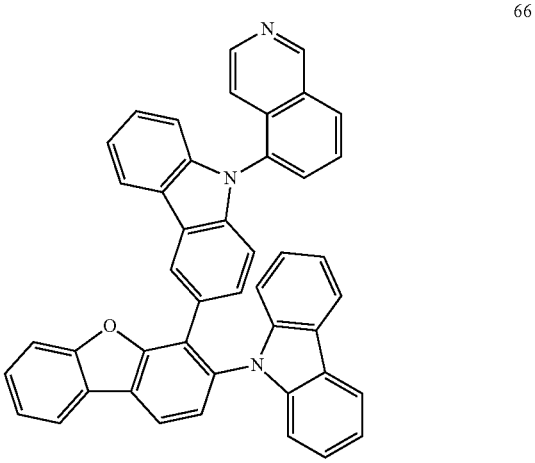
66
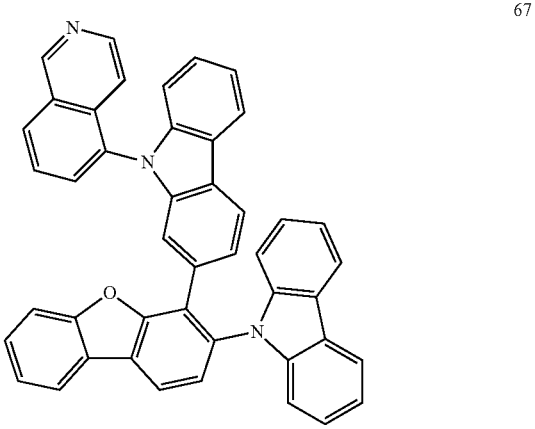
67

205
-continued
68
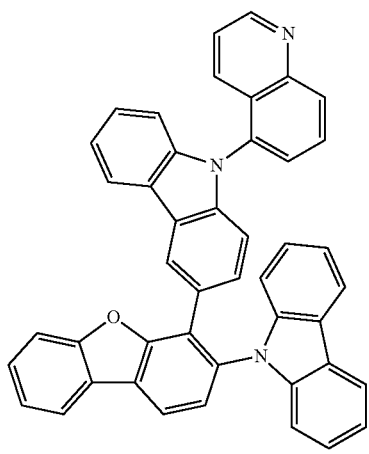
69
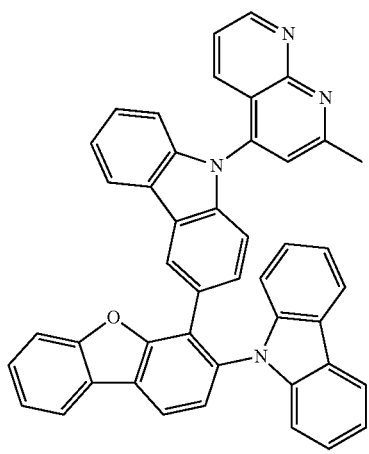
70
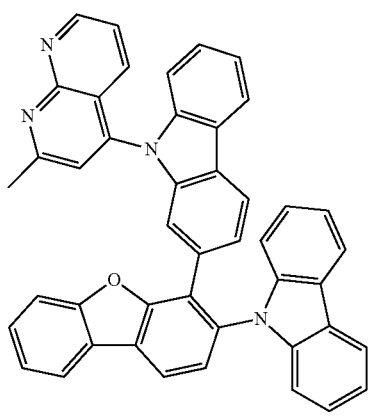
206
-continued
71
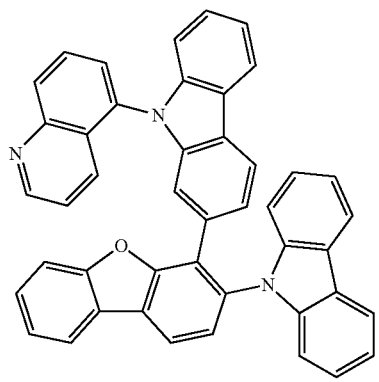
72
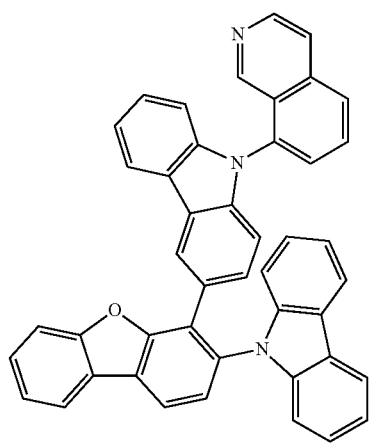
73
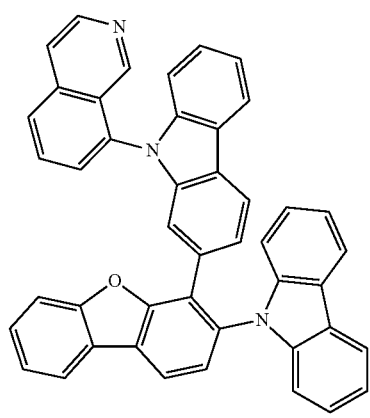

207
-continued
74
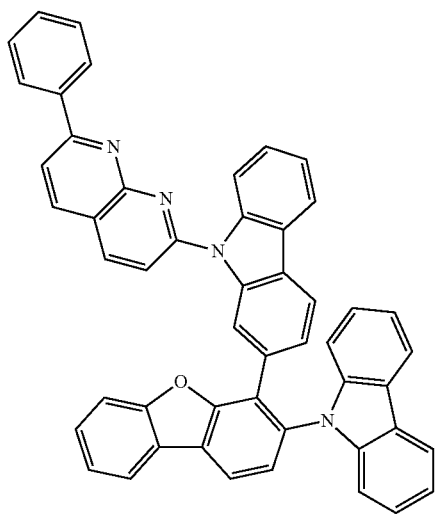
75
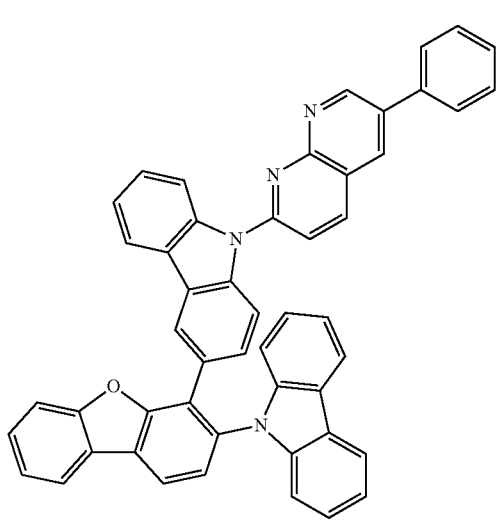
76
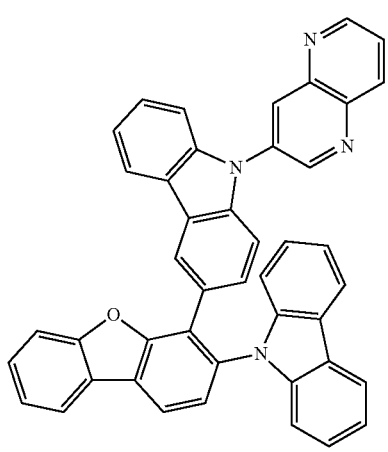
208
-continued
77
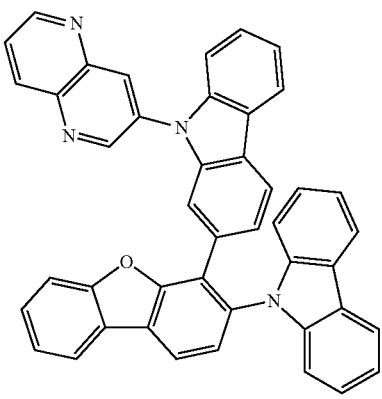
78
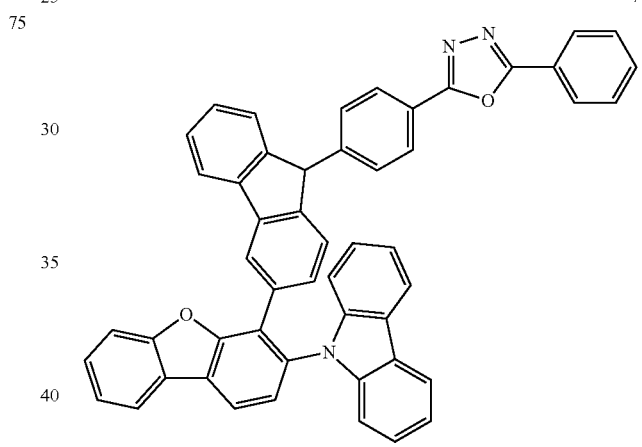
79
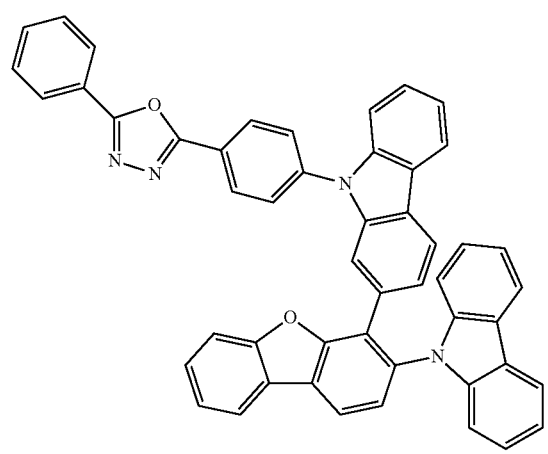

80
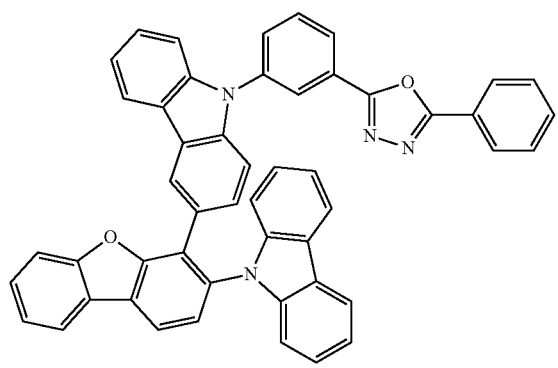
81
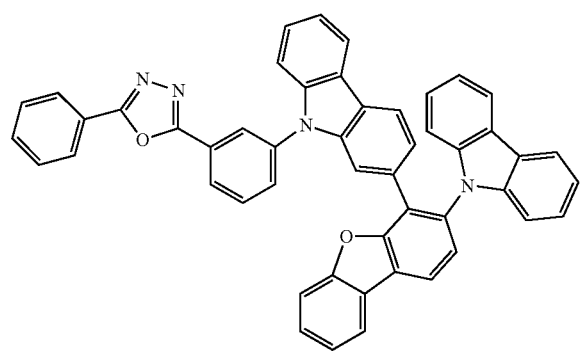
82
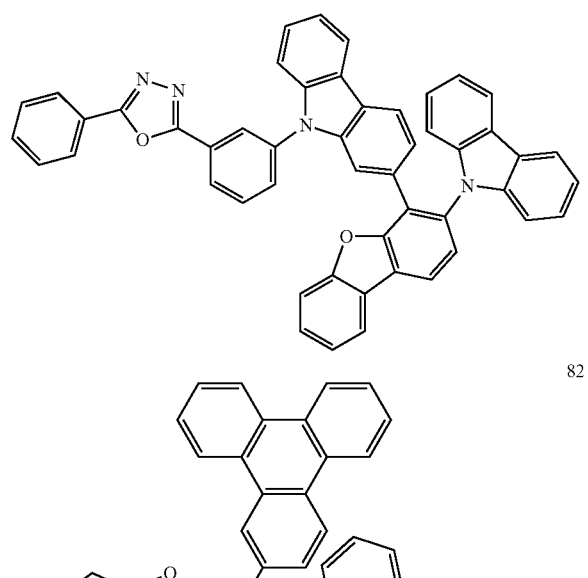
83
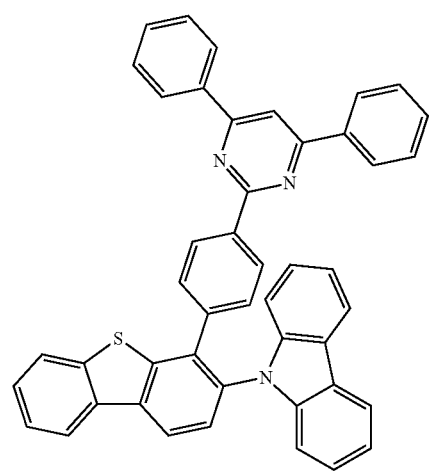
84
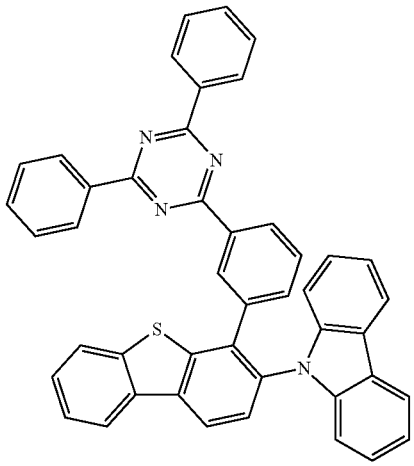
85
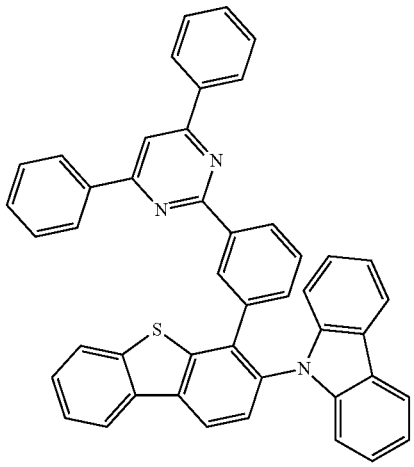
86
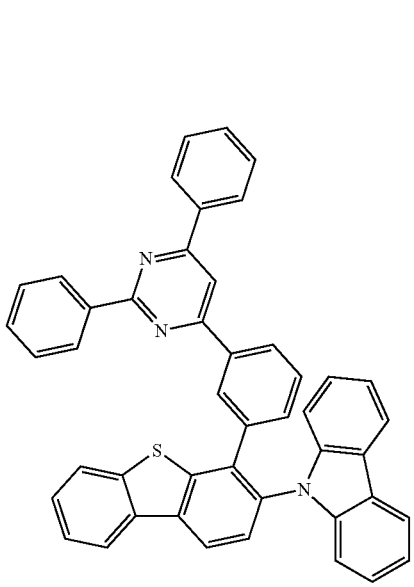

87
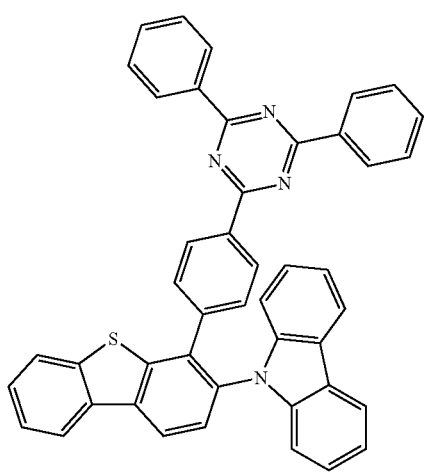
88
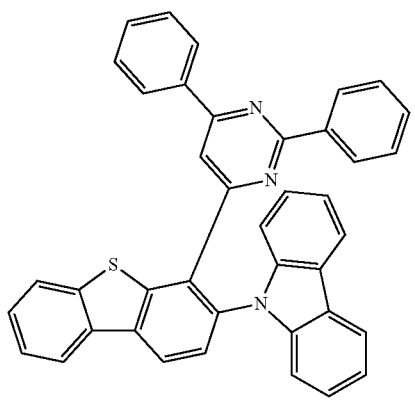
89
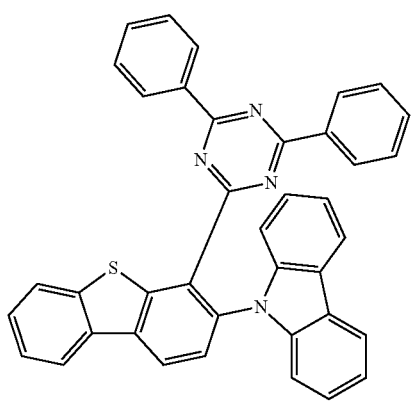
90
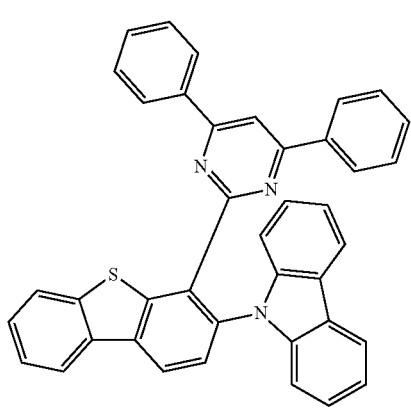
91
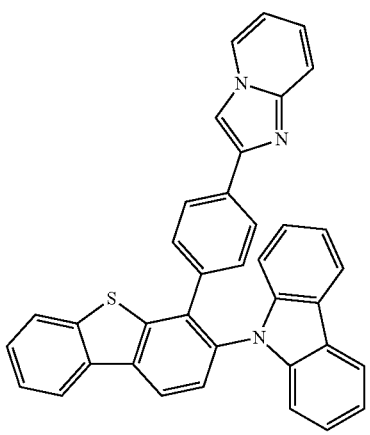
92
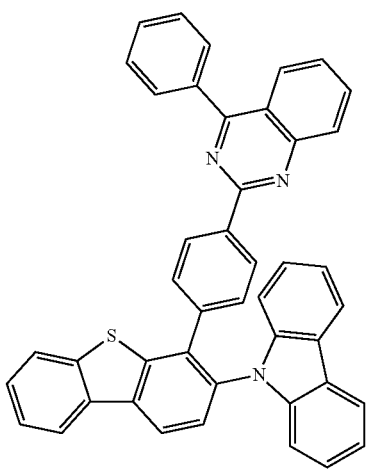
93
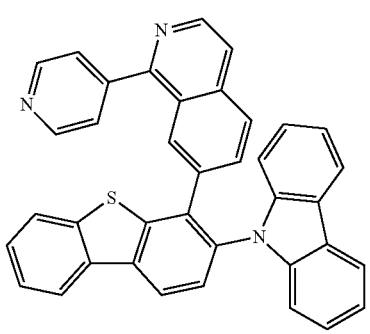

213
-continued
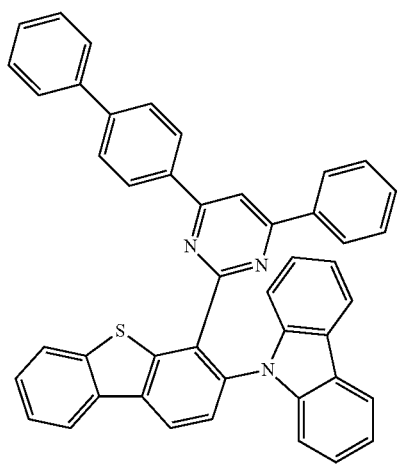
214
-continued
94
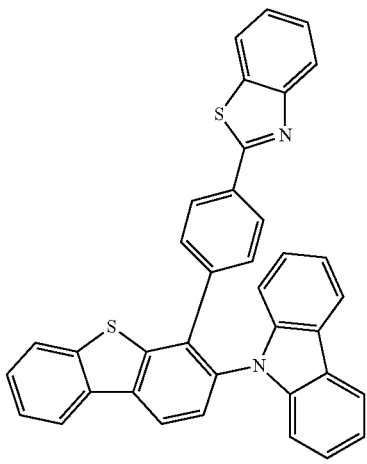
95
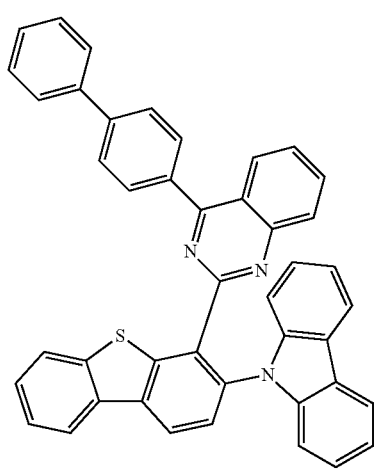
97
98
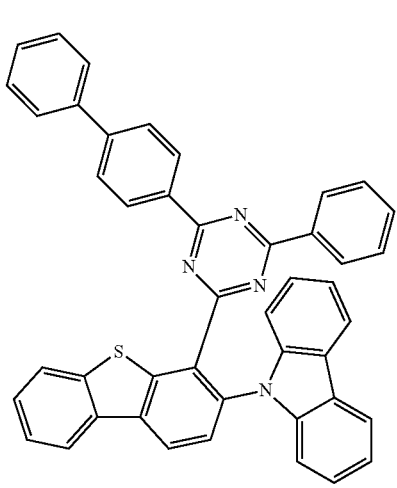
96
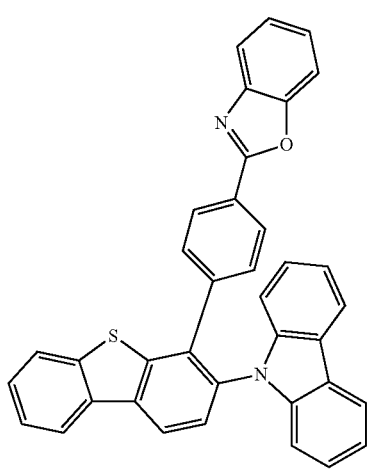
99
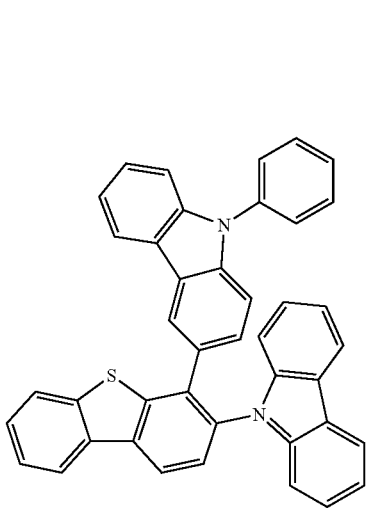

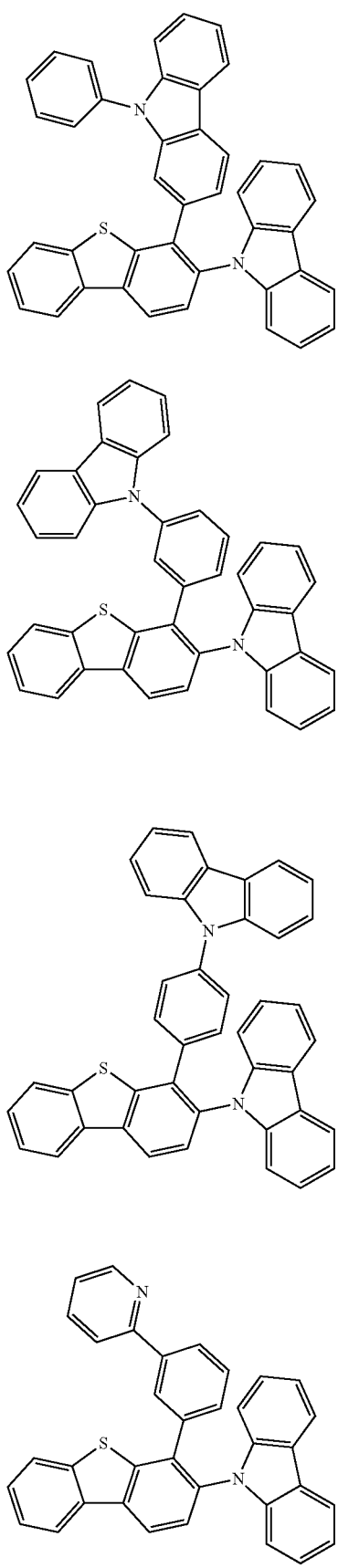
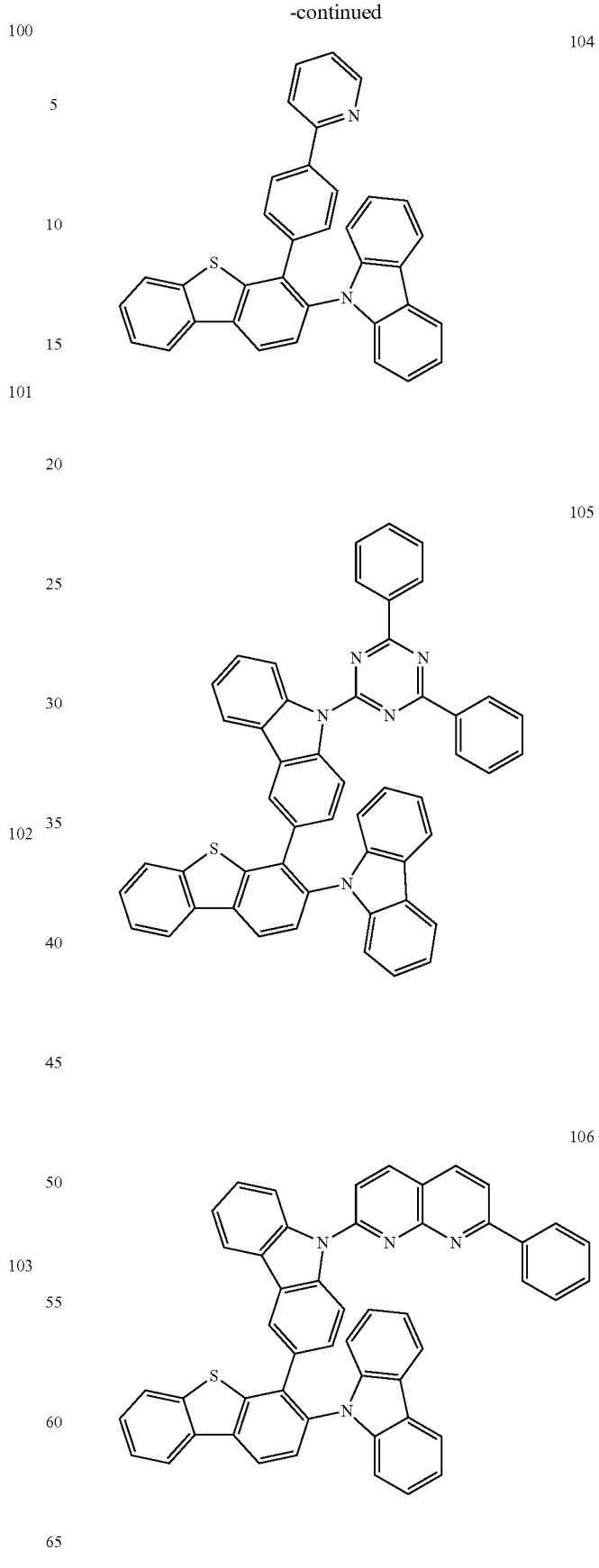

107
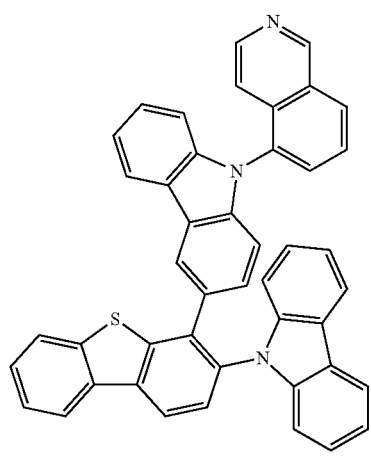
108
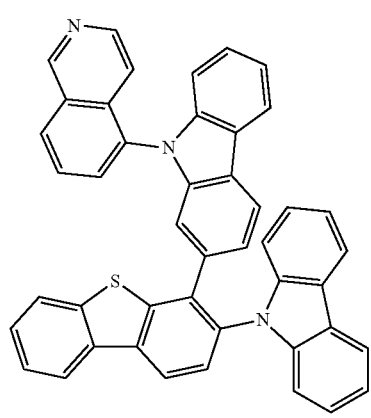
109
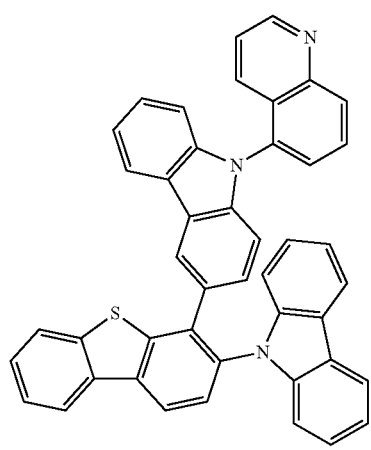
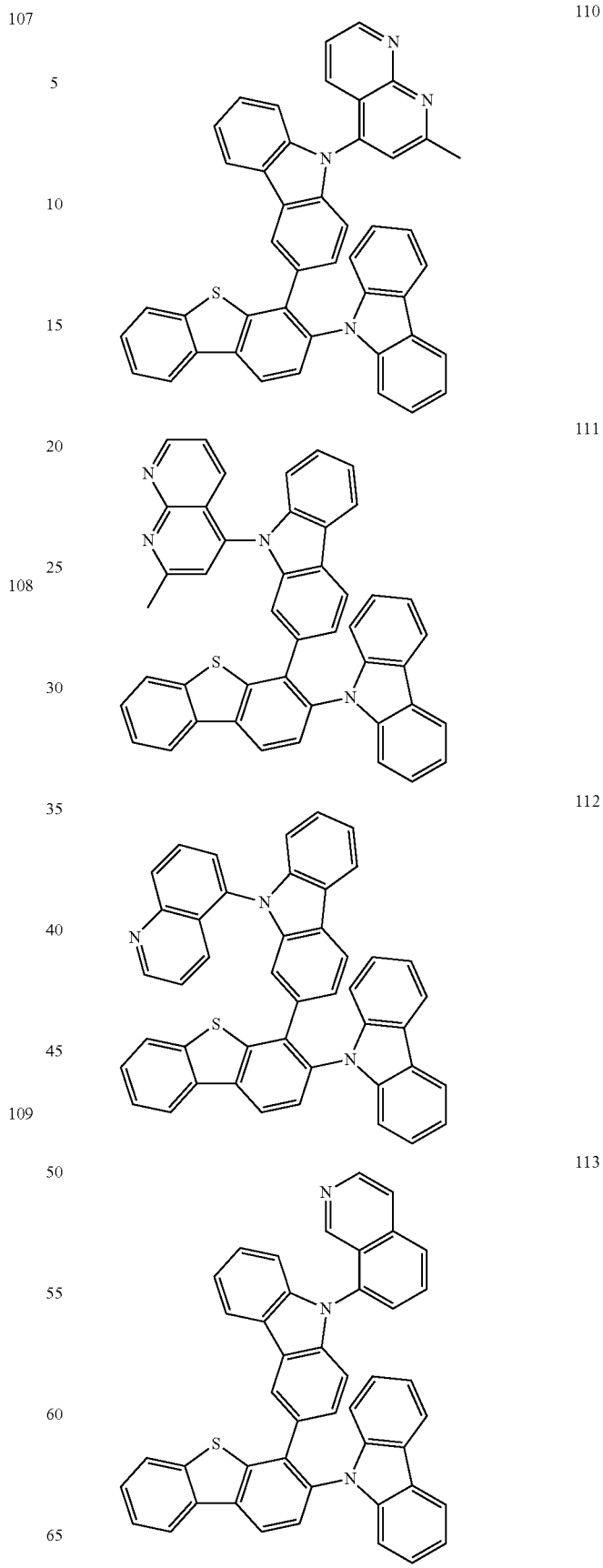

-continued
114
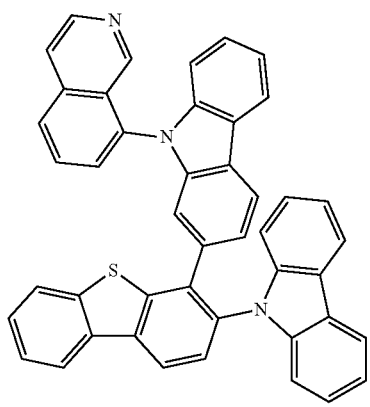
115
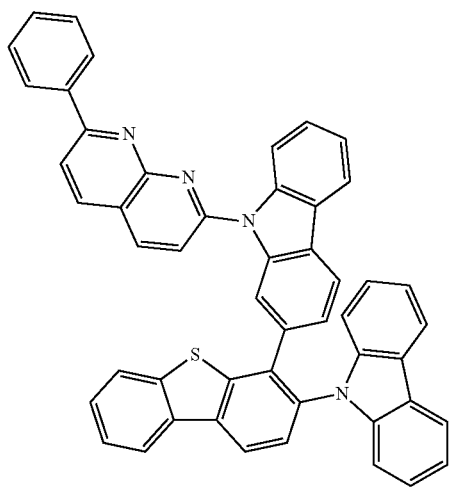
116
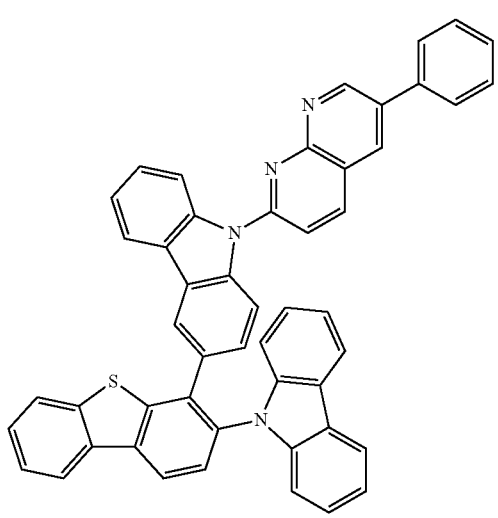
-continued
117
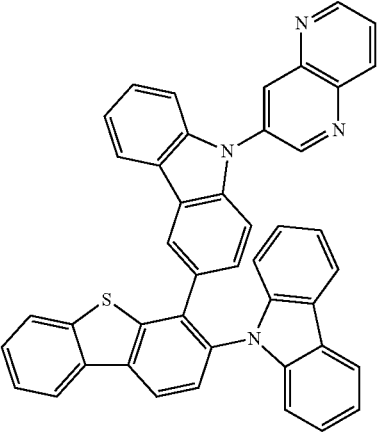
118
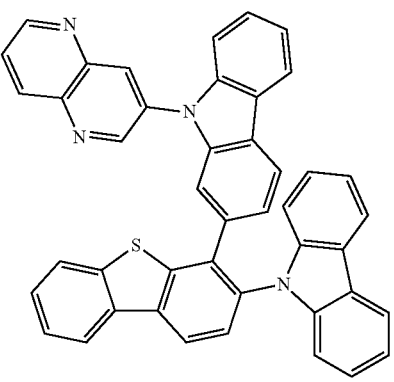
119
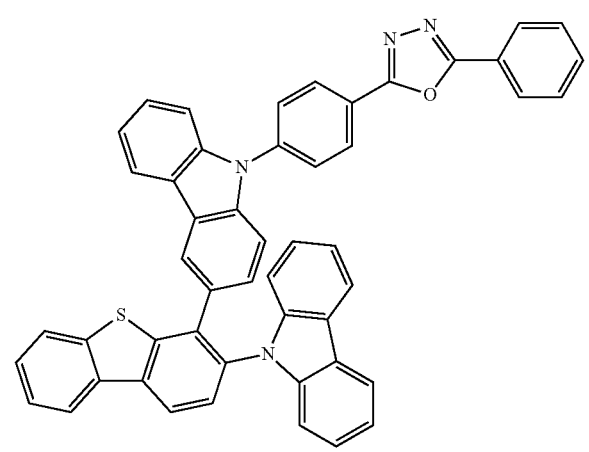

120
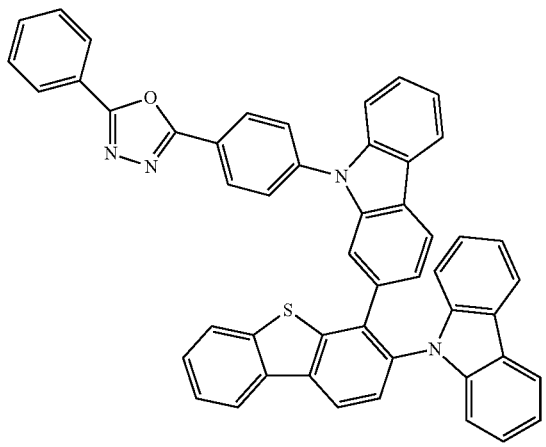
121
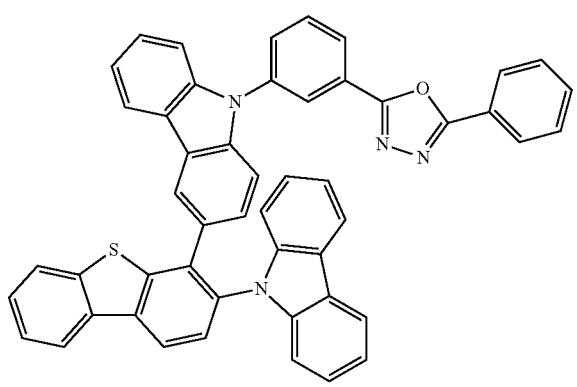
122
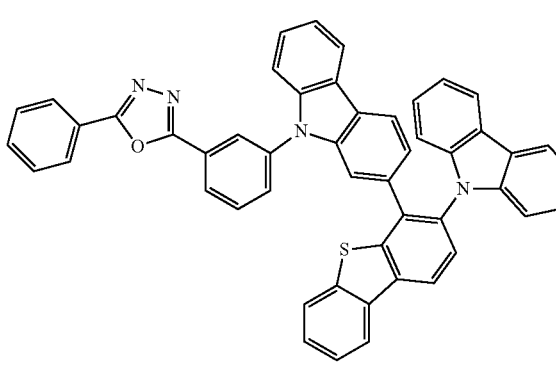
123
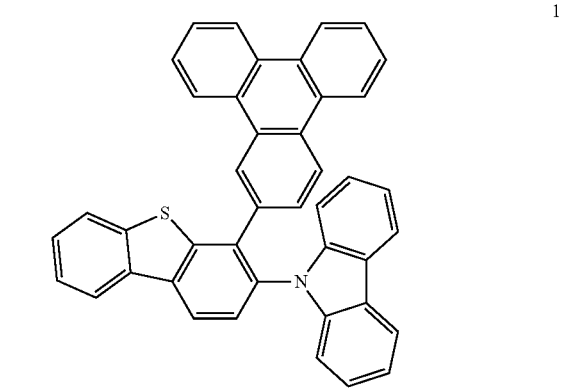
124
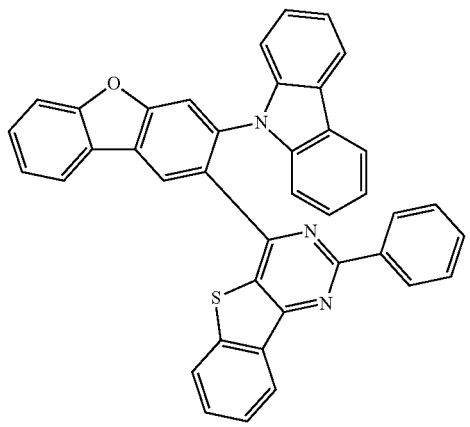
125
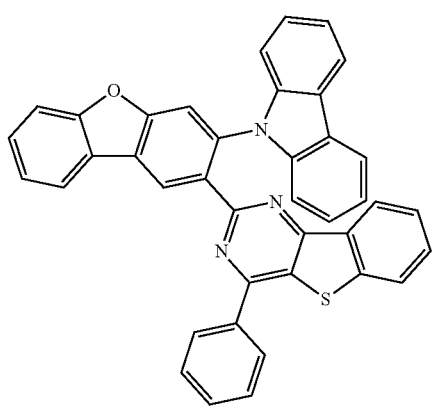
126
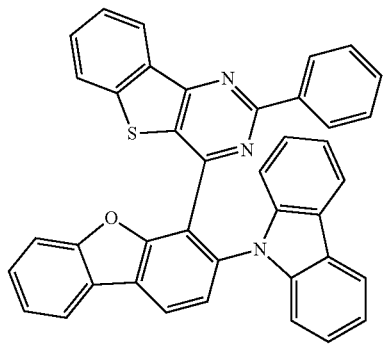
127
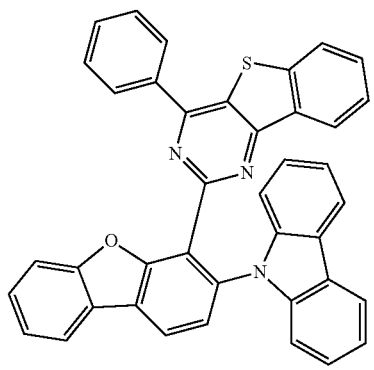

223
-continued

128
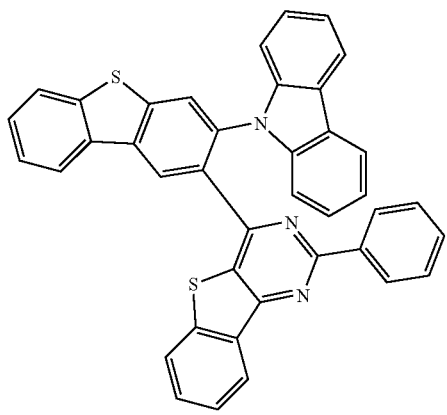

129
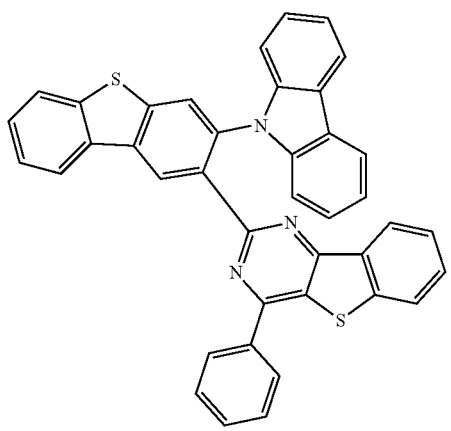

130
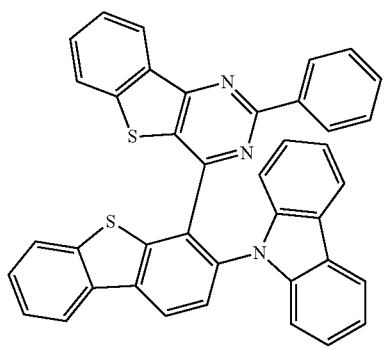

131
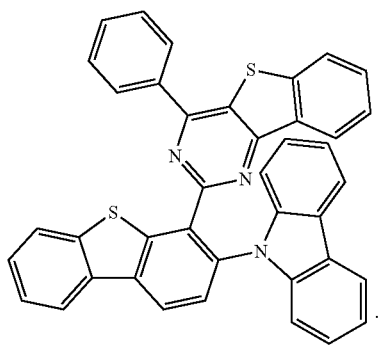

224

14. An organic light-emitting device comprising:
a first electrode;
a second electrode; and
an organic layer disposed between the first electrode and the second electrode,
wherein the organic layer comprises an emission layer and at least one carbazole compound of Formula 1 of claim 1.

15. The organic light-emitting device of claim 14, wherein
the first electrode is an anode,
the second electrode is a cathode, and
the organic layer comprises
i) a hole transport region disposed between the first electrode and the emission layer, wherein the hole transport region comprises at least one of a hole injection layer, a hole transport layer, and an electron blocking layer, and
ii) an electron transport region disposed between the emission layer and the second electrode, wherein the electron transport region comprises at least one of a hole blocking layer, an electron transport layer, and an electron injection layer.

16. The organic light-emitting device of claim 14, wherein the emission layer comprises the at least one carbazole compound represented by Formula 1.

17. The organic light-emitting device of claim 14, wherein the emission layer comprises a first host and a second host, wherein
the first host and the second host are different from each other,
the emission layer comprises the at least one carbazole compound represented by Formula 1,
the first host comprises at least one carbazole compound represented by Formula 1, wherein at least one of $R_2$ to $R_4$ is independently selected from
a pyridinyl group, a pyrazinyl group, a pyrimidinyl group, a pyridazinyl group, a quinolinyl group, an isoquinolinyl group, a naphthyridinyl group, a quinoxalinyl group, a quinazolinyl group, a benzothiazolyl group, an isobenzothiazolyl group, a benzoxazolyl group, an isobenzooxazolyl group, an oxadiazolyl group, a triazinyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, and
a pyridinyl group, a pyrazinyl group, a pyrimidinyl group, a pyridazinyl group, a quinolinyl group, an isoquinolinyl group, a naphthyridinyl group, a quinoxalinyl group, a quinazolinyl group, a benzothiazolyl group, an isobenzothiazolyl group, a benzoxazolyl group, an isobenzooxazolyl group, an oxadiazolyl group, a triazinyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, each substituted with at least one of a deuterium, —F, —Cl, —Br, —I, a hydroxyl group, a cyano group, a nitro group, an amino group, an amidino group, a hydrazine group, a hydrazone group, carboxylic acid group or a salt thereof, a sulfonic acid group or a salt thereof, a phosphoric acid group or a salt thereof, $C_1$-$C_{20}$ alkyl group, $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$), the second host comprises at least one carbazole compound represented by Formula 1 in which at least one of $R_2$ to $R_4$ is independently selected from a thiophenyl group, a furanyl group, a carbazolyl group, acridinyl, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, and a thiophenyl group, a furanyl group, a carbazolyl group, acridinyl, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$), wherein $Q_{33}$ to $Q_{35}$ are each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

18. The organic light-emitting device of claim 14, wherein the emission layer comprises host 1 and host 2, wherein
the host 1 and the host 2 are different from each other,
the emission layer comprises the at least one carbazole compound represented by Formula 1,
the host 1 comprises a carbazole compound represented by Formula 1, and
the host 2 comprises at least one of a first compound represented by Formula 41 and a second compound represented by Formula 61:

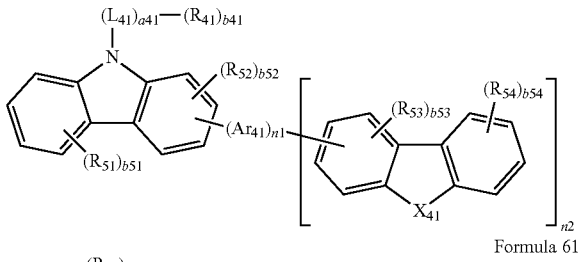

Formula 41

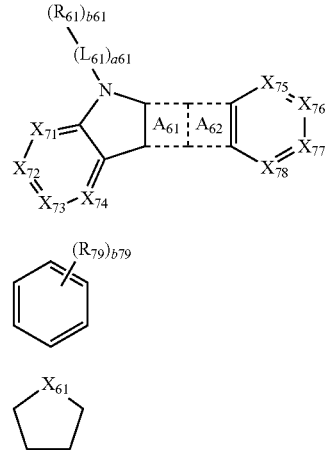

Formula 61

Formula 61A

Formula 61B wherein, in Formulae 41, 61, 61A, and 61B, $X_{41}$ is N-[($L_{42}$)$_{a42}$-($R_{42}$)$_{b42}$], S, O, S(=O), S(=O)$_2$, C(=O), C($R_{43}$)($R_{44}$), Si($R_{43}$)($R_{44}$), P($R_{43}$), P(=O)($R_{43}$), or C=N($R_{43}$);

ring $A_{61}$ in Formula 61 is represented by Formula 61A;
ring $A_{62}$ in Formula 61 is represented by Formula 61B;
$X_{61}$ is N-[($L_{62}$)$_{a62}$-($R_{62}$)$_{b62}$], S, O, S(=O), S(=O)$_2$, C(=O), C($R_{63}$)($R_{64}$), Si($R_{63}$)($R_{64}$), P($R_{63}$), P(=O)($R_{63}$), or C=N($R_{63}$);
$X_{71}$ is C($R_{71}$) or N;
$X_{72}$ is C($R_{72}$) or N;
$X_{73}$ is C($R_{73}$) or N;
$X_{74}$ is C($R_{74}$) or N;
$X_{75}$ is C($R_{75}$) or N;
$X_{76}$ is C($R_{76}$) or N;
$X_{77}$ is C($R_{77}$) or N;
$X_{78}$ is C($R_{78}$) or N;
$Ar_{41}$, $L_{41}$, $L_{42}$, $L_{61}$, and $L_{62}$ are each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent nonaromatic condensed polycyclic group, and a substituted or unsubstituted divalent nonaromatic condensed heteropolycyclic group;
n1 and n2 are each independently an integer selected from 0 to 3;
a41, a42, a61, and a62 are each independently an integer selected from 0 to 3;
$R_{41}$ to $R_{44}$, $R_{51}$ to $R_{54}$, $R_{61}$ to $R_{64}$, and $R_{71}$ to $R_{79}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent nonaromatic condensed polycyclic group, a substituted or unsubstituted monovalent nonaromatic condensed heteropolycyclic group, —N($Q_1$)($Q_2$), —Si($Q_3$)($Q_4$)($Q_5$), and —B($Q_6$)($Q_7$);

b41, b42, b51 to b54, b61, b62, and b79 are each independently an integer selected from 1 to 3;

at least one of substituents of the substituted $C_1$-$C_{60}$ alkylene group, the substituted $C_2$-$C_{60}$ alkenylene group, the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —N($Q_{11}$)($Q_{12}$), —Si($Q_{13}$)($Q_{14}$)($Q_{15}$), and —B($Q_{16}$)($Q_{17}$), a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, and a monovalent nonaromatic condensed heteropolycyclic group, a $C_3$-$C_{10}$ cycloalkyl group, a $C_2$—C heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, and a monovalent nonaromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent nonaromatic condensed polycyclic group, and a monovalent aromatic condensed heteropolycyclic group.

19. The organic light-emitting device of claim 18, wherein at least one of $R_2$ to $R_4$ in Formula 1 is independently selected from a pyridinyl group, a pyrazinyl group, a pyrimidinyl group, a pyridazinyl group, a quinolinyl group, an isoquinolinyl group, a naphthyridinyl group, a quinoxalinyl group, a quinazolinyl group, a benzothiazolyl group, an isobenzothiazolyl group, a benzoxazolyl group, an isobenzooxazolyl group, an oxadiazolyl group, a triazinyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, and a pyridinyl group, a pyrazinyl group, a pyrimidinyl group, a pyridazinyl group, a quinolinyl group, an isoquinolinyl group, a naphthyridinyl group, a quinoxalinyl group, a quinazolinyl group, a benzothiazolyl group, an isobenzothiazolyl group, a benzoxazolyl group, an isobenzooxazolyl group, an oxadiazolyl group, a triazinyl group, an imidazopyridinyl group, an imidazopyrimidinyl group, a pyridobenzofuranyl group, a pyrimidobenzofuranyl group, a pyridobenzothiophenyl group, and a pyrimidobenzothiophenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$); and at least one of $R_{41}$, $R_{42}$, and $R_{52}$ in Formula 41, and at least one of $R_{61}$ and $R_{62}$ in Formula 61 is independently selected from a thiophenyl group, a furanyl group, a carbazolyl group, acridinyl, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group and an ovalenyl group, and a thiophenyl group, a furanyl group, a carbazolyl group, acridinyl, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid group or a salt thereof, a $C_1$-$C_{20}$ alkyl group, a $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$), wherein $Q_{33}$ to $Q_{35}$ are each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

20. The organic light-emitting device of claim 18, wherein at least one of $R_2$ to $R_4$ in Formula 1 is independently selected from a thiophenyl group, a furanyl group, a carbazolyl group, acridinyl, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, and a thiophenyl group, a furanyl group, a carbazolyl group, acridinyl, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$); and at least one of $R_{41}$, $R_{42}$, and $R_{52}$ in Formula 41 and at least one of $R_{61}$ and $R_{62}$ in Formula 61 are each independently selected from a pyrrolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, phenanthridinyl, phenanthrolinyl, phenazinyl, a benzoimidazolyl group, an isobenzothiazolyl group, a benzoxazolyl group, an isobenzooxazolyl group, a triazolyl group, a tetrazolyl group, an oxadiazolyl group, a triazinyl group, an imidazopyridinyl group, and an imidazopyrimidinyl group, and a pyrrolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, phenanthridinyl, phenanthrolinyl, phenazinyl, a benzoimidazolyl group, an isobenzothiazolyl group, a benzoxazolyl group, an isobenzooxazolyl group, a triazolyl group, a tetrazolyl group, an oxadiazolyl group, a triazinyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a $C_1$-$C_{20}$ alkyl group-substituted phenyl group, a phenyl group-substituted phenyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, and —Si($Q_{33}$)($Q_{34}$)($Q_{35}$), wherein $Q_{33}$ to $Q_{35}$ are each independently selected from a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

* * * * *